US006284755B1

(12) United States Patent
deSolms et al.

(10) Patent No.: US 6,284,755 B1
(45) Date of Patent: Sep. 4, 2001

(54) INHIBITORS OF PRENYL-PROTEIN TRANSFERASE

(75) Inventors: S. Jane deSolms, Norristown; Samuel L. Graham, Schwenksville; Anthony W. Shaw, Lansdale; Terrence M. Ciccarone, Telford; Gerald E. Stokker, Gwynedd Valley, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/456,153

(22) Filed: Dec. 7, 1999

Related U.S. Application Data

(60) Provisional application No. 60/111,416, filed on Dec. 8, 1998, and provisional application No. 60/129,282, filed on Apr. 14, 1999.

(51) Int. Cl.$^7$ .................................................... A01N 43/46
(52) U.S. Cl. ............................... 514/212.03; 514/212.08; 540/524; 540/531
(58) Field of Search ........................ 514/212.08; 540/524

(56) References Cited

U.S. PATENT DOCUMENTS

| 4,006,243 | 2/1977 | Strehlke et al. | 424/273 |
|---|---|---|---|
| 4,916,144 | 4/1990 | Strehlke et al. | 514/326 |
| 5,739,132 | 4/1998 | Ishida et al. | 514/247 |
| 5,756,528 | 5/1998 | Anthony et al. | 514/399 |
| 5,780,488 | 7/1998 | Bergman et al. | 514/357 |
| 5,780,492 | 7/1998 | Dinsmore et al. | 514/397 |

FOREIGN PATENT DOCUMENTS

| 0 875 506 A1 | 11/1998 | (EP) . |
|---|---|---|
| 928788 | 7/1999 | (EP) . |
| WO 97/16443 | 5/1997 | (WO) . |
| WO 97/17070 | 5/1997 | (WO) . |
| WO 97/21701 | 6/1997 | (WO) . |
| WO 97/30992 | 8/1997 | (WO) . |
| WO 97/44350 | 11/1997 | (WO) . |
| WO 98/02436 | 1/1998 | (WO) . |
| WO 98/32741 | 7/1998 | (WO) . |
| WO 98/34921 | 8/1998 | (WO) . |
| WO 98/40383 | 9/1998 | (WO) . |
| WO 98/49157 | 11/1998 | (WO) . |
| WO 99/01434 | 1/1999 | (WO) . |
| WO 99/20611 | 4/1999 | (WO) . |
| WO 99/20612 | 4/1999 | (WO) . |
| WO 99/55725 | 11/1999 | (WO) . |

OTHER PUBLICATIONS

John D. Roberts and Marjorie C. Caserio, "Basic Principles of Organic Chemistry", Benjamin, New York, 1964, p. 969.*

Rosanio, S. et al, Thromb. Haemost., 1999, 82 Suppl. 1, 164–170.*

Draetta, G. and Pagano, M. in "Annual Reports in Medicinal Chemistry, vol. 31", 1996, Academic Press, San Diego, pp. 241–246.*

Bolton, G.L. et al, in "Annual Reports in Medicinal Chemistry, vol. 29", 1994, Academic Press, San Diego, pp. 165–174.*

Arch. Pharm. (Weinheim), vol. 322, pp. 515–516 (1989), by M. Muller, et al.

Curr. Opin. Chem. Biol. vol. 2, No. 1, pp. 40–48 (1998), by M. H. Gelb, et al.

Exp. Opin. Ther. Patents, vol. 9, No. 9, pp. 1263–1280 (1999), by T. M. Williams.

Eur. J. Med. Chem—Chimica Therapeutica, vol. 15, No. 4, (1980), pp. 375–385, by G. Bradley, et al.

Exp. Opin. Ther. Patents, vol. 6, No. 12 (1996), pp. 1295–1304, by S. L. Graham, et al.

Exp. Opin. Ther. Patents, vol. 5, No. 12 (1995), pp. 1269–1285, by S. L. Graham.

J. of Biol. Chem., vol. 268, No. 11 (1993), pp. 7617–7620, by J. B. Gibbs, et al.

J. of Biol. Chem., vol. 266, No. 24 (1991), pp. 15575–15578, by J. L. Goldstein, et al.

J. of Biol. Chem., vol. 269, No. 44 (1994), pp. 27705–27714, by G. L. James, et al.

Nature Medicine, vol. 1, No. 8 (1995), pp. 792–797, by N.E. Kohl, et al.

Science, vol. 260 (1993), pp. 1934–1937, by N. E. Kohl, et al.

Biochemistry, vol. 31 (1992), pp. 3800–3807, by D. L. Pompliano, et al.

Cancer Research, vol. 55 (1995), pp. 5302–5309, by L. Sepp–Lorenzino.

Proc. Natl. Acad. Sci. USA, vol. 91 (1994), pp. 9141–9144, by N. E. Kohl, et al.

* cited by examiner

Primary Examiner—Mark L. Berch
Assistant Examiner—Thomas McKenzie
(74) Attorney, Agent, or Firm—Dianne Pecoraro; Mark R. Daniel

(57) ABSTRACT

The present invention is directed to azepan-2-one compounds which inhibit prenyl-protein transferase, particularly farnesyl-protein transferase (Ftase), and the prenylation of the oncogene protein Ras. The invention is further directed to chemotherapeutic compositions containing the compounds of this invention and methods for inhibiting prenyl-protein transferase and the prenylation of the oncogene protein Ras.

35 Claims, No Drawings

SEQUENCE LISTING

```
<160> NUMBER OF SEQ ID NOS: 21

<210> SEQ ID NO 1
<211> LENGTH: 4
<212> TYPE: PRT
<213> ORGANISM: Homosapien

<400> SEQUENCE: 1

Cys Val Leu Leu
 1

<210> SEQ ID NO 2
<211> LENGTH: 15
<212> TYPE: PRT
<213> ORGANISM: Homosapien

<400> SEQUENCE: 2

Gly Lys Lys Lys Lys Lys Lys Ser Lys Thr Lys Cys Val Ile Met
 1               5                  10                  15
```

```
<210> SEQ ID NO 3
<211> LENGTH: 52
<212> TYPE: DNA
<213> ORGANISM: Artificial Sequence
<220> FEATURE:
<223> OTHER INFORMATION: completely synthesized

<400> SEQUENCE: 3
gagagggaat cgggcccttt cctgcatgct gctgctgctg ctgctgctgg gc        52

<210> SEQ ID NO 4
<211> LENGTH: 41
<212> TYPE: DNA
<213> ORGANISM: Artificial Sequence
<220> FEATURE:
<223> OTHER INFORMATION: completely synthesized

<400> SEQUENCE: 4
gagagagctc gaggttaacc cgggtgcgcg gcgtcggtgg t                    41

<210> SEQ ID NO 5
<211> LENGTH: 42
<212> TYPE: DNA
<213> ORGANISM: Artificial Sequence
<220> FEATURE:
<223> OTHER INFORMATION: completely synthesized

<400> SEQUENCE: 5
gagagagtct agagttaacc cgtggtcccc gcgttgcttc ct                   42

<210> SEQ ID NO 6
<211> LENGTH: 43
<212> TYPE: DNA
<213> ORGANISM: Artificial Sequence
<220> FEATURE:
<223> OTHER INFORMATION: completely synthesized

<400> SEQUENCE: 6
gaagaggaag cttggtaccg ccactgggct gtaggtggtg gct                  43

<210> SEQ ID NO 7
<211> LENGTH: 27
<212> TYPE: DNA
<213> ORGANISM: Artificial Sequence
<220> FEATURE:
<223> OTHER INFORMATION: completely synthesized

<400> SEQUENCE: 7
ggcagagctc gtttagtgaa ccgtcag                                    27

<210> SEQ ID NO 8
<211> LENGTH: 27
<212> TYPE: DNA
<213> ORGANISM: Artificial Sequence
<220> FEATURE:
<223> OTHER INFORMATION: completely synthesized

<400> SEQUENCE: 8
gagagatctc aaggacggtg actgcag                                    27

<210> SEQ ID NO 9
<211> LENGTH: 86
<212> TYPE: DNA
<213> ORGANISM: Artificial Sequence
<220> FEATURE:
```

<223> OTHER INFORMATION: completely synthesized

<400> SEQUENCE: 9
tctcctcgag gccaccatgg ggagtagcaa gagcaagcct aaggacccca gccagcgccg    60
gatgacagaa tacaagcttg tggtgg    86

<210> SEQ ID NO 10
<211> LENGTH: 33
<212> TYPE: DNA
<213> ORGANISM: Artificial Sequence
<220> FEATURE:
<223> OTHER INFORMATION: completely synthesized

<400> SEQUENCE: 10
cacatctaga tcaggacagc acagacttgc agc    33

<210> SEQ ID NO 11
<211> LENGTH: 41
<212> TYPE: DNA
<213> ORGANISM: Artificial Sequence
<220> FEATURE:
<223> OTHER INFORMATION: completely synthesized

<400> SEQUENCE: 11
tctcctcgag gccaccatga cagaatacaa gcttgtggtg g    41

<210> SEQ ID NO 12
<211> LENGTH: 38
<212> TYPE: DNA
<213> ORGANISM: Artificial Sequence
<220> FEATURE:
<223> OTHER INFORMATION: completely synthesized

<400> SEQUENCE: 12
cactctagac tggtgtcaga gcagcacaca cttgcagc    38

<210> SEQ ID NO 13
<211> LENGTH: 38
<212> TYPE: DNA
<213> ORGANISM: Artificial Sequence
<220> FEATURE:
<223> OTHER INFORMATION: completely synthesized

<400> SEQUENCE: 13
gagagaattc gccaccatga cggaatataa gctggtgg    38

<210> SEQ ID NO 14
<211> LENGTH: 33
<212> TYPE: DNA
<213> ORGANISM: Artificial Sequence
<220> FEATURE:
<223> OTHER INFORMATION: completely synthesized

<400> SEQUENCE: 14
gagagtcgac gcgtcaggag agcacacact tgc    33

<210> SEQ ID NO 15
<211> LENGTH: 22
<212> TYPE: DNA
<213> ORGANISM: Artificial Sequence
<220> FEATURE:
<223> OTHER INFORMATION: completely synthesized

<400> SEQUENCE: 15
ccgccggcct ggaggagtac ag    22

<210> SEQ ID NO 16
<211> LENGTH: 38
<212> TYPE: DNA
<213> ORGANISM: Artificial Sequence
<220> FEATURE:
<223> OTHER INFORMATION: completely synthesized

<400> SEQUENCE: 16
gagagaattc gccaccatga ctgagtacaa actggtgg               38

<210> SEQ ID NO 17
<211> LENGTH: 32
<212> TYPE: DNA
<213> ORGANISM: Artificial Sequence
<220> FEATURE:
<223> OTHER INFORMATION: completely synthesized

<400> SEQUENCE: 17
gagagtcgac ttgttacatc accacacatg gc                     32

<210> SEQ ID NO 18
<211> LENGTH: 21
<212> TYPE: DNA
<213> ORGANISM: Artificial Sequence
<220> FEATURE:
<223> OTHER INFORMATION: completely synthesized

<400> SEQUENCE: 18
gttggagcag ttggtgttgg g                                 21

<210> SEQ ID NO 19
<211> LENGTH: 38
<212> TYPE: DNA
<213> ORGANISM: Artificial Sequence
<220> FEATURE:
<223> OTHER INFORMATION: completely synthesized

<400> SEQUENCE: 19
gagaggtacc gccaccatga ctgaatataa acttgtgg               38

<210> SEQ ID NO 20
<211> LENGTH: 36
<212> TYPE: DNA
<213> ORGANISM: Artificial Sequence
<220> FEATURE:
<223> OTHER INFORMATION: completely synthesized

<400> SEQUENCE: 20
ctctgtcgac gtatttacat aattacacac tttgtc                 36

<210> SEQ ID NO 21
<211> LENGTH: 24
<212> TYPE: DNA
<213> ORGANISM: Artificial Sequence
<220> FEATURE:
<223> OTHER INFORMATION: completely synthesized

<400> SEQUENCE: 21
gtagttggag ctgttggcgt aggc                              24

INHIBITORS OF PRENYL-PROTEIN TRANSFERASE

DOMESTIC PRIORITY CLAIM

This application claims the benefit of U.S. Provisional Application No. 60/111,416 and 60/129,282, filed Dec. 8, 1998 and Apr. 14, 1999, respectively, which are now abandoned.

BACKGROUND OF THE INVENTION

The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. Such enzymes may be generally termed prenyl-protein transferases. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyiso-prenoids including farnesyl pyrophosphate. Farnesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been reported that farnesyl-protein transferase inhibitors are inhibitors of proliferation of vascular smooth muscle cells and are therefore useful in the prevention and therapy of arteriosclerosis and diabetic disturbance of blood vessels (JP H7-112930).

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001 and EP 0 675 112 A1).

It is, therefore, an object of this invention to develop compounds that will inhibit prenyl-protein transferase and thus, the post-translational isoprenylation of proteins. It is a further object of this invention to develop chemotherapeutic compositions containing the compounds of this invention and methods for producing the compounds of this invention.

SUMMARY OF THE INVENTION

The present invention comprises non-prodrug compounds which inhibit prenyl-protein transferase. Further contained in this invention are chemo-therapeutic compositions containing these prenyl-protein transferase inhibitors and methods for their production.

The compounds of this invention are illustrated by the formulae I and A:

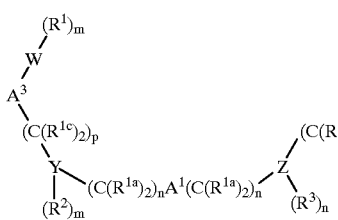

I

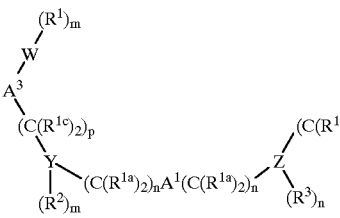

A

DETAILED DESCRIPTION OF THE INVENTION

The compounds of this invention are useful in the inhibition of prenyl-protein transferase. In a first embodiment of this invention, the inhibitors of prenyl-protein transferase are illustrated by the formula I:

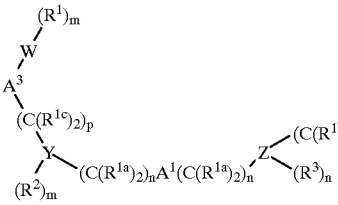

I wherein:

$R^{1a}$, $R^{1b}$ and $R^{1c}$ are independently selected from:
 a) hydrogen,
 b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^9S(O)_q$—, CN, $NO_2$, $R^8C(O)$—, $R^8OC(O)$—, $(R^8)_2NC(O)$—, —$N(R^{15})_2$, —$OR^{15}$, —$N(R^8)S(O)_qR^8$ or $N_3$;
 c) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$R^1$ is independently selected from:
 a) H,
 b) unsubstituted or substituted $C_1$–$C_6$ alkyl,
 c) unsubstituted or substituted aryl,
 d) unsubstituted or substituted heterocycle,
 e) —($C_1$–$C_6$ alkyl)$N(R^8)_2$,
 f) —$R^8C(O)R^8$,
 g) —($C_1$–$C_6$ alkyl)$OR^8$,
 h) —$N(R^8)_2$,
 i) —$OR^8$,
 j) —$R^8NHC(O)R^8$,
 k) —$R^8C(O)N(R^8)_2$,
 l) $CF_3$,
 m) halo,
 n) —$C(O)OR^8$,
 o) $C_2$–$C_6$ alkynyl,
 p) $C_2$–$C_6$ alkenyl,
 q) perfluoroalkyl,
 r) $N_3$,
 s) $NO_2$,
 t) CN,
 u) $R^9S(O)_q$—,
 v) —($C_1$–$C_6$ alkyl)$NR^8C(O)N(R^8)_2$, and
 w) —($C_1$–$C_6$ alkyl)$R^{14}$;

$R^2$ is independently selected from:
 a) hydrogen,
 b) CN,
 c) $NO_2$,
 d) halogen,
 e) aryl, unsubstituted or substituted,
 f) heteroaryl, unsubstituted or substituted,
 g) $C_1$–$C_6$ alkyl, unsubstituted or substituted,
 h) $OR^8$,
 i) $N_3$,
 j) $R^9S(O)_q$,
 k) $R^8HC$=$CH$—, and
 l) $R^8C$≡$C$—;

$R^3$ is independently selected from:
 a) H,
 b) CN,
 c) $NO_2$,
 d) halogen,
 e) $C_1$–$C_6$ alkyl, unsubstituted or substituted,
 f) $OR^8$,
 g) aryl, unsubstituted or substituted,
 h) heteroaryl, unsubstituted or substituted, and
 i) $CF_3$;

$R^5$ and $R^6$ are independently selected from:
 a) H,
 b) CN,
 c) $NO_2$,
 d) halogen,
 e) $C_1$–$C_6$ alkyl, unsubstituted or substituted,
 f) $N_3$,
 g) $R^9S(O)_q$,
 h) —$HC$=$CH_2$,
 i) $HC$≡$C$—,
 j) aryl, unsubstituted or substituted,
 k) heterocycle, unsubstituted or substituted,
 l) $CF_3O$—,
 m) $CF_3CH_2O$—,
 n) $C_3$–$C_{10}$ cycloalkyl,
 o) $CF_3$,
 p) —($C_1$–$C_6$ alkyl)$N(R^8)_2$,
 q) —($C_1$–$C_6$ alkyl)$OR^8$,
 r) $OR^8$,
 s) $N(R^8)_2$,
 t) —$C(O)(C_1$–$C_6$ alkyl),
 u) —($C_1$–$C_6$ alkyl)$C(O)R^8$,
 v) —$C(O)O(C_1$–$C_6$ alkyl),
 w) —$C(O)N(R^8)_2$,
 x) —($C_1$–$C_6$ alkyl)$NR^8C(O)N(R^8)_2$,
 y) —($C_1$–$C_6$ alkyl)$NR^8C(O)R^8$,
 z) —$C_2$–$C_6$ alkynyl,
 aa) —$C_2$–$C_6$ alkenyl,
 bb) —($C_1$–$C_6$ alkyl)$N_3$,
 cc) —($C_1$–$C_6$ alkyl)$NR^8S(O)_q$, and
 dd) —($C_1$–$C_6$ alkyl)$NR^8(C_1$–$C_6$ alkyl)$N(R^8)_2$;

$R^8$ is independently selected from hydrogen, unsubstituted or substituted $C_1$–$C_6$ alkyl, unsubstituted or substituted aralkyl, unsubstituted or substituted heterocycle and unsubstituted or substituted aryl;

R⁹ is independently selected from unsubstituted or substituted $C_1$–$C_6$ alkyl, unsubstituted or substituted benzyl and unsubstituted or substituted aryl;

$R^{14}$ is unsubstituted saturated heterocycle;

$R^{15}$ is independently selected from
  a) hydrogen, unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^9S(O)_2$—, $R^8C(O)$—, $R^8OC(O)$—, $(R^8)_2NC(O)$—, and
  b) $C_1$–$C_6$ alkyl, unsubstituted or substituted by unsubstituted or substituted aryl, unsubstituted or substituted heterocycle, $C_3$–$C$ 10 cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$A^1$ and $A^2$ are independently selected from:
  a) a bond,
  b) —HC=CH—,
  c) —C≡C—,
  d) O,
  e) $S(O)_q$,
  f) OC(O),
  g) C(O),
  h) C(O)O, and
  i) $NR^8$;

$A^3$ is selected from a bond, —C(=O)—,

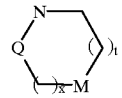

and $C_3$–$C_6$ cycloalkyl;

M is selected from $CH_2$, $NR^8$, O or $S(O)_q$;

Q is selected from $S(O)_q$, $CH_2$, C(=S), C(=NR⁸) or C(=O);

W is selected from:
  a) heterocycle, and
  b) aryl;

Y is selected from:
  a) aryl, and
  b) heterocycle;

Z is selected from:
  a) aryl,
  b) heterocycle,
  c) $C_3$–$C_6$ cycloalkyl, and
  d) a bond;

m is 0, 1, 2, 3 or 4;

n is 0, 1, 2, 3 or 4;

p is 0, 1, 2, 3 or 4;

q is 0, 1 or 2;

r is 0, 1, 2, 3, or 4;

s is 0, 1, 2, 3 or 4;

t is 0, 1, 2 or 3;

x is 0, 1, 2 or 3;

provided that the moiety

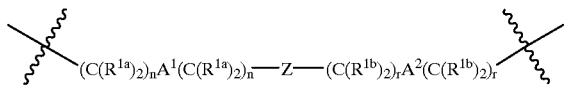

does not represent a bond; and
provided that if attachment of

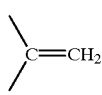

to the rest of the molecule is through a nitrogen ring atom, then $A^1$ is $NR^8$, O, or $S(O)_q$;

or a pharmaceutically acceptable salt, an optical isomer or stereoisomer thereof.

Another embodiment of the compounds of this invention is illustrated by the formula A:

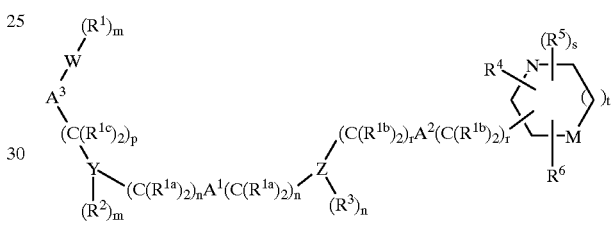

A wherein:

$R^{1a}$, $R^{1b}$ and $R^{1c}$ are independently selected from:
  a) hydrogen,
  b) unsubstituted or substituted aryl; unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, $N(R^8)_2$, $(R^8)_2NC(O)$—, $C(O)N(R^8)$—, or $N_3$;
  c) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$R^1$ is selected from:
  a) H,
  b) unsubstituted or substituted $C_1$–$C_6$ alkyl,
  c) unsubstituted or substituted aryl,
  d) unsubstituted or substituted heterocycle,
  e) —($C_1$–$C_6$ alkyl)$N(R^8)_2$,
  f) —$R^8C(O)R^8$,
  g) —($C_1$–$C_6$ alkyl)$OR^8$,
  h) —$N(R^8)_2$,
  i) —$OR^8$,
  j) —$R^8NHC(O)R^8$,
  k) —$R^8C(O)N(R^8)_2$,
  l) $CF_3$,
  m) halo,
  n) —$C(O)OR^8$,
  o) $C_2$–$C_6$ alkynyl,
  p) $C_2$–$C_6$ alkenyl,
  q) perfluoroalkyl,
  r) $N_3$,
  s) $NO_2$, t) CN, and
u) $R^9S(O)_q$—;

$R^2$ is selected from:
a) hydrogen,
b) CN,
c) $NO_2$,
d) halogen,
e) aryl, unsubstituted or substituted,
f) heteroaryl, unsubstituted or substituted,
g) $C_1$–$C_6$ alkyl, unsubstituted or substituted,
h) $OR^8$,
i) $N_3$,
j) $R^9S(O)_q$,
k) $R^8HC=CH$—, and
l) $R^8C\equiv C$—;

$R^3$ is selected from:
a) H,
b) CN,
c) $NO_2$,
d) halogen,
e) $C_1$–$C_6$ alkyl, unsubstituted or substituted,
f) $OR^8$,
g) aryl, unsubstituted or substituted,
h) heteroaryl, unsubstituted or substituted, and
i) $CF_3$;

$R^4$ is selected from:
a) H,
b) =O, or
c) =S;

$R^5$ is selected from:
a) H,
b) CN,
c) $NO_2$,
d) halogen,
e) $C_1$–$C_6$ alkyl, unsubstituted or substituted,
f) $N_3$,
g) $R^9S(O)_q$,
h) —$HC=CH_2$,
i) $HC\equiv C$—,
j) aryl, unsubstituted or substituted,
k) heterocycle, unsubstituted or substituted,
l) $CF_3O$—,
m) $CF_3CH_2O$—,
n) $C_3$–$C_{10}$ cycloalkyl,
o) $CF_3$,
p) —($C_1$–$C_6$ alkyl)$N(R^8)_2$,
q) —($C_1$–$C_6$ alkyl)$OR^8$,
r) $OR^8$,
s) $N(R^8)_2$,
t) —C(O)($C_1$–$C_6$ alkyl), and
u) —($C_1$—$C_6$ alkyl)$C(O)R^8$;

$R^6$ is selected from:
a) H,
b) $C_1$–$C_6$ alkyl, unsubstituted or substituted,
c) $OR^8$, and
d) —C(O)($C_1$–$C_6$ alkyl);

$R^8$ is independently selected from hydrogen, unsubstituted or substituted $C_1$–$C_6$ alkyl, unsubstituted or substituted benzyl, unsubstituted or substituted heterocycle and unsubstituted or substituted aryl;

$R^9$ is independently selected from unsubstituted or substituted $C_1$–$C_6$ alkyl or unsubstituted or substituted benzyl and unsubstituted or substituted aryl;

$A^1$ and $A^2$ are independently selected from:
a) a bond,
b) —HC=CH—,
c) —C≡C—,
d) O,
e) $S(O)_q$,
f) OC(O),
g) C(O),
h) C(O)O, and
i) $NR^8$;

$A^3$ is selected from a bond, —C(=O)—,

and $C_3$–$C_6$ cycloalkyl;

M is selected from $CH_2$, NH, O or S;

W is selected from:
a) hydrogen,
b) heterocycle, and
c) aryl;

Y is selected from:
a) aryl, and
b) heterocycle;

Z is selected from:
a) aryl,
b) heterocycle,
c) $C_3$–$C_6$ cycloalkyl, and
d) a bond;

m is 0, 1, 2, 3 or 4;

n is 0, 1, 2, 3 or 4;

p is 0, 1, 2, 3 or 4;

q is 0, 1 or 2;

r is 0, 1, 2, 3, or 4;

s is 0, 1, 2, 3 or 4;

t is 0, 1, 2 or 3;

or a pharmaceutically acceptable salt, an optical isomer or stereoisomer thereof In a further embodiment, the compounds of the instant invention are illustrated by formula A:

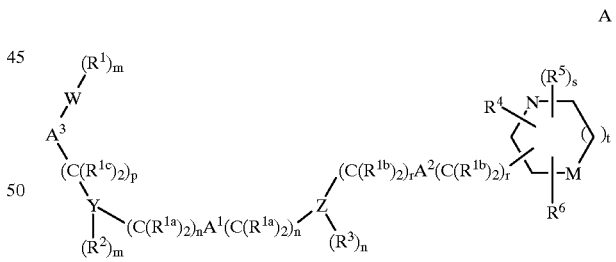

wherein:
$R^{1a}$, $R^{1b}$ and $R^{1c}$ are independently selected from:
a) hydrogen,
b) unsubstituted or substituted aryl; unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, $N(R^8)_2$, $(R^8)_2NC(O)$—, $C(O)N(R^8)$—, or $N_3$;
c) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$R^1$ is selected from:
a) H,
b) unsubstituted or substituted $C_1$–$C_6$ alkyl,
c) unsubstituted or substituted aryl,
d) unsubstituted or substituted heterocycle,
e) —($C_1$–$C_6$ alkyl)N($R^8$)$_2$,
f) —($C_1$–$C_6$ alkyl)C(O)$R^8$,
g) —($C_1$–$C_6$ alkyl)O$R^8$,
h) —N($R^8$)$_2$,
i) —O$R^8$,
j) —($C_1$–$C_6$ alkyl)NHC(O)$R^8$,
k) —($C_1$–$C_6$ alkyl)C(O)N($R^8$)$_2$,
l) $CF_3$, and
m) halo;

$R^2$ is selected from:
a) hydrogen,
b) CN,
c) $NO_2$,
d) halogen,
e) aryl, unsubstituted or substituted,
f) heteroaryl, unsubstituted or substituted,
g) $C_1$–$C_6$ alkyl, unsubstituted or substituted,
h) O$R^8$,
i) $N_3$,
j) $R^9S(O)_q$,
k) $R^8HC$=CH—, and
l) $R^8C$≡C—;

$R^3$ is selected from:
a) H,
b) CN,
c) $NO_2$,
d) halogen,
e) $C_1$–$C_6$ alkyl, unsubstituted or substituted,
f) O$R^8$,
g) aryl, unsubstituted or substituted,
h) heteroaryl, unsubstituted or substituted, and
i) $CF_3$;

$R^4$ is selected from:
a) H,
b) =O, or
c) =S;

$R^5$ is selected from:
a) H,
b) CN,
c) $NO_2$,
d) halogen,
e) $C_1$–$C_6$ alkyl, unsubstituted or substituted,
f) $N_3$,
g) $R^9S(O)_q$,
h) —HC=$CH_2$,
i) HC≡C—,
j) aryl, unsubstituted or substituted,
k) heterocycle, unsubstituted or substituted,
l) $CF_3O$—,
m) $CF_3CH_2O$—,
n) $C_3$–$C_{10}$ cycloalkyl,
o) $CF_3$,
p) —($C_1$–$C_6$ alkyl)N($R^8$)$_2$,
q) —($C_1C_6$ alkyl)O$R^8$,
r) O$R^8$,
s) N($R^8$)$_2$,
t) —C(O)($C_1$–$C_6$ alkyl), and
u) —($C_1$–$C_6$ alkyl)C(O)$R^8$;

$R^6$ is selected from:
a) H,
b) $C_1$–$C_6$ alkyl, unsubstituted or substituted,
c) O$R^8$, and
d) —C(O)($C_1$–$C_6$ alkyl);

$R^8$ is independently selected from hydrogen, unsubstituted or substituted $C_1$–$C_6$ alkyl, benzyl and unsubstituted or substituted aryl;

$R^9$ is independently selected from unsubstituted or substituted $C_1$–$C_6$ alkyl, benzyl and unsubstituted or substituted aryl;

$A^1$ is selected from:
a) a bond,
b) —HC=CH—,
c) —C≡C—,
d) O,
e) $S(O)_q$,
f) OC(O),
g) C(O),
h) C(O)O, and
i) $NR^8$;

$A^2$ is selected from:
a) a bond,
b) O,
c) $S(O)_q$,
d) C(O), and
e) $NR^8$;

$A^3$ is selected from a bond, —C(=O)—,

and $C_3$–$C_6$ cycloalkyl;

M is selected from $CH_2$ or NH;

W is selected from:
a) heterocycle, and
b) aryl;

Y is selected from:
a) aryl, and
b) heterocycle;

Z is selected from:
a) aryl,
b) heterocycle, and
c) a bond;

m is 0, 1, 2, 3 or 4;
n is 0, 1, 2, 3 or 4;
p is 0, 1, 2, 3 or 4;
q is 0, 1 or 2;
r is 0, 1, 2, 3, or 4;
s is 0, 1, 2, 3 or 4; and
t is 0, 1, 2 or 3;

or a pharmaceutically acceptable salt, an optical isomer or stereoisomer thereof.

Another embodiment of the compounds of this invention is illustrated by formula B:

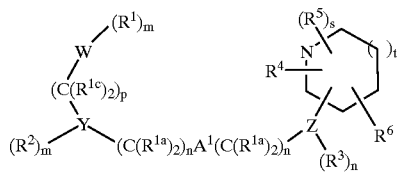

wherein:

$R^{1a}$ and $R^{1c}$ are independently selected from:
  a) hydrogen,
  b) unsubstituted or substituted aryl; unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, $N(R^8)_2$, $(R^8)_2NC(O)$—, $C(O)N(R^8)$—, or $N_3$;
  c) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$R^1$ is selected from:
  a) H,
  b) unsubstituted or substituted $C_1$–$C_6$ alkyl,
  c) unsubstituted or substituted aryl,
  d) unsubstituted or substituted heterocycle,
  e) —$(C_1$–$C_6$ alkyl)$N(R^8)_2$,
  f) —$(C_1$–$C_6$ alkyl)$C(O)R^8$,
  g) —$(C_1$–$C_6$ alkyl)$OR^8$,
  h) —$N(R^8)_2$,
  i) —$OR^8$,
  j) —$(C_1$–$C_6$ alkyl)$NHC(O)R^8$,
  k) —$(C_1$–$C_6$ alkyl)$C(O)N(R^8)_2$,
  l) $CF_3$, and
  m) halo;

$R^2$ is selected from:
  a) hydrogen,
  b) CN,
  c) $NO_2$,
  d) halogen,
  e) aryl, unsubstituted or substituted,
  f) heteroaryl, unsubstituted or substituted,
  g) $C_1$–$C_6$ alkyl, unsubstituted or substituted,
  h) $OR^8$,
  i) $N_3$,
  j) $R^9S(O)_q$,
  k) $R^8HC$=CH—, and
  l) $R^8C$≡C—;

$R^3$ is selected from:
  a) H,
  b) CN,
  c) $NO_2$,
  d) halogen,
  e) $C_1$–$C_6$ alkyl, unsubstituted or substituted,
  f) $OR^8$,
  g) aryl, unsubstituted or substituted,
  h) heteroaryl, unsubstituted or substituted, and
  i) $CF_3$;

$R^4$ is selected from:
  a) H,
  b) =O, or
  c) =S;

$R^5$ is selected from:
  a) H,
  b) CN,
  c) $NO_2$,
  d) halogen,
  e) $C_1$–$C_6$ alkyl, unsubstituted or substituted,
  f) $N_3$,
  g) $R^9S(O)_q$,
  h) —HC=$CH_2$,
  i) HC≡C—,
  j) aryl, unsubstituted or substituted,
  k) heterocycle, unsubstituted or substituted,
  l) $CF_3O$—,
  m) $CF_3CH_2O$—,
  n) $C_3$–$C_{10}$ cycloalkyl,
  o) $CF_3$,
  p) —$(C_1$–$C_6$ alkyl)$N(R^8)_2$,
  q) —$(C_1$–$C_6$ alkyl)$OR^8$,
  r) $OR^8$,
  s) $N(R^8)_2$,
  t) —$C(O)(C_1$–$C_6$ alkyl), and
  u) —$(C_1$–$C_6$ alkyl)$C(O)R^8$;

$R^6$ is selected from:
  a) H,
  b) $C_1$–$C_6$ alkyl, unsubstituted or substituted,
  c) $OR^8$, and
  d) —$C(O)(C_1$–$C_6$ alkyl);

$R^8$ is independently selected from hydrogen, unsubstituted or substituted $C_1$–$C_6$ alkyl, benzyl and unsubstituted or substituted aryl;

$R^9$ is independently selected from unsubstituted or substituted $C_1$–$C_6$ alkyl, benzyl and unsubstituted or substituted aryl;

$A^1$ is selected from:
  a) a bond,
  b) —HC=CH—,
  c) —C≡C—,
  d) O,
  e) $S(O)_q$,
  f) OC(O),
  g) C(O),
  h) C(O)O, and
  i) $NR^8$;

W is selected from:
  a) heterocycle, and
  b) aryl;

Y is selected from:
  a) aryl, and
  b) heterocycle;

Z is selected from:
  a) aryl, and
  b) heterocycle;

m is 0, 1, 2, 3 or 4;

n is 0, 1, 2, 3 or 4;

p is 0, 1, 2, 3 or 4;

q is 0, 1 or 2;

s is 0, 1, 2, 3 or 4; and t is 0, 1, 2 or 3;

or a pharmaceutically acceptable salt, an optical isomer or stereoisomer thereof.

Another embodiment of the compounds of this invention is illustrated by the formula II:

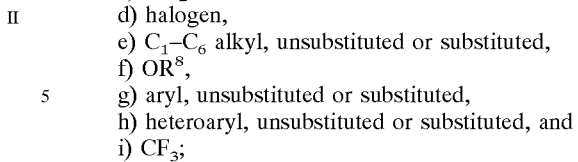

wherein:

$R^{1c}$ is independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^9S(O)_q$—, CN, $NO_2$, $R^8C(O)$—, $R^8OC(O)$—, $(R^8)_2NC(O)$—, —$N(R^{15})_2$, —$OR^{15}$, —$N(R^8)S(O)_qR^8$ or $N_3$;
c) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$R^1$ is independently selected from:
a) H,
b) unsubstituted or substituted $C_1$–$C_6$ alkyl,
c) unsubstituted or substituted aryl,
d) unsubstituted or substituted heterocycle,
e) —$(C_1$–$C_6$ alkyl$)N(R^8)_2$,
f) —$R^8C(O)R^8$,
g) —$(C_1$–$C_6$ alkyl$)OR^8$,
h) —$N(R^8)_2$,
i) —$OR^8$,
j) —$R^8NHC(O)R^8$,
k) —$R^8C(O)N(R^8)_2$,
l) $CF_3$,
m) halo,
n) —$C(O)OR^8$,
o) $C_2$–$C_6$ alkynyl,
p) $C_2$–$C_6$ alkenyl,
q) perfluoroalkyl,
r) $N_3$,
s) $NO_2$,
t) CN,
u) $R^9S(O)_q$—,
v) —$(C_1$–$C_6$ alkyl$)NR^8C(O)N(R^8)_2$, and
w) —$(C_1$–$C_6$ alkyl$)R^{14}$;

$R^2$ is independently selected from:
a) hydrogen,
b) CN,
c) $NO_2$,
d) halogen,
e) aryl, unsubstituted or substituted,
f) heteroaryl, unsubstituted or substituted,
g) $C_1$–$C_6$ alkyl, unsubstituted or substituted,
h) $OR^8$,
i) $N_3$,
j) $R^9S(O)_q$,
k) $R^8HC$=CH—, and
l) $R^8C$≡C—;

$R^3$ is independently selected from:
a) H,
b) CN,
c) $NO_2$,
d) halogen,
e) $C_1$–$C_6$ alkyl, unsubstituted or substituted,
f) $OR^8$,
g) aryl, unsubstituted or substituted,
h) heteroaryl, unsubstituted or substituted, and
i) $CF_3$;

$R^5$ and $R^6$ are independently selected from:
a) H,
b) CN,
c) $NO_2$,
d) halogen,
e) $C_1$–$C_6$ alkyl, unsubstituted or substituted,
f) $N_3$,
g) $R^9S(O)_q$,
h) —HC=$CH_2$,
i) HC≡C—,
j) aryl, unsubstituted or substituted,
k) heterocycle, unsubstituted or substituted,
l) $CF_3O$—,
m) $CF_3CH_2$—,
n) $C_3$–$C_{10}$ cycloalkyl,
o) $CF_3$,
p) —$(C_1$–$C_6$ alkyl$)N(R^8)_2$,
q) —$(C_1$–$C_6$ alkyl$)OR^8$,
r) $OR^8$,
s) $N(R^8)_2$,
t) —$C(O)(C_1$–$C_6$ alkyl),
u) —$(C_1$–$C_6$ alkyl$)C(O)R^8$,
v) —$C(O)O(C_1$–$C_6$ alkyl),
w) —$C(O)N(R^8)_2$,
x) —$(C_1$–$C_6$ alkyl$)NR^8C(O)N(R^8)_2$,
y) —$(C_1$–$C_6$ alkyl$)NR^8C(O)R^8$,
z) —$C_2$–$C_6$ alkynyl,
aa) —$C_2$–$C_6$ alkenyl,
bb) —$(C_1$–$C_6$ alkyl$)N_3$,
cc) —$(C_1$–$C_6$ alkyl$)NR^8S(O)_q$, and
dd) —$(C_1$–$C_6$ alkyl$)NR^8(C_1$–$C_6$ alkyl$)N(R^8)_2$;

$R^8$ is independently selected from hydrogen, unsubstituted or substituted $C_1$–$C_6$ alkyl, unsubstituted or substituted aralkyl, unsubstituted or substituted heterocycle and unsubstituted or substituted aryl;

$R^9$ is independently selected from unsubstituted or substituted $C_1$–$C_6$ alkyl, unsubstituted or substituted benzyl and unsubstituted or substituted aryl;

$R^{14}$ is unsubstituted saturated heterocycle;

$R^{15}$ is independently selected from
a) hydrogen, unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^9S(O)_2$—, $R^8C(O)$—, $R^8OC(O)$—, $(R^8)_2NC(O)$—, and
b) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$A^1$ and $A^2$ are independently selected from:
a) a bond,
b) —HC=CH—,
c) —C≡C—,
d) O,
e) $S(O)_q$,
f) OC(O),
g) C(O),
h) C(O)O, and
i) $NR^8$;

$A^3$ is selected from a bond, —C(=O)—, $$\diagdown_{\diagup} C{=}CH_2$$

and $C_3$–$C_6$ cycloalkyl;

M is selected from $CH_2$, $NR^8$, O or $S(O)_q$;

Q is selected from $S(O)_q$, $CH_2$, C(=S), C(=$NR^8$) or C(=O);

W is a heterocycle;

Y is selected from
  a) aryl, and
  b) heterocycle;

Z is selected from
  a) aryl, and
  b) heterocycle;

m is 0, 1, 2, 3 or 4;
n is 0, 1, 2, 3 or 4;
p is 0, 1, 2, 3 or 4;
q is 0, 1 or 2;
r is 0, 1, 2, 3, or 4;
s is 0, 1, 2, 3 or 4;
t is 0, 1, 2 or 3;
x is 0, 1, 2 or 3;

provided that if attachment of

[structure]

to the rest of the molecule is through a nitrogen ring atom, then $A^1$ is $NR^8$, O, or $S(O)_q$;

or a pharmaceutically acceptable salt, an optical isomer or stereoisomer thereof.

Another embodiment of the compounds of this invention is illustrated by the formula III:

[structure III]

wherein:

$R^{1a}$ and $R^{1c}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^9S(O)_q$—, CN, $NO_2$, $R^8C(O)$—, $R^8OC(O)$—, $(R^8)_2NC(O)$—, —$N(R^{15})_2$, —$OR^{15}$, —$N(R^8)S(O)_qR^8$ or $N_3$;
  c) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$R^1$ is independently selected from:
  a) H,
  b) unsubstituted or substituted $C_1$–$C_6$ alkyl,
  c) unsubstituted or substituted aryl,
  d) unsubstituted or substituted heterocycle,
  e) —($C_1$–$C_6$ alkyl)$N(R^8)_2$,
  f) —$R^8C(O)R^8$,
  g) —($C_1$–$C_6$ alkyl)$OR^8$,
  h) —$N(R^8)_2$,
  i) —$OR^8$,
  j) —$R^8NHC(O)R^8$,
  k) —$R^8C(O)N(R^8)_2$,
  l) $CF_3$,
  m) halo,
  n) —$C(O)OR^8$,
  o) $C_2$–$C_6$ alkynyl,
  p) $C_2$–$C_6$ alkenyl,
  q) perfluoroalkyl,
  r) $N_3$,
  s) $NO_2$,
  t) CN,
  u) $R^9S(O)_q$—,
  v) —($C_1$–$C_6$ alkyl)$NR^8C(O)N(R^8)_2$, and
  w) —($C_1$–$C_6$ alkyl)$R^{14}$;

$R^2$ is independently selected from:
  a) hydrogen,
  b) CN,
  c) $NO_2$,
  d) halogen,
  e) aryl, unsubstituted or substituted,
  f) heteroaryl, unsubstituted or substituted,
  g) $C_1$–$C_6$ alkyl, unsubstituted or substituted,
  h) $OR^8$,
  i) $N_3$,
  j) $R^9S(O)_q$,
  k) $R^8HC$=CH—, and
  l) $R^8C$≡C—;

$R^3$ is independently selected from:
  a) H,
  b) CN,
  c) $NO_2$,
  d) halogen,
  e) $C_1$–$C_6$ alkyl, unsubstituted or substituted,
  f) $OR^8$,
  g) aryl, unsubstituted or substituted,
  h) heteroaryl, unsubstituted or substituted, and
  i) $CF_3$;

$R^5$ and $R^6$ are independently selected from:
  a) H,
  b) CN,
  c) $NO_2$,
  d) halogen,
  e) $C_1$–$C_6$ alkyl, unsubstituted or substituted,
  f) $N_3$,
  g) $R^9S(O)_q$,
  h) —HC=$CH_2$,
  i) HC≡C—,
  j) aryl, unsubstituted or substituted,
  k) heterocycle, unsubstituted or substituted,
  l) $CF_3O$—,
  m) $CF_3CH_2O$—,
  n) $C_3$–$C_{10}$ cycloalkyl,
  o) $CF_3$,
  p) —($C_1$–$C_6$ alkyl)$N(R^8)_2$,
  q) —($C_1$–$C_6$ alkyl)$OR^8$,
  r) $OR^8$,
  s) $N(R^8)_2$,
  t) —$C(O)(C_1$–$C_6$ alkyl), u) —(C$_1$-C$_6$ alkyl)C(O)R$^8$,
v) —C(O)O(C$_1$-C$_6$ alkyl),
w) —C(O)N(R$^8$)$_2$,
x) —(C$_1$-C$_6$ alkyl)NR$^8$C(O)N(R$^8$)$_2$,
y) —(C1-C$_6$ alkyl)NR$^8$C(O)R$^8$,
z) —C$_2$-C$_6$ alkynyl,
aa) —C$_2$-C$_6$ alkenyl,
bb) —(C$_1$-C$_6$ alkyl)N$_3$,
cc) —(C$_1$-C$_6$ alkyl)NR$^8$S(O)$_q$, and
dd) —(C$_1$-C$_6$ alkyl)NR$^8$(C$_1$-C$_6$ alkyl)N(R$^8$)$_2$;

R$^8$ is independently selected from hydrogen, unsubstituted or substituted C$_1$-C$_6$ alkyl, unsubstituted or substituted aralkyl, unsubstituted or substituted heterocycle and unsubstituted or substituted aryl;

R$^9$ is independently selected from unsubstituted or substituted C$_1$-C$_6$ alkyl, unsubstituted or substituted benzyl and unsubstituted or substituted aryl;

R$^{14}$ is unsubstituted saturated heterocycle;

R$^{15}$ is independently selected from
a) hydrogen, unsubstituted or substituted aryl, unsubstituted or substituted heterocycle, C$_3$-C$_{10}$ cycloalkyl, C$_2$-C$_6$ alkenyl, C$_2$-C$_6$ alkynyl, R$^9$S(O)$_2$—, R$^8$C(O)—, R$^8$OC(O)—, (R$^8$)$_2$NC(O)—, and
b) C$_1$-C$_6$ alkyl, unsubstituted or substituted by unsubstituted or substituted aryl, unsubstituted or substituted heterocycle, C$_3$-C$_{10}$ cycloalkyl, C$_2$-C$_6$ alkenyl, C$_2$-C$_6$ alkynyl, R$^8$O—, R$^9$S(O)$_q$—, CN, R$^8$C(O)—, R$^8$OC(O)—, N(R$^8$)$_2$, N$_3$, or R$^8$C(O)O—;

A$^1$ is selected from:
a) a bond,
b) —HC=CH—,
c) —C≡C—,
d) O,
e) S(O)$_q$,
f) OC(O),
g) C(O),
h) C(O)O, and
i) NR$^8$;

A$^3$ is selected from a bond, —C(=O)—,

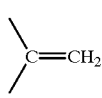

and C$_3$-C$_6$ cycloalkyl;

M is selected from CH$_2$, NR8, O or S(O)$_q$;

Q is selected from S(O)$_q$, CH$_2$, C(=S), C(=NR$^8$) or C(=O);

W is a heterocycle selected from pyrrolidinyl, imidazolyl, pyridyl, triazolyl, pyridonyl, 2-oxopiperidinyl, indolyl, quinolinyl, isoquinolinyl, and tetrahydroimidazopyridinyl, Y is selected from:
a) aryl, and
b) pyridyl;

Z is selected from:
a) aryl, and
b) pyridyl;

m is 0, 1, 2, 3 or 4;
n is 0, 1, 2, 3 or 4;
p is 0, 1, 2, 3 or 4;
q is 0, 1 or 2;
s is 0, 1, 2, 3 or 4;
t is 0, 1, 2 or 3;
x is 0, 1, 2 or 3;

provided that if attachment of

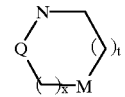

to the rest of the molecule is through a nitrogen ring atom, then A$^1$ is NR$^8$, O, or S(O)$_q$;

or a pharmaceutically acceptable salt, an optical isomer or stereoisomer thereof.

Another embodiment of the compounds of this invention is illustrated by the formula C:

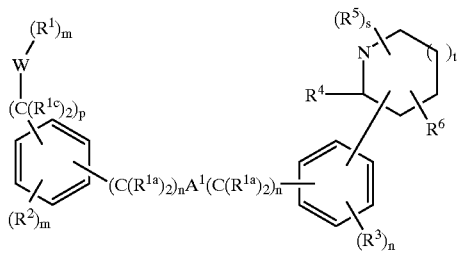

wherein:

R$^{1a}$ and R$^{1c}$ are independently selected from:
a) hydrogen,
b) unsubstituted or substituted aryl; unsubstituted or substituted heterocycle, C$_3$-C$_{10}$ cycloalkyl, C$_2$-C$_6$ alkenyl, C$_2$-C$_6$ alkynyl, R$^8$O—, R$^9$S(O)$_q$—, CN, NO$_2$, R$^8$C(O)—, R$^8$OC(O)—, N(R$^8$)$_2$, (R$^8$)$_2$NC(O)—, C(O)N(R$^8$)—, or N$_3$;
c) C$_1$-C$_6$ alkyl, unsubstituted or substituted by unsubstituted or substituted aryl, unsubstituted or substituted heterocycle, C$_3$-C$_{10}$ cycloalkyl, C$_2$-C$_6$ alkenyl, C$_2$-C$_6$ alkynyl, R$^8$O—, R$^9$S(O)$_q$—, CN, R$^8$C(O)—, R$^8$OC(O)—, N(R$^8$)$_2$, N$_3$, or R$^8$C(O)O—;

R$^1$ is selected from:
a) H,
b) unsubstituted or substituted C$_1$-C$_6$ alkyl,
c) unsubstituted or substituted aryl,
d) unsubstituted or substituted heterocycle,
e) —(C$_1$-C$_6$ alkyl)N(R$^8$)$_2$,
f) —(C$_1$-C$_6$ alkyl)C(O)R$^8$,
g) —(C$_1$-C$_6$ alkyl)OR$^8$,
h) —N(R$^8$)$_2$,
i) —OR$^8$,
j) —(C$_1$-C$_6$ alkyl)NHC(O)R$^8$,
k) —(C$_1$-C$_6$ alkyl)C(O)N(R$^8$)$_2$,
l) CF$_3$, and
m) halo;

R$^2$ is selected from:
a) hydrogen,
b) CN,
c) NO$_2$,
d) halogen,
e) aryl, unsubstituted or substituted,
f) heteroaryl, unsubstituted or substituted,
g) C$_1$-C$_6$ alkyl, unsubstituted or substituted,
h) OR$^8$,
i) N$_3$,
j) R$^9$S(O)$_q$,
k) R$^8$HC=CH—, and
l) R$^8$C≡C—;

$R^3$ is selected from:
a) H,
b) CN,
c) $NO_2$,
d) halogen,
e) $C_1$–$C_6$ alkyl, unsubstituted or substituted,
f) $OR^8$,
g) aryl, unsubstituted or substituted,
h) heteroaryl, unsubstituted or substituted, and
i) $CF_3$;

$R^4$ is selected from:
a) H,
b) =O, or
c) =S;

$R^5$ is selected from:
a) H,
b) CN,
c) $NO_2$,
d) halogen,
e) $C_1$–$C_6$ alkyl, unsubstituted or substituted,
f) $N_3$,
g) $R^9S(O)_q$,
h) —HC=$CH_2$,
i) HC≡C—,
j) aryl, unsubstituted or substituted,
k) heterocycle, unsubstituted or substituted,
l) $CF_3O$—,
m) $CF_3CH_2O$—,
n) $C_3$–$C_{10}$ cycloalkyl,
o) $CF_3$,
p) —($C_1$–$C_6$ alkyl)$N(R^8)_2$,
q) —($C_1$–$C_6$ alkyl)$OR^8$,
r) $OR^8$,
s) $N(R^8)_2$,
t) —C(O)($C_1$–$C_6$ alkyl), and
u) —($C_1$–$C_6$ alkyl)$C(O)R^8$;

$R^6$ is selected from:
a) H,
b) $C_1$–$C_6$ alkyl, unsubstituted or substituted,
c) $OR^8$, and
d) —C(O)($C_1$–$C_6$ alkyl);

$R^8$ is independently selected from hydrogen, unsubstituted or substituted $C_1$–$C_6$ alkyl, benzyl and unsubstituted or substituted aryl;

$R^9$ is independently selected from unsubstituted or substituted $C_1$–$C_6$ alkyl, benzyl and unsubstituted or substituted aryl;

$A^1$ is selected from:
a) a bond,
b) —HC=CH—,
c) —C≡C—,
d) O,
e) $S(O)_q$,
f) OC(O),
g) C(O),
h) C(O)O, and
i) $NR^8$;

W is selected from:
a) heterocycle, and
b) aryl;

m is 0, 1, 2, 3 or 4;
n is 0, 1, 2, 3 or 4;
p is 0, 1, 2, 3 or 4;
q is 0, 1 or 2;
s is 0, 1, 2, 3 or 4; and
t is 0, 1, 2 or 3;
or a pharmaceutically acceptable salt, an optical isomer or stereoisomer thereof.

Another embodiment of the compounds of this invention is illustrated by formula IV:

IV wherein:
$R^{1c'}$ is selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl;
c) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$R^{1c''}$ is selected from:
a) hydrogen,
b) $N(R^{15})_2$, and
c) $OR^{15}$;

$R^1$ is independently selected from:
a) H,
b) unsubstituted or substituted $C_1$–$C_6$ alkyl,
c) unsubstituted or substituted aryl,
d) unsubstituted or substituted heterocycle,
e) —($C_1$–$C_6$ alkyl)$N(R^8)_2$,
f) —$R^8C(O)R^8$,
g) —($C_1$–$C_6$ alkyl)$OR^8$,
h) —$N(R^8)_2$,
i) —$OR^8$,
j) —$R^8NHC(O)R^8$,
k) —$R^8C(O)N(R^8)_2$,
l) $CF_3$,
m) halo,
n) —$C(O)OR^8$,
o) $C_2$–$C_6$ alkynyl,
p) $C_2$–$C_6$ alkenyl,
q) perfluoroalkyl,
r) $N_3$,
s) $NO_2$,
t) CN,
u) $R^9S(O)_q$—,
v) —($C_1$–$C_6$ alkyl)$NR^8C(O)N(R^8)_2$, and
w) —($C_1$–$C_6$alkyl)$R^{14}$;

$R^2$ is independently selected from:
a) hydrogen,
b) CN,
c) $NO_2$,
d) halogen,
e) aryl, unsubstituted or substituted,
f) heteroaryl, unsubstituted or substituted,
g) $C_1$–$C_6$ alkyl, unsubstituted or substituted,
h) $OR^8$,
i) $N_3$,
j) $R^9S(O)_q$, k) $R^8HC=CH—$, and
l) $R^8C\equiv C—$;

$R^3$ is independently selected from:
a) H,
b) CN,
c) $NO_2$,
d) halogen,
e) $C_1$–$C_6$ alkyl, unsubstituted or substituted,
f) $OR^8$,
g) aryl, unsubstituted or substituted,
h) heteroaryl, unsubstituted or substituted, and
i) $CF_3$;

$R^5$ is independently selected from:
a) H,
b) CN,
c) $NO_2$,
d) halogen,
e) $C_1$–$C_6$ alkyl, unsubstituted or substituted,
f) $N_3$,
g) $R^9S(O)_q$,
h) —$HC=CH_2$,
i) $HC\equiv C—$,
j) aryl, unsubstituted or substituted,
k) heterocycle, unsubstituted or substituted,
l) $CF_3O—$,
m) $CF_3CH_2O—$,
n) $C_3$–$C_{10}$ cycloalkyl,
o) $CF_3$,
p) —$(C_1$–$C_6$ alkyl$)N(R^8)_2$,
q) —$(C_1$–$C_6$ alkyl$)OR^8$,
r) $OR^8$,
s) $N(R^8)_2$,
t) —$C(O)(C_1$–$C_6$ alkyl),
u) —$(C_1$–$C_6$ alkyl$)C(O)R^8$,
v) —$C(O)O(C_1$–$C_6$ alkyl),
w) —$C(O)N(R^8)_2$,
x) —$(C_1$–$C_6$ alkyl$)NR^8C(O)N(R^8)_2$,
y) —$(C_1$–$C_6$ alkyl$)NR^8C(O)R^8$,
z) —$C_2$–$C_6$ alkynyl,
aa) —$C_2$–$C_6$ alkenyl,
bb) —$(C_1$–$C_6$ alkyl$)N_3$,
cc) —$(C_1$–$C_6$ alkyl$)NR^8S(O)_q$, and
dd) —$(C_1$–$C_6$ alkyl$)NR^8(C_1$–$C_6$ alkyl$)N(R^8)_2$;

$R^6$ is selected from
a) H,
b) $C_1$–$C_6$ alkyl, unsubstituted or substituted,
c) aryl, unsubstituted or substituted,
d) heterocycle, unsubstituted or substituted,
e) $C_3$–$C_{10}$ cycloalkyl,
f) —$(C_1$–$C_6$ alkyl$)N(R^8)_2$,
g) —$(C_1$–$C_6$ alkyl$)OR^8$,
h) —$C(O)(C_1$–$C_6$ alkyl),
i) —$(C_1$–$C_6$ alkyl$)C(O)R^8$,
j) —$C(O)O(C_1$–$C_6$ alkyl),
k) —$C(O)N(R^8)_2$,
l) —$(C_1$–$C_6$ alkyl$)NR^8C(O)N(R^8)_2$,
m) —$(C_1$–$C_6$ alkyl$)NR^8C(O)R^8$,
n) —$C_2$–$C_6$ alkynyl,
o) —$C_2$–$C_6$ alkenyl,
p) —$(C_1$–$C_6$ alkyl$)N_3$,
q) —$(C_1$–$C_6$ alkyl$)NR^8S(O)_q$, and
r) —$(C_1$–$C_6$ alkyl$)NR^8(C_1$–$C_6$ alkyl$)N(R^8)_2$;

$R^8$ is independently selected from hydrogen, unsubstituted or substituted $C_1$–$C_6$ alkyl, unsubstituted or substituted aralkyl, unsubstituted or substituted heterocycle and unsubstituted or substituted aryl;

$R^9$ is independently selected from unsubstituted or substituted $C_1$–$C_6$ alkyl, unsubstituted or substituted benzyl and unsubstituted or substituted aryl;

$R^{14}$ is unsubstituted saturated heterocycle;

$R^{15}$ is independently selected from
a) hydrogen, unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^9S(O)_2$—, $R^8C(O)$—, $R^8OC(O)$—, $(R^8)_2NC(O)$—, and
b) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$A^1$ is selected from
a) O,
b) $S(O)_q$,
c) C(O), and
d) $NR^8$;

M is selected from $CH_2$, $NR^8$, O or $S(O)_q$;

Q is selected from $S(O)_q$, $CH_2$, $C(=S)$, $C(=NR^8)$ or $C(=O)$;

W is a heterocycle selected from imidazolyl, triazolyl or pyridyl;

Y is selected from phenyl or pyridyl;

Z is selected from phenyl or pyridyl;

m is 0, 1, 2, 3 or 4;
n is 0, 1, 2, 3 or 4;
q is 0, 1 or 2;
s is 0, 1, 2, 3 or 4;
t is 0, 1, 2 or 3;
x is 0, 1, 2 or 3;

provided that if attachment of

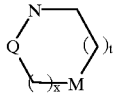

to the rest of the molecule is through a nitrogen ring atom, then $A^1$ is $NR^8$, O, or $S(O)_q$;

or a pharmaceutically acceptable salt, an optical isomer or stereoisomer thereof.

Another embodiment of the compounds of this invention is illustrated by formula D:

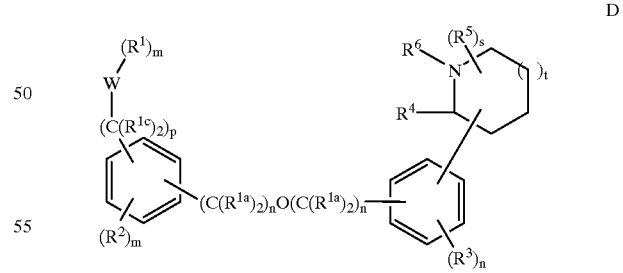

D $R^{1a}$ and $R^{1c}$ are independently selected from:
a) hydrogen,
b) unsubstituted or substituted aryl; unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, $N(R^8)_2$, $(R^8)_2NC(O)$—, $C(O)N(R^8)$—, or $N_3$;
c) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$R^1$ is selected from:
  a) H,
  b) unsubstituted or substituted $C_1$–$C_6$ alkyl,
  c) unsubstituted or substituted aryl,
  d) unsubstituted or substituted heterocycle,
  e) —($C_1$–$C_6$ alkyl)$N(R^8)_2$,
  f) —($C_1$–$C_6$ alkyl)$C(O)R^8$,
  g) —($C_1$–$C_6$ alkyl)$OR^8$,
  h) —$N(R^8)_2$,
  i) —$OR^8$,
  j) —($C_1$–$C_6$ alkyl)$NHC(O)R^8$,
  k) —($C_1$–$C_6$ alkyl)$C(O)N(R^8)_2$,
  l) $CF_3$, and
  m) halo;

$R^2$ is selected from:
  a) hydrogen,
  b) CN,
  c) $NO_2$,
  d) halogen,
  e) aryl, unsubstituted or substituted,
  f) heteroaryl, unsubstituted or substituted,
  g) $C_1$–$C_6$ alkyl, unsubstituted or substituted,
  h) $OR^8$,
  i) $N_3$,
  j) $R^9S(O)_q$,
  k) $R^8HC=CH$—, and
  l) $R^8C\equiv C$—;

$R^3$ is selected from:
  a) H,
  b) CN,
  c) $NO_2$,
  d) halogen,
  e) $C_1$–$C_6$ alkyl, unsubstituted or substituted,
  f) $OR^8$,
  g) aryl, unsubstituted or substituted,
  h) heteroaryl, unsubstituted or substituted, and
  i) $CF_3$;

$R^4$ is selected from:
  a) H, or
  b) =O;

$R^5$ is selected from:
  a) H,
  b) CN,
  c) $NO_2$,
  d) halogen,
  e) $C_1$–$C_6$ alkyl, unsubstituted or substituted,
  f) $N_3$,
  g) $R^9S(O)_q$,
  h) —$HC=CH_2$,
  i) $HC\equiv C$—,
  j) aryl, unsubstituted or substituted,
  k) heterocycle, unsubstituted or substituted,
  l) $CF_3O$—,
  m) $CF_3CH_2O$—,
  n) $C_3$–$C_{10}$ cycloalkyl,
  o) $CF_3$,
  p) —($C_1$–$C_6$ alkyl)$N(R^8)_2$,
  q) —($C_1$–$C_6$ alkyl)$OR^8$,
  r) $OR^8$,
  s) $N(R^8)_2$,
  t) —$C(O)(C_1$–$C_6$ alkyl), and
  u) —($C_1$–$C_6$ alkyl)$C(O)R^8$;

$R^6$ is selected from:
  a) H,
  b) $C_1$–$C_6$ alkyl, unsubstituted or substituted, and
  c) —$C(O)(C_1$–$C_6$ alkyl);

$R^8$ is independently selected from hydrogen, unsubstituted or substituted $C_1$–$C_6$ alkyl, benzyl and unsubstituted or substituted aryl;

$R^9$ is independently selected from unsubstituted or substituted $C_1$–$C_6$ alkyl, benzyl and unsubstituted or substituted aryl;

m is 0, 1, 2, 3 or 4;
n is 0, 1, 2, 3 or 4;
p is 0, 1, 2, 3 or 4;
q is 0, 1 or 2;
s is 0, 1, 2, 3 or 4; and
t is 0, 1, 2, or 3;

or a pharmaceutically acceptable salt, an optical isomer or stereoisomer thereof.

Specific examples of the compounds of the invention are:
  4-imidazol-1-ylmethyl-2-[2-(2-oxo-piperidin-1-yl)-phenoxy]-benzonitrile
  4-imidazol-1-ylmethyl-2-[3-(2-oxo-piperidin-1-yl)-phenoxy]-benzonitrile
  4-imidazol-1-ylmethyl-2-[4-(2-oxo-piperidin-1-yl)-phenoxy]-benzonitrile
  4-imidazol-1-ylmethyl-2-[2-(3-methyl-2-oxo-piperidin-1-yl)-phenoxy]-benzonitrile
  4-Imidazol-1-ylmethyl-2-[2-(2-oxo-pyrrolidin-1-yl)-phenoxy]-benzonitrile
  4-imidazol-1-ylmethyl-2-(3-morpholin-4-yl-phenoxy)-benzonitrile
  4-imidazol-1-ylmethyl-2-(3-piperidin-1-ylmethyl-phenoxy)-benzonitrile
  4-imidazol-1-ylmethyl-2-[3-(2-oxo-azepan-1-yl)-phenoxy]-benzonitrile
  2-[2-(3,3-dimethyl-2-oxo-piperidin-1-yl)-phenoxy]-4-imidazol-1-ylmethyl-benzonitrile
  2-[3-(3-ethyl-1-methyl-2-oxo-azepan-3-yl)-phenoxy]-4-imidazol-1-ylmethyl-benzonitrile
  2-[3-(3(S)-ethyl-1-methyl-2-oxo-azepan-3-yl)-phenoxy]-4-imidazol-1-ylmethyl-benzonitrile
  2-[3-(3(R)-ethyl-1-methyl-2-oxo-azepan-3-yl)-phenoxy]-4-imidazol-1-ylmethyl-benzonitrile 2-[3-(3-ethyl-1-methyl-2-oxo-azepan-3-yl)-phenoxy]-4-(2-methyl-imidazol-1-yl)methyl-benzonitrile
  2-[3-(3-ethyl-1-methyl-2-oxo-azepan-3-yl)-phenoxy]-4-(5-methyl-imidazol-1-yl)methyl-benzonitrile
  2-[3-(3-ethyl-1-methyl-2-oxo-azepan-3-yl)-phenoxy]-4-(2,5-dimethyl-imidazol-1-yl)methyl-benzonitrile
  2-[3-(3-ethyl-1-methyl-2-oxo-azepan-3-yl)-phenoxy]-4-[1,2,4]triazol-4-ylmethyl-benzonitrile
  2-[3-(3-ethyl-1-methyl-2-oxo-azepan-3-yl)-phenoxy]-4-[1,2,4]triazol-1-ylmethyl-benzonitrile
  4-imidazol-1-ylmethyl-2-[3-(1-methyl-2-oxo-azepan-3-yl)-phenoxy]-benzonitrile
  4-imidazol-1-ylmethyl-2-[3-(1-methyl-2-oxo-azocan-3-yl)-phenoxy]-benzonitrile
  4-imidazol-1-ylmethyl-2-[3-(1-methyl-2-oxo-piperidin-3-yl)-phenoxy]-benzonitrile
  4-imidazol-1-ylmethyl-2-[3-(1-methyl-2-oxo-pyrrolidin-3-yl)-phenoxy]-benzonitrile 4-imidazol-1-ylmethyl-2-[3-(3-ethyl-1-methyl-2-oxo-piperidin-3-yl)-phenoxy]-benzonitrile 4-imidazol-1-ylmethyl-2-[3-(2-oxo-azepan-3-yl)-phenoxy]-benzonitrile 2-[3-(3-hydroxymethyl-1-methyl-2-oxo-azepan-3-yl)-phenoxy]-4-imidazol-1-ylmethyl-benzonitrile 2-[3-(3-cyclopropylmethyl-1-methyl-2-oxo-azepan-3-yl)-phenoxy]-4-imidazol-1-ylmethyl-benzonitrile 2-[4-bromo-3-(3-cyclopropylmethyl-1-methyl-2-oxo-azepan-3-yl)-phenoxy]-4-imidazol-1-ylmethyl-benzonitrile 2-[3-(3-methoxymethyl-1-methyl-2-oxo-azepan-3-yl)-phenoxy]-4-imidazol-1-ylmethyl-benzonitrile 2-[3-(3-ethyl-2-oxo-azepan-3-yl)-phenoxy]-4-imidazol-1-ylmethyl-benzonitrile 2-[3-(3-ethyl-azepan-3-yl)-phenoxy]-4-imidazol-1-ylmethyl-benzonitrile 2-[3-(1-acetyl-3-ethyl-azepan-3-yl)-phenoxy]-4-imidazol-1-ylmethyl-benzonitrile 3-[3-(2-cyano-5-imidazol-1-ylmethyl-phenoxy)-phenyl]-3-ethyl-azepane-1-carboxylic acid-tert-butyl ester 4-[5-(2-amino-ethyl)-2-methyl-imidazol-1-ylmethyl]-2-[3-(3-ethyl-1-methyl-2-oxo-azepan-3-yl)-phenoxy]-benzonitrile 2-[3-(3-ethyl-1-methyl-2-oxo-azepan-3-yl)-phenoxy]-4-[2-methyl-5-(2-morpholin-4-yl-ethyl)-imidazol-1-ylmethyl]-benzonitrile N-[2-(3-{4-cyano-3-[3-(3-ethyl-1-methyl-2-oxo-azepan-3-yl)-phenoxy]-benzyl}-2-methyl-3H-imidazol-4-yl)-ethyl]-acetamide 3-ethyl-3-[3-(3-imidazol-1-ylmethyl-phenoxy)-phenyl]-1-methyl-azepan-2-one 2-[3-(3-ethyl-1-methyl-2-oxo-azepan-3-yl)-phenoxy]-4-(3-methyl-3-H-imidazol-4-ylmethyl)-benzonitrile 2-[3-(3-ethyl-1-methyl-2-oxo-azepan-3-yl)-phenoxy]-4-(3H-imidazol-4-ylmethyl)-benzonitrile 2-[3-(3-ethyl-1-methyl-2-oxo-azepan-3-yl)-phenoxy]-4-[hydroxy-(3-methyl-3-H-imidazol-4-yl)-methyl]-benzonitrile 4-[amino-(3-methyl-3-H-imidazol-4-yl)-methyl]-2-[3-(3-ethyl-1-methyl-2-oxo-azepan-3-yl)-phenoxy]-benzonitrile 2-[3-(3-ethyl-1-methyl-2-oxo-azepan-3-yl)-benzyl]-4-(3-methyl-3H-imidazole-4-carbonyl)-benzonitrile 2-[3-(3-ethyl-1-methyl-2-oxo-azepan-3-yl)-phenoxy]-4-(hydroxy-pyridin-3-yl-methyl)-benzonitrile 2-[3-(3-ethyl-1-methyl-2-oxo-azepan-3-yl)-phenoxy]-4-pyridin-3-ylmethyl-benzonitrile 2-[3-(3-ethyl-1-methyl-2-oxo-azepan-3-yl)-phenoxy]-4-pyridin-2-ylmethyl-benzonitrile 2-[3-(3-ethyl-1-methyl-2-oxo-azepan-3-yl)-phenoxy]-4-[1-hydroxy-1-(3-methyl-3H-imidazol-4-yl)-ethyl]-benzonitrile 2-[3-(3R)-ethyl-1-methyl-2-oxo-azepan-3-yl)-phenoxy]-4-[1-(R)amino-1-(3-methyl-3H-imidazol-4-yl)-ethyl]-benzonitrile 2-[3-(3S)-ethyl-1-methyl-2-oxo-azepan-3-yl)-phenoxy]-4-[1-(S)amino-1-(3-methyl-3H-imidazol-4-yl)-ethyl]-benzonitrile 2-[3-(3S)-ethyl-1-methyl-2-oxo-azepan-3-yl)-phenoxy]-4-[1-(R)amino-1-(3-methyl-3H-imidazol-4-yl)-ethyl]-benzonitrile 2-[3-(3R)-ethyl-1-methyl-2-oxo-azepan-3-yl)-phenoxy]-4-[1-(S)amino-1-(3-methyl-3H-imidazol-4-yl)-ethyl]-benzonitrile 2-[3-3(R)-n-butyl-1-methyl-2-oxo-azepan-3-yl)-phenoxy]-4-[1-(R)amino-1-(3-methyl-3H-imidazol-4-yl)-ethyl]-benzonitrile 2-[3-3(S)-n-butyl-1-methyl-2-oxo-azepan-3-yl)-phenoxy]-4-[1-(S)amino-1-(3-methyl-3H-imidazol-4-yl)-ethyl]-benzonitrile 2-[3-3(S)-n-butyl-1-methyl-2-oxo-azepan-3-yl)-phenoxy]-4-[1-(R)amino-1-(3-methyl-3H-imidazol-4-yl)-ethyl]-benzonitrile 2-[3-3(R)-n-butyl-1-methyl-2-oxo-azepan-3-yl)-phenoxy]-4-[1-(S)amino-1-(3-methyl-3H-imidazol-4-yl)-ethyl]-benzonitrile 2-[3-3(R)-cyclopropylmethyl-1-methyl-2-oxo-azepan-3-yl)-phenoxy]-4-[1-(R)amino-1-(3-methyl-3H-imidazol-4-yl)-ethyl]-benzonitrile 2-[3-3(S)-cyclopropylmethyl-1-methyl-2-oxo-azepan-3-yl)-phenoxy]-4-[1-(S)amino-1-(3-methyl-3H-imidazol-4-yl)-ethyl]-benzonitrile 2-[3-3(R)-cyclopropylmethyl-1-methyl-2-oxo-azepan-3-yl)-phenoxy]-4-[1-(S)amino-1-(3-methyl-3H-imidazol-4-yl)-ethyl]-benzonitrile 2-[3-3(S)-cyclopropylmethyl-1-methyl-2-oxo-azepan-3-yl)-phenoxy]-4-[1-(R) amino-1-(3-methyl-3H-imidazol-4-yl)-ethyl]-benzonitrile 2-[3-3(R)-cyclopropylethyl-1-methyl-2-oxo-azepan-3-yl)-phenoxy]-4-[1-(R)-amino-1-(3-methyl-3H-imidazol-4-yl)-ethyl]-benzonitrile 2-[3-3(S)-cyclopropylethyl-l1-methyl-2-oxo-azepan-3-yl)-phenoxy]-4-[1-(S)-amino-(3-methyl-3H-imidazol-4-yl)-ethyl]-benzonitrile 2-[3-3(R)-cyclopropylethyl-1-methyl-2-oxo-azepan-3-yl)-phenoxy]-4-[1-(S)-amino-1-(3-methyl-3H-imidazol-4-yl)-ethyl]-benzonitrile 2-[3-3(S)-cyclopropylethyl-1-methyl-2-oxo-azepan-3-yl)-phenoxy]-4-[1-(R)-amino-1-(3-methyl-3H-imidazol-4-yl)-ethyl]-benzonitrile 2-[3-3(R)-propyl-1-methyl-2-oxo-azepan-3-yl)-phenoxy]-4-[1-(R)-amino-1-(3-methyl-3H-imidazol-4-yl)-ethyl]-benzonitrile 2-[3-3(S)-propyl-1-methyl-2-oxo-azepan-3-yl)-phenoxy]-4-[1-(S)amino-1-(3-methyl-3H-imidazol-4-yl)-ethyl]-benzonitrile 2-[3-3(R)-propyl-1-methyl-2-oxo-azepan-3-yl)-phenoxy]-4-[1-(S)amino-1-(3-methyl-3H-imidazol-4-yl)-ethyl]-benzonitrile 2-[3-3(S)-propyl-1-methyl-2-oxo-azepan-3-yl)-phenoxy]-4-[1-(R)-amino-1-(3-methyl-3H-imidazol-4-yl)-ethyl]-benzonitrile 2-[3-3(R)-methoxymethyl-1-methyl-2-oxo-azepan-3-yl)-phenoxy]-4-[1-(R)-amino-1-(3-methyl-3H-imidazol-4-yl)-ethyl]-benzonitrile 2-[3-3(S)-methoxymethyl-1-methyl-2-oxo-azepan-3-yl)-phenoxy]-4-[1-(S)-amino-1-(3-methyl-3H-imidazol-4-yl)-ethyl]-benzontrile 2-[3-3(R)-methoxymethyl-1-methyl-2-oxo-azepan-3-yl)-phenoxy]-4-[1-(S)-amino-1-(3-methyl-3H-imidazol-4-yl)-ethyl]-benzonitrile 2-[3-3(S)-methoxymethyl-1-methyl-2-oxo-azepan-3-yl)-phenoxy]-4-[1-(R)-amino-1-(3-methyl-3H-imidazol-4-yl)-ethyl]-benzonitrile 2-[3-3(R)-ethoxymethyl-1-methyl-2-oxo-azepan-3-yl)-phenoxy]-4-[1-(R)-amino-1-(3-methyl-3H-imidazol-4-yl)-ethyl]-benzonitrile 2-[3-3(S)-ethoxymethyl-1-methyl-2-oxo-azepan-3-yl)-phenoxy]-4-[1-(S)-amino-1-(3-methyl-3H-imidazol-4-yl)-ethyl]-benzonitrile 2-[3-3(R)-ethoxymethyl-1-methyl-2-oxo-azepan-3-yl)-phenoxy]-4-[1-(S)-amino-1-(3-methyl-3H-imidazol-4-yl)-ethyl]-benzonitrile 2-[3-3(S)-ethoxymethyl-1-methyl-2-oxo-azepan-3-yl)-phenoxy]-4-[1-(R)-amino-1-(3-methyl-3H-imidazol-4-yl)-ethyl]-benzonitrile 2-[3-3(R)-cyclopropylmethyl-1-methyl-2-oxo-piperidin-3-yl)-phenoxy]-4-[1-(R)amino-1-(3-methyl-3H-imidazol-4-yl)-ethyl]-benzonitrile 2-[3-3 (S)-cyclopropylmethyl-1-methyl-2-oxo-piperidin-3-yl)-phenoxy]-4-[1-(S)amino-1-(3-methyl-3H-imidazol-4-yl)-ethyl]-benzonitrile 2-[3-3(R)-cyclopropylmethyl-1-methyl-2-oxo-piperidin-3-yl)-phenoxy]-4-[1-(S)amino-1-(3-methyl-3H-imidazol-4-yl)-ethyl]-benzonitrile 2-[3-3(S-cyclopropylmethyl-1-methyl-2-oxo-piperidin-3-yl)-phenoxy]-4-[1-(R)amino-1-(3-methyl-3H-imidazol-4-yl)-ethyl]-benzonitrile 2-[3-3(R)-benzyl-1-methyl-2-oxo-piperidin-3-yl)-phenoxy]-4-[1-(R)amino-1-(3-methyl-3H-imidazol-4-yl)-ethyl]-benzonitrile 2-[3-3(S)-benzyl-1-methyl-2-oxo-piperidin-3-yl)-phenoxy]-4-[1-(S)amino-1-(3-methyl-3H-imidazol-4-yl)-ethyl]-benzonitrile 2-[3-3(R)-benzyl-1-methyl-2-oxo-piperidin-3-yl)-phenoxy]-4-[1-(S)amino-1(3-methyl-3H-imidazol-4-yl)-ethyl]-benzonitrile 2-[3-3(S)-benzyl-1-methyl-2-oxo-piperidin-3-yl)-phenoxy]-4-[1-(R)amino-1-(3-methyl-3H-imidazol-4-yl)-ethyl]-benzonitrile 2-[3-methyl-1-methyl-2-oxo-azepan-3-yl)-phenoxy]-4-[1-amino-1-(3-methy-3H-imidazol-4-yl)-ethyl]-benzonitrile 2-[3-(3-ethyl-1-methyl-2-oxo-azepan-3-yl)-phenoxy]-4-[1-(3-methyl-3-H-imidazol-4-yl)-vinyl]-benzonitrile 2-[3-(3-ethyl-1-methyl-2-oxo-azepan-3-yl)-phenoxy]-4-[1-(3-methyl-3-H-imidazol-4-yl)-cyclopropyl]-benzonitrile 2-[3-N,N-dimethylaminomethyl-1-methyl-2-oxo-azepan-3-yl)-phenoxy]-4-[1-hydroxy-1-(3-methyl-3H-imidazol-4-yl)-ethyl]-benzonitrile 2-[3-N,N-dimethylaminomethy-1-methyl-2-oxo-azepan-3-yl)-phenoxy]-4-[-amino-1-(3-methyl-3H-imidazol-4-yl)-ethyl]-benzonitrile 2-[3-(3-N,N-dimethylaminomethyl-1-methyl-2-oxo-azepan-3-yl)-phenoxy]-4-[1-(3-methyl-3-H-imidazol-4-yl)-vinyl]-benzonitrile 4-[5-(2-N,N-dimethylaminoethyl)-2-methyl-imidazol-1-ylmethyl]-2-[3-(3S-ethyl-1-methyl-2-oxo-azepan-3-yl)-phenoxy]-benzonitrile 4-[5-(2-N,N-dimethylaminoethyl)-2-methyl-imidazol-1-ylmethyl]-2-[3-(3R-ethyl-1-methyl-2-oxo-azepan-3-yl)-phenoxy]-benzonitrile

[2-(3-{4-cyano-3-[3-(3S-ethyl-1-methyl-2-oxo-azepan-3-yl)-phenoxy]-benzyl}-2-methyl-3H-imidazol-4-yl)-ethyl]-urea

[2-(3-{4-cyano-3-[3-(3R-ethyl-1-methyl-2-oxo-azepan-3-yl)-phenoxy]-benzyl}-2-methyl-3H-imidazol-4-yl)-ethyl]-urea 2-[3-(3-ethyl-1-methyl-2-oxo-azepan-3-yl)-phenoxy]-4-pyridin-N-oxide-3-ylmethyl-benzonitrile 2-[3-1-methyl-2-oxo-pyrrolidin-3-yl)-phenoxy]-4-[1-amino-1-(3-methyl-3H-imidazol-4-yl)-ethyl]-benzonitrile 2-[3-(1-methyl-2-oxo-azepan-3-yl)-phenoxy]-4-[1-amino-1-(3-methyl-3H-imidazol-4-yl)-ethyl]-benzonitrile 2-[3-(3-hydroxymethyl-1-methyl-2-oxo-azepan-3-yl)-phenoxy]-4-[1-amino-1-(3-methyl-3H-imidazol-4-yl)-ethyl]-benzonitrile 2-[3-(3-cyclopropylmethyl-1-methyl-2-oxo-pyrrolidin-3-yl)-phenoxy]-4-[1-amino-1-(3-methyl-3H-imidazol-4-yl)-ethyl]-benzonitrile 2-[3-3(R)-cyclopropylmethyl-1-methyl-2-oxo-pyrrolidin-3-yl)-phenoxy]-4-[1-(R)-amino-1-(3-methyl-3H-imidazol-4-yl)-ethyl]-benzonitrile 2-[3-3(S)-cyclopropylmethyl-1-methyl-2-oxo-pyrrolidin-3-yl)-phenoxy]-4-[1-(S)-amino-1-(3-methyl-3H-imidazol-4-yl)-ethyl]-benzonitrile 2-[3-3(R)-cyclopropylmethyl-1-methyl-2-oxo-pyrrolidin-3-yl)-phenoxy]-4-[1-(S)-amino-1-(3-methyl-3H-imidazol-4-yl)-ethyl]-benzonitrile 2-[3-3(S)-cyclopropylmethyl-1-methyl-2-oxo-pyrrolidin-3-yl)-phenoxy]-4-[-(R)amino-1-(3-methyl-3H-imidazol-4-yl)-ethyl]-benzonitrile 2-[3-3(R)-benzyl-1-methyl-2-oxo-pyrrolidin-3-yl)-phenoxy]-4-[1-(R)-amino-1-(3-methyl-3H-imidazol-4-yl)-ethyl]-benzonitrile 2-[3-3(S)-benzyl-1 -methyl-2-oxo-pyrrolidin-3-yl)-phenoxy]-4-[1-(S)-amino-1-(3-methyl-3H-imidazol-4-yl)-ethyl]-benzonitrile 2-[3-3(R)-benzyl-1-methyl-2-oxo-pyrrolidin-3-yl)-phenoxy]-4-[1-(S)-amino-1-(3-methyl-3H-imidazol-4-yl)-ethyl]-benzonitrile 2-[3-3(S)-benzyl-1-methyl-2-oxo-pyrrolidin-3-yl)-phenoxy]-4-[1-(R-amino-1-(3-methyl-3H-imidazol-4-yl)-ethyl]-benzonitrile 4-[1-(4-allyl-5-bromo-pyridin-3-yl)-1-hydroxy-ethyl]-2-[3-(3-ethyl-[1-methyl-2-oxo-azepan-3-yl)-phenoxy]-benzonitrile 1-tert-butyl-3(R)-[1-{4-cyano-3-[3-(3R-ethyl-1-methyl-2-oxo-azepan-3-yl)-phenoxy]-phenyl}-1-(3-methyl-3H-imidazol-4-yl)-ethyl]-urea 1-tert-butyl-3(S)-[1-{4-cyano-3-[3-(3S-ethyl-1-methyl-2-oxo-azepan-3-yl)-phenoxy]-phenyl}-1-(3-methyl-3H-imidazol-4-yl)-ethyl]-urea 1-tert-butyl-3(R)-[1-{4-cyano-3-[3-(3S-ethyl-1-methyl-2-oxo-azepan-3-yl)-phenoxy]-phenyl}-1-(3-methyl-3H-imidazol-4-yl)-ethyl]-urea 1-tert-butyl-3(S)-[1-{4-cyano-3-[3-(3R-ethyl-1-methyl-2-oxo-azepan-3-yl)-phenoxy]-phenyl}-1-(3-methyl-3H-imidazol-4-yl)-ethyl]-urea 1-[1-{4-cyano-3(R)-[3-(3R-ethyl-1-methyl-2-oxo-azepan-3-yl)-phenoxy]-phenyl}-1-(3-methyl-3H-imidazol-4-yl)-ethyl]-3-methyl-urea 1-[1-{4-cyano-3(S)-[3-(3S-ethyl-1-methyl-2-oxo-azepan-3-yl)-phenoxy]-phenyl}-1-(3-methyl-3H-imidazol-4-yl)-ethyl]-3-methyl-urea 1-[1-{4-cyano-3(R)-[3-(3S-ethyl-1-methyl-2-oxo-azepan-3-yl)-phenoxy]-phenyl}-1-(3-methyl-3H-imidazol-4-yl)-ethyl]-3-methyl-urea 1-[1-{4-cyano-3(S)-[3-(3R-ethyl-1-methyl-2-oxo-azepan-3-yl)-phenoxy]-phenyl}-1-(3-methyl-3H-imidazol-4-yl)-ethyl]-3-methyl-urea 1-[1-{4-cyano-3(R)-[3-(3S-ethyl-1-methyl-2-oxo-azepan-3-yl)-phenoxy]-phenyl}-1-(3-methyl-3H-imidazol-4-yl)-ethyl]-3-phenyl-urea 1-[1-{4-cyano-3(S)-[3-(3S-ethyl-1-methyl-2-oxo-azepan-3-yl)-phenoxy]-phenyl}-1-(3-methyl-3H-imidazol-4-yl)-ethyl]-3-phenyl-urea 1-[1-{4-cyano-3(R)-[3-(3R-ethyl-1-methyl-2-oxo-azepan-3-yl)-phenoxy]-phenyl}-1-(3-methyl-3H-imidazol-4-yl)-ethyl]-3-phenyl-urea 1-[1-{4-cyano-3(R)-[3-(3S-ethyl-1-methyl-2-oxo-azepan-3-yl)-phenoxy]-phenyl}-1-(3-methyl-3H-imidazol-4-yl)-ethyl]-3-phenyl-urea

[1-{4-cyano-3(R)-[3-(3R-ethyl-1-methyl-2-oxo-azepan-3-yl)-phenoxy]-phenyl}-1-(3-methyl-3H-imidazol-4-yl)-ethyl]-urea

[3-{4-cyano-3(S)-[3-(3S-ethyl-1-methyl-2-oxo-azepan-3-yl)-phenoxy]-phenyl}-1-(3-methyl-3H-imidazol-4-yl)-ethyl]-urea

[1-{4-cyano-3(R)-[3-(3S-ethyl-1-methyl-2-oxo-azepan-3-yl)-phenoxy]-phenyl}-1-(3-methyl-3H-imidazol-4-yl)-ethyl]-urea

[1-{4-cyano-3(S)-[3-(3R-ethyl-1-methyl-2-oxo-azepan-3-yl)-phenoxy]-phenyl}-1-(3-methyl-3H-imidazol-4-yl)-ethyl]-urea N-[1-{4-cyano-3-[3-(3-ethyl-1-methyl-2-oxo-azepan-3-yl)-phenoxy]-phenyl}-1(3-methyl-3H-imidazol-4-yl)-ethyl]-acetamide 2-[3-(3S-ethyl-1-methyl-2-oxo-azepan-3-yl)-phenoxy]-4-[1-methylamino-1-(3-methyl-3H-imidazol-4-yl)-ethyl]-benzonitrile 2-[3-(3R-ethyl-1-methyl-2-oxo-azepan-3-yl)-phenoxy]-4-[1-methylamino-1-(3-methyl-3H-imidazol-4-yl)-ethyl]-benzonitrile 2-[3-(3S-ethyl-1-methyl-2-oxo-azepan-3-yl)-phenoxy]-4-[1(R)-methylamino-1-(3-methyl-3H-imidazol-4-yl)-ethyl]-benzonitrile 2-[3-(3S-ethyl-1-methyl-2-oxo-azepan-3-yl)-phenoxy]-4-1(S)-methylamino-1-(3-methyl-3H-imidazol-4-yl)-ethyl]-benzonitrile 2-[5-(3S-ethyl-1-methyl-2-oxo-azepan-3-yl)-2-iodo-phenoxy]-4-imidazol-1-ylmethyl-benzonitrile 2-[5-(3R-ethyl-1-methyl-2-oxo-azepan-3-yl)-2-iodo-phenoxy]-4-imidazol-1-ylmethyl-benzonitrile 2-[5-(3S-ethyl-1-methyl-2-oxo-azepan-3-yl)-2-bromo-phenoxy]-4-imidazol-1-ylmethyl-benzonitrile 2-[5-(3R-ethyl-1-methyl-2-oxo-azepan-3-yl)-2-bromo-phenoxy]-4-imidazol-1-ylmethyl-benzonitrile 4-[1-amino-1-(3-methyl-3H-imidazol-4-yl)-ethyl]-2-[2-dimethyl aminomethyl-5-(3S-ethyl-1-methyl-2-oxo-azepan-3-yl)-phenoxy]-benzonitrile 2-[3-(3-ethyl-1-methyl-2-oxo-azepan-3-yl)-phenoxy]-4-(4,5,6,7-tetrahydro-3H-imidazo[4,5-]pyridin-4-yl)-benzontrile 2-[3-ethyl-2-oxo-azepan-3-yl)-phenoxy]-4-[1-amino-1-(3-methyl-3H-imidazol-4-yl)-ethyl]-benzonitrile 4-[1-amino-1-(3-methyl-3H-imidazol-4-yl)-ethyl]-2-{3-[3-ethyl-1-(3-hydroxy-propyl)-2-oxo-azepan-3-yl]-phenoxy}-benzonitrile 4-[1-amino-1-(3-methyl-3H-imidazol-4-yl)-ethyl]-2-{3-[3-ethyl-1-propyl-2-oxo-azepan-3-yl]-phenoxy}-benzonitrile 2-{3-[1-(2-amino-ethyl)-3-ethyl-2-oxo-azepan-3-yl]-phenoxy}-4-[1-amino-1(3-methyl-3H-imidazol-4-yl)-ethyl]-benzonitrile {2-[3-(3-{5-[1-amino-1-(3-methyl-3H-imidazol-4-yl)-ethyl]2-cyano-phenoxy}-phenyl)-3-ethyl-2-oxo-azepan-1-yl]-ethyl}-urea N-{2-[3-(3-{5-[1-amino-1-(3-methyl-3H-imidazol-4-yl)-ethyl]2-cyano-phenoxy}-phenyl)-3-ethyl-2-oxo-azepan-1-yl]-ethyl}-N'-methyl urea 4-[1(R)-amino-1-(3-methyl-3H-imidazol-4-yl)-ethyl]-2-{3-[1-methyl-2-oxo-3(R)-(3,3,3-trifluoro-propyl)-azepan-3-yl]-phenoxy}-benzonitrile 4-[1(S)-amino-1-(3-methyl-3H-imidazol-4-yl)-ethyl]-2-{3-[1-methyl-2-oxo-3(S)-(3,3,3-trifluoro-propyl)-azepan-3-yl]-phenoxy}-benzonitrile 4-[1(R)-amino-1-(3-methyl-3H-imidazol-4-yl)-ethyl]-2-{3-[1-methyl-2-oxo-3(S)-(3,3,3-trifluoro-propyl)-azepan-3-yl]-phenoxy}-benzonitrile 4-[1(S)-amino-1-(3-methyl-3H-imidazol-4-yl)-ethyl]-2-{3-[1-methyl-2-oxo-3(R)-(3,3 ,3-trifluoro-propyl)-azepan-3-yl]-phenoxy}-benzonitrile 4-[1-amino-1-(3-methyl-3H-imidazol-4-yl)-ethyl]-2-{3-[1-(2-dimethylamino-ethyl)-3-ethyl-2-oxo-azepan-3-yl]-phenoxy}-benzonitrile 4-[1-(R or S) amino-1-(3-methyl-3H-imidazol-4-yl)-ethyl]-2-{3-[1-(2-hydroxyethyl)-3-ethyl-2-oxo-azepan-3-yl]-phenoxy}-benzonitrile 4-[1-amino-1-(3-methyl-3H-imidazol-4-yl)-ethyl]-2-{3-[1-(2-methoxyethyl)3R-ethyl-2-oxo-azepan-3-yl]-phenoxy}-benzonitrile 4-Imidazol-1-ylmethyl-2-[3-(1-methyl-7-oxo-azepan-2-yl)-phenoxy]-benzonitrile hydrochloride 4-[1-Amino-1-(3-methyl-3H-imidazol-4-yl)-ethyl]-2-[3-(4-methyl-3-oxo-2-propyl-morpholin-2-yl)-phenoxy]-benzonitrile 4-[1-amino-1-(3-methyl-3H-imidazol-4-yl)-ethyl]-2-[3-(morpholine-4-sulfonyl)-phenoxy]-benzonitrile 4-[1-amino-1-(3-methyl-3H-imidazol-4-yl)-ethyl]-2-{3-[1-(2-methoxyethyl)-3R-ethyl-2-oxo-azepan-3-yl]-phenoxy}-benzonitrile;

2-[3-(3R-ethyl-1-methyl-2-oxo-azepan-3-yl)-phenoxy]-4-[5-(2-morpholin-4-yl-ethyl-imidazol-1-ylmethyl benzonitrile;

or a pharmaceutically acceptable salt, an optical isomer or stereoisomer thereof.

The preferred compounds of the instant invention are:

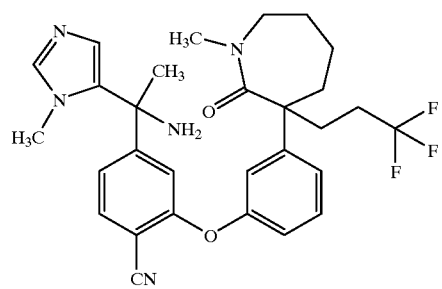

2-{3-[1-methyl-2-oxo-3-(R or S)-(3,3,3-trifluoro-propyl)-azepan-3-yl]-phenoxy}-4-[1(R or S)-amino-1-(3-methyl-3H-imidazol-4-yl)-ethyl]-benzonitrile;

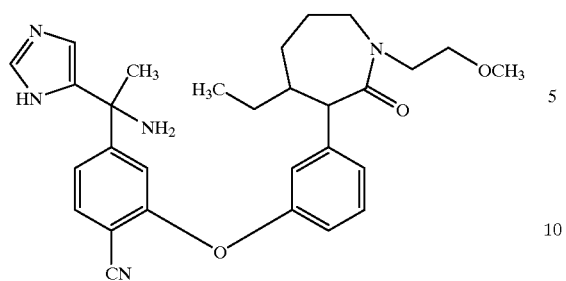

4-[1-amino-1-(3-methyl-3H-imidazol-4-yl)-ethyl]-2-{3-[1-(2-methoxyethyl)-3R-ethyl-2-oxo-azepan-3-yl]-phenoxy}-benzonitrile;

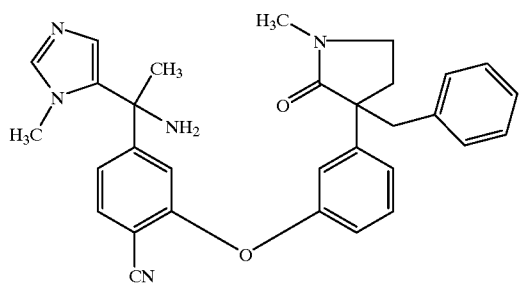

2-[3(R or S)-3(R or S)-benzyl-1-methyl-2-oxo-pirrolidin-3-yl)-phenoxy]-4-[1-amino-1-(3-methyl-3H-imidazol-4-yl)-ethyl]-benzonitrile;

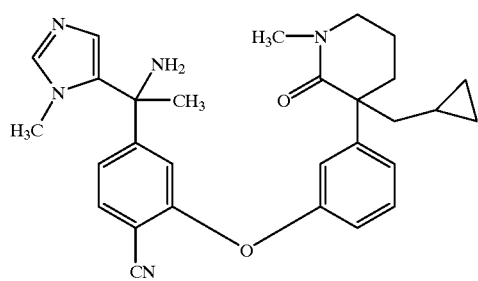

2-[3-(3-(cyploroylmethyl-1-methyl-2-oxo-piperidin-3-yl)-phenoxy]-4-[1-amino-1-(3-methyl-3H-imidazol-4-yl)-ethyl]-benzonitrile;

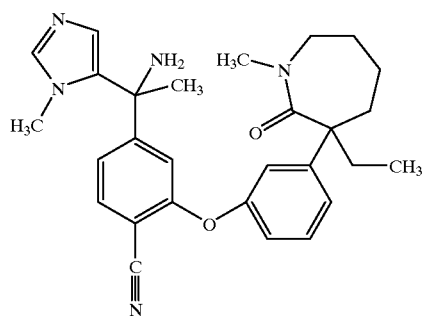

2-[3-(3-ethyl-1-methyl-2-oxo-azepan-3-yl)-phenoxy]-4-[1-amino-1-(3-methyl-3H-imidazol-4-yl)-ethyl]-benzonitrile

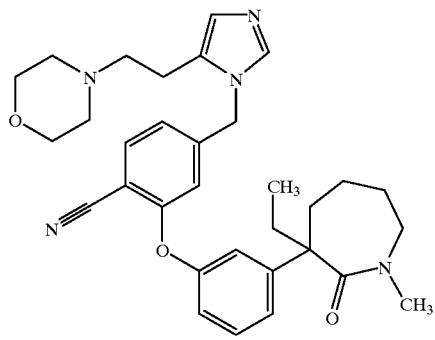

2-[3-(3R-ethyl-1-methyl-2-oxo-azepan-3-yl)-phenoxy]-4-[5-(2-morpholin-4-yl-ethyl)-imidazol-1-ylmethyl benzonitrile;

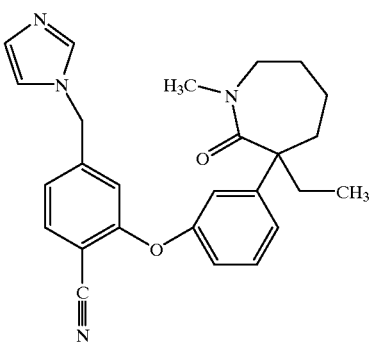

(±) 2-[3-(3-ethyl-1-methyl-2-oxo-azepan-3-yl)-phenoxy]-4-imidazol-1-ylmethyl-benzonitrile;

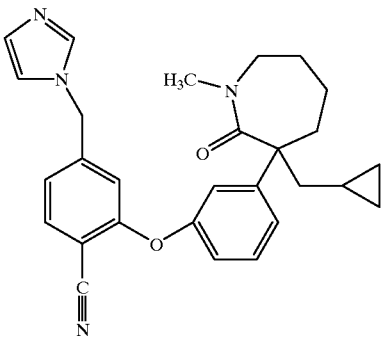

2-[3-(3-cyclopropylmethyl-1-methyl-2-oxo-azepan-3-yl)-phenoxy]-4-imidazol-1-ylmethyl-benzonitrile;

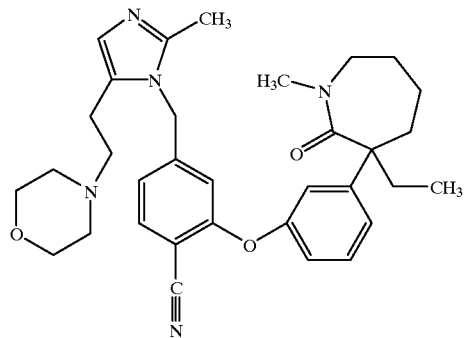

2-[3-(3-ethyl-1-methyl-2-oxo-azepan-3-yl)-phenoxy]-4-
[2-methyl-5-(2-morpholin-4-yl-ethyl)-imidazol-1-
ylmethyl]-benzonitrile;

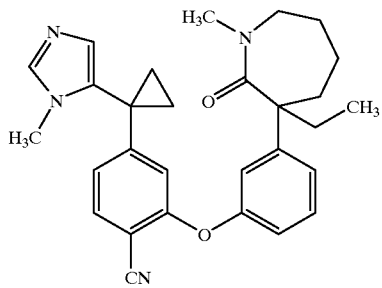

2-[3-(3-ethyl-1-methyl-2-oxo-azepan-3-yl)-phenoxy]-4-
[1-(3-methyl-3-H-imidazol-4-yl)-cyclopropyl]-
benzonitrile

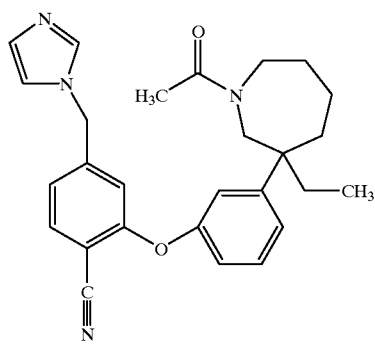

2-[3-(1-acetyl-3-ethyl-azepan-3-yl)-phenoxy]-4-
imidazol-1-ylmethyl-benzonitrile;

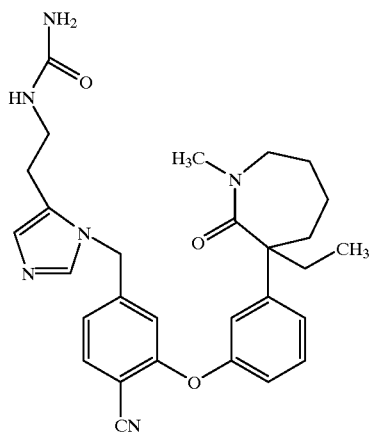

[2-(3-{4-cyano-3-[3-(3-ethyl-1-methyl-2-oxo-azepan-3-
yl)-phenoxy]-benzyl}-2-methyl-3H-imidazol-4-yl)-
ethyl]-urea

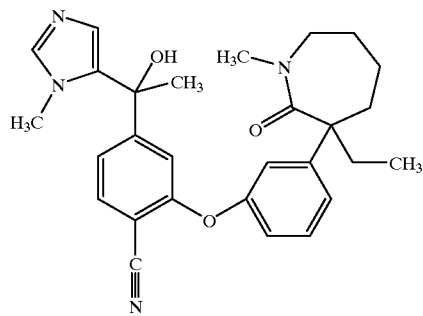

2-[3-(3-ethyl-1-methyl-2-oxo-azepan-3-yl)-phenoxy]-4-
[1-hydroxy-1-(3-methyl-3H-imidazol-4-yl)-ethyl]-
berizonitrile

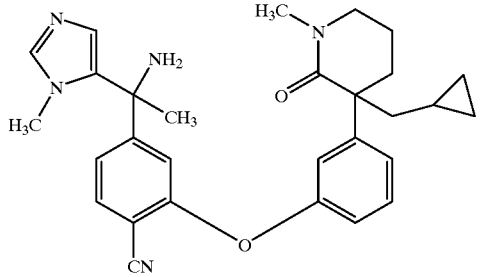

2-[3-(3-cyclopropylmethyl-1-methyl-2-oxo-azepan-3-
yl)-phenoxy]-4-[1-amino-1-(3-methyl-3H-imidazol-4-
yl)-ethyl]-benzonitrile

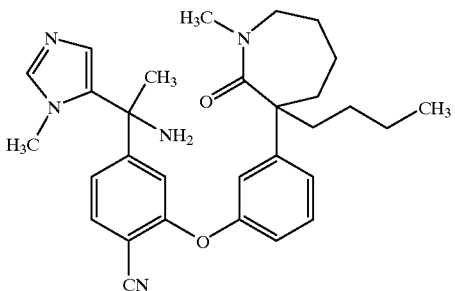

2-[3-(3-n-butyl-1-methyl-2-oxo-azepan-3-yl)-phenoxy]-4-[1-amino-1-(3-methyl-3H-imidazol-4-yl)-ethyl]-benzonitrile

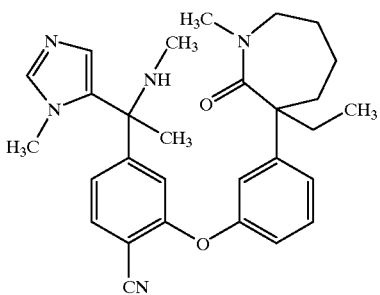

2-[3-(3-ethyl-1-methyl-2-oxo-azepan-3-yl)-phenoxy]-4-[1-methylamino-1-(3-methyl-3H-imidazol-4-yl)-ethyl]-benzonitrile

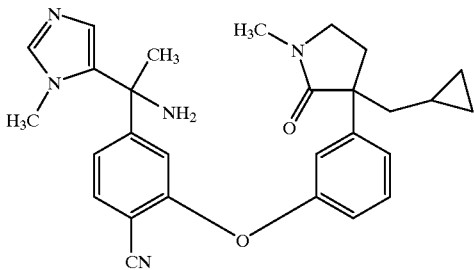

2-[3-(3-cyclopropylmethyl-1-methyl-2-oxo-pyrrolidin-3-yl)-phenoxy]-4-[1-amino-1-(3-methyl-3H-imidazol-4-yl)-ethyl]-benzonitrile

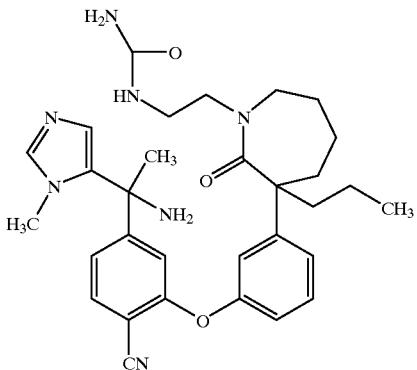

{2-[3-(3-{5-[1-amino-1-(3-methyl-3H-imidazol-4-yl)-ethyl]2-cyano-phenoxy}-phenyl)-3-ethyl-2-oxo-azepan-1-yl]-ethyl}-urea or a pharmaceutically acceptable salt, an optical isomer or stereoisomer thereof.

The compounds of the present invention may have asymmetric centers and occur as racemates, racemic mixtures, and as individual diastereomers, with all possible isomers, including optical isomers, being included in the present invention. When any variable, term or substituent (e.g. aryl, heterocycle, n, $R^{1a}$ etc.) occurs more than one time in any formula or generic structure, its definition on each occurrence is independent from the definition at every other occurrence. Also, combinations of substituents/or variables are permissible only if such combinations result in stable compounds.

As used herein, "alkyl" is intended to include both branched and straight-chain saturated aliphatic hydrocarbon groups having 1 to 6 carbon atoms, unless otherwise specified; "alkoxy" represents an alkyl group having 1 to 4 carbon atoms, unless otherwise indicated, attached through an oxygen bridge. "Halogen" or "halo" as used herein means fluoro, chloro, bromo and iodo.

As used herein, "aryl" is intended to mean any stable monocyclic, bicyclic or tricyclic carbon ring of up to 7 members in each ring, wherein at least one ring is aromatic. Examples of such aryl elements include phenyl, naphthyl, tetrahydronaphthyl, indanyl, indanonyl, biphenyl, tetralinyl, tetralonyl, fluorenonyl, phenanthryl, anthryl or acenaphthyl.

As used herein, "aralkyl" is intended to mean an aryl moiety, as defined above, attached through a $C_1$–$C_6$ alkyl linker, where alkyl is defined above. Examples of aralkyls inlcude, but are not limited to, benzyl, naphthylmethyl and phenylpropyl.

As used herein, "heteroaralkyl" is intended to mean a heteroaryl moiety, as defined below, attached through a $C_1$–$C_6$ alkyl linker, where alkyl is defined above. Examples of heteroaralkyls include, but are not limited to, 2-pyridylmethyl, 2-morpholinylethyl, 2-imidazolylethyl, 2-quinolinylmethyl, 2-imidazolylmethyl and the like.

The term heterocycle or heterocyclic, as used herein, represents a stable 5- to 7-membered monocyclic or stable 8- to 11-membered bicyclic hetero-cyclic ring which is either saturated or unsaturated, and which consists of carbon atoms and from one to four heteroatoms selected from the group consisting of N, O, and S, and including any bicyclic group in which any of the above-defined hetero-cyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, benzopyrazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperdinyl, 2-oxopyrrolidinyl, 2-oxopyridyl, 2-oxoquinolinyl, piperidyl, piperazinyl, pyridyl, pyridinyl-N-oxide, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroimidazopyridinyl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

Examples of a "saturated heterocycle" may include, but are not limited to, morpholinyl, piperidinyl, piperazinyl, pyrrolidinyl, thiamorpholinyl, and the like.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heteroaryl elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroimidazopyridinyl, tetrahydroisoquinolinyl, tetrahydroquinolinyl, thiazolyl, thienofuryl, thienothienyl, and thienyl.

As used herein, the terms "substituted $C_1$–$C_6$ alkyl" and "substituted $C_1$–$C_6$ alkoxy" are intended to include the branch or straight-chain alkyl group of the specified number of carbon atoms, wherein the carbon atoms may be substituted with F, Cl, Br, $CF_3$, $N_3$, $NO_2$, $NH_2$, oxo, —OH, —O($C_1$–$C_6$ alkyl), $S(O)_{0-2}$, ($C_1$–$C_6$ alkyl) $S(O)_{0-2}$—, ($C_1$–$C_6$ alkyl)$S(O)_{0-2}$($C_1$–$C_6$ alkyl)-, $C_3$–$C_{10}$ cycloalkyl, $C_2$–$C_6$ alkenyl, $C_2$–$C_6$ alkynyl, —C(O)NH, ($C_1$–$C_6$ alkyl) C(O)NH—, $H_2NC(O)NH$—, $H_2NC(NH)$—, ($C_1$–$C_6$ alkyl) C(O)—, —O($C_1$–$C_6$ alkyl)$CF_3$, ($C_1$–$C_6$ alkyl)OC(O)—, ($C_1$–$C_6$ alkyl)O ($C_1$–$C_6$ alkyl)—, ($C_1$–$C_6$ alkyl)C(O)$_2$ ($C_1$–$C_6$ alkyl)—, ($C_1$–$C_6$ alkyl)OC(O)NH—, aryl, benzyl, heterocycle, aralkyl, heteroaralkyl, halo-aryl, halo-benzyl, halo-heterocycle, cyano-aryl, cyano-benzyl and cyano-heterocycle.

As used herein, the terms "substituted aryl", "substituted heteroaryl", "substituted aralkyl", substituted heteroaralkyl", "substituted benzyl" and "substituted hetrocycle" are intended to include the cyclic group containing from 1 to 3 substitutents in addition to the point of attachment to the rest of the compound. Such substitutents are preferably selected from the group which includes but is not limited to F, Cl, Br, $CF_3$, $NH_2$, $N(C_1$–$C_6$ alkyl)$_2$, $NO_2$, CN, $N_3$, $C_1$–$C_{20}$ alkyl, $C_1$–$C_6$ alkoxy, —OH, —O($C_1$–$C_6$ alkyl), $S(O)_{0-2}$, ($C_1$–$C_6$ alkyl)$S(O)_{0-2}$—, ($C_1$–$C_6$ alkyl) $S(O)_{0-2}$ ($C_1$–$C_6$ alkyl)—, ($C_1$–$C_6$ alkyl)C(O)NH—, $H_2NC(O)NH$—, $H_2N$—C(NH)—, ($C_1$–$C_6$ alkyl)C(O)—, ($C_1$–$C_6$ alkyl)OC (O)—, ($C_1$–$C_6$ alkyl)O($C_1$–$C_6$ alkyl)—, ($C_1$–$C_6$ alkyl)C(O) $_2$($C_1$–$C_6$ alkyl)—, ($C_1$–$C_6$ alkyl)OC(O)NH—, aryl, aralkyl, heteroaryl, heteroaralkyl, halo-aryl, halo-aralkyl, halo-heterocycle, halo-heteroaralkyl, cyano-aryl, cyano-aralkyl, cyano-heterocycle and cyano-heteroaralkyl.

Examples of the moiety

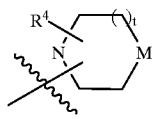

include, but are not limited to,

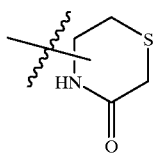 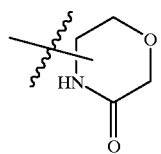

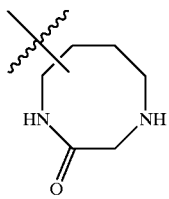 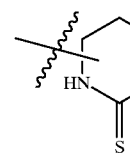 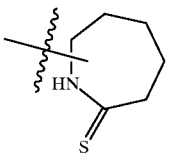

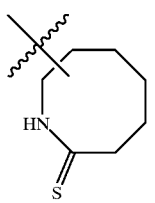 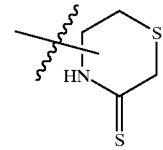 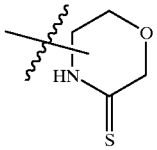

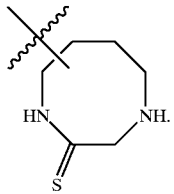

Examples of the moiety

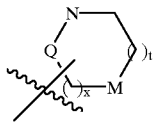

include, but are not limited to,

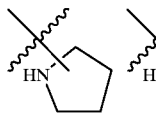 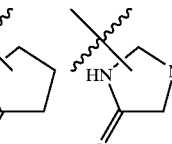 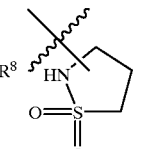

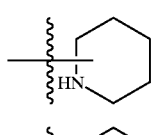 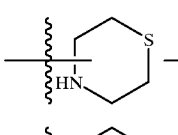 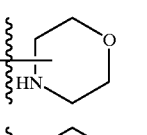

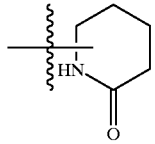 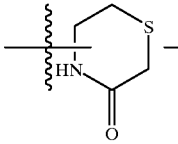 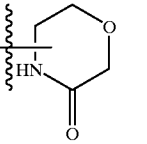

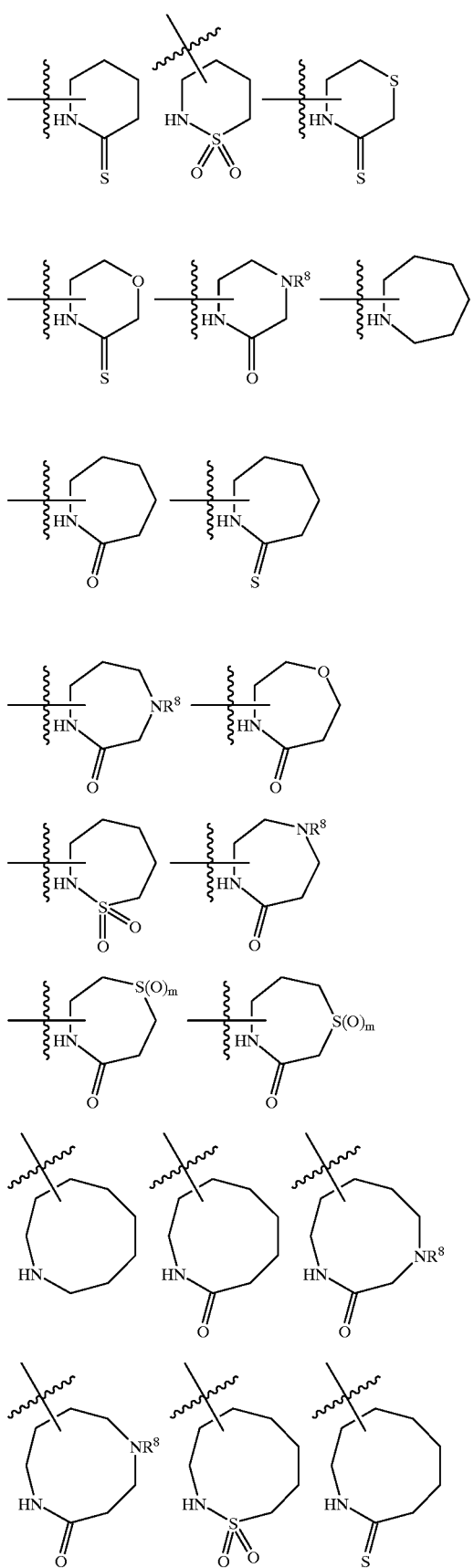
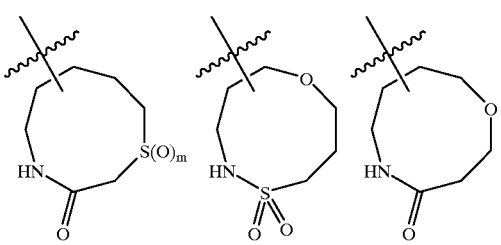
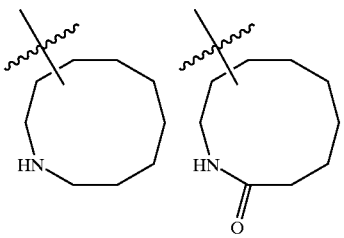
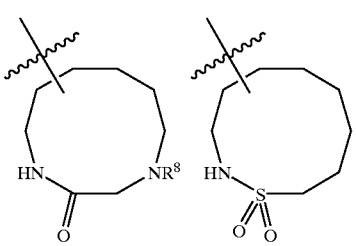
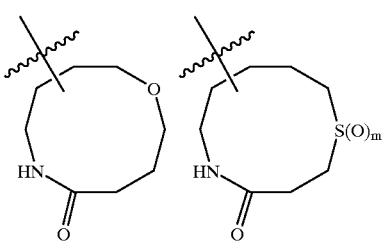

As used herein for substituent $A^3$, examples of "$C_3$–$C_6$ cycloalkyl" include, but are not limited to:

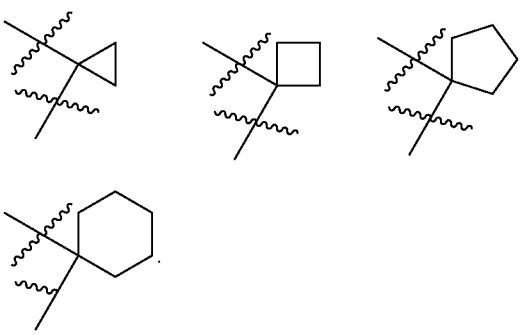

Lines drawn into the ring systems from substituents (such as from $R^2$, $R^3$, $R^4$ etc.) indicate that the indicated bond may be attached to any of the substitutable ring carbon atoms or heteroatoms.

Preferably, $R^{1c}$ is independently selected from: hydrogen, unsubstituted or substituted $C_1$–$C_6$ alkyl, unsubstituted or substituted aryl, unsubstituted or substituted heterocycle, —OR$^{15}$, or —N(R$^{15}$)$_2$.

Preferably, R$^{1c''}$ is selected from N(R$^{15}$)$_2$ or OR$^{15}$.

Preferably, R$^1$ is independently selected from H, halo, unsubstituted or substituted C$_1$–C$_6$ alkyl, —OR$^8$, —N(R$^8$)$_2$, —(C$_1$–C$_6$ alkyl)N(R$^8$)$_2$, unsubstituted or substituted aryl, unsubstituted or substituted heterocycle, —(C$_1$–C$_6$ alkyl)NR$^8$C(O) N(R$^8$)$_2$, or (C$_1$–C$_6$ alkyl)R$^{14}$. Preferably, R$^1$ is not C$_1$–C$_6$ alkyl substituted with unsubstituted or substituted aryl.

Preferably, R$^2$ is independently selected from H, OR$^8$, CN, unsubstituted or substituted aryl or halogen. Most preferably, R$^2$ is CN.

Preferably, R$^3$ is independently selected from hydrogen, halogen, CN, NO$_2$, and unsubstituted or substituted C$_1$–C$_6$ alkyl.

Preferably, R$^4$ of formulae A–D is selected from H or =O.

Preferably, R$^5$ is independently selected from hydrogen, halogen, unsubstituted or substituted C$_1$–C$_6$ alkyl, unsubstituted or substituted aryl, unsubstituted or substituted heterocycle, —(C$_1$–C$_6$ alkyl)N(R$^8$)$_2$, C(O)N(R$^8$)$_2$ or —(C$_1$–C$_6$ alkyl)OR$^8$.

Preferably, A$^1$ and A$^2$ are independently selected from: a bond, O, —NR$^8$, C(O) and S(O)$_q$. Most preferably, A$^1$ is O, —NR$^8$, C(O) or S(O)$_q$ and A$^2$ is a bond.

Preferably, A$^3$ is selected from a bond,

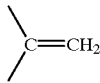

or C$_3$–C$_6$ cycloalkyl.

Preferably, M of formulae I–III is selected from CH$_2$ or NR$^8$.

Preferably, Q of formulae I–III is selected from C(=O), CH$_2$, or S(O)$_m$.

Preferably, W is a heterocycle. Most preferably, W is imidazolyl, pyridyl.

Preferably, Y is selected from phenyl or pyridyl. Most preferably, Y is phenyl.

Preferably, Z is selected from aryl, a bond or heteroaryl. Most preferably, Z is phenyl or pyridyl.

Preferably, m, n, p, q, r and s are independently 0, 1, or 2.

Preferably, t is 1, 2 or 3. Most preferably, t is 2.

Preferably, x of formulae I–III is selected from 0, 1 or 2.

Preferably, (C(R$^{1a}$)$_2$)$_n$A$^1$(C(R$^{1a}$)$_2$)n represents O, —NR$^8$, C(O), S(O)$_q$ or C$_1$–C$_6$ alkyl. More preferably, (C(R$^{1a}$)$_2$)$_n$A$^1$ (C(R$^{1a}$)$_2$)$_n$ represents O, —NR$^8$, C(O) or S(O)$_q$.

Preferably, (C(R$^{1b}$)$_2$)$_r$A$^2$(C(R$^{1b}$)$_2$)$_r$ represents a bond or C$_1$–C$_6$ alkyl. More preferably, (C(R$^{1b}$)$_2$)$_r$A$^2$(C(R$^{1b}$)$_2$)$_r$ represents a bond.

Preferably, (CH$_2$)$_n$A$^1$(CH$_2$)$_n$ represents O, —NR$^8$, C(O), S(O)$_q$ or C$_1$–C$_6$ alkyl. More preferably, (CH$_2$)$_n$A$^1$(CH$_2$)$_n$ represents O, —NR$^8$, C(O) or S(O)$_q$.

Preferably, (CH$_2$)$_r$A$^2$(CH$_2$)$_r$ represents a bond or C$_1$–C$_6$ alkyl. More preferably, (CH$_2$)$_r$A$^2$(CH$_2$)$_r$ represents a bond.

Preferably, the ring system

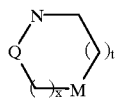

is attached to the rest of the molecule through a non-nitrogen ring atom.

Preferably, the moiety

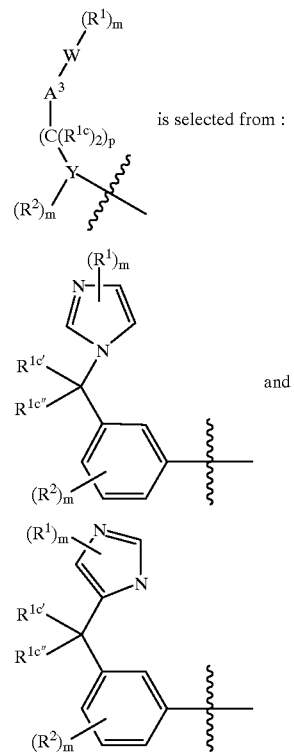

is selected from:

It is intended that the definition of any substituent or variable (e.g., R$^{1a}$, R$^3$, m, p, etc.) at a particular location in a molecule is independent of its definitions elsewhere in that molecule. Thus, —C(R$^{1a}$)$_2$ represents —CH$_2$, —CHCH$_3$, —CHC$_2$H$_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Abbreviations which may be used in the description of the chemistry and in the Examples that follow include:

| | |
|---|---|
| Ac$_2$O | Acetic anhydride; |
| AIBN | 2,2'-azobisiobutyronitrile |
| Boc | t-Butoxycarbonyl; |
| CBz | Carbobenzyloxy; |
| DBU | 1,8-diazabicyclo[5.4.0]undec-7-ene; |
| DMAP | 4-Dimethylaminopyridine; |
| DME | 1,2-Dimethoxyethane; |
| DMF | Dimethylformamide; |
| DMSO | Methyl sulfoxide; |
| DTT | Dithiothreitol; |
| EDC | 1-(3-dimethylaminopropyl)-3-ethyl-carbodiimide-hydrochloride; |
| EDTA | Ethylenediaminetetraacetic acid; |
| Et$_3$N | Triethylamine; |
| EtOAc | Ethyl acetate; |
| EtOH | Ethanol; |
| FAB | Fast atom bombardment; |
| HEPES | 4-(2-hydroxyethyl)-1-piperazineethanesulfonic acid; |
| HOBT | 1-Hydroxybenzotriazole hydrate; |
| HOOBT | 3-Hydroxy-1,2,2-benzotriazin-4(3H)-one; |
| HPLC | High-perfomance liquid chromatography; |
| MCPBA | m-Chloroperoxybenzoic acid; |
| MeOH | methanol; |
| MsCl | Methanesulfonyl chloride; |
| NaHMDS | Sodium bis(trimethylsilyl)amide; |
| NBS | N-bromosuccinimide; |
| PMSF | a toluenesulfonyl chloride; |
| Py or pyr | Pyridine; |
| RPLC | Reverse Phase Liquid Chromatography; |
| TFA | Trifluoroacetic acid; |
| THF | Tetrahydrofuran. |

These reactions may be employed in a linear sequence to provide the compounds of the invention or they may be used to synthesize fragments which are subsequently joined by the alkylation reactions described in the Schemes.

Synopsis of Schemes

Schemes 1 to 18 describe the synthesis of compounds of formula A. The starting materials can be obtained from commercial sources or they can be obtained using standard transformations (e.g. esterification of the hydroxy acid) from commercially available materials.

In Scheme 1, amino-hydroxybenzoates of type 1 can be converted to the corresponding iodide 2 by treatment with acidic aqueous NaNO$_2$ followed by the addition of KI. The phenol may then be alkylated by treatment with a base such as NaH or Cs$_2$CO$_3$ in an organic solvent (for example DMF) followed by the addition of an electrophile to yield 3. Reduction of the ester of 3 using, for example, LiBH$_4$ in THF then yields the alcohol 4 which can in turn be treated with Zn(CN)$_2$ in DMF and a palladium catalyst to give 5. The alcohol of 5 can be converted into a leaving group of 6 in a number of ways. One such procedure involves reaction of the alcohol with a sulfonyl chloride in the presence of an organic base (e.g. triethylamine) in an organic solvent such as dichloromethane. A second method requires the reaction of the alcohol with CBr$_4$ and a phosphine such as triphenyl phosphine in an organic solvent such as dichloromethane. A third method involves reaction of the alcohol with N-bromosuccinimide and dimethyl sulfide in dichloromethane. The reaction of 6 with imidazole in a polar solvent such as DMF then affords compounds of formula 7. In addition, 6 upon reaction with 4-iodo-1-tritylimidazole in THF with 1,2-dibromoethane, Zn and NiCl$_2$(PPh$_3$)$_2$ gives a compound of formula 8. Subsequent methanolysis of 8 yields compounds of formula 9. Treating a compound of formula 8 with a suitably substituted alkyl or aralkyl halide or mesylate, followed by methanolysis yields a compound of formula 10.

An alternative route for the synthesis of compounds of formula 7 is shown in Scheme 2. Iodo-hydroxybenzoic acids of structure 2 may be converted to the corresponding cyano 11. The ester may be reduced by treating 11 with LiBH$_4$ (and THF) to produce the alcohol 12. The primary hydroxyl can be converted into a leaving group by reacting the alcohol with CBr$_4$ and a phosphine, such as triphenyl phosphine (in an organic solvent such as dichloromethane). The reaction of 13 with imidazole affords 14, which can be converted to 7 by treatment with a base, such as Cs$_2$CO$_3$, and a suitably substituted alkyl or aralkyl halide or mesylate.

Scheme 3 illustrates one route for the synthesis of compounds of formula 21. The bromotoluene 15 can be treated with KMnO$_4$ to yield the bromofluorobenzoic acid 16. The acid 16 can be reduced with BH$_3$ in THF to give the bromobenzene 17. The bromobenzene 17 can be converted to the corresponding cyanobenzene 18 by treating 17 with Zn(CN)$_2$ and a palladium catalyst. The alcohol of intermediate 18 can be converted into a leaving group by reacting the alcohol with NBS and DMS to produce 19. Treatment of 19 with a nitrogen-containing hetero-cycle yields 20. Compounds of formula 21 can be obtained by treating 20 with Cs$_2$CO$_3$ or KF/Alumina and a phenol.

Scheme 4 describes one route for preparing compounds of formulae 27 and 28. Compound 18 is oxidized with pyridine-sulfoxide complex, for example, to aldehyde 22. Treatment of compound 22 with a Grignard reagent R$^c$MgBr provides compound 23. Oxidation of 23 gives ketone 24 which is treated with 4-iodo-1-tritylimidazole and EtMgBr to obtain alcohol 25. Subsequent protection of alcohol 25, quaternization, and removal of the protecting groups provides compound 26. Compound 26 is converted to compounds of formula 27 by treatment with R$^b$OH and a base such as Cs$_2$CO$_3$ or KF on alumina. Compounds of formula 27 are converted to compounds of formula 28 by treatment with SOCl$_2$ followed by ammonia.

Scheme 4A depicts the synthesis of compounds of formula 29, where the nitrogen atom attached to benzylic carbon is substituted, using sulfonyl chloride and a substituted amine to convert compound 27 to compound 29.

Scheme 5 illustrates an alternate way of preparing intermediate 25. The aldehyde 22 is treated with 4-iodo-1-tritylimidazole and EtMgBr to obtain the alcohol 30. The alcohol 30 was then converted to the ketone 31 using MnO$_2$. Intermediate 25 was obtained by treating the ketone 31 with a substituted MgBr.

Scheme 6 illustrates several routes using compounds of formula 32 to prepare various amide, urea, carbamate and sulfonamide derivatives (33–36).

Scheme 7 describes a route for the chiral preparation of compounds of formula 40. Using the commercially available t-butyl sulfinamide and techniques described in the literature (J. A. Ellman et al., *J. Org. Chem.*, 1999, vol. 64, p. 1278–1284), intermediates of formula 39 are prepared as single enantiomers. Treating 39 with an alcohol and cesium carbonate or KF/alumina yields compounds of formula 40 as single enantiomers.

Another route for the chiral synthesis of intermediate 39, which uses a protected imidazolyl group, is described in Scheme 8.

Schemes 9 and 10 illustrate alternate ways of preparing compounds of formula 37. Scheme 9 uses techniques known in the literature (P. Molina et al., *Tetrahedron Letters*, vol. 37, N. 52, p. 9353–9356) to prepare intermediate 45. Scheme 10 illustrates an alternative route to compounds of formula 37.

Schemes 11 and 12 illustrate the synthesis of compounds of formula 49 and 50, using techniques previously described above.

Schemes 13 and 14 illustrate syntheses of compounds of the formulae 53, 55, and 56 wherein substituent W is present as a pyridyl moiety. Similar synthetic strategies for preparing compounds that incorporate other heterocyclic moieties for variable W are also well known in the art.

Schemes 15–17 depict the preparation of various lactam phenols using an allyl compound 58 as a common intermediate. In Scheme 15 compound 58 is hydrogenated and deprotected to give compound 60. In Scheme 16 compound 58 is hydroborated to provide compound 61. Ozonolysis and reduction of 58 yields compound 62. Deprotection of 59 and 61 give 63 which can be further elaborated to the amino derivative 65. Scheme 17 illustrates modifications of the amino compound 65 by reductive alkylation, acylation, sulfonylation or carbamylation to provide compounds 66, 67, 68, and 69, respectively.

Scheme 18 illustrates a method to prepare sultam phenols of formula 75. By treating compound 70 with $MgSO_2$ in THF and sulfonyl chloride, compound 71 is obtained. Compound 71 is converted to the substituted sulfonamide 72, which is then treated with NaH to obtain the compounds of formula 73. Compound 73 is treated with a suitably substituted halide and base to provide intermediate 74. Intermediate 74 is deprotected to give a sultam phenol of formula 75.

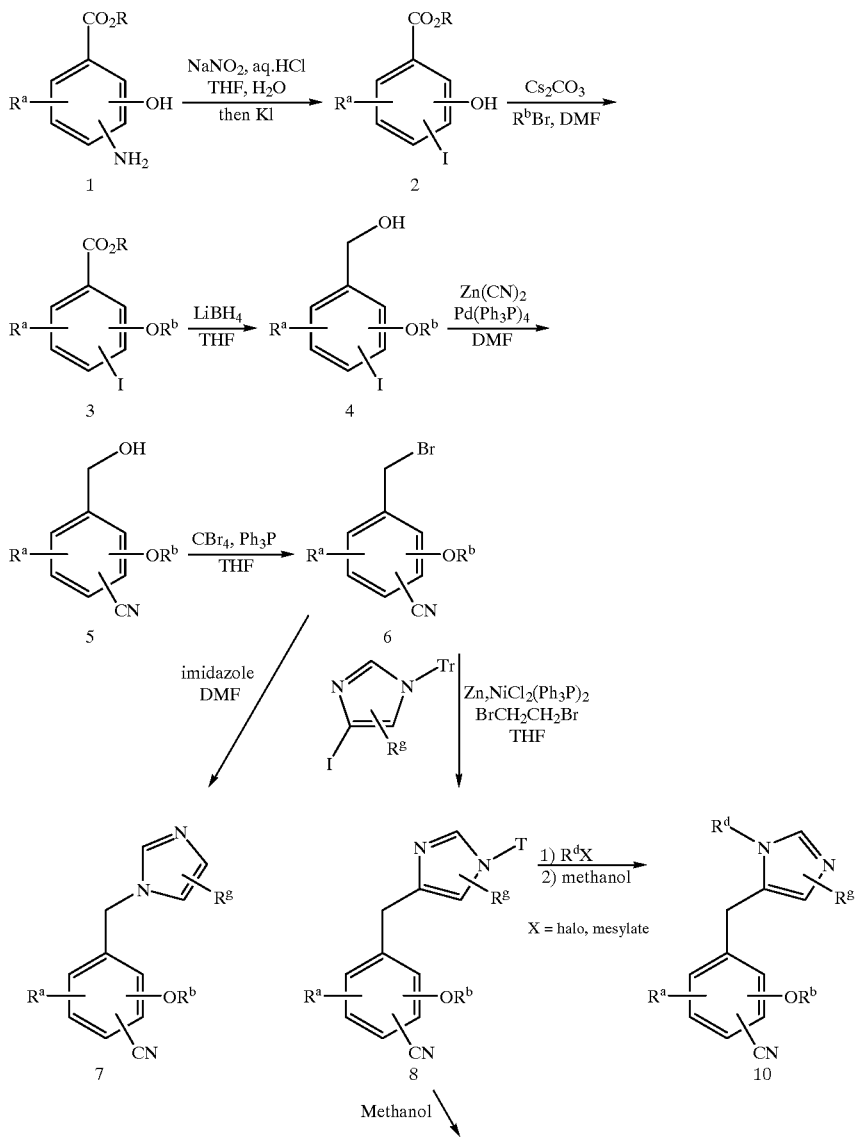

SCHEME 1

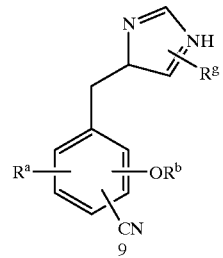
SCHEME 2
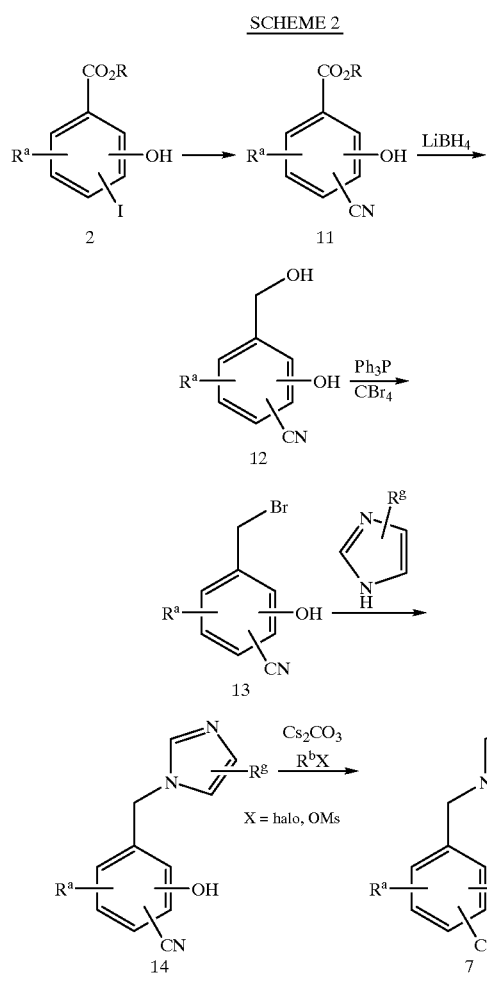
SCHEME 3
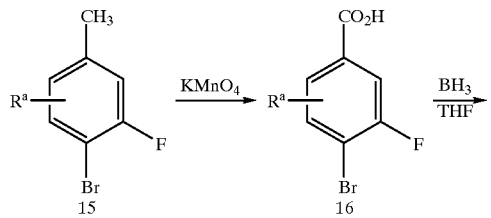
-continued
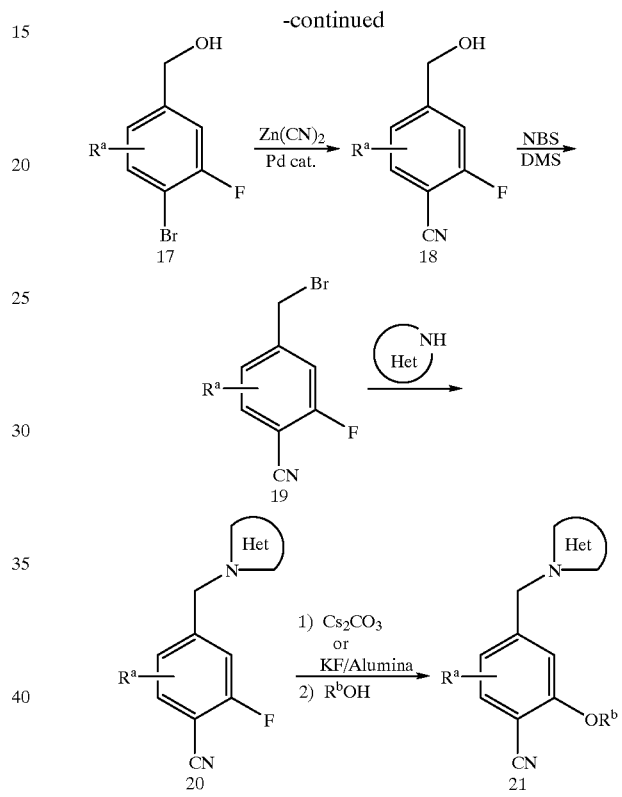
SCHEME 4
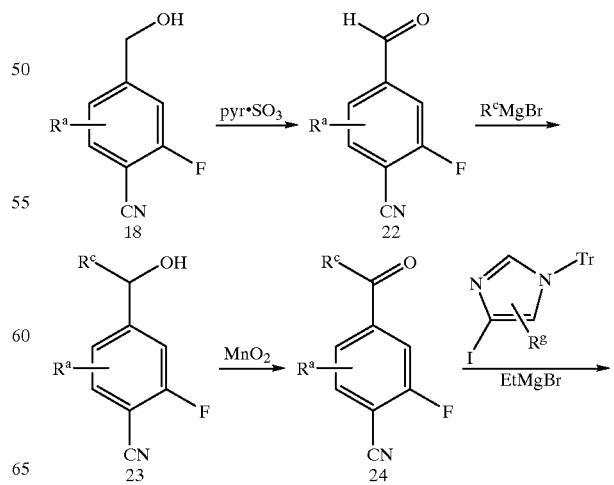

-continued
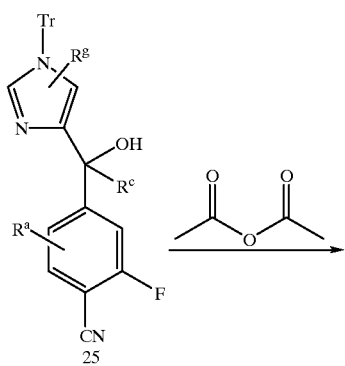
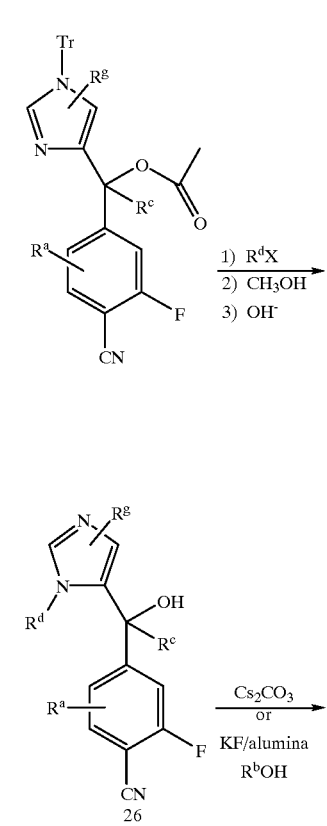
SCHEME 4A
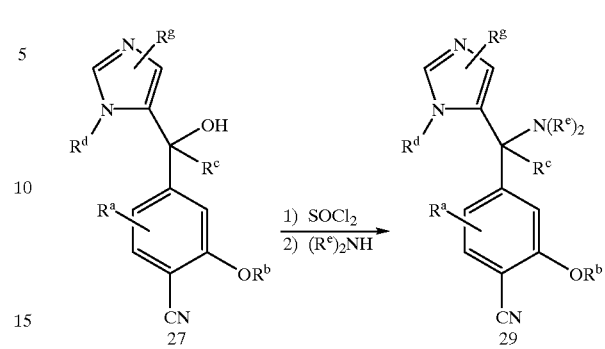
SCHEME 5
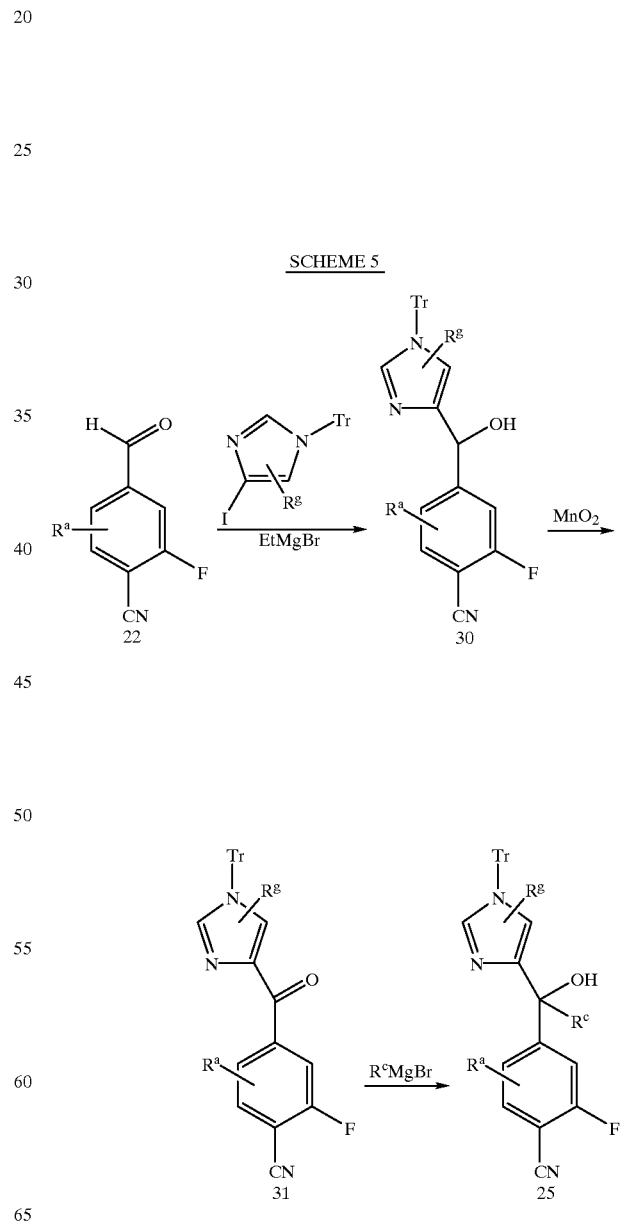

SCHEME 6
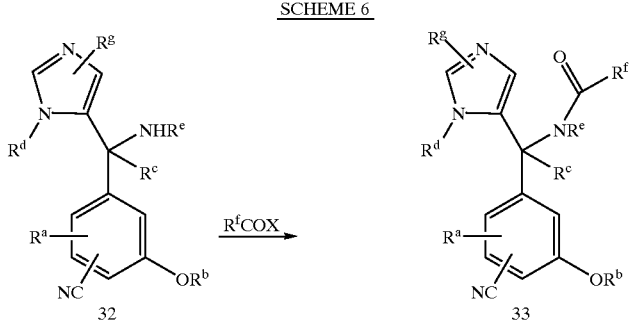
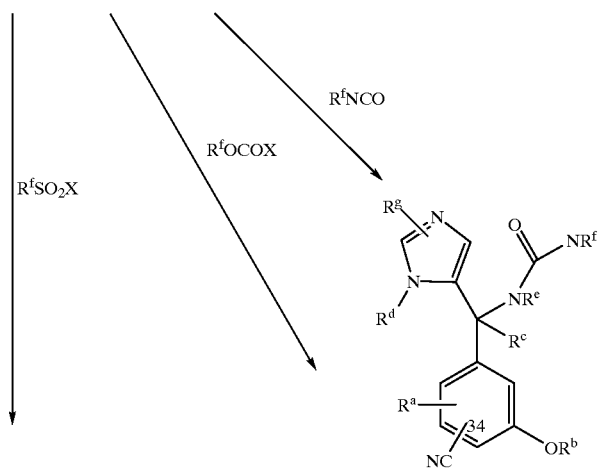
SCHEME 7
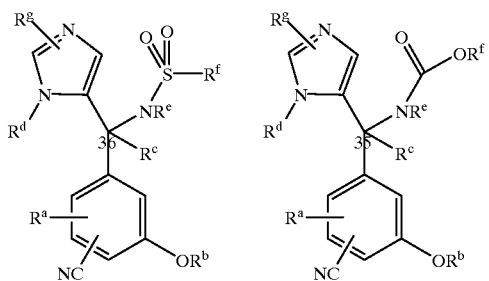
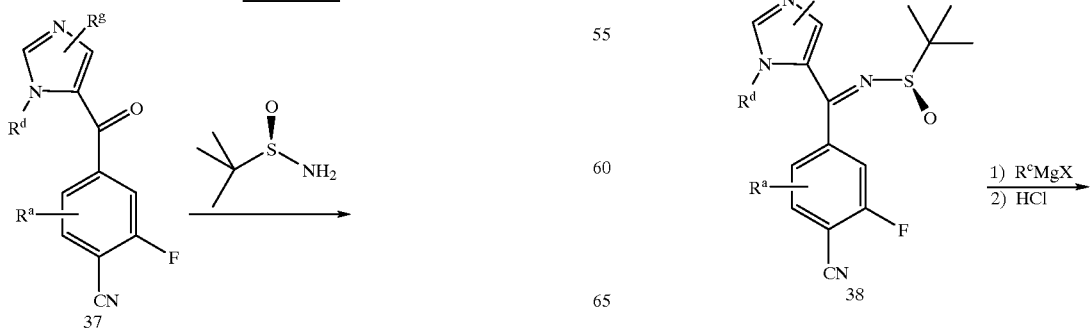
-continued

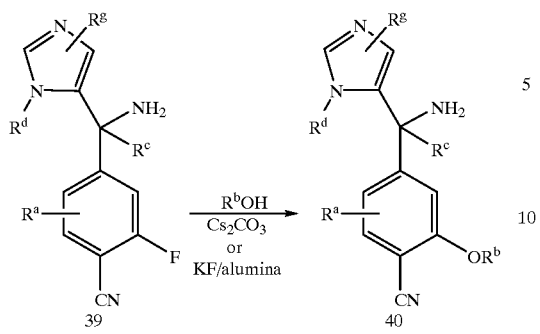
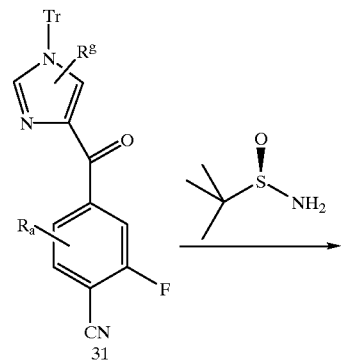
SCHEME 8
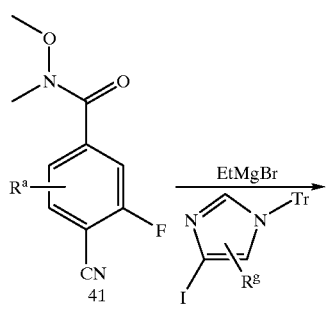
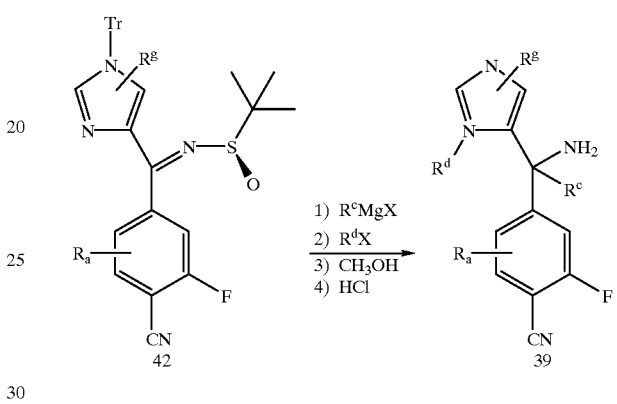
SCHEME 9
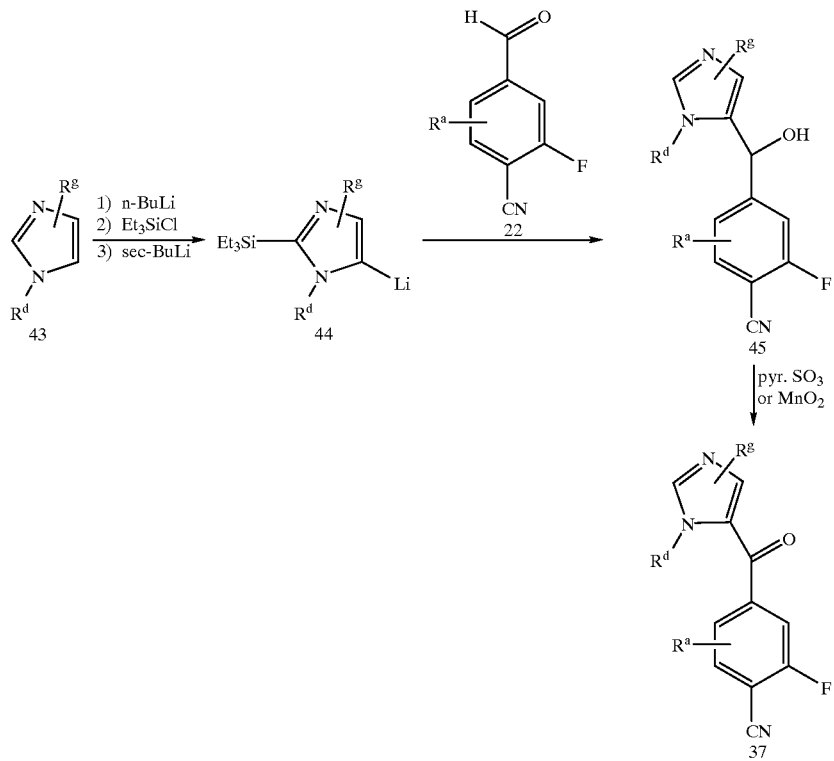

SCHEME 10
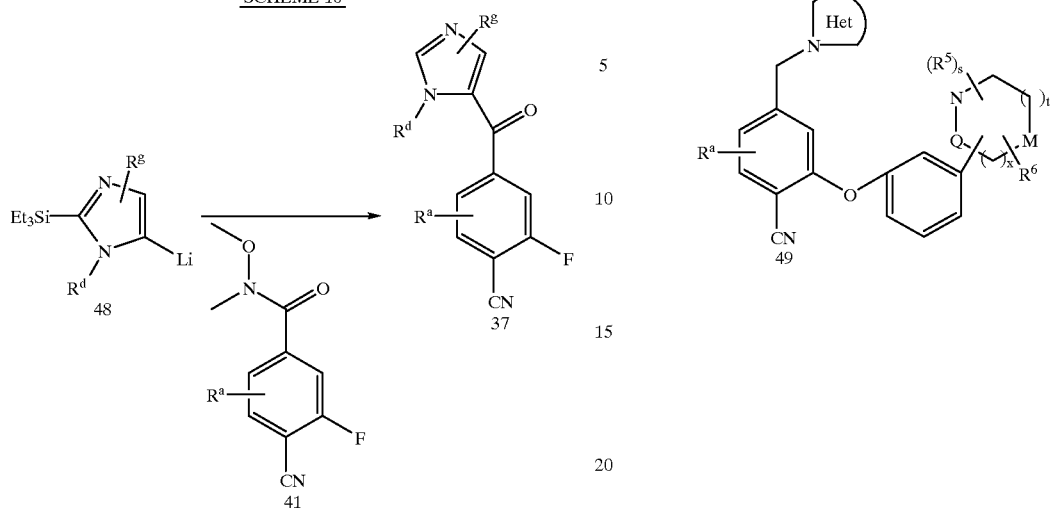
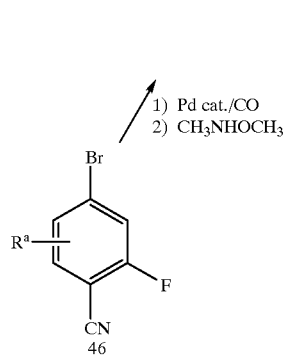
SCHEME 11
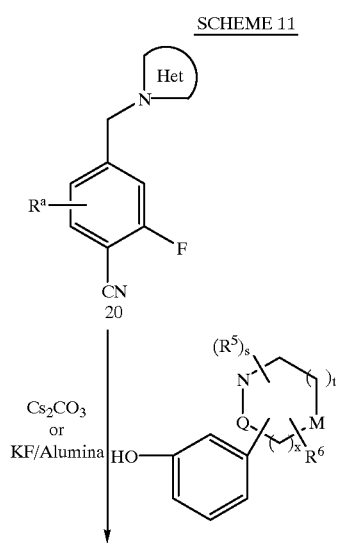
SCHEME 12

SCHEME 13
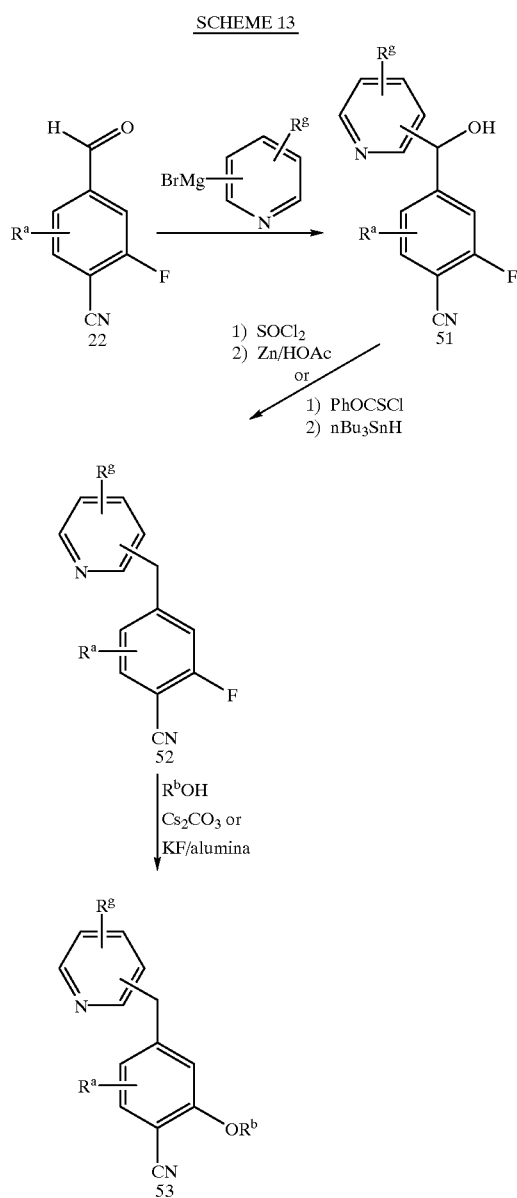
SCHEME 14
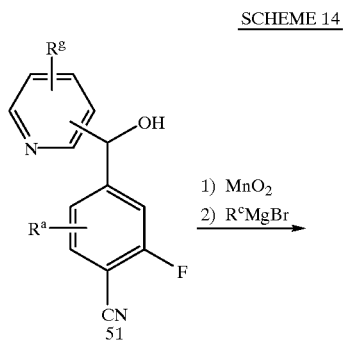
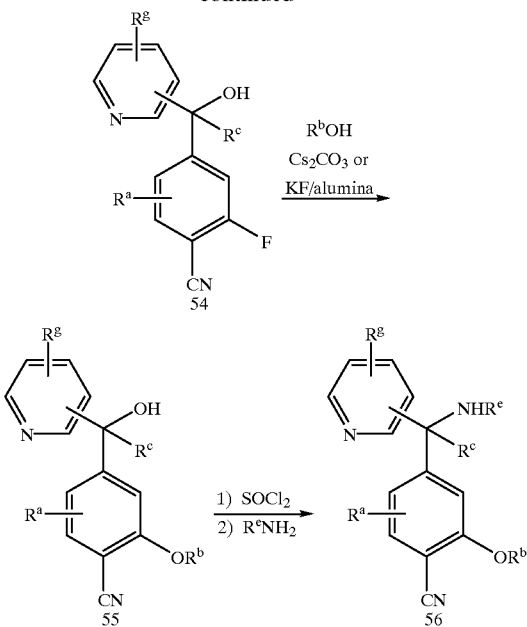
SCHEME 15
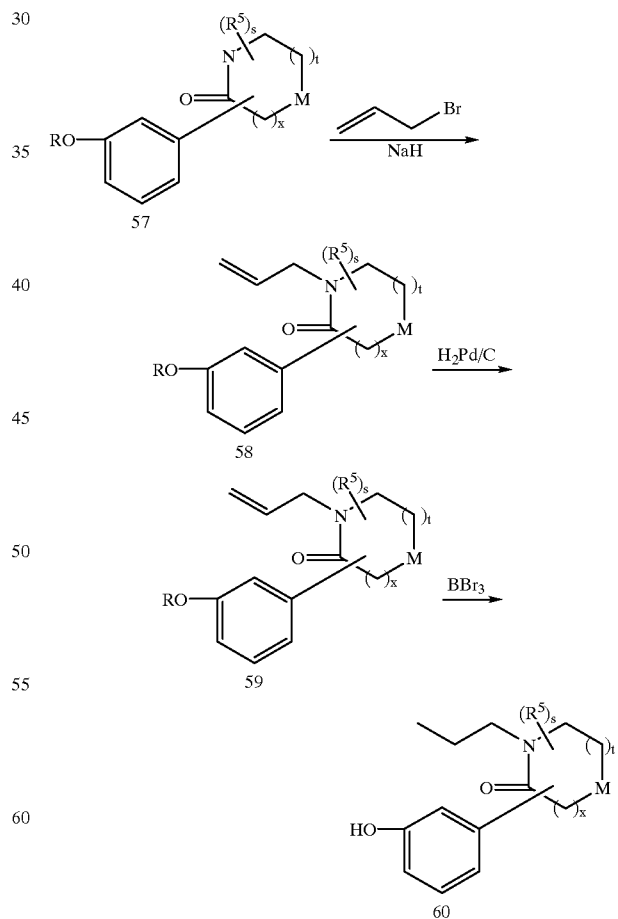

SCHEME 16
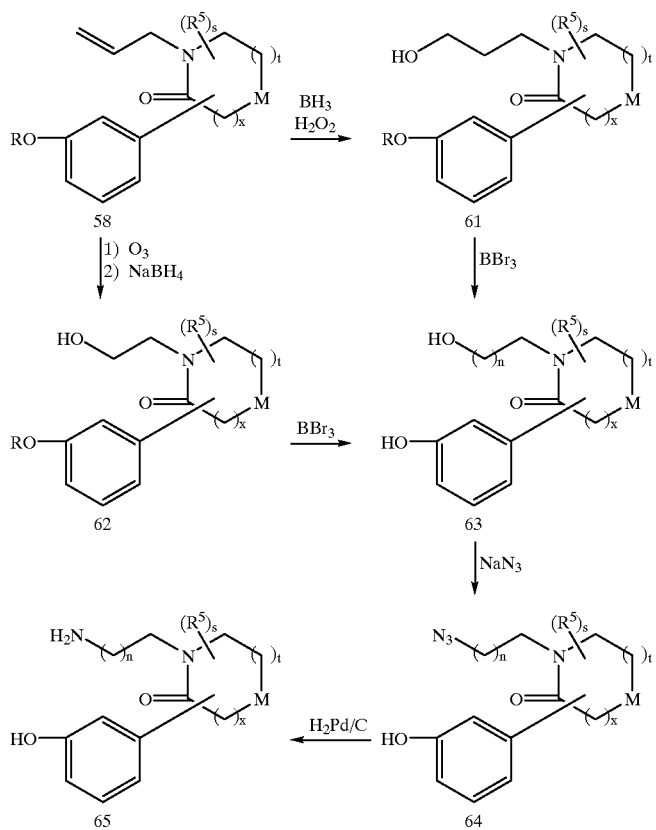
SCHEME 17
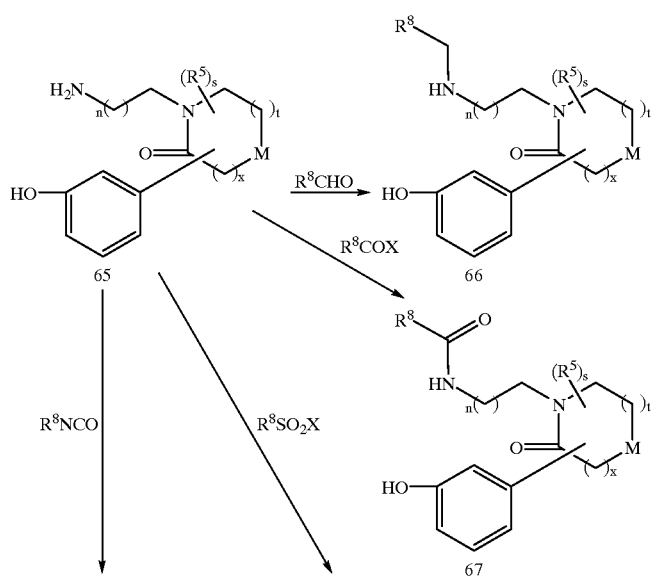

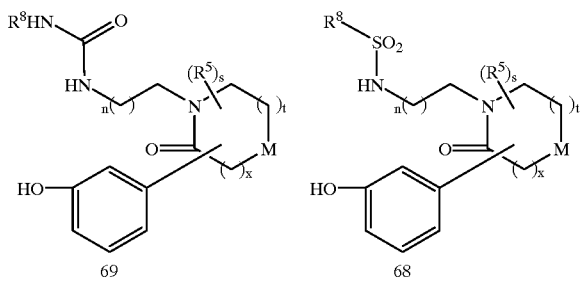

SCHEME 18

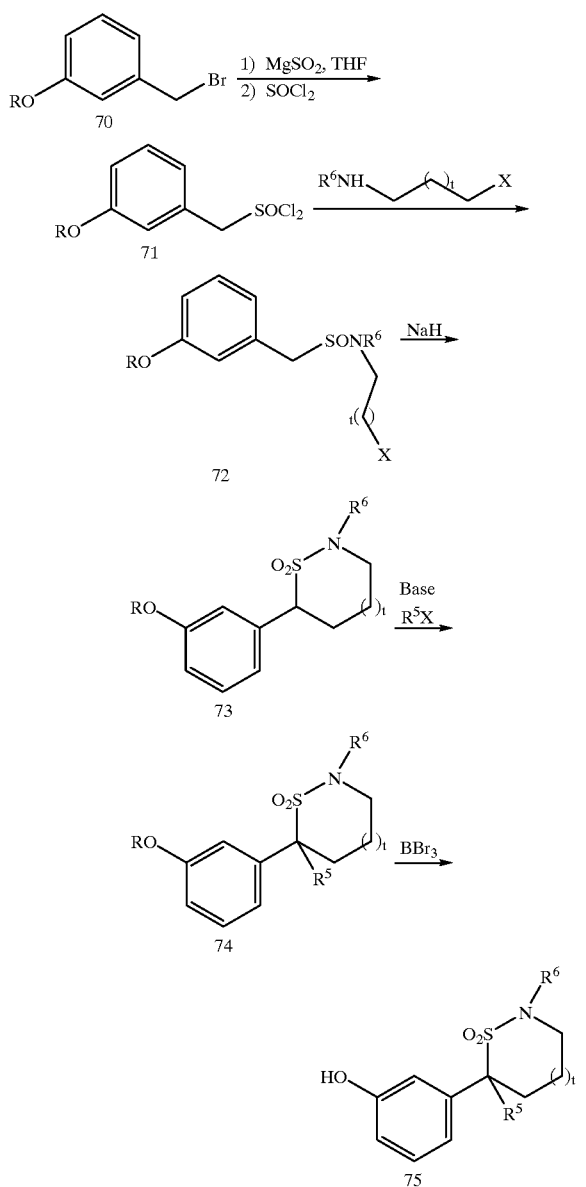

In the above Schemes, it is understood that
R independently represents an alkyl or an aryl;
$R^a$ independently represents $R^2$ or protected precursors thereof;

$R^b$ independently represents the following moiety:

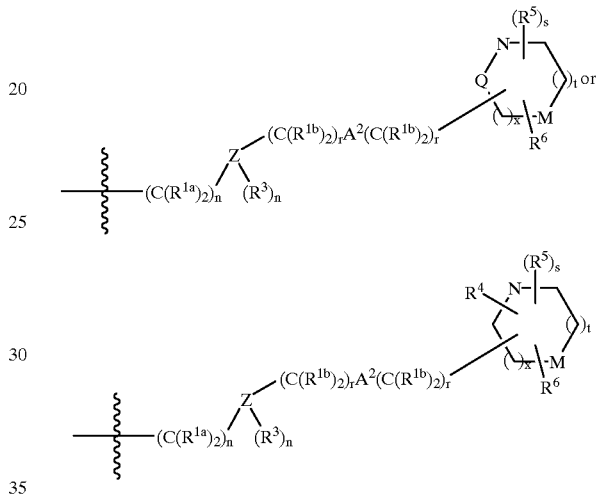

$R^c$ independently represents $R^{1c}$ or protected precursors thereof;
$R^d$ and $R^g$ independently represents $R^1$ or protected precursors thereof;
$R^e$ and $R^f$ independently represent $R^8$ or protected precursors thereof; and
X is independently represents a halide.

In order to simplify the structures described in the above schemes, mutiple designations of a substituent (i.e. $R^a$, $R^b$, $R^c$, $R^d$, $R^e$, $R^f$ and $R^g$) have not been included. However, it is understood that there may be several, independently selected substitutients around each of the rings described hereinabove, as seen in formulae I–III and A–D, hereinabove.

In a preferred embodiment of the instant invention the compounds of the invention are selective inhibitors of farnesyl-protein transferase. A compound is considered a selective inhibitor of farnesyl-protein transferase, for example, when its in vitro farnesyl-protein transferase inhibitory activity, as assessed by the assay described in Example 60 is at least 100 times greater than the in vitro activity of the same compound against geranylgeranyl-protein transferase-type I in the assay described in Example 61. Preferably, a selective compound exhibits at least 1000 times greater activity against one of the enzymatic activities when comparing geranylgeranyl-protein transferase-type I inhibition and farnesyl-protein transferase inhibition.

It is also preferred that the selective inhibitor of farnesyl-protein transferase is further characterized by:
b) an $IC_{50}$ (a measure of in vitro inhibitory activity) for inhibition of the prenylation of newly synthesized K-Ras protein more than about 100-fold higher than the $IC_{50}$ for the inhibition of the farnesylation of hDJ protein.

When measuring such $IC_{50}$s the assays described in Examples 65 and 66 may be utilized.

It is also preferred that the selective inhibitor of farnesyl-protein transferase is further characterized by:

c) an $IC_{50}$ (a measurement of in vitro inhibitory activity) for inhibition of K4B-Ras dependent activation of MAP kinases in cells at least 100-fold greater than the $IC_{50}$ for inhibition of the farnesylation of the protein hDJ in cells.

It is also preferred that the selective inhibitor of farnesyl-protein transferase is further characterized by:

d) an $IC_{50}$ (a measurement of in vitro inhibitory activity) against H-Ras dependent activation of MAP kinases in cells at least 1000-fold lower than the inhibitory activity ($IC_{50}$) against H-ras-CVLL (SEQ.ID.NO.: 1) dependent activation of MAP kinases in cells.

When measuring Ras dependent activation of MAP kinases in cells the assays described in Example 64 may be utilized.

In another preferred embodiment of the instant invention the compounds of the invention are dual inhibitors of farnesyl-protein transferase and geranylgeranyl-protein transferase type I. Such a dual inhibitor may be termed a Class II prenyl-protein transferase inhibitor and will exhibit certain characteristics when assessed in in vitro assays, which are dependent on the type of assay employed.

In a SEAP assay, such as described in Example 64, it is preferred that the dual inhibitor compound has an in vitro inhibitory activity ($IC_{50}$) that is less than about 12 mM against K4B-Ras dependent activation of MAP kinases in cells.

The Class II prenyl-protein transferase inhibitor may also be characterized by:

a) an $IC_{50}$ (a measurement of in vitro inhibitory activity) for inhibiting K4B-Ras dependent activation of MAP kinases in cells between 0.1 and 100 times the $IC_{50}$ for inhibiting the farnesylation of the protein hDJ in cells; and b) an $IC_{50}$ (a measurement of in vitro inhibitory activity) for inhibiting K4B-Ras dependent activation of MAP kinases in cells greater than 5-fold lower than the inhibitory activity ($IC_{50}$) against expression of the SEAP protein in cells transfected with the pCMV-SEAP plasmid that constitutively expresses the SEAP protein.

The Class II prenyl-protein transferase inhibitor may also be characterized by:

a) an $IC_{50}$ (a measurement of in vitro inhibitory activity) against H-Ras dependent activation of MAP kinases in cells greater than 2 fold lower but less than 20,000 fold lower than the inhibitory activity ($IC_{50}$) against H-ras-CVLL (SEQ.ID.NO.: 1) dependent activation of MAP kinases in cells; and b) an $IC_{50}$ (a measurement of in vitro inhibitory activity) against H-ras-CVLL dependent activation of MAP kinases in cells greater than 5-fold lower than the inhibitory activity ($IC_{50}$) against expression of the SEAP protein in cells transfected with the pCMV-SEAP plasmid that constitutively expresses the SEAP protein.

The Class II prenyl-protein transferase inhibitor may also be characterized by:

a) an $IC_{50}$ (a measurement of in vitro inhibitory activity) against H-Ras dependent activation of MAP kinases in cells greater than 10-fold lower but less than 2,500 fold lower than the inhibitory activity ($IC_{50}$) against H-ras-CVLL (SEQ.ID.NO.: 1) dependent activation of MAP kinases in cells; and b) an $IC_{50}$ (a measurement of in vitro inhibitory activity) against H-ras-CVLL dependent activation of MAP kinases in cells greater than 5 fold lower than the inhibitory activity ($IC_{50}$) against expression of the SEAP protein in cells transfected with the pCMV-SEAP plasmid that constitutively expresses the SEAP protein.

A method for measuring the activity of the inhibitors of prenyl-protein transferase, as well as the instant combination compositions, utilized in the instant methods against Ras dependent activation of MAP kinases in cells is described in Example 64.

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, src, abl, lck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. *Cancer Research*, 55:4575–4580 (1995)). Such anti-angiogenesis properties of the instant compounds may also be useful in the treatment of certain forms of vision deficit related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. *Science*, 256:1331–1333 (1992).

The compounds of the instant invention are also useful in the prevention of restenosis after percutaneous transluminal coronary angioplasty by inhibiting neointimal formation (C. Indolfi et al. *Nature medicine*, 1:541–545(1995).

The instant compounds may also be useful in the treatment and prevention of polycystic kidney disease (D. L. Schaffler et al. *American Journal of Pathology*, 142:1051–1060 (1993) and B. Cowley, Jr. et al.*FASEB Journal*, 2:A3160 (1988)).

The instant compounds may also be useful for the treatment of fungal infections.

The instant compounds may also be useful as inhibitors of proliferation of vascular smooth muscle cells and therefore useful in the prevention and therapy of arteriosclerosis and diabetic vascular pathologies.

The compounds of the instant invention may also be useful in the prevention and treatment of endometriosis, uterine fibroids, dysfunctional uterine bleeding and endometrial hyperplasia.

In such methods of prevention and treatment, the prenyl-protein transferase inhibitor may also be co-administered with other well known therapeutic agents that are selected for their particular usefulness against the condition that is being treated. For example, the prenyl-protein transferase inhibitor may be useful in further combination with drugs known to supress the activity of the ovaries and slow the growth of the endometrial tissue. Such drugs include but are not limited to oral contraceptives, progestins, danazol and GnRH (gonadotropin-releasing hormone) agonists.

Administration of the prenyl-protein transferase inhibitor may also be combined with surgical treatment of endometriosis (such as surgical removal of misplaced endometrial tissue) where appropriate.

The instant compounds may also be useful as inhibitors of corneal inflammation. These compounds may improve the treatment of corneal opacity which results from cauterization-induced corneal inflammation. The instant compounds may also be useful in reducing corneal edema and neovascularization. (K. Sonoda et al., *Invest. Ophthalmol. Vis. Sci.*, 1998, vol. 39, p 2245–2251).

The compounds of this invention may be administered to mammals, preferably humans, either alone or, preferably, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

As used herein, the term "composition" is intended to encompass a product comprising the specified ingredients in the specific amounts, as well as any product which results, directly or indirectly, from combination of the specific ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropyl-cellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyl-eneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formnulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula A may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula A are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention may also be co-administered with other well known therapeutic agents that are selected for their particular usefulness against the condition that is being treated. For example, the compounds of the instant invention may also be co-administered with other well known cancer therapeutic agents that are selected for their particular usefulness against the condition that is being treated. Included in such combinations of therapeutic agents are combinations of the instant farnesyl-protein transferase inhibitors and an antineoplastic agent. It is also understood that such a combination of antineoplastic agent and inhibitor of farnesyl-protein transferase may be used in conjunction with other methods of treating cancer and/or tumors, including radiation therapy and surgery.

Examples of an antineoplastic agent include, in general, microtubule-stabilizing agents (such as paclitaxel (also known as Taxol®), docetaxel (also known as Taxotere®), epothilone A, epothilone B, desoxyepothilone A, desoxyepothilone B or their derivatives); microtubule-disruptor agents; alkylating agents, anti-metabolites; epidophyllotoxin; an antineoplastic enzyme; a topoisomerase inhibitor; procarbazine; mitoxantrone; platinum coordination complexes; biological response modifiers and growth inhibitors; hormonal/anti-hormonal therapeutic agents and haematopoietic growth factors.

Example classes of antineoplastic agents include, for example, the anthracycline family of drugs, the vinca drugs, the mitomycins, the bleomycins, the cytotoxic nucleosides, the taxanes, the epothilones, discodermolide, the pteridine family of drugs, diynenes and the podophyllotoxins. Particularly useful members of those classes include, for example, doxorubicin, carminomycin, daunorubicin, aminopterin, methotrexate, methopterin, dichloro-methotrexate, mitomycin C, porfiromycin, herceptin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, cisplatin, carboplatin, cyclophosphamide, bleomycin, tamoxifen, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

The preferred class of antineoplastic agents is the taxanes and the preferred antineoplastic agent is paclitaxel.

Radiation therapy, including x-rays or gamma rays which are delivered from either an externally applied beam or by implantation of tiny radioactive sources, may also be used in combination with the instant inhibitor of farnesyl-protein transferase alone to treat cancer.

Additionally, compounds of the instant invention may also be useful as radiation sensitizers, as described in WO 97/38697, published on Oct. 23, 1997, and herein incorporated by reference.

The instant compounds may also be useful in combination with other inhibitors of parts of the signaling pathway that links cell surface growth factor receptors to nuclear signals initiating cellular proliferation. Thus, the instant compounds may be utilized in combination with farnesyl pyrophosphate competitive inhibitors of the activity of farnesyl-protein transferase or in combination with a compound which has Raf antagonist activity. The instant compounds may also be co-administered with compounds that are selective inhibitors of geranylgeranyl protein transferase.

In particular, if the compound of the instant invention is a selective inhibitor of farnesyl-protein transferase, co-administration with a compound(s) that is a selective inhibitor of geranylgeranyl protein transferase may provide an improved therapeutic effect.

In particular, the compounds disclosed in the following patents and publications may be useful as farnesyl pyrophosphate-competitive inhibitor component of the instant composition: U.S. Ser. Nos. 08/254,228 and 08/435,047. Those patents and publications are incorporated herein by reference.

In practicing methods of this invention, which comprise administering, simultaneously or sequentially or in any order, two or more of a protein substrate-competitive inhibitor and a farnesyl pyrophosphate-competitive inhibitor, such administration can be orally or parenterally, including intravenous, intramuscular, intraperitoneal, subcutaneous, rectal and topical routes of administration. It is preferred that such administration be orally. It is more preferred that such administration be orally and simultaneously. When the protein substrate-competitive inhibitor and farnesyl pyrophosphate-competitive inhibitor are administered sequentially, the administration of each can be by the same method or by different methods.

The instant compounds may also be useful in combination with an integrin antagonist for the treatment of cancer, as described in U.S. Ser. No. 09/055,487, filed Apr. 6, 1998, which is incorporated herein by reference.

As used herein the term an integrin antagonist refers to compounds which selectively antagonize, inhibit or counteract binding of a physiological ligand to an integrin(s) that is involved in the regulation of angiogenisis, or in the growth and invasiveness of tumor cells. In particular, the term refers to compounds which selectively antagonize, inhibit or counteract binding of a physiological ligand to the αvβ3 integrin, which selectively antagonize, inhibit or counteract binding of a physiological ligand to the αvβ5 integrin, which antagonize, inhibit or counteract binding of a physiological ligand to both the αvβ3 integrin and the αvβ5 integrin, or which antagonize, inhibit or counteract the activity of the particular integrin(s) expressed on capillary endothelial cells. The term also refers to antagonists of the α1β1, α2β1, α5β1, α6β1 and α6β4 integrins. The term also refers to antagonists of any combination of αvβ3 integrin, αvβ5, α1β1, α2β1, α5β1, α6β1 and α6β4 integrins. The instant compounds may also be useful with other agents that inhibit angiogenisis and thereby inhibit the growth and invasiveness of tumor cells, including, but not limited to angiostatin and endostatin.

The instant compounds may also be useful in combination with an inhibitor of 3-hydroxy-3-methylglutaryl-CoA reductase (HMG-CoA reductase) for the treatment of cancer. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30–33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938; 4,294,926; 4,319,039), simvastatin (ZOCOR®; see U.S. Pat. Nos. 4,444,784; 4,820,850; 4,916,239), pravastatin (PRAVACHOL®; see U.S. Pat. Nos. 4,346,227; 4,537,859; 4,410,629; 5,030,447 and 5,180,589), fluvastatin (LESCOL®; see U.S. Pat. Nos. 5,354,772; 4,911,165; 4,929,437; 5,189,164; 5,118,853; 5,290,946; 5,356,896), atorvastatin (LIPITOR®; see U.S. Pat. Nos. 5,273,995; 4,681,893; 5,489,691; 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85–89 (Feb. 5, 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

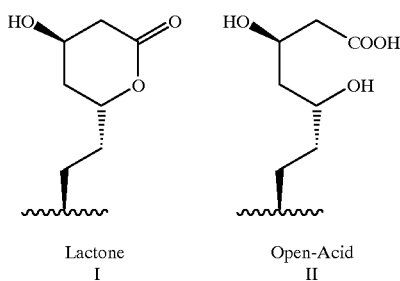

Lactone
I

Open-Acid
II

In HMG-CoA reductase inhibitor's where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamnine, N-methylglucamine, lysine, arginine, omithine, choline, N,N'-dibenzylethylenediamine, chioroprocaine, diethanolamine, procaine, N-benzylphenethyl amine, 1-p-chlorobenzyl-2-pyrrolidine-1'-yl-methylbenzimidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

Similarly, the instant compounds may be useful in combination with agents that are effective in the treatment and prevention of NF-1, restenosis, polycystic kidney disease, infections of hepatitis delta and related viruses and fungal infections.

If formulated as a fixed dose, such combination products employ the combinations of this invention within the dosage range described above and the other pharmaceutically active agent(s) within its approved dosage range. Combinations of the instant invention may alternatively be used sequentially with known pharmaceutically acceptable agent(s) when a multiple combination formulation is inappropriate.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immuno-logical, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

Example 1

Preparation of 4-imidazol-1-ylmethyl-2-[2-(2-oxo-piperidin-1-yl)-phenoxy]-benzonitrile Step A: Preparation of 4-Bromo-3-fluorobenzoic Acid 4-Bromo-3-fluorotoluene (40.0 g, 0.212 mol) was heated at 90° C. in $H_2O$ (200 mL)-pyridine (200 mL) with mechanical stirring under Ar. Potassium permanganate ($KMnO_4$) (67 g, 0.424 mol) was added portionwise over 3 h. After 4 h, an HPLC of a filtered sample indicated 50% conversion to the acid. An additional 30 g of $KMnO_4$ was added and heating continued overnight. HPLC indicated 81% conversion. Further $KMnO_4$ was added portionwise with reaction monitoring by HPLC until >95% conversion was obtained. The reaction mixture was filtered through Celite, the filter pad washed with $H_2O$, aq NaOH and EtOH. The filtrate was concentrated to a small volume, then partitioned between 3N NaOH solution and diethyl ether. The aqueous basic layer was separated, cooled in an ice-$H_2O$ bath and acidified slowly with 6N HCl solution to precipitate the white solid product. This was collected by suction filtration and dried at 40° C. in a vacuum oven overnight to give the title compound. mp 190–192° C.

$^1$H NMR ($CDCl_3$) δ 7.83 (dd, 1H, J=2, 9 Hz), 7.78 (dd, 1H, J=2, 8 Hz), 7.67–7.71 (m, 1H).

Step B: Preparation of 4-bromo-3-fluorobenzyl Alcohol

4-Bromo-3-fluorobenzoic acid, as described above, (40.8 g, 0.187 mol) was dissolved in THF (250 ml) with magnetic stirring under Ar in an ice-$H_2O$ bath. The cloudy solution was treated dropwise with borane-THF complex (1 M) (374 mL, 0.374 mol) over a 1 h period maintaining the internal temperature at <10° C. The reaction mixture was left to warm to ambient temperature overnight, then cooled in an ice-$H_2O$ bath and treated dropwise with $H_2O$ (150 mL). The THF was removed on a rotary evaporator, and the residue partitioned between EtOAc and $H_2O$. The aqueous layer was extracted with EtOAc (3×100 mL), the organic layers combined, washed with brine, and dried ($Na_2SO_4$), filtered, and concentrated to give the title compound as an oil which solidified on standing.

$^1$H NMR ($CDCl_3$) δ 7.52 (t, 1H, J=8 Hz), 7.16 (d, 1H, J=9 Hz), 7.02 (d, 1H, J=8 Hz), 4.67 (s, 2H), 1.47 (br s, 1H).

Step C: Preparation of 2-fluoro-4-hydroxymethylbenzonitrile

4-Bromo-3-fluorobenzyl alcohol, as described in Step B above, (20 g, 0.097 mol) was dissolved in DMF (100 mL) then placed under high vacuum for 15 min. The solution was then purged with Ar for 15 min. While purging continued, zinc cyanide (8 g, 0.068 mol) and the catalyst, $Pd[(PPh_2)]_4$, (5.63 g, 0.0049 mol) were added. The reaction mixture was heated at 95° C. under Ar for 18 h, then cooled to ambient temperature and added to $H_2O$. The mixture was extracted with EtOAc, then washed with 1M HCl, $H_2O$, brine, and dried ($Na_2SO_4$). Filtration and concentration to dryness gave the title compound as a white solid after chromatography (silica gel, hexane:EtOAc, 6.5:3.5).

$^1$H NMR ($CDCl_3$) δ 7.61 (t, 1H, J=8 Hz), 7.23–7.29 (m, 2H), 4.80 (d, 2H, J=6 Hz), 1.93 (t, 1H, J=6 Hz).

Step D: Preparation of 4-Bromomethyl-2-fluoro-benzonitrile

N-Bromosuccinimide (6.6 g, 0.037 mol) was dissolved in $CH_2Cl_2$ (150 mL), cooled to 0° C. and treated with dimethylsulfide (3.27 mL, 0.0446 mol). The solution was cooled to −20° C. then treated dropwise with a solution of 2-fluoro-4-hydroxymethylbenzonitrile, as described in Step C above, (3.74 g, 0.0248 mol) in $CH_2Cl_2$ (30 mL). After the addition, the reaction mixture was stirred at 0° C. for 2 h then left to warm to ambient temperature overnight. The reaction mixture was added to ice/$H_2O$, extracted with EtOAc, the organic layer separated, washed with brine and dried ($MgSO_4$). Filtration and concentration to dryness gave the title compound which was purified after chromatography (silica gel, 5–10% EtOAc/hexane).

$^1$H NMR ($CDCl_3$) δ 7.61 (dd, 1H, J=8, 8 Hz), 7.26–7.30 (m, 2H), 4.45 (s, 2H).

Step E: Preparation of 2-fluoro-4-imidazol-1-ylmethyl-benzonitrile

4-Bromomethyl-2-fluoro-benzonitrile, as described in Step D above, (3.44 g, 16.0 mmol) and imidazole (5.47 g, 80.3 mmol) were dissolved in DMF (40 mL) and stirred at ambient temperature for 2 h. The DMF was removed in vacuo and the residue was partitioned between EtOAc (300 mL) and aqueous saturated $NaHCO_3$ solution. The organic layer was separated, washed with $NaHCO_3$ solution, $H_2O$, brine, and dried ($MgSO_4$). Filtration and concentration to dryness gave the title compound after chromatography (silica gel, 1–2% $CH_3OH/CH_2Cl_2$).

$^1$H NMR ($CDCl_3$) δ 7.62 (dd, 1H, J=8.5, 9.5 Hz), 7.57 (s, 1H), 7.16 (s, 1H), 7.00 (d, 1H, J=8.5 Hz), 6.94 (d, 1H, J=9.5 Hz), 6.91 (s, 1H), 5.21 (s, 2H).

Step F: Preparation of 2-(2-oxo-piperidin-1-yl)-phenol

To a solution of 2-aminophenol (1.09 g, 0.01 mol), $Et_3N$ (4.46 mL, 0.032 mol) and 4-dimethylaminopyridine (0.122 g, 0.001 mol) in $CHCl_3$ (20 mL) in an ice-$H_2O$ bath was added dropwise 5-bromovaleryl chloride (2.95 mL, 0.022 mol) with stirring. After 2 hr, the reaction mixture was washed with 1N HCl until the aqueous layer was acidic, then washed with $H_2O$, aqueous saturated $NaHCO_3$ solution, brine, and dried ($Na_2SO_4$). Filtration and concentration to dryness gave a yellow oil which solidifed on standing. This bisacylated product was dissolved in DMF (20 mL) and heated at 80° C. with cesium carbonate (4.89 g, 0.015 mol) for 3 hr, then partitioned between EtOAc and ice water. The aqueous layer was extracted with EtOAc (3×), the organics combined, washed with $H_2O$, aqueous saturated $NaHCO_3$ solution, brine, and dried ($Na_2SO_4$). Filtration and concentration to dryness gave a crude product which was treated with 1N NaOH solution (12 mL, 0.012 mol) in THF (20 mL)—$H_2O$ (10 mL) with stirring at ambient temperature for 2 hr. The reaction mixture was neutralized with 1N HCl (12 mL, 0.012 mol), concentrated, and extracted with EtOAc (3×), the organics combined, washed with $H_2O$, aqueous saturated $NaHCO_3$ solution, brine, and dried ($Na_2SO_4$). Filtration and concentration to dryness gave the title compound.

Step G: Preparation of 4-imidazol-1-ylmethyl-2-[2-(2-oxo-piperidin-1-yl)-phenoxy]-benzonitrile 2-Fluoro-4-imidazol-1-ylmethyl-benzonitrile (as described in Step E above) (0.080 g, 0.4 mmol), 2-(2-oxo-piperidin-1-yl)-phenol (as described in Step F above) (0.091 g, 0.5 mmol) and cesium carbonate (0.261 g, 0.8 mmol) were combined in DMF (2.0 mL) and heated at 50° C. for 18 hr. The reaction mixture was partitioned between EtOAc and a minimum volume of $H_2O$. Additional product was salted out from the aqueous layer with solid NaCl, and extracted into EtOAc. The organic layers were combined, dried ($Na_2SO_4$), filtered and concentrated to give the title compound after RP HPLC on a Waters Prep Pak column eluting with a 0.1% TFA/$H_2O$: 0.1% TFA/$CH_3CN$ gradient followed by conversion to the free base.

FAB MS 373 (M+1). Analysis calculated for $C_{22}H_{20}N_4O_2$.0.45 $H_2O$: C, 69.43; H, 5.54; N, 14.72; Found: C, 69.41; H, 5.46; N, 14.67.

Using the methods described above, but substituting the requisite phenol for 2-(2-oxo-piperidin-1-yl)-phenol in Step G, the following compounds were prepared:

4-imidazol-1-ylmethyl-2-(3-morpholin-4-yl-phenoxy)-benzonitrile

FAB MS 361 (M+1).
4-imidazol-1-ylmethyl-2-(3-piperidin-1-ylmethyl-phenoxy)-benzonitrile FAB MS 373 (M+1).
4-imidazol-1-ylmethyl-2-[3-(2-oxo-azepan-1-yl)-phenoxy]-benzonitrile Analysis calculated for $C_{23}H_{22}N_4O_2$.0.30 $C_2H_5OH$.0.50 HCl: C, 62.30; H, 5.61; N,12.32; Found: C, 62.32; H, 5.82; N,12.35.

Using the methods described above, but substituting the requisite phenol for 2-(2-oxo-piperidin-1-yl)-phenol in Step G, the following compounds are prepared:
4-imidazol-1-ylmethyl-2-[3-(2-oxo-piperidin-1-yl)-phenoxy]-benzonitrile
4-imidazol-1-ylmethyl-2-[4-(2-oxo-piperidin-1-yl)-phenoxy]-benzonitrile

Example 2

Preparation of 4-imidazol-1-ylmethyl-2-[2-(3-methyl-2-oxo-piperidin-1-yl)-phenoxy]-benzonitrile Step A: Preparation of 2-(3-methyl-2-oxo-piperidin-1-yl)-phenol Lithium diethylamide (2M solution in THF) (3.92 mL, 7.84 mmol) was added to a solution of 2-(2-oxo-piperidin-1-yl)-phenol (as described in Example 1, Step F) (0.50 g, 2.61 mmol) in THF (5 mL) at −78° C. with stirring under Ar. After 30 min, iodomethane (0.488 mL, 7.84 mmol) was added and the reaction left to come to room temperature overnight. The reaction was treated with $H_2O$, concentrated to remove the THF, then partitioned between diethyl ether and $H_2O$. The organic layer was separated, washed with brine, dried ($Na_2SO_4$), filtered, and concentrated to dryness to give the title compound after chromatography (silica gel, 1% $CH_3OH$, 29% EtOAc, 70% hexane).

$^1$H NMR ($CDCl_3$) δ 7.14–7.23 (m, 3H), 7.52 (dd, 1H, J=1.5, 8 Hz), 6.93–6.98 (m, 1H), 3.70–3.85 (m, 2H), 2.63–2.72 (m, 1H), 2.08–2.17 (m, 1H), 1.89–2.05 (m, 2H), 1.60–1.70 (m, 1H), 1.36 (d, 3H, J=7 Hz).

Step B: Preparation of 4-imidazol-1-ylmethyl-2-[2-(3-methyl-2-oxo-piperidin-1-yl)-phenoxy]-benzonitrile Following the procedure outlined in Example 1, Step G, but substituting the phenol of Step A for the phenol used in Example 1, Step G, the title compound was prepared.

FAB MS 387(M+1). Analysis calculated for $C_{25}H_{26}N_4O_2$.1.85 HCl.0.35 $Et_2O$: C, 61.07; H, 5.75; N, 11.66; Found: C, 60.98; H, 5.93; N, 11.68.

Using the procedures outlined above, but resubmitting 2-(3-methyl-2-oxo-piperidin-1-yl)-phenol to the conditions of Step A to give 2-(3,3-dimethyl-2-oxo-piperidin-1-yl)-phenol, the following compound was prepared:
2-[2-(3,3-dimethyl-2-oxo-piperidin-1-yl)-phenoxy]-4-imidazol-1-ylmethyl-benzonitrile FAB MS 401(M+1). Analysis calculated for $C_{24}H_{24}N_4O_2$.1.65 HCl.0.70 $Et_2O$: C, 62.80; H, 6.42; N, 10.93; Found: C, 62.84; H, 6.10; N, 10.94.

Example 3

Preparation of 2-[3-(3-ethyl-1-methyl-2-oxo-azepan-3-yl)-phenoxy]-4-imidazol-1-ylmethyl-benzonitrile hydrochloride 2-Fluoro-4-imidazol-1-ylmethyl-benzonitrile (as described in Example 1, Step E) (0.045 g, 0.222 mmol), 3-ethyl-3-(3-hydroxy-phenyl)-1-methyl-azepan-2-one, commercially available from Maybridge, (0.055 g, 0.222 mmol), $KF.Al_2O_3$ (0.136 g) and 18-Crown-6 (0.006 g, 0.023 mmol) were refluxed in $CH_3CN$ (2.5 mL) under Ar for 48 hr. The solution was filtered, concentrated in vacuo, and purified using reverse phase chromatography (95/5–5/95 $H_2O$/$CH_3CN$ with 0.1% TFA, flow=65 mL/min). The compound was converted to the free base using satd. NaHCO$_3$ solution, extracting with CH$_2$Cl$_2$ (3×), drying (MgSO$_4$), filtering and treating with 1N HCl ethereal solution to give the title compound.

FAB MS (M+1)=429; Analysis calculated for C$_{26}$H$_{28}$N$_4$O$_2$.1.05 HCl.0.05 H$_2$O: C, 66.76; H, 6.28; N, 11.98; Found: C, 66.80; H, 6.17; N, 11.69.

Chromatography of racemic 2-[3-(3-ethyl-1-methyl-2-oxo-azepan-3-yl)-phenoxy]-4-imidazol-1-ylmethyl-benzonitrile by Normal Phase LC on a Chirasil AD Column Provided Both Enantiomer A:

FAB MS (M+1)=429; Analysis calculated for C$_{26}$H$_{28}$N$_4$O$_2$.1.50 HCl.1.25 H$_2$O: C, 61.74; H, 6.38; N, 11.08; Found: C, 61.77; H, 6.39; N, 11.25.

and Enantiomer B:

FAB MS (M+1)=429; Analysis calculated for C$_{26}$H$_{28}$N$_4$O$_2$.1.00 HCl.1.95 H$_2$O: C, 62.44; H, 6.63; N, 11.20; Found: C, 62.43; H, 6.70; N, 11.46.

Using the procedure outlined above, but substituting the appropriate commercially available phenols for the 3-ethyl-3-(3-hydroxy-phenyl)-1-methyl-azepan-2-one, the following compounds were prepared:

4-Imidazol-1-ylmethyl-2-[2-(2-oxo-pyrrolidin-1-yl)-phenoxy]-benzonitrile FAB MS (M+1)=359; Analysis calculated for C$_{21}$H$_{18}$N$_4$O$_2$.1.00 HCl.1.00 H$_2$O: C, 61.08; H, 5.13; N, 13.57; Found: C, 61.05; H, 5.23; N, 13.28.

Using the procedures above but substituting the appropriate nitrogen-containing heterocycle for imidazole in Example 1, Step E, the following compounds were prepared:

2-[3-(3-ethyl-1-methyl-2-oxo-azepan-3-yl)-phenoxy]-4-(2-methyl-imidazol-1-yl)methyl-benzonitrile

FAB MS (M+1)=443.

2-[3-(3-ethyl-1-methyl-2-oxo-azepan-3-yl)-phenoxy]-4-(5-methyl-imidazol-1-yl)methyl-benzonitrile

FAB MS (M+1)=443.

2-[3-(3-ethyl-1-methyl-2-oxo-azepan-3-yl)-phenoxy]-4-(2,5-dimethyl-imidazol-1-yl)methyl-benzonitrile

FAB MS (M+1)=457.

2-[3-(3-ethyl-1-methyl-2-oxo-azepan-3-yl)-phenoxy]-4-[1,2,4]triazol-4-ylmethyl-benzonitrile

FAB MS (M+1)=430.

2-[3-(3-ethyl-1-methyl-2-oxo-azepan-3-yl)-phenoxy]-4-[1,2,4]triazol-1-ylmethyl-benzonitrile

FAB MS (M+1)=430.

Example 4

Preparation of 4-imidazol-1-ylmethyl-2-[3-(1-methyl-2-oxo-azepan-3-yl)-phenoxy]-benzonitrile hydrochloride Step A: Preparation of 3-(3-methoxy-phenyl)-1-methyl-azepan-2-one To 1.6 M n-BuLi in hexane (31.3 mL, 50 mmol) at 0° C. was added a solution of 2,2,6,6-tetramethyl piperidine (8.43 mL, 50 mmol) in anh. THF (100 mL) over 5 min. N-methylcaprolactam (6.41 mL, 50 mmol) in anhydrous THF (20 mL) was added. After stirring the reaction mixture for 10 min, a further portion of 1.6M n-BuLi in hexane (31.3 mL, 50 mmol) was added, the mixture was stirred for 10 min, and 2-chloroanisole (6.34 mL, 50 mmol) was added. After stirring for 30 min under Ar, the reaction was quenched with H$_2$O, stirred for 30 min, concentrated in vacuo, diluted with EtOAc and washed with 5N HCl (100 mL) and brine. The organic layer was dried (MgSO$_4$), concentrated and purified using SiO$_2$ chromatography (10% EtOAc/CH$_2$Cl$_2$) to give the title compound.

Step B: Preparation of 3-(3-hydroxy-phenyl)-1-methyl-azepan-2-one 3-(3-Methoxy-phenyl)-1-methyl-azepan-2-one (as described in Step A above) (1.067 g, 4.58 mmol) was refluxed in 48% HBr (5 mL) for 1 h. The reaction was diluted with EtOAc, washed with H$_2$O, brine, dried (MgSO$_4$), and concentrated to give the title compound.

Step C: Preparation of 4-imidazol-1-ylmethyl-2-[3-(1-methyl-2-oxo-azepan-3-yl)-phenoxy]-benzonitrile hydrochloride 2-Fluoro-4-imidazol-1-ylmethyl-benzonitrile (as described in Example 1, Step E) (0.100 g, 0.497 mmol), 3-(3-hydroxy-phenyl)-1-methyl-azepan-2-one (0.141 g, 0.646 mmol), KF.Al$_2$O$_3$ (0.141 g) and 18-Crown-6 (0.014 g, 0.053 mmol) were refluxed in CH$_3$CN (8 mL) under Ar for 48 h. The solution was filtered, concentrated in vacuo, and purified using reverse phase chromatography (95/5–5/95 H$_2$O/CH$_3$CN with 0.1% TFA, flow=65 mL/min). The compound was converted to its free base using satd. NaHCO$_3$ solution, extracted with CH$_2$Cl$_2$ (3×), dried (MgSO$_4$), filtered and treated with 1N HCl ethereal solution to give the title compound.

FAB MS (M+1)=401. Analysis calculated for C$_{24}$H$_{24}$N$_4$O$_2$.1.00 HCl.0.65 H$_2$O.0.20 CH$_2$Cl$_2$: C, 62.55; H, 5.58; N, 12.06; Found: C, 62.86; H, 5.61; N, 11.67.

Using the procedures outlined above but substituting the appropriate N-methylated lactam for N-methylcaprolactam, the following compounds were prepared:

4-imidazol-1-ylmethyl-2-[3-(1-methyl-2-oxo-azepan-3-yl)-phenoxy]-benzonitrile

FAB MS (M+1)=415; Analysis calculated for C$_{25}$H$_{26}$N$_4$O$_2$.1.85 HCl.0.35 (C$_2$H$_5$)$_2$O: C, 62.42; H, 6.22; N, 11.03; Found: C, 62.42; H, 6.15; N, 11.01.

4-imidazol-1-ylmethyl-2-[3-(1-methyl-2-oxo-piperidin-3-yl)-phenoxy]-benzonitrile FAB MS (M+1)=387.

4-imidazol-1-ylmethyl-2-[3-(1-methyl-2-oxo-pyrrolidin-3-yl)-phenoxy]-benzonitrile

FAB MS (M+1)=373.

Quenching the reaction in Step A with ethyl iodide instead of H$_2$O, provided:

4-imidazol-1-ylmethyl-2-[3-(3-ethyl-1-methyl-2-oxo-piperidin-3-yl)-phenoxy]-benzonitrile

FAB MS (M+1)=415.

Example 5

Preparation of 4-Imidazol-1-ylmethyl-2-[3-(2-oxo-azepan-3-yl)-phenoxy]-benzonitrile hydrochloride Step A: Preparation of 1-trimethylsilanyl-azepan-2-one Caprolactam, commercially available from Maybridge, (10.0 g, 88.0 mmol), Et$_3$N (14.8 mL, 106 mmol) and chlorotrimethylsilane (13.5 mL, 106 mmol) were dissolved in toluene (60 mL) and refluxed under Ar for 3 h. The reaction was filtered and concentrated to give the title compound.

Step B: Preparation of 3-(3-methoxy-phenyl)-azepan-2-one

To 1.6 M n-BuLi in hexane (31.3 mL, 50 mmol) at 0° C. was added a solution of 2,2,6,6-tetramethyl piperidine (8.43 mL, 50 mmol) in anhydrous THF (100 mL) over 5 min. 1-Trimethylsilanyl-azepan-2-one (as described in Step A above) (9.26 g, 50 mmol) in anhydrous THF (20 mL) was added. After stirring the reaction mixture for 10 min a further portion of 1.6M n-BuLi in hexane (31.3 mL, 50 mmol) was added, the mixture stirred for 10 min, and 2-chloroanisole (6.34 mL, 50 mmol) was added. After stirring for 30 min under Ar, the reaction was quenched with H$_2$O, stirred for 30 min, concentrated in vacuo, diluted with EtOAc, washed with 5N HCl (100 mL) and brine. The organic layer was dried (MgSO$_4$), concentrated and purified using SiO$_2$ chromatography (0.5% MeOH/CH$_2$Cl$_2$) to give the title compound.

Step C: Preparation of 3-(3-hydroxy-phenyl)-azepan-2-one

A 1M solution of BBr$_3$ (1.0 mL, 1.00 mmol) in CH$_2$Cl$_2$ was added to 3-(3-methoxy-phenyl)-azepan-2-one (as described in Step B above) (0.200 g, 0.912 mmol) dissolved in anhydrous CH$_2$Cl$_2$ (5 mL) at −78° C. After 30 hr of stirring at RT, the reaction was quenched with H$_2$O, extracted with CH$_2$Cl$_2$ (3×), dried (MgSO$_4$), concentrated and purified using reverse phase chromatography (95/5–5/95 H$_2$O/CH$_3$CN with 0.1% TFA, flow=65 mL/min) to give the title compound.

Step D: Preparation of 4-imidazol-1-ylmethyl-2-[3-(2-oxo-azepan-3-yl)-phenoxy]-benzonitrile hydrochloride 2-Fluoro-4-imidazol-1-ylmethyl-benzonitrile (as described in Example 1, Step E) (0.039 g, 0.194 mmol), 3-(3-hydroxy-phenyl)-azepan-2-one (as described in Step C above) (0.040 g, 0.646 mmol), KF.Al$_2$O$_3$ (0.048 g) and 18-Crown-6 (0.004 g, 0.015 mmol) were refluxed in CH$_3$CN (6 mL) under Ar for 72 h. The solution was filtered, concentrated in vacuo, and purified using reverse phase chromatography (95/5–5/95 H$_2$O/CH$_3$CN with 0.1% TFA, flow=65 mL/min). The compound was converted to its free base using satd. NaHCO$_3$ solution, extracted with CH$_2$Cl$_2$ (3×), dried (MgSO$_4$), filtered and treated with 1N HCl ethereal solution to give the title compound.

FAB MS(M+1)=387. Analysis calculated for C$_{23}$H$_{22}$N$_4$O$_2$.1.00 HCl.0.40 CH$_2$Cl$_2$: C, 61.51; H, 5.25; N, 12.26; Found: C, 61.47; H, 5.21; N, 11.94.

Example 6

Preparation of 2-[3-(3-hydroxymethyl-1-methyl-2-oxo-azepan-3-yl)-phenoxy]-4-imidazol-1-ylmethyl-benzonitrile hydrochloride Step A: Preparation of 3-methoxymethyl-3-(3-methoxy-phenyl)-1-methyl-azepan-2-one To 1.6 M n-BuLi in hexane (3.38 mL, 5.42 mmol) at 0° C. was added a solution of 2,2,6,6-tetramethyl piperidine (0.91 mL, 5.42 mmol) in anh. THF (10 mL) over 5 min. A solution of 3-(3-methoxy-phenyl)-1-methyl-azepan-2-one (as described in Example 4, Step A) (0.632 g, 2.71 mmol) in anhydrous THF (10 mL) was added and stirred OC for 1 h. Iodomethyl methyl ether (0.275 mL, 3.25 mmol) was added. After stirring for 30 min, the reaction was quenched with H$_2$O, concentrated in vacuo, diluted with EtOAc, washed with 5N HCl (100 mL), water and brine. The organic layer was dried (MgSO$_4$) and concentrated to give the title compound.

Step B: Preparation of 3-hydroxymethyl-3-(3-hydroxy-phenyl)-1-methyl-azepan-2-one A 1M solution of BBr$_3$(1.48 mL, 1.48 mmol) in CH$_2$Cl$_2$ was added to 3-methoxymethyl-3-(3-methoxy-phenyl)-1-methyl-azepan-2-one (as described in Step A above) (0.391 g, 1.35 mmol) dissolved in anh. CH$_2$Cl$_2$ (5 mL) at −78° C. After 24 h of stirring at RT, the reaction was quenched with H$_2$O, extracted with CH$_2$Cl$_2$ (3×), dried (MgSO$_4$), concentrated and purified using SiO$_2$ chromatography (1–1.5% MeOH/CH$_2$Cl$_2$with HOAc) to give the title compound.

Step C: Preparation of 2-[3-(3-hydroxymethyl-1-methyl-2-oxo-azepan-3-yl)-phenoxy]-4-imidazol-1-ylmethyl-benzonitrile hydrochloride 2-Fluoro-4-imidazol-1-ylmethyl-benzonitrile (as described in Example 1, Step E) (0.089 g, 0.441 mmol), 3-hydroxymethyl-3-(3-hydroxy-phenyl)-1-methyl-azepan-2-one (0.100 g, 0.401 mmol), KF.Al$_2$O$_3$ (0.120 g) and 18-crown-6 (0.10 g, 0.038 mmol) were refluxed in CH$_3$CN (5 mL) under Ar for 24 h. The solution was filtered, concentrated in vacuo, and purified using reverse phase chromatography (95/5–5/95 H$_2$O/CH$_3$CN with 0.1% TFA, flow=65 mL/min). The compound was converted to its free base using satd. NaHCO$_3$ solution, extracted with CH$_2$Cl$_2$ (3×), dried (MgSO$_4$), filtered and treated with 1N HCl ethereal solution to give the title compound. FAB MS (M+1)=431.

Analysis calculated for C$_{25}$H$_{26}$N$_4$O$_3$.1.00 HCl.1.25 H$_2$O.0.15 CH$_2$Cl$_2$: C, 60.14; H, 5.98; N, 11.16; Found: C, 60.15; H, 5.96; N, 11.01.

Using the procedures above but substituting cyclopropylmethyl bromide for iodomethyl methyl ether in Step A, the following compound was prepared:

2-[3-(3–Cyclopropylmethyl-1-methyl-2-oxo-azepan-3-yl)-phenoxy]-4-imidazol-1-ylmethyl-benzonitrile hydrochloride FAB MS (M+1)=455. Analysis calculated for C$_{28}$H$_{30}$N$_4$O$_3$.1.25 HCl.0.55 H$_2$O: C, 65.93; H, 6.39; N, 10.99; Found: C, 65.95; H, 6.39; N, 10.67.

Chromatographic isolation of a brominated byproduct from the demethylation with BBr3 in Step B gave the following:

2-[4-Bromo-3-(3-cyclopropylmethyl-1-methyl-2-oxo-azepan-3-yl)-phenoxy]-4-imidazol-1-ylmethyl-benzonitrile hydrochloride FAB MS (M+1)=533. Analysis calculated for C$_{28}$H$_{29}$BrN$_4$O$_3$.1.90 CF$_3$CO$_2$H.1.85 H$_2$O: C, 48.75; H, 4.45; N, 7.15; Found: C, 48.76; H, 4.43; N, 7.39.

Example 7

Preparation of 2-[3-(3-methoxymethyl-1-methyl-2-oxo-azepan-3-yl)-phenoxy]-4-imidazol-1-ylmethyl-benzonitrile hydrochloride Step A: Preparation of 3-methoxymethyl-3-(3-hydroxy-phenyl)-1-methyl-azepan-2-one 3-Methoxymethyl-3-(3-methoxy-phenyl)-1-methyl-azepan-2-one (as described in Example 6, Step A) (0.391 g, 1.48 mmol) and LiI (0.500 g, 3.73 mol) were heated in collidine (3.5 mL) at 200° C. for 10 h. The reaction mixture was cooled, diluted with EtOAc, washed with 1N HCl (2×), H$_2$O, brine, dried (MgSO$_4$) and concentrated to give the title compound.

Step B: Preparation of 2-[3-(3-methoxymethyl-1-methyl-2-oxo-azepan-3-yl)-phenoxy]-4-imidazol-1-ylmethyl-benzonitrile hydrochloride 2-Fluoro-4-imidazol-1-ylmethyl-benzonitrile (as described in Example 1, Step E) (0.098 g, 0.488 mmol), 3-methoxymethyl-3-(3-hydroxy-phenyl)-1-methyl-azepan-2-one (as described in Step A above) (0.129 g, 0.488 mmol), KF.Al$_2$O$_3$ (0.155 g) and 18-Crown-6 (0.13 g, 0.049 mmol) were refluxed in CH$_3$CN (10 mL) under Ar for 72 h. The solution concentrated in vacuo, diluted with EtOAc, washed with satd. NaHCO$_3$ solution, H$_2$O, brine, dried (MgSO$_4$) and purified using SiO$_2$ chromatography (1–2% MeOH/CH$_2$Cl$_2$ with NH$_4$OH). The compound treated with 1N HCl ethereal solution to give the title compound. FAB MS (M+1)=445.

Analysis calculated for C$_{26}$H$_{28}$N$_4$O$_3$.1.40 HCl.1.05 H$_2$O: C, 60.69; H, 6.17; N, 10.89; Found: C, 60.68; H, 6.16; N, 10.66.

Example 8

Preparation of 2-[3-(3-ethyl-2-oxo-azepan-3-yl)-phenoxy]-4-imidazol-1-ylmethyl-benzonitrile Step A: Preparation of 3-ethyl-3-(3-methoxy-phenyl)-azepan-2-one To 1.6 M n-BuLi in hexane (31.3 mL, 50 mmol) at 0° C. was added a solution of 2,2,6,6-tetramethyl piperidine (8.43 mL, 50 mmol) in anhydrous THF (100 mL) over 5 min. 1-Trimethylsilanyl-azepan-2-one (as described in Example 5, Step A) (9.26 g, 50 mmol) in anhydrous THF (20 mL) was added. After stirring the reaction mixture for 10 min, a further portion of 1.6M n-BuLi in hexane (31.3 mL, 50 mmol) was added, the mixture stirred for 10 min, and 2-chloroanisole (6.34 mL, 50 mmol) was added. After stirring for 30 min under Ar, ethyl iodide (3.90 mL, 48.7 mmol) was added, the reaction mixture was stirred for 30 min, quenched with $H_2O$, concentrated in vacuo, diluted with EtOAc, and washed with 5N HCl (100 mL) and brine. The organic layer was dried ($MgSO_4$), concentrated and purified using $SiO_2$ chromatography (10–15% EtOAc/$CH_2Cl_2$) to give the title compound.

Step B: Preparation of 3-ethyl-3-(3-hydroxy-phenyl)-azepan-2-one

A 1M solution of $BBr_3$ (7.1 mL, 7.1 mmol) in $CH_2Cl_2$ was added to 3-ethyl-3-(3-methoxy-phenyl)-azepan-2-one (as described in Step A above) (0.800 g, 0.323 mmol) dissolved in anhydrous $CH_2Cl_2$ (5 mL) at −78° C. After 48 h of stirring at room temperature, the reaction was quenched with $H_2O$, extracted with $CH_2Cl_2$ (3×), dried ($MgSO_4$), concentrated and purified using reverse phase chromatography (95/5–5/95 $H_2O/CH_3CN$ with 0.1% TFA, flow=65 mL/min) to give the title compound.

Step C: Preparation of 2-[3-(3-ethyl-2-oxo-azepan-3-yl)-phenoxy]-4-imidazol-1-ylmethyl-benzonitrile 2-Fluoro-4-imidazol-1-ylmethyl-benzonitrile (as described in Example 1, Step E) (0.065 g, 0.325 mmol), 3-ethyl-3-(3-hydroxy-phenyl)-azepan-2-one (as described in Step B above) (0.076 g, 0.325 mmol), $KF.Al_2O_3$ (0.091 g) and 18-Crown-6 (0.008 g, 0.030 mmol) were refluxed in $CH_3CN$ (8 mL) under Ar for 72 h. The solution was filtered, concentrated in vacuo, and purified using $SiO_2$ chromatography (0.5–3.0% MeOH/$CH_2Cl_2$). The compound was treated with 1N HCl ethereal solution to give the title compound.

FAB MS (M+1)=415. Analysis calculated for $C_{25}H_{26}N_4O_2$.1.00 HCl.0.10 $H_2O$.0.40 $CH_2Cl_2$: C, 62.67; H, 5.80; N, 11.51; Found: C, 62.72; H, 5.58; N, 11.36.

Example 9

Preparation of 2-[3-(3-ethyl-azepan-3-yl)-phenoxy]-4-imidazol-1-ylmethyl-benzonitrile bishydrochloride Step A: Preparation of 3-ethyl-3-(3-methoxy-phenyl)-azepane 3-Ethyl-3-(3-methoxy-phenyl)-azepan-2-one (as described in Example 8, Step A) (1.05 g, 4.24 mmol) in anhydrous THF (4.2 mL) was added to a solution of $LiAlH_4$ (0.193 g, 5.09 mmol) in anhydrous THF (4.2 mL) and refluxed for 24 h. The solution was cooled, quenched with $H_2O$ (0.18 mL), 15% NaOH (0.18 mL), $H_2O$ (0.54 mL), filtered and concentrated. The residue was purified using reverse phase chromatography (95/5–5/95 $H_2O/CH_3CN$ with 0.1% TFA, flow=65 mL/min) and converted to its free base using saturated $NaHCO_3$ solution, extracted with $CH_2Cl_2$ (3×) and dried ($MgSO_4$) to give the title compound.

Step B: Preparation of 3-(3-ethyl-azepan-3-yl)-phenol

A 1M solution of $BBr_3$ (2.56 mL, 2.56 mmol) in $CH_2Cl_2$ was added to 3-ethyl-3-(3-methoxy-phenyl)-azepane (as described in Example 8, Step A) (0.300 g, 0.1.28 mmol) dissolved in anhydrous $CH_2Cl_2$ (10 mL) at −78° C. After 20 h of stirring at room temperature, the reaction was quenched with sat. $NaHCO_3$ solution, extracted with $CH_2Cl_2$ (3×), dried ($MgSO_4$) and concentrated to give the title compound.

Step C: Preparation of 2-[3-(3-ethyl-azepan-3-yl)-phenoxy]-4-imidazol-1-ylmethyl-benzonitrile bishydrochloride 2-Fluoro-4-imidazol-1-ylmethyl-benzonitrile (as described in Example 1, Step E) (0.113 g, 0.560 mmol), 3-(3-ethyl-azepan-3-yl)-phenol (as described in Step B above) (0.123 g, 0.560 mmol), $KF.Al_2O_3$ (0.148 g) and 18-Crown-6 (0.012 g, 0.038 mmol) were refluxed in $CH_3CN$ (5 mL) under Ar for 24 h. The solution was filtered, concentrated in vacuo, and purified using reverse phase chromatography (95/5–5/95 $H_2O/CH_3CN$ with 0.1% TFA, flow=65 mL/min). The compound was converted to its free base using saturated $NaHCO_3$ solution, extracted with $CH_2Cl_2$ (3×), dried ($MgSO_4$), filtered and treated with 1N HCl ethereal solution to give the title compound. FAB MS (M+1)=401.

Analysis calculated for $C_{25}H_{28}N_4O_1$.2.00 HCl.0.10 $H_2O$.0.45 $CH_2Cl_2$: C, 59.53; H, 6.11; N, 10.91; Found: C, 59.55; H, 6.13; N, 10.59.

Example 10

Preparation of 2-[3-(1-acetyl-3-ethyl-azepan-3-yl)-phenoxy]-4-imidazol-1-ylmethyl-benzonitrile hydrochloride 2-[3-(3-Ethyl-azepan-3-yl)-phenoxy]-4-imidazol-1-ylmethyl-benzonitrile bistrifluoroacetate (as described in Example 9) (0.116 g, 0.184 mmol), $Et_3N$ (0.103 mL, 0.736 mmol) and acetyl chloride (0.020 mL, 0.276 mmol) were dissolved in anhydrous. $CH_2Cl_2$ (5 mL). After 1 h, the reaction was concentrated in vacuo, and purified using reverse phase chromatography (95/5–5/95 $H_2O/CH_3CN$ with 0.1% TFA, flow=65 mL/min). The compound was converted to its free base using saturated $NaHCO_3$ solution, extracted with $CH_2Cl_2$ (3×), dried ($MgSO_4$), filtered and treated with 1N HCl ethereal solution to give the title compound.

FAB MS (M+1)=443. Analysis calculated for $C_{27}H_{30}N_4O_2$.1.00 HCl.0.35 $H_2O$.0.40 $CH_2Cl_2$: C, 63.37; H, 6.31; N, 10.79; Found: C, 63.44; H, 6.42; N, 10.39.

2-[3-(3-ethyl-azepan-3-yl)-phenoxy]-4-imidazol-1-ylmethyl-benzonitrile was acylated with $Boc_2O$ to give 3-[3-(2-cyano-5-imidazol-1-ylmethyl-phenoxy)-phenyl]-3-ethyl-azepane-1-carboxylic Acid-tert-butyl Ester FAB MS (M+1)=501. Analysis calculated for $C_{30}H_{36}N_4O_3$.0.40 $H_2O$: C, 70.95; H, 7.30; N, 11.03; Found: C, 70.92; H, 7.00; N, 10.73.

Example 11

Preparation of 4-[5-(2-amino-ethyl)-2-methyl-imidazol-1-ylmethyl]-2-[3-(3-ethyl-1-methyl-2-oxo-azepan-3-yl)-phenoxy]-benzonitrile dihydrochloride Step A: Preparation of {2-[3-(4-cyano-3-fluoro-benzyl)-2-methyl-3H-imidazol-4-yl]-ethyl}-carbamic Acid tert-butyl Ester To a solution of $N^G$-pivaloyloxymethyl-$N^a$-phthaloyl-histamine (J. C. Emmett, F. H. Holloway, and J. L. Turner, *J. Chem. Soc., Perkin Trans.* 1, 1341, (1979)) (4.59 g, 0.0124 mmol) in acetonitrile (40 mL) was added 2-fluoro-4-imidazol-1-ylmethyl-benzonitrile (as described in Example 1, Step E) (2.8 g, 0.013 mmol) and the mixture was heated to reflux for 18 hr. A white solid precipitate formed which after cooling to 0° C. was collected by filtration to obtain the quaternary salt. This intermediate was dissolved in EtOH (100 mL), hydrazine (1.46 mL, 0.046 mmol) was added, and the mixture was heated at reflux for 4 hr. A white precipitate was observed and the reaction was cooled to 25° C. Dimethylphthalate (11.4 mL, 0.0699 mmol) was added and the mixture was again refluxed for 18 hr. After cooling to 25° C. the precipitate was removed by filtration and washed with EtOAc. The filtrate was evaporated in vacuo and the residue was dissolved in THF (125 mL) and H$_2$O (25 mL). To this solution was added solid Na$_2$CO$_3$ (4.0 g, 0.0377 mol) and BOC$_2$O (4.47 g, 0.020 mol) and the reaction was stirred for 18 hr. The THF was removed in vacuo and the mixture was partitioned with EtOAc and saturated NaHCO$_3$. The EtOAc layer was washed with brine, dried with MgSO$_4$, and evaporated in vacuo to obtain the title product after chromatography (silica gel, CH$_2$Cl$_2$:MeOH:NH$_4$OH/97:3:0.3).

Step B: Preparation of [2-(3-{4-cyano-3-[3-(3-ethyl-1-methyl-2-oxo-azepan-3-yl)-phenoxy]-benzyl}-2-methyl-3H-imidazol-4-yl)-ethyl]-carbamic Acid tert-butyl Ester Following the procedure outlined in Example 2, but using {2-[3-(4-cyano-3-fluoro-benzyl)-2-methyl-3H-imidazol-4-yl]-ethyl}-carbamic acid tert-butyl ester (as described in Step A above) (0.60 g, 1.67 mmol) and 3-ethyl-3-(3-hydroxy-phenyl)-1-methyl-azepan-2-one (0.41 g, 1.67 mmol), the title compound was obtained after chromatography (CH$_2$Cl$_2$:CH$_3$OH:NH$_4$OH, 98:2:0.2).

Step C: Preparation of 4-[5-(2-amino-ethyl)-2-methyl-imidazol-1-ylmethyl]-2-[3-(3-ethyl-1-methyl-2-oxo-azepan-3-yl)-phenoxy]-benzonitrile dihydrochloride To a solution of [2-(3-{4-cyano-3-[3-(3-ethyl-1-methyl-2-oxo-azepan-3-yl)-phenoxy]-benzyl}-2-methyl-3H-imidazol-4-yl)-ethyl]-carbamic acid tert-butyl ester (as described in Step B above) (0.2 g, 0.41 mmol) in CH$_2$Cl$_2$ (6.0 mL) was added TFA (3.0 mL) and the solution was stirred for 0.5 hr. The solvents were removed in vacuo and the crude product was purified by preparative HPLC. Conversion to the HCl salt yielded the title compound.

FAB mass spectrum m/e 486 (m+1). Analysis calculated for C$_{29}$H$_{35}$N$_5$O$_2$.2.2 HCl: C, 61.55; H, 6.63; N, 12.38; Found: C, 61.56; H, 6.45; N, 11.83.

Example 12

Preparation of 2-[3-(3-ethyl-1-methyl-2-oxo-azepan-3-yl)-phenoxy]-4-[2-methyl-5-(2-morpholin-4-yl-ethyl)-imidazol-1-ylmethyl]-benzonitrile To a solution of 4-[5-(2-amino-ethyl)-2-methyl-imidazol-1-ylmethyl]-2-[3-(3-ethyl-1-methyl-2-oxo-azepan-3-yl)-phenoxy]-benzonitrile dihydrochloride (as described in Example 11) (0.25 g, 0.456 mmol) in acetonitrile (35.0 mL) and triethylamine (1.8 mL) was added 2-bromoethyl ether (0.133 mL, 1.06 mmol) and the mixture was refluxed for 48 hr. The solvents were removed in vacuo to obtain the title compound after purification by preparative HPLC.

FAB mass spectrum m/e 556 (m+1). Analysis calculated for C$_{33}$H$_{41}$N$_5$O$_3$.0.8 H$_2$O: C, 69.51; H, 7.53; N, 12.28; Found: C, 69.51; H, 7.28; N, 12.13.

Example 13

Preparation of N-[2-(3-{4-cyano-3-[3-(3-ethyl-1-methyl-2-oxo-azepan-3-yl)-phenoxy]-benzyl}-2-methyl-3H-imidazol-4-yl)-ethyl]-acetamide To a solution of 4-[5-(2-amino-ethyl)-2-methyl-imidazol-1-ylmethyl]-2-[3-(3-ethyl-1-methyl-2-oxo-azepan-3-yl)-phenoxy]-benzonitrile dihydrochloride (as described in Example 11) (0.06 g, 0.108 mmol) in CH$_2$Cl$_2$ (3.0 mL) was added triethylamine (0.06 mL, 0.43 mmol) and acetyl chloride (0.010 mL, 0.14 mmol). After stirring for 2 hr, the solvents were removed in vacuo and the residue was partitioned with EtOAc and saturated NaHCO$_3$. The EtOAc was dried with brine and MgSO$_4$ and evaporated in vacuo to obtain the title compound.

FAB mass spectrum m/e 528 (m+1).

Example 14

Preparation of 3-ethyl-3-[3-(3-imidazol-1-ylmethyl-phenoxy)-phenyl]-1-methyl-azepan-2-one hydrochloride Step A: Preparation of 3-[3-(3-ethyl-1-methyl-2-oxo-azepan-3-yl)-phenoxy]-benzaldehyde 3-Ethyl-3-(3-hydroxy-phenyl)-1-methyl-azepan-2-one (as described in Example 8, Step B) (0.10 g, 0.4 mmol), 3-formylphenyl-boronic acid (0.12 g, 0.8 mmol), cupric acetate (0.073 g, 0.4 mmol) and powdered 4A molecular sieves (0.12 g) were combined under Ar, diluted with anhydrous CH$_2$Cl$_2$ (2 mL) and pyridine (0.162 mL, 2.0 mmol) and stirred at ambient temperature for 48 hrs. The reaction mixture was filtered, and the filtrated concentrated to dryness and partitioned between EtOAc and H$_2$O. The aqueous layer was washed with EtOAc, the organics combined, washed with H$_2$O, 10% aqueous NaOH solution, H$_2$O, brine, and dried (Na$_2$SO$_4$). Filtration and concentration to dryness gave the title compound as a white solid after trituration with diethyl ether/hexane.

Step B: Preparation of 3-ethyl-3-[3-hydroxymethyl-phenoxy)-phenyl]-1-methyl-azepan-2-one 3-[3-(3-Ethyl-1-methyl-2-oxo-azepan-3-yl)-phenoxy]-benzaldehyde (as described in Step A above) (0.096 g, 0.273 mmol) in absolute ethanol (2 mL) was treated with sodium borohydride (0.010 g, 0.273 mmol) with stirring at ambient temperature. After 2 hrs the reaction was quenched with H$_2$O, concentrated to remove the EtOH, and the residue partitioned between EtOAc and H$_2$O. The aqueous layer was washed with EtOAc, the organics combined, washed with brine, and dried (Na$_2$SO$_4$). Filtration and concentration to dryness gave the title compound as a colorless oil which solidified on standing.

Step C: Preparation of 3-ethyl-3-[3-(3-imidazol-1-ylmethyl-phenoxy)-phenyl]-1-methyl-azepan-2-one hydrochloride 3-ethyl-3-[3-hydroxymethyl-phenoxy)-phenyl]-1-methyl-azepan-2-one (as described in Step B above) (0.090 g, 0.26 mmol) and N,N'-carbonyldiimidazole (0.176 g,1.04 mmol) and imidazole (0.027 g, 0.4 mmol) were dissolved in acetonitrile (10 mL) and heated at 80° C. for 48 hrs. The reaction mixture was concentrated to dryness and purified on a Waters RP HPLC Prep Pak eluting with 0.1% TFA/H$_2$O: 0.1% TFA/CH$_3$CN to give the title compound after conversion to the hydrochloride salt.

FAB mass spectrum m/e 404 (m+1). Analysis calculated for C$_{25}$H$_{29}$N$_3$O$_2$.1.0 HCl.0.85 H$_2$O: C, 65.94; H, 7.02; N, 9.23; Found: C, 66.18; H, 6.95; N, 8.83.

Example 15

Preparation of 2-[3-(3-ethyl-1-methyl-2-oxo-azepan-3-yl)-phenoxy]-4-(3-methyl-3-H-imidazol-4-ylmethyl)-benzonitrile hydrochloride Step A: Preparation of 2-fluoro-4-(1-trityl-1H-imidazol-4-ylmethyl)-benzonitrile Zinc (0.301 g, 4.63 mmol) and dibromoethane (0.040 mL, 0.463 mmol) were stirred in anhydrous THF (2 mL) under Ar for 1.5 h. A solution of 4-bromomethyl-2-fluoro-benzonitrile (as described in Example 1, Step D) (0.546 g, 2.55 mmol) in anhydrous THF (1 mL) was added dropwise and stirred for 1 h. A mixture of 4-iodo-1-trityl-1H-imidazole (0.808 g, 1.85 mmol) and NiCl$_2$ (PPh3)$_2$ (0.120 g, 0.183 mmol) were added together to the reaction. After stirring overnight under Ar, the reaction was quenched with NH$_4$Cl (9 mL), stirred for 2 h, extracted with CH$_2$Cl$_2$ (3×), dried (MgSO$_4$), concentrated and purified using SiO$_2$ chromatography (0.5% MeOH/CH$_2$Cl$_2$ w/NH$_4$OH) to give the title compound.

Step B: Preparation of 2-[3-(3-ethyl-1-methyl-2-oxo-azepan-3-yl)-phenoxy]-4-(1-trityl-1H-imidazol-4-ylmethyl)-benzonitrile 2-Fluoro-4-(1-trityl-1H-imidazol-4-ylmethyl)-benzonitrile (as described in Step A above) (0.348 g, 0.784 mmol), 3-ethyl-3-(3-hydroxy-phenyl)-1-methyl-azepan-2-one (as described in Example 8, Step B) (0.194 mg, 0.784 mmol), KF.Al$_2$O$_3$ (0.232 g) and 18-Crown-6 (0.020 g, 0.076 mmol) were refluxed in CH$_3$CN (15 mL) under Ar for 48 h. The solution was concentrated in vacuo, diluted with EtOAc, washed with 1N NaOH solution, water, brine, dried (MgSO$_4$), concentrated and purified using SiO$_2$ chromatography (1.0% MeOH/CH$_2$Cl$_2$) to give the title compound.

Step C: Preparation of 2-[3-(3-ethyl-1-methyl-2-oxo-azepan-3-yl)-phenoxy]-4-(3-methyl-3-H-imidazol-4-ylmethyl)-benzonitrile hydrochloride 2-[3-(3-Ethyl-1-methyl-2-oxo-azepan-3-yl)-phenoxy]-4-(1-trityl-1H-imidazol-4-ylmethyl)-benzonitrile (as described in Step B above) (0.100 g, 0.149 mmol) and dimethyl sulfate (0.014 mL, 0.149 mmol) were dissolved in EtOAc (10 mL) and heated at 60° C. for 18 h under Ar. The reaction was concentrated in vacuo, triturated with Et$_2$O, dissolved in MeOH (15 mL) and refluxed for 1 h. The solution was concentrated in vacuo and purified using reverse phase chromatography (95/5–5/95 H$_2$O/CH$_3$CN with 0.1% TFA, flow=65 mL/min). The compound was converted to its free base using saturated NaHCO$_3$ solution, extracted with CH$_2$Cl$_2$ (3×), dried (MgSO$_4$), filtered and treated with 1N HCl ethereal solution to give the title compound.

FAB MS (M+1)=443.

Example 16

Preparation of 2-[3-(3-ethyl-1-methyl-2-oxo-azepan-3-yl)-phenoxy]-4-(3H-imidazol-4-ylmethyl)-benzonitrile hydrochloride 2-[3-(3-ethyl-1-methyl-2-oxo-azepan-3-yl)-phenoxy]-4-(1-trityl-1H-imidazol-4-ylmethyl)-benzonitrile (as described in Example 15, Step B) (0.074 g, 0.110 mmol) and triethylsilane (0.140 mL, 0.828 mmol) were stirred in CH$_2$Cl$_2$ (5 mL) and TFA (2.5 mL) for 1 h. The solution was concentrated in vacuo and purified using reverse phase chromatography (95/5–5/95 H$_2$O/CH$_3$CN with 0.1% TFA, flow=65 mL/min). The compound was converted to its free base using saturated NaHCO$_3$ solution, extracted with CH$_2$Cl$_2$ (3×), dried (MgSO$_4$), filtered and treated with 1N HCl ethereal solution to give the title compound.

FAB MS (M+1)=429.

Example 17

Preparation of 2-[3-(3-ethyl-1-methyl-2-oxo-azepan-3-yl)-phenoxy]-4-[hydroxy-(3-methyl-3-H-imidazol-4-yl)-methyl]-benzonitrile Step A: Preparation of 2-Fluoro-4-formylbenzonitrile 2-Fluoro-4-hydroxymethylbenzonitrile (as described in Example 1, Step C) (10 g, 0,066 mol) and triethylamine (32.3 mL, 0.231 mol) were dissolved in CH$_2$Cl$_2$ (100 mL)—DMSO (20 mL) at <5° C. with stirring and treated dropwise with a solution of pyridine·SO$_3$ complex (31.5 g, 0.198 mol) in DMSO (70 mL) maintaining the reaction mixture temperature at <10° C. The reaction mixture was stirred at 5° C. for 1 hr after the addition, then at 20° C. for 1 hr, then partitioned between CH$_2$Cl$_2$ and H$_2$O. The organic layer was separated, washed well with H$_2$O, brine, and dried (Na$_2$SO$_4$). Filtration and concentration gave the title compound after purification by chromatography (silica gel, hexane:EtOAc, 3:1).

$^1$H NMR (CDCl$_3$) δ 10.06 (d, 1H, J=2 Hz), 7.86 (dd, 1H, J=5,8 Hz), 7.798 (dd, 1H, J=1, 8 Hz), 7.728 (dd, 1H, J=1, 8 Hz).

Step B: Preparation of 2-fluoro-4-[hydroxy-(1-trityl-1H-imidazol-4-yl)-methyl]-benzonitrile To a solution of 4-iodo-1-trityl-1H-imidazole (5.00 g, 11.5 mmol) in anhydrous CH$_2$Cl$_2$ (30 mL) was added a 3.0M solution of ethylmagnesium bromide (6.58 mL, 19.7 mmol) with stirring under Ar. After 3 h, the reaction mixture was cooled to −78° C. and a solution of 2-fluoro-4-formyl-benzonitrile (as described in Step A above) (1.70g, 11.5 mmol) dissolved in CH$_2$Cl$_2$ (20 mL) was added dropwise. The reaction was allowed to warm to room temperature over 2 h, quenched with saturated NH$_4$Cl solution, diluted with satd. NaHCO$_3$ solution to pH=8.5, and extracted with CH$_2$Cl$_2$ (3×). The combined organic layers were dried (MgSO$_4$), concentrated and purified using SiO$_2$ chromatography (0–1% MeOH/CH$_2$Cl$_2$) to yield the title compound.

Step C: Preparation of acetic Acid (4-cyano-3-fluoro-phenyl)-(1-trityl-1H-imidazol-4-yl)-methyl Ester 2-Fluoro-4-[hydroxy-(1-trityl-1H-imidazol-4-yl)-methyl]-benzonitrile (as described in Step B above) (4.05 g, 8.81 mmol), pyridine (2.14 mL, 26.4 mmol), and acetic anhydride (12.5 mL, 132 mmol) were stirred in anhydrous DMF (60 mL) for 3 h under Ar. The reaction was concentrated in vacuo, diluted with EtOAc (250 mL), washed with H$_2$O (2×), brine, dried (MgSO$_4$) and concentrated to give the title compound.

Step D: Preparation of acetic Acid (4-cyano-3-fluoro-phenyl)-(3-methyl-3H-imidazol-4-yl)-methyl Ester Acetic acid (4-cyano-3-fluoro-phenyl)-(1-trityl-1H-imidazol-4-yl)-methyl ester (as described in Step C above) (4.60 g, 9.17 mmol) and dimethyl sulfate (0.83 mL, 8.81 mmol) were dissolved in EtOAc (20 mL) and heated at 60° C. overnight under Ar. The reaction was concentrated in vacuo, diluted with MeOH (30 mL), and refluxed for 1 h. Concentrated in vacuo and purified using SiO$_2$ chromatography (0.5–4% MeOH/CH$_2$Cl$_2$ with NH$_4$OH) to give the title compound.

Step E: Preparation of 2-fluoro-4-[hydroxy-(3-methyl-3H-imidazol-4-yl)-methyl]-benzonitrile Acetic acid (4-cyano-3-fluoro-phenyl)-(3-methyl-3H-imidazol-4-yl)-methyl ester (as described in Step C above) (1.26 g, 4.59 mmol) and NaOH (5.5 mL, 5.5 mmol) were dissolved in THF (15 mL) and H$_2$O (25 mL). After 1 h, the reaction was diluted with satd. NaHCO$_3$ solution, extracted with CH$_2$Cl$_2$ (3×), dried (MgSO$_4$) and concentrated to give the title compound.

Step F: Preparation of 2-[3-(3-ethyl-1-methyl-2-oxo-azepan-3-yl)-phenoxy]-4-[hydroxy-(3-methyl-3-H-imidazol-4-yl)-methyl]-benzonitrile 2-Fluoro-4-[hydroxy-(3-methyl-3H-imidazol-4-yl)-methyl]-benzonitrile (as described in Step E above) (0.162 g, 0.700 mmol), 3-ethyl-3-(3-hydroxy-phenyl)-1-methyl-azepan-2-one (0.173 g, 0.700 mmol) and KF.Al$_2$O$_3$ (0.208 g) and 18-Crown-6 (0.017 g, 0.064 mmol) were dissolved in anhydrous CH$_3$CN (7 mL) and refluxed under Ar for 24 h. The reaction was filtered, concentrated and purified using SiO$_2$ chromatography (1–3% MeOH/CH$_2$Cl$_2$).

FAB MS (M+1)=459.

Example 18

Preparation of 4-[amino-(3-methyl-3-H-imidazol-4-yl)-methyl]-2-[3-(3-ethyl-1-methyl-2-oxo-azepan-3-yl)-phenoxy]-benzonitrile 2-[3-(3-ethyl-1-methyl-2-oxo-azepan-3-yl)-phenoxy]-4-[hydroxy-(3-methyl-3-H-imidazol-4-yl)-methyl]- benzonitrile (as described in Example 17) (0.093 g, 0.202 mmol) was dissolved in $SOCl_2$ (5 mL) and stirred at room temperature for 2 h under Ar. The solution was concentrated in vacuo and azeotroped with $CH_2Cl_2$ (3×). The solid was dissolved in $CHCl_3$ (20 mL) and cooled to −78° C. $NH_3$ (g) was bubbled through the solution and stirred for 16 h while warming to room temperature under Ar. The solution was concentrated in vacuo and purified using reverse phase chromatography (95/5–5/95 $H_2O/CH_3CN$ with 0.1% TFA, flow=65 mL/min). The compound was converted to its free base using saturated $NaHCO_3$ solution, extracted with $CH_2Cl_2$ (3×), dried ($MgSO_4$), filtered and concentrated to give the title compound. FAB MS (M+1)=458.

Analysis calculated for $C_{27}H_{31}N_5O_2 \cdot 0.35\ H_2O$: C, 69.90; H, 6.89; N, 15.10; Found: C, 69.95; H, 7.08; N, 14.72.

Example 19

Preparation of 2-[3-(3-ethyl-1-methyl-2-oxo-azepan-3-yl)-benzyl]-4-(3-methyl-3H-imidazole-4-carbonyl)-benzonitrile trifluoroacetate Step A: Preparation of 2-fluoro-4-[amino-(3-methyl-3H-imidazol-4-yl)-methyl]-benzonitrile 2-Fluoro-4-[hydroxy-(3-methyl-3H-imidazol-4-yl)-methyl]-benzonitrile (0.542 g, 2.31 mmol) was dissolved in $SOCl_2$ (15 mL) and stirred at room temperature for 2 h under $Ar_2$. The solution was concentrated in vacuo and azeotroped with $CH_2Cl_2$ (3×). The solid was dissolved in $CHCl_3$ (30 mL) and cooled to −78° C. $NH_3$ (g) was bubbled through the solution and stirred for 16 h while warming to room temperature under Ar. After concentration to dryness and chromatography (silica gel, 1–2% $CH_3OH/CH_2Cl_2$ with $NH_3$), the title compound was obtained.

Step B: Preparation of 2-[3-(3-ethyl-1-methyl-2-oxo-azepan-3-yl)-benzyl]-4-(3-methyl-3H-imidazole-4-carbonyl)-benzonitrile trifluoroacetate 2-Fluoro-4-[amino-(3-methyl-3H-imidazol-4-yl)-methyl]-benzonitrile (as described in Step A above) (0.012 g, 0.052 mmol), 3-ethyl-3-(3-hydroxy-phenyl)-1-methyl-azepan-2-one (0.014 g, 0.056 mmol), $KF \cdot Al_2O_3$ (0.020 g) and 18-Crown-6 (0.001 g) were dissolved in anhydrous $CH_3CN$ (2 mL) and refluxed under Ar for 24 h. The reaction was filtered, concentrated and purified using RP LC on a VYDAC column eluting with 0.1% $TFA/H_2O$: 0.1% TFA/$CH_3CN$ to give the title compound.

FAB MS (M+1)=457.

Example 20

Preparation of 2-[3-(3-ethyl-1-methyl-2-oxo-azepan-3-yl)-phenoxy]-4-(hydroxy-pyridin-3-yl-methyl)-benzonitrile Step A: Preparation of 4-Bromo-3-fluorobenzaldehyde To a well-stirred mixture of 4-bromo-3-fluorobenzyl alcohol (as described in Example 1, Step B) (10.25 g, 0.05 mol), TEMPO (0.781 g, 0.005 mol) and tetrabutylammonium fluoride (1.39 g, 0.005 mol) in $CH_2Cl_2$ (200 mL) and a solution of 0.5M $NaHCO_2$/0.05M $K_2CO_3$ (200 mL) was added N-chlorosuccinimide (9.35 g, 0.07 mol). After 6 hrs, the layers were separated, the aqueous layer back-washed with $CH_2Cl_2$ (2×50 mL), the organics combined and dried ($Na_2SO_4$). The solution was filtered, concentrated to half its volume, then chromatographed (silica gel, $CH_2Cl_2$) to give the title compound.

$^1$H NMR ($CDCl_3$) δ 9.96 (s, 1H), 7.78 (dd, 1H, J=2, 8 Hz), 7.62 (dd, 1H, J=2, 8 Hz), 7.56 (dd, 1H, J=2, 8 Hz).

Step B: Preparation of (4-bromo-3-fluoro-phenyl)-pyridin-3-yl-methanol

To a solution of 3-bromopyridine (0.986 mL, 10.23 mmol) in diethyl ether (20 mL) at −78° C. was added n-butyl lithium (1.6M/hexane, 7.0 mL, 11.25 mmol) dropwise and the mixture was stirred for 0.5 hr. A turbid solution of magnesium bromide, preformed with magnesium (0.372 g, 15.3 mmol) and dibromoethane (1.3 mL, 15.3 mmol) in THF (20 mL) at −78° C. for 20 min., was added. The resulting mixture was stirred at −78° C. for 15 min. and then at 0° C. for 20 min. To this mixture was added 4-bromo-3-fluorobenzaldehyde (as described in Step A above) (1.6 g, 7.88 mmol) in THF (10 mL) at 0° C. and the reaction was stirred for 15 min. at ° C. and at 25° C. for 2 hr. The reaction was cooled to 0° C. and quenched with saturated $NH_4Cl$. The mixture was partitioned with EtOAc and the organic layer was washed with water, brine and dried over $MgSO_4$. The solvents were removed in vacuo to obtain the title compound after chromatography (silica gel, $CH_2Cl_2$:MeOH:$NH_4OH$ 98:2:0.2).

Step C: Preparation of 2-fluoro-4-(hydroxy-pyridin-3-yl-methyl)-benzonitrile

Using the procedure described in Example 1, Step C, the title compound was prepared starting with (4-bromo-3-fluoro-phenyl)-pyridin-3-yl-methanol (1.0 g, 3.54 mmol).

Step D: Preparation of 2-[3-(3-ethyl-1-methyl-2-oxo-azepan-3-yl)-phenoxy]-4-(hydroxy-pyridin-3-yl-methyl)-benzonitrile Using the procedure described in Example 2, the crude title compound was prepared starting with 2-fluoro-4-(hydroxy-pyridin-3-yl-methyl)-benzonitrile (as described in Step C above) (0.075 g, 0.329 mmol) and 3-ethyl-3-(3-hydroxy-phenyl)-1-methyl-azepan-2-one (0.082 g, 0.329 mmol). Purification by preparative HPLC and conversion to the free base yielded the title compound.

FAB mass spectrum m/e 456 (m+1). Analysis calculated for $C_{28}H_{29}N_3O_3 \cdot 0.55\ H_2O$: C, 72.25; H, 6.52; N, 9.03; Found: C, 72.23; H, 6.44; N, 8.71.

Example 21

Preparation of 2-[3-(3-ethyl-1-methyl-2-oxo-azepan-3-yl)-phenoxy]-4-pyridin-3-ylmethyl-benzonitrile hydrochloride Step A: Preparation of thiocarbonic acid O-[(4-cyano-3-fluoro-phenyl)-pyridin-3-yl-methyl]Ester O-phenyl Ester To a solution of 2-fluoro-4-(hydroxy-pyridin-3-yl-methyl)-benzonitrile (as described in Example 20, Step C) (0.4 g, 1.75 mmol) in $CH_2Cl_2$ (25.0 mL) at 0° C. was added phenyl thionochloroformate (0.388 mL, 2.8 mmol) and DMAP (0.471 g, 3.86 mmol). The solution was stirred at 25° C. for 3 hr. The reaction was partitioned with saturated $NaHCO_3$ and $CH_2Cl_2$. The $CH_2Cl_2$ layer was washed with brine, dried with $MgSO_4$, and evaporated in vacuo to obtain the title compound after chromatography (silica gel, $CH_2Cl_2$:MeOH 99:1).

Step B: Preparation of 2-fluoro-4-pyridin-3-ylmethyl-benzonitrile

To a solution of thiocarbonic acid O-[(4-cyano-3-fluoro-phenyl)-pyridin-3-yl-methyl]ester O-phenyl ester (as described in Step A above) (0.5 g, 1.37 mmol) in benzene (2.0 mL) was added AIBN (0.18 g, 1.1 mmol) and tri-n-butyltinhydride (1.09 mL, 4.0 mmol) and the solution was heated to refluxed for 2 hr. The solvents were removed in vacuo to obtain the title compound after chromatography (silica gel, $CH_2Cl_2$:MeOH 99:1).

Step C: Preparation of 2-[3-(3-ethyl-1-methyl-2-oxo-azepan-3-yl)phenoxy]-4-pyridin-3-ylmethyl-benzonitrile hydrochloride Using the procedure described in Example 2, the crude title compound was prepared starting with 2-fluoro-4- pyridin-3-yl-methyl-benzonitrile (as described in Step B above) (0.075 g, 0.354 mmol) and 3-ethyl-3-(3-hydroxyphenyl)-1-methyl-azepan-2-one (0.087 g, 0.354 mmol). Purification by preparative HPLC and conversion to the HCl salt yielded the title compound.

FAB mass spectrum m/e 440 (m+1). Analysis calculated for $C_{28}H_{29}N_3O_2 \cdot 1.05\ H_2O \cdot 1.25\ HCl$: C, 66.71; H, 6.47; N, 8.34; Found: C, 67.02; H, 6.47; N, 7.95.

Example 22

Preparation of 2-[3-(3-ethyl-1-methyl-2-oxo-azepan-3-yl)-phenoxy]-4-pyridin-2-ylmethyl-benzonitrile hydrochloride Step A: Preparation of (4-bromo-3-fluoro-phenyl)-pyridin-2-yl-methanol To a solution of n-butyllithium (2.5 M/hexane, 0.98 mL, 2.46 mmol) in THF (7 mL) at −78° C. was added 2-bromopyridine (0.235 mL, 2.46 mmol) dropwise. The mixture was stirred at −78° C. for 1 hr. This solution was added via cannula to a solution of 4-bromo-3-fluorobenzaldehyde (as described in Example 20, Step A) (0.5 g, 2.46 mmol) in THF (5 mL) at −78° C. The resulting solution was stirred at −78° C. for 15 min. and at 25° C. for 2 hr. The reaction was cooled to 0° C. and quenched with saturated NH$_4$Cl. The mixture was partitioned with EtOAc and the organic layer was washed with water, brine and dried over MgSO$_4$. The solvents were removed in vacuo to obtain the title compound after chromatography (silica gel, CH$_2$Cl$_2$:MeOH 99:1).

Step B: Preparation of 2-fluoro-4-(hydroxy-pyridin-2-yl-methyl)-benzonitrile

Using the procedure described in Example 1, Step C, the title compound was prepared starting with (4-bromo-3-fluoro-phenyl)-pyridin-2-yl-methanol (0.28 g, 0.993 mmol). The product was purified and isolated by pouring the reaction into H$_2$O and partitioning with EtOAc. The EtOAc was washed with 1M HCl which now contains the product. The HCl layer was adjusted to pH=9 with solid Na$_2$CO$_3$ and extracted twice with EtOAc. The EtOAc layers were combined and washed with brine, dried with MgSO$_4$ and evaporated in vacuo to obtain the title compound.

Step C: Preparation of 2-[(4-bromo-3-fluoro-phenyl)-chloro-methyl]-pyridine

To a solution of 2-fluoro-4-(hydroxy-pyridin-2-yl-methyl)-benzonitrile (as described in Step B above) (0.27 g, 0.957 mmol) in CHCl$_3$ (15 mL) was added thionyl chloride (0.104 mL, 1.44 mmol) and the solution was refluxed for 1 hr. The reaction was cooled and evaporated in vacuo. The residue was partitioned with EtOAc and 50% Na$_2$CO$_3$. The EtOAc was washed with H$_2$O, brine, dried with MgSO$_4$ and evaporated in vacuo to obtain the title compound which was used without further purification.

Step D: Preparation of 2-(4-bromo-3-fluoro-benzyl)-pyridine

To a solution of 2-[(4-bromo-3-fluoro-phenyl)-chloro-methyl]-pyridine (as described in Step C above) (0.29 g, 0.965 mmol) in HOAc (10 mL) was added zinc powder (0.315 g, 4.82 mmol) and the mixture was refluxed for 1 hr. The HOAc was removed in vacuo and the residue was partitioned with EtOAc and saturated NaHCO$_3$. The EtOAc was washed with H$_2$O, brine, dried with MgSO$_4$, and evaporated in vacuo to obtain the title compound which was used without further purification.

Step E: Preparation of 2-fluoro-4-pyridin-2-ylmethyl-benzonitrile

Using the procedure described in Example 1, Step C, the title compound was prepared starting with (4-bromo-3-fluoro-phenyl)-pyridin-3-yl-methanol (0.27 g).

Step F: Preparation of 2-[3-(3-ethyl-1-methyl-2-oxo-azepan-3-yl)-phenoxy]-4-pyridin-2-ylmethyl-benzonitrile hydrochloride Using the procedure described in Example 2, the title compound was prepared starting with compound 2-fluoro-4-pyridin-2-ylmethyl-benzonitrile (as described in Step E above) (0.16 g, 0.754 mmol) and 3-ethyl-3-(3-hydroxyphenyl)-1-methyl-azepan-2-one (0.186 g, 0.754 mmol).

FAB mass spectrum m/e 440 (m+1). Analysis calculated for $C_{28}H_{29}\ N_3O_2 \cdot 0.85\ H_2O \cdot 1.15\ HCl$: C, 67.69; H, 6.46; N, 8.46; Found: C, 67.64; H, 6.47; N, 8.09.

Example 23

Preparation of 2-[3-(3-ethyl-1-methyl-2-oxo-azepan-3-yl)-phenoxy]-4-[1-hydroxy-1-(3-methyl-3H-imidazol-4-yl)-ethyl]-benzonitrile 2-[3-(3-Ethyl-1-methyl-2-oxo-azepan-3-yl)-phenoxy]-4-(3-methyl- 3H-imidazole-4-carbonyl)-benzonitrile (Example 19) (0.216 g, 0.473 mmol) was dissolved in anhydrous THF (10 mL) and a 3.0 M solution of MeMgBr (1.10 mL, 3.30 mmol) was added and stirred at RT. The reaction was quenched with NH$_4$Cl after 1 h, concentrated, diluted with EtOAc, washed with satd. NaHCO$_3$ solution, water, brine, dried (MgSO$_4$), concentrated and purified using SiO$_2$ chromatography (1–3% MeOH/CH$_2$Cl$_2$ w/NH$_4$OH) to give the title compound. FT/ICR MS (M+1)=473.

Example 24

Preparation of 2-[3-(3-ethyl-1-methyl-2-oxo-azepan-3-yl)-phenoxy]-4-[1-amino-1-(3-methyl-3H-imidazol-4-yl)-ethyl]-benzonitrile 2-[3-(3-ethyl-1-methyl-2-oxo-azepan-3-yl)-phenoxy]-4-[1-hydroxy-1-(3-methyl-3H-imidazol-4-yl)-ethyl]-benzonitrile (as described in Example 23) (0.099 g, 0.209 mmol) was dissolved in SOCl$_2$ (5 mL) and stirred at RT for 2 h. The solution was concentrated in vacuo and azeotroped with anhydrous CH$_2$Cl$_2$ (3×). The solid was dissolved in CHCl$_3$ (5 mL) and cooled to −78° C. NH$_3$ (g) was bubbled through the solution and stirred for 2 h while warming to RT under Ar. The solution was concentrated in vacuo and purified using reverse phase chromatography (95/5–5/95 H$_2$O/CH$_3$CN with 0.1% TFA, flow=65 mL/min). The compound was converted to its free base using saturated NaHCO$_3$ solution, extracted with CH$_2$Cl$_2$ (3×), dried (MgSO$_4$), filtered and treated with 1N HCl ethereal solution to give the title compound. FAB MS (M+1)=472. Analysis calculated for $C_{28}H_{33}N_5O_2 \cdot 0.35\ EtOAc$: C, 70.28; H, 7.18; N, 13.94; Found: C, 70.37; H, 7.29; N, 13.88.

Example 24A

Preparation of 2-[3-(3R-ethyl-1-methyl-2-oxo-azepan-3-yl)-phenoxy]-4-[1-(R or S)(+)amino-1-(3-methyl-3H-imidazol-4-yl)-ethyl]-benzonitrile Step A: Preparation of (+) and (−)-3-ethyl-3-(3-methoxyphenyl)-1-methyl-azepan-2-one Racemic 3-ethyl-3-(3-methoxy-phenyl)-1-methyl-azepan-2-one was prepared as described in Example 5, but substituting N-methylcaprolactam for caprolactam in Step A and quenching the reaction of Step B with ethyl iodide instead of water. This procedure is described in the literature (A. C. White et al., *Eur. J. Med. Chem. Chimica Therapeutica*, 15[4], 375–385 (1980)). The racemic product was separated on an HPLC chiracel AD column eluting with 90:10 hexane:ethanol to give R(+)-3-ethyl-3-(3-methoxyphenyl)-1-methyl-azepan-2-one [a]$_D$+59.8° (c=1, CCl$_4$) and S(−)-3-ethyl-3-(3-methoxy-phenyl)-1-methyl-azepan-2-one [a]$_D$−60.8° (c=1, CCl$_4$).

Step B: Preparation of S(−) 3-ethyl-3-(3-hydroxy-phenyl)-1-methyl-azepan-2-one

1M BBr$_3$ in CH$_2$Cl$_2$ (77.7 mL, 0.0777 mol) was added to a solution of S(−)-3-Ethyl-3-(3-methoxy-phenyl)-1-methyl-azepan-2-one (as described above in Step A) (6.04 g, 0.026 mol) in CH$_2$Cl$_2$ (400 mL) cooled to 0° C. in an ice-H$_2$O bath. After 3.5 hours, the reaction was added to a saturated NaHCO$_3$ solution and the layers separated. The aqueous layer was washed with CH$_2$Cl$_2$ (3×50 mL). The organic layers were combined, washed with brine and dried with Na$_2$SO$_4$. Filtration and concentration to dryness gave the title compound.

[a]$_D$−43.0° (c=1, EtOH).

R-(+)-3-ethyl-3-(3-hydroxy-phenyl)-1-methyl-azepan-2-one was prepared in a like manner using the enantiomer obtained in Step A.

[a]$_D$+46.9° (c=1, EtOH).

Step C: Preparation of 2-Fluoro-4-(3-methyl-3H-imidazole-4-carbonyl)-benzonitrile 2-Fluoro-4-[hydroxy-(3-methyl-3H-imidazol-4-yl)-methyl]-benzonitrile (as described in Example 17, Step E) (0.655 g, 2.83 mmol) and MnO$_2$ (1.23 g, 14.2 mmol) were stirred in CH$_2$Cl$_2$ (50 mL) and CH$_3$CN (5 mL) for 3 h. The solution was filtered and concentrated to yield the title compound.

Step D: Preparation of 2-fluoro-4-[1-hydroxy-1-(3-methyl-3H-imidazol-4-yl)-ethyl]-benzonitrile 2-Fluoro-4-(3-methyl-3H-imidazole-4-carbonyl)-benzonitrile (as described above in Step C) (0.603 g, 2.63 mmol) was dissolved in anhydrous THF (30 mL). A solution of 3.0M MeMgBr in diethyl ether (2.55 mL, 7.65 mmol) was added and stirred for 15 min. The reaction was quenched with NH$_4$Cl solution, diluted with CH$_2$Cl$_2$ and saturated NaHCO$_3$ solution and seperated. The aqueous layer was back extracted with CH$_2$Cl$_2$ (3×), the combined organic layers dried (MgSO$_4$) and concentrated to give the title compound.

Step E: Preparation of 2-fluoro-4-[1-amino-1-(3-methyl-3H-imidazol-4-yl)-ethyl]-benzonitrile 2-Fluoro-4-[1-hydroxy-1-(3-methyl-3H-imidazol-4-yl)-ethyl]-benzonitrile (as described above in Step D) (1.88 g, 0.0078 mol) was added to SOCl$_2$ (25 mL) in an ice-H$_2$O bath, and stirred at RT for 45 min. The solution was concentrated in vacuo and azeotroped with anhydrous CH$_2$Cl$_2$ (3×). The solid was dissolved in CH$_2$Cl$_2$ (20 mL) and cooled to −78° C. NH$_3$ (g) was bubbled through the solution to double the volume, then the solution was stirred for 2 hours while warning to RT under Ar. The solution was concentrated in vacuo, and partitioned between H$_2$O and CH$_2$Cl$_2$. The aqueous layer was back extracted with CH$_2$Cl$_2$. The organic layers were combined, and dried with MgSO$_4$. Filtration and concentration gave the title compound.

Step F: Preparation of (+) and (−)-2-fluoro-4-[1-amino-1-(3-methyl-3H-imidazol-4-yl)-ethyl]-benzonitrile Racemic 2-fluoro-4-[1-amino-1-(3-methyl-3H-imidazol-4-yl)-ethyl]-benzonitrile (as described above in Step E) was separated on an HPLC chiracel OD column eluting with 60:40 ethanol:hexane to give (+)-2-fluoro-4-[1-amino-1-(3-methyl-3H-imidazol-4-yl)-ethyl]-benzonitrile [a]$_D$+99.6° (c=1,EtOH) and (−)-2-fluoro-4-[1-amino-1-(3-methyl-3H-imidazol-4-yl)-ethyl]-benzonitrile [a]$_D$−111.6° (c=1, EtOH).

Step G: Preparation of a diastereomer of 2-[3-(3-ethyl-1-methyl-2-oxo-azepan-3-yl)-phenoxy]-4-[1-amino-1-(3-methyl-3H-imidazol-4-yl)-ethyl]-benzonitrile Following the methods described in Example 24, (3R)-Ethyl-3-(3-hydroxy-phenyl)-1-methyl-azepan-2-one and (+)-2-fluoro-4-[1-amino-1-(3-methyl-3H-imidazol-4-yl)-ethyl]-benzonitrile (as described above in Step F) were reacted to give 2-[3-(3R)-ethyl-1-methyl-2-oxo-azepan-3-yl)-phenoxy]-4-[1-(R or S)(+)amino 1-(3-methyl-3H-imidazol-4-yl)-ethyl]-benzonitrile.

FAB MS (M+1)=472. Analysis calculated for C$_{28}$H$_{33}$N$_5$O$_2$.0.65 H$_2$O: C, 69.58; H, 7.15; N, 14.49; Found: C, 69.57; H, 6.90; N, 14.23.

Example 24B

Following the methods described in Example 24A, (3R)-Ethyl-3-(3-hydroxy-phenyl)-1-methyl-azepan-2-one and (−)-2-fluoro-4-[1-amino-1-(3-methyl-3H-imidazol-4-yl)-ethyl]-benzonitrile were reacted to give 2-[3-(3R)-ethyl-1-methyl-2-oxo-azepan-3-yl)-phenoxy]-4-[1-(R or S)(−) amino-1-(3-methyl-3H-imidazol-4-yl)-ethyl]-benzonitrile.

FAB MS (M+1)=472. Analysis calculated for C$_{28}$H$_{33}$N$_5$O$_2$: C, 71.31; H, 7.05; N, 14.85; Found: C, 71.36; H, 6.95; N, 14.58.

Example 24C

Following the methods described in Example 24A, (3S)-Ethyl-3-(3-hydroxy-phenyl)-1-methyl-azepan-2-one and (+)-2-fluoro-4-[1-amino-1-(3-methyl-3H-imidazol-4-yl)-ethyl]-benzonitrile were reacted to give 2-[3-(3S)-ethyl-1-methyl-2-oxo-azepan-3-yl)-phenoxy]-4-[1-(R or S)(+) amino-1-(3-methyl-3H-imidazol-4-yl)-ethyl]-benzonitrile.

FAB MS (M+1)=472. Analysis calculated for C$_{28}$H$_{33}$N$_5$O$_2$.0.20 H$_2$O.0.25 CH$_2$Cl$_2$: C, 68.34; H, 6.88; N, 14.11; Found: C, 68.49; H, 7.00; N, 13.72.

Example 24D

Following the methods described in Example 24A, (3S)-Ethyl-3-(3-hydroxy-phenyl)-1-methyl-azepan-2-one and (−)-2-fluoro-4-[1-amino-1-(3-methyl-3H-imidazol-4-yl)-ethyl]-benzonitrile were reacted to give 2-[3-(3S)-ethyl-1-methyl- 2-oxo-azepan-3-yl)-phenoxy]-4-[1-(R or S)(−) amino-1-(3-methyl-3H-imidazol-4-yl)-ethyl]-benzonitrile.

FAB MS (M+1)=472. Analysis calculated for C$_{28}$H$_{33}$N$_5$O$_2$.0.85 H$_2$O: C, 69.06; H, 7.18; N, 14.38; Found: C, 68.72; H, 6.92; N, 14.77.

Example 24E

Preparation of (−)-2-fluoro-4-[1-amino-1-(3-methyl-3H-imidazol-4-yl)-ethyl]-benzonitrile The following is an alternate way of preparing (−)-2-fluoro-4-[1-amino-1-(3-methyl-3H-imidazol-4-yl)-ethyl]-benzonitrile:

Step A: Preparation of N-[(4-cyano-3-fluoro-phenyl)-(3-methyl-3H-imidazol-4-yl)-methylene]-2-methylpropanesulfinamide 2-Fluoro-4-(3-methyl-3H-imidazole-4-carbonyl)-benzonitrile (as described in Example 24A, Step C) (2.56 g, 11.2 mmol), titanium(IV) ethoxide (7.02 mL, 33.5 mmol) and commercially available (R)-(+)-2-methyl-2-propanesulfinamide (1.35 g, 11.17 mmol) were dissolved in anhydrous THF (100 mL) and heated at 75° C. for 7 days. The solution was cooled, diluted with brine (100 mL), filtered through a celite pad and washed generously with EtOAc and H$_2$O. The filtrate was separated, dried (MgSO$_4$), and purified using SiO$_2$ chromatography (0–3% MeOH/CH$_2$Cl$_2$) to give the title compound.

Step B: Preparation of N-[1-(4-cyano-3-fluoro-phenyl)-1-(3-methyl-3H-imidazol-4-yl)-ethyl]-2-methylpropanesulfinamide N-[(4-cyano-3-fluoro-phenyl)-(3-methyl-3H-imidazol-4-yl)-methylene]-2-methylpropanesulfinamide (as described above in Step B) (1.50 g, 4.51 mmol) was dissolved in anhydrous THF (30 mL) at 0° C. to which a 3.0M solution of MeMgBr (4.50 mL, 13.5 mmol) in Et$_2$O was added. The reaction was quenched with aq. NH$_4$Cl solution, diluted with saturated NaHCO$_3$ solution and extracted with CH$_2$Cl$_2$ (3×). The combined organic layers were dried (MgSO$_4$), filtered, concentrated, and recrystallized from 95% EtOAc/Hexane to give the title compound.

Step C: Preparation of (−)-4-[1-amino-1-(3-methyl-3H-imidazol-4-yl)-ethyl]-2-fluoro-benzonitrile Bishydrochloride A cold methanolic HCl solution (50 mL) was added to N-[1-(4-cyano-3-fluoro-phenyl)-1-(3-methyl-3H-imidazol-4-yl)-ethyl]-2-methylpropanesulfinamide (as described above in Step B) (0.880 g, 2.51 mmol) dissolved in MeOH (50 mL) and stirred for 1 h at RT. After concentration and trituration with EtOAc the title compound was obtained as a bis HCl salt as confirmed by chiral HPLC.

Using the procedure described above, but substituting (S)-(−)-2-methyl-2-propanesulfinamide for (R)-(+)-2-methyl-2-propanesulfinamide in Step A, (+)-2-fluoro-4-[1-amino-1-(3-methyl-3H-imidazol-4-yl)-ethyl]-benzonitrile was obtained.

Example 25

Preparation of the diastereomers of 2-[3-3(R or S)-n-butyl-1-methyl-2-oxo-azepan-3-yl)-phenoxy]-4-[1-(R or S)amino-1-(3-methyl-3H-imidazol-4-yl)-ethyl]-benzonitrile Using the methods described in Example 24A, but substituting racemic 3-n-butyl-3-(3-methoxy-phenyl)-1-methyl-azepan-2-one (prepared as described in Example 6, Step A, but using n-butyl bromide in place of iodomethyl methylether), the following compounds were prepared, wherein the "(−)" and "(+)" represent the optical rotation of the starting intermediates that are combined to obtain the compounds below:

2-[3-3(R or S)(+)-n-butyl-1-methyl-2-oxo-azepan-3-yl)-phenoxy]-4-[1-(R or S)(+) amino-1-(3-methyl-3H-imidazol-4-yl)-ethyl]-benzonitrile

FAB MS (M+1)=500;

2-[3-3(R or S)(+)-n-butyl-1-methyl-2-oxo-azepan-3-yl)-phenoxy]-4-[1-(R or S)(−)amino-1-(3-methyl-3H-imidazol-4-yl)-ethyl]-benzonitrile FAB MS (M+1)=500. Analysis calculated for C$_{30}$H$_{39}$N$_5$O$_2$.2.80 CF$_3$CO$_2$H: C, 52.21; H, 4.90; N, 8.55; Found: C, 52.19; H, 4.69; N, 8.34.

2-[3-3(R or S)(−)-n-butyl-1-methyl-2-oxo-azepan-3-yl)-phenoxy]-4-[1-(R or S)(−) amino-1-(3-methyl-3H-imidazol-4-yl)-ethyl]-benzonitrile FAB MS (M+1)=500; Analysis calculated for C$_{30}$H$_{39}$N$_5$O$_2$.2.50 CF$_3$CO$_2$H.1.0 H$_2$O: C, 52.36; H, 5.21; N, 8.73; Found: C, 52.35; H, 4.82; N, 8.45.

2-[3-3(R or S)(−)-n-butyl-1-methyl-2-oxo-azepan-3-yl)-phenoxy]-4-[1-(R or S)(+)amino-1-(3-methyl-3H-imidazol-4-yl)-ethyl]-benzonitrile

FAB MS (M+1)=500.

Example 25A

Preparation of the diastereomers of 2-{3-[1-methyl-2-oxo-3-(R or S)-(3,3,3-trifluoro-propyl)-azepan-3-yl]-phenoxy}-4-[1(R or S)-amino-1-(3-methyl-3H-imidazol-4-yl)-ethyl]-benzonitrile Using the methods described in Example 24A, but substituting racemic (3,3,3-trifluoro-propyl)-3-(3-methoxy-phenyl)-1-methyl-azepan-2-one (prepared as described in Example 6, Step A, but using 3,3,3-trifluoro-propyl bromide in place of iodomethyl methylether), the following compounds were prepared, wherein the "(−)" and "(+)" represent the optical rotation of the starting intermediates that are combined to obtain the compounds below:

2-{3-[1-methyl-2-oxo-3-(R or S)(+)-(3,3,3-trifluoro-propyl)-azepan-3-yl]-phenoxy}-4-[1(R or S)(+)-amino-1-(3-methyl-3H-imidazol-4-yl)-ethyl]-benzonitrile

FAB MS (M+1)=540.

2-{3-[1-methyl-2-oxo-3-(R or S)(−)-(3,3,3-trifluoro-propyl)-azepan-3-yl]-phenoxy}-4-[1(R or S)(−)-amino-1-(3-methyl-3H-imidazol-4-yl)-ethyl]-benzonitrile

FAB MS (M+1)=540.

2-{3-[1-methyl-2-oxo-3-(R or S)(+)-(3,3,3-trifluoro-propyl)-azepan-3-yl]-phenoxy}-4-[1(R or S)(−)-amino-1-(3-methyl-3H-imidazol-4-yl)-ethyl]-benzonitrile

FAB MS (M+1)=540.

2-{3-[1-methyl-2-oxo-3-(R or S)(−)-(3,3,3-trifluoro-propyl)-azepan-3-yl]-phenoxy}-4-[1(R or S)(+)-amino-1-(3-methyl-3H-imidazol-4-yl)-ethyl]-benzonitrile

FAB MS (M+1)=540.

Example 26

Preparation of the diastereomers of 2-[3-3(R or S)-cyclopropylmethyl-1-methyl-2-oxo-azepan-3-yl)-phenoxy]-4-[1-(R or S)amino-1-(3-methyl-3H-imidazol-4-yl)-ethyl]-benzonitrile Using the methods described in Example 24A, but substituting racemic 3-cyclopropylmethyl-3-(3-methoxy-phenyl)-1-methyl-azepan-2-one (prepared as described in Example 6, Step A, but using cyclopropylmethyl bromide in place of iodomethyl methylether), the following compounds were prepared, wherein the "(−)" and "(+)" represent the optical rotation of the starting intermediates that are combined to obtain the compounds below:

2-[3-3(R or S)(−)-cyclopropylmethyl-1-methyl-2-oxo-azepan-3-yl)-phenoxy]-4-[1-(R or S)(+)amino-1-(3-methyl-3H-imidazol-4-yl)-ethyl]-benzonitrile FAB MS (M+1)=498; HRMS measured 498.2866; theoretical 498.2863.

2-[3-3(R or S)(+)-cyclopropylmethyl-1-methyl-2-oxo-azepan-3-yl)-phenoxy]-4-[1-(R or S)(+)amino-1-(3-methyl-3H-imidazol-4-yl)-ethyl]-benzonitrile FAB MS (M+1)=498; HRMS measured 498.2851; theoretical 498.2863.

2-[3-3(R or S)(−)-cyclopropylmethyl-1-methyl-2-oxo-azepan-3-yl)-phenoxy]-4-[1-(R or S)(+)amino-1-(3-methyl-3H-imidazol-4-yl)-ethyl]-benzonitrile FAB MS (M+1)=498; HRMS measured 498.2845; theoretical 498.2863.

2-[3-3(R or S)(+)-cyclopropylmethyl-1-methyl-2-oxo-azepan-3-yl)-phenoxy]-4-[1-(R or S)(−)amino-1-(3-methyl-3H-imidazol-4-yl)-ethyl]-benzonitrile FAB MS (M+1)=498; Analysis calculated for C$_{30}$H$_{35}$N$_5$O$_2$.0.35 H$_2$O: C, 71.50; H, 7.14; N, 13.90; Found: C, 71.37; H, 7.39; N, 14.28.

Example 26A

Preparation of the diastereomers of 2-[3-3(R or S)-cyclopropylethyl-1-methyl-2-oxo-azepan-3-yl)-phenoxy]-4-[1-(R or S)amino-1-(3-methyl-3H-imidazol-4-yl)-ethyl]-benzonitrile Using the methods described in Example 24A, but substituting racemic 3-cyclopropylethyl-3-(3-methoxy-phenyl)-

1-methyl-azepan-2-one (prepared as described in Example 6, Step A, but using cyclopropylmethyl bromide in place of iodomethyl methylether), the following compounds were prepared, wherein the "(−)" and "(+)" represent the optical rotation of the starting intermediates that are combined to obtain the compounds below:

2-[3-3(R or S)(−)-cyclopropylmethyl-1-methyl-2-oxo-azepan-3-yl)-phenoxy]-4-[1-(R or S)(+)amino-1-(3-methyl-3H-imidazol-4-yl)-ethyl]-benzonitrile
FAB MS (M+1)=512.

2-[3-3(R or S)(+)-cyclopropylethyl-1-methyl-2-oxo-azepan-3-yl)-phenoxy]-4-[1-(R or S)(+)amino-1-(3-methyl-3H-imidazol-4-yl)-ethyl]-benzonitrile
FAB MS (M+1)=512.

2-[3-3(R or S)(−)-cyclopropylethyl-1-methyl-2-oxo-azepan-3-yl)-phenoxy]-4-[1-(R or S)(+)amino-1-(3-methyl-3H-imidazol-4-yl)-ethyl]-benzonitrile
FAB MS (M+1)=512.

2-[3-3(R or S)(+)-cyclopropylethyl-1-methyl-2-oxo-azepan-3-yl)-phenoxy]-4-[1-(R or S)(−)amino-1-(3-methyl-3H-imidazol-4-yl)-ethyl]-benzonitrile
FAB MS (M+1)=512.

Example 26B

Preparation of the diastereomers of 2-[3-3(R or S)-propyl-1-methyl-2-oxo-azepan-3-yl)-phenoxy]-4-[1-(R or S)amino-1-(3-methyl-3H-imidazol-4-yl)-ethyl]-benzonitrile Using the methods described in Example 24A, but substituting racemic 3-propyl-3-(3-methoxy-phenyl)-1-methyl-azepan-2-one (prepared as described in Example 6, Step A, but using propyl bromide in place of iodomethyl methylether), the following compounds were prepared, wherein the "(−)" and "(+)" represent the optical rotation of the starting intermediates that are combined to obtain the compounds below:

2-[3-3(R or S)(−)-propyl-1-methyl-2-oxo-azepan-3-yl)-phenoxy]-4-[1-(R or S)(+)amino-1-(3-methyl-3H-imidazol-4-yl)-ethyl]-benzonitrile
FAB MS (M+1)=486.

2-[3-3(R or S)(+)-propyl-1-methyl-2-oxo-azepan-3-yl)-phenoxy]-4-[1-(R or S)(+)amino-1-(3-methyl-3H-imidazol-4-yl)-ethyl]-benzonitrile
FAB MS (M+1)=486.

2-[3-3(R or S)(−)-propyl-1-methyl-2-oxo-azepan-3-yl)-phenoxy]-4-[1-(R or S)(+)amino-1-(3-methyl-3H-imidazol-4-yl)-ethyl]-benzonitrile
FAB MS (M+1)=486.

2-[3-3(R or S)(+)-propyl-1-methyl-2-oxo-azepan-3-yl)-phenoxy]-4-[1-(R or S)(−)amino-1-(3-methyl-3H-imidazol-4-yl)-ethyl]-benzonitrile
FAB MS (M+1)=486.

Example 26C

Preparation of the diastereomers of 2-[3-3(R or S)-methoxymethyl-1-methyl-2-oxo-azepan-3-yl)-phenoxy]-4-[1-(R or S)amino-1-(3-methyl-3H-imidazol-4-yl)-ethyl]-benzonitrile Using the methods described in Example 24A, but substituting racemic 3-methoxymethyl-3-(3-methoxy-phenyl)-1-methyl-azepan-2-one (Example 6, Step A), the following compounds were prepared, wherein the "(−)" and "(+)" represent the optical rotation of the starting intermediates that are combined to obtain the compounds below:

2-[3-3(R or S)(−)-methoxymethyl-1-methyl-2-oxo-azepan-3-yl)-phenoxy]-4-[1-(R or S)(+)amino-1-(3-methyl-3H-imidazol-4-yl)-ethyl]-benzonitrile
FAB MS (M+1)=488.

2-[3-3(R or S)(+)-methoxymethyl-1-methyl-2-oxo-azepan-3-yl)-phenoxy]-4-[1-(R or S)(+)amino-1-(3-methyl-3H-imidazol-4-yl)-ethyl]-benzonitrile FAB MS (M+1)=488.

2-[3-3(R or S)(−)-methoxymethyl-1-methyl-2-oxo-azepan-3-yl)-phenoxy]-4-[1-(R or S)(+)amino-1-(3-methyl-3H-imidazol-4-yl)-ethyl]-benzonitrile
FAB MS (M+1)=488.

2-[3-3(R or S)(+)-methoxymethyl-1-methyl-2-oxo-azepan-3-yl)-phenoxy]-4-[1-(R or S)(−)amino-1-(3-methyl-3H-imidazol-4-yl)-ethyl]-benzonitrile
FAB MS (M+1)=488.

Example 26D

Preparation of the diastereomers of 2-[3-3(R or S)-ethoxymethyl-1-methyl-2-oxo-azepan-3-yl)-phenoxy]-4-[1-(R or S)amino-1-(3-methyl-3H-imidazol-4-yl)-ethyl]-benzonitrile Using the methods described in Example 24A, but substituting racemic 3-cyclopropylethyl-3-(3-methoxy-phenyl)-1-methyl-azepan-2-one (prepared as described in Example 6, Step A, but using bromomethyl ethylether in place of iodomethyl methylether), the following compounds were prepared, wherein the "(−)" and "(+)" represent the optical rotation of the starting intermediates that are combined to obtain the compounds below:

2-[3-3(R or S)(−)-ethoxymethyl-1-methyl-2-oxo-azepan-3-yl)-phenoxy]-4-[1-(R or S)(+)amino-1-(3-methyl-3H-imidazol-4-yl)-ethyl]-benzonitrile
FAB MS (M+1)=502.

2-[3-3(R or S)(+)-ethoxymethyl-1-methyl-2-oxo-azepan-3-yl)-phenoxy]-4-[1-(R or S)(+)amino-1-(3-methyl-3H-imidazol-4-yl)-ethyl]-benzonitrile
FAB MS (M+1)=502.

2-[3-3(R or S)(−)-ethoxymethyl-1-methyl-2-oxo-azepan-3-yl)-phenoxy]-4-[1-(R or S)(+)amino-1-(3-methyl-3H-imidazol-4-yl)-ethyl]-benzonitrile
FAB MS (M+1)=502.

2-[3-3(R or S)(+)-ethoxymethyl-1-methyl-2-oxo-azepan-3-yl)-phenoxy]-4-[1-(R or S)(−)amino-1-(3-methyl-3H-imidazol-4-yl)-ethyl]-benzonitrile
FAB MS (M+1)=502.

Example 27

Preparation of the diastereomers of 2-[3-3(R or S)-cyproylmethyl-1-methyl-2-oxo-piperidin-3-yl)-phenoxy]-4-[1-(R or S)amino-1-(3-methyl-3H-imidazol-4-yl)-ethyl]-benzonitrile Using the methods described in Example 24A, but substituting racemic 3-cyclopropylmethyl-3-(3-methoxy-phenyl)-1-methyl-piperidin-2-one (prepared using techniques described in Example 4, Step A, and in Example 6, Step A, but using N-methyl-2-piperidinone instead of N-methylcaprolactam in Example 4 and cyclo-propylmethyl bromide in place of iodomethyl methylether in Example 6), the following compounds were prepared, wherein the "(−)" and "(+)" represent the optical rotation of the starting intermediates that are combined to obtain the compounds below:

2-[3-3(R or S)(−)-cyclopropylmethyl-1-methyl-2-oxo-piperidin-3-yl)-phenoxy]-4-[1-(R or S)(+)amino-1-(3-methyl-3H-imidazol-4-yl)-ethyl]-benzonitrile
FAB MS (M+1)=484.

2-[3-3(R or S)(+)-cyclopropylmethyl-1-methyl-2-oxo-piperidin-3-yl)-phenoxy]-4-[1-(R or S)(+)amino-1-(3-methyl-3H-imidazol-4-yl)-ethyl]-benzonitrile FAB MS (M+1)=484.
2-[3-3(R or S)(−)-cyclopropylmethyl-1-methyl-2-oxo-piperidin-3-yl)-phenoxy]-4-[1-(R or S)(−)amino-1-(3-methyl-3H-imidazol-4-yl)-ethyl]-benzonitrile
FAB MS (M+1)=484.
2-[3-3(R or S)(+)-cyclopropylmethyl-1-methyl-2-oxo-piperidin-3-yl)-phenoxy]-4-[1-(R or S)(−)amino-1-(3-methyl-3H-imidazol-4)-ethyl]-benzonitrile
FAB MS (M+1)=484.

Example 27A

Preparation of the diastereomers of 2-[3-3(R or S)-benzyl-1-methyl-2-oxo-piperidin-3-yl)-phenoxy]-4-[-(R or S)amino-1-(3-methyl-3H-imidazol-4-yl)-ethyl]-benzonitrile Using the methods described in Example 24A, but substituting racemic 3-benzyl-3-(3-methoxy-phenyl)-1-methyl-piperidin-2-one (prepared using techniques described in Example 4, Step A, and in Example 6, Step A, but using N-methyl-2-piperidinone instead of N-methylcaprolactam in Example 4 and benzyl bromide in place of iodomethyl methylether in Example 6), the following compounds were prepared, wherein the "(−)" and "(+)" represent the optical rotation of the starting intermnediates that are combined to obtain the compounds below :
2-[3-3(R or S)(−)-benzyl-1-methyl-2-oxo-piperidin-3-yl)-phenoxy]-4-[1-(R or S)(+)amino-1-(3-methyl-3H-imidazol-4-yl)-ethyl]-benzonitrile
FAB MS (M+1)=520.
2-[3-3(R or S)(+)-benzyl-1-methyl-2-oxo-piperidin-3-yl)-phenoxy]-4-[1-(R or S)(+)amino-1-(3-methyl-3H-imidazol-4-yl)-ethyl]-benzonitrile
FAB MS (M+1)=520.
2-[3-3(R or S)(−)-benzyl-1-methyl-2-oxo-piperidin-3-yl)-phenoxy]-4-[1-(R or S)(−)amino-1-(3-methyl-3H-imidazol-4-yl)-ethyl]-benzonitrile
FAB MS (M+1)=520.
2-[3-3(R or S)(+)-benzyl-1-methyl-2-oxo-piperidin-3-yl)-phenoxy]-4-[1-(R or S)(−)amino-1-(3-methyl-3H-imidazol-4-yl)-ethyl]-benzonitrile
FAB MS (M+1)=520.

Example 28

Preparation of 2-[3-methyl-1-methyl-2-oxo-azepan-3-yl)-phenoxy]-4-[1-amino-1-(3-methyl-3H-imidazol-4-yl)-ethyl]-benzontrile Using the methods described in Example 24A, but substituting racemic 3-methyl-3-(3-hydroxy-phenyl)-1-methyl-azepan-2-one (prepared as described in Example 4, Step A and in Example 6, Step A, but using methyl iodide in place of iodomethyl methylether), and racemic 2-fluoro-4-[1-amino-1-(3-methyl-3H-imidazol-4-yl)-ethyl]-benzonitrile (Example 24A, Step F), the following compound was prepared:
2-[3-methyl-1-methyl-2-oxo-azepan-3-yl)-phenoxy]-4-[1-amino-1-(3-methyl-3H-imidazol-4-yl)-ethyl]-benzonitrile
FAB MS (M+1)=458.

Example 29

Preparation of 2-[3-(3-ethyl-1-methyl-2-oxo-azepan-3-yl)-phenoxy]-4-[1-(3-methyl-3-H-imidazol-4-yl)-vinyl]-benzonitrile Step A: Preparation of 2-fluoro-4-formylbenzonitrile
2-Fluoro-4-hydroxymethylbenzonitrile (as described in Example 9, Step C) (10 g, 0,066 mol) and triethylamine (32.3 mL, 0.231 mol) were dissolved in $CH_2Cl_2$ (100 mL)-DMSO (20 mL) at <5° C. with stirring and treated dropwise with a solution of pyridine•$SO_3$ complex (31.5 g, 0.198 mol) in DMSO (70 mL). The reaction mixture was maintained at a temperature <10° C. The reaction mixture was stirred at 5° C. for 1 hr after the addition, then at 20° C. for 1 hr, then partitioned between $CH_2Cl_2$ and $H_2O$. The organic layer was separated, washed well with $H_2O$, brine, and dried ($Na_2SO_4$). Filtration and concentration gave the title compound after purification by chromatography (silica gel, hexane:EtOAc, 3:1).
$^1$H NMR ($CDCl_3$) δ 10.06 (d, 1H, J=2 Hz), 7.86 (dd, 1H, J=5,8 Hz), 7.798 (dd, 1H, J=1, 8 Hz), 7.728 (dd, 1H, J=1, 8 Hz).

Step B: Preparation of 2-fluoro-4-[hydroxy-(1-trityl-1H-imidazol-4-yl)-methyl]-benzonitrile
To a solution of 4-iodo-1-trityl-1H-imidazole (5.00 g, 11.5 mmol) in anhydrous $CH_2Cl_2$ (30 mL) was added a 3.0M solution of ethylmagnesium bromide (6.58 mL, 19.7 mmol) with stirring under Ar. After 3 h, the reaction mixture was cooled to −78° C. and a solution of 2-fluoro-4-formyl-benzonitrile (as described in Step A above) (1.70 g, 11.5 mmol) dissolved in $CH_2Cl_2$ (20 mL) was added dropwise. The reaction was allowed to warm to RT over 2 h, quenched with saturated $NH_4Cl$ solution, diluted with satd. $NaHCO_3$ solution to pH=8.5, and extracted with $CH_2Cl_2$ (3×). The combined organic layers were dried ($MgSO_4$), concentrated and purified using $SiO_2$ chromatography (0–1% MeOH/$CH_2Cl_2$) to yield the title compound.

Step C: Preparation of Acetic Acid (4-cyano-3-fluoro-phenyl)-(1-trityl-1H-imidazol-4-yl)-methyl Ester
2-Fluoro-4-[hydroxy-(1-trityl-1H-imidazol-4-yl)-methyl]-benzonitrile (as described in Step B above) (4.05 g, 8.81 mmol), pyridine (2.14 mL, 26.4 mmol), and acetic anhydride (12.5 mL, 132 mmol) were stirred in anhydrous DMF (60 mL) for 3 h under Ar. The reaction was concentrated in vacuo, diluted with EtOAc (250 mL), washed with $H_2O$ (2×), brine, dried ($MgSO_4$) and concentrated to give the title compound.

Step D: Preparation of Acetic Acid (4-cyano-3-fluoro-phenyl)-(3-methyl-3H-imidazol-4-yl)-methyl Ester
Acetic acid (4-cyano-3-fluoro-phenyl)-(1-trityl-1H-imidazol-4-yl)-methyl ester (as described in Step C above) (4.60 g, 9.17 mmol) and dimethyl sulfate (0.83 mL, 8.81 mmol) were dissolved in EtOAc (20 mL) and heated at 60° C. overnight under Ar. The reaction was concentrated in vacuo, diluted with MeOH (30 mL), and refluxed for 1 hr, concentrated in vacuo and purified using $SiO_2$ chromatography (0.5–4% MeOH/$CH_2Cl_2$ with $NH_4OH$) to give the title compound.

Step E: Preparation of 2-fluoro-4-[hydroxy-(3-methyl-3H-imidazol-4-yl)-methyl]-benzonitrile
Acetic acid (4-cyano-3-fluoro-phenyl)-(3-methyl-3H-imidazol-4-yl)-methyl ester (as described in Step D above) (1.26 g, 4.59 mmol) and NaOH (5.5 mL, 5.5 mmol) were dissolved in THF (15 mL) and $H_2O$ (25 mL). After 1h, the reaction was diluted with satd. $NaHCO_3$ solution, extracted with $CH_2Cl_2$ (3×), dried ($MgSO_4$) and concentrated to give the title compound.

Step F: Preparation 2-fluoro-4-[1-(3-methyl-3-H-imidazol-4-yl)-vinyl]-benzonitrile
Thionyl chloride (15 mL) was added to a suspension of 2-fluoro-4-[hydroxy-(3-methyl-3H-imidazol-4-yl)-methyl]-benzonitrile (as described in Step E above) (0.268 g) in $CHCl_3$ (10 mL)—benzene (30 mL) and the reaction mixture was heated at reflux for 2 hr. The reaction mixture was concentrated to dryness, dissolved in $CH_2Cl_2$, and re-concentrated to give the title compound.

FAB MS (M+1) 228. $^1$H NMR (CDCl$_3$) δ 7.81 (s, 1H), 7.15–7.23 (m, 1H), 7.11 (s, 1H), 5.85 (s, 1H), 5.63 (s, 1H), 3.40 (s, 3H).

Step G: Preparation of 2-[3-(3-ethyl-1-methyl-2-oxo-azepan-3-yl)-phenoxy]-4-[1-(3-methyl-3-H-imidazol-4-yl)-vinyl]-benzonitrile Using the procedure described in Example 3, the title compound was prepared starting with 2-fluoro-4-[1-(3-methyl-3-H-imidazol-4-yl)-vinyl]-benzonitrile (as described in Step F above) and 3-ethyl-3-(3-hydroxy-phenyl)-1-methyl-azepan-2-one.

FAB mass spectrum m/e 455 (m+1). Analysis calculated for C$_{28}$H$_{30}$N$_4$O$_2$·0.70 H$_2$O·1.30 HCl: C, 65.35; H, 6.41; N, 10.89; Found: C, 65.36; H, 6.41; N, 10.53.

Example 30

Preparation of 2-[3-(3-ethyl-1-methyl-2-oxo-azepan-3-yl)-phenoxy]-4-[1-(3-methyl-3-H-imidazol-4-yl)-cyclopropyl]-benzonitrile Step A: Preparation of 2-fluoro-4-[1-(3-methyl-3-H-imidazol-4-yl)-cyclopropyl]-benzonitrile To a suspension of sodium hydride (60% dispersion) (0.040 g, 1.05 mmol) in dry DMF (2 mL) at ambient temperature under Ar was added trimethylsulfoxonium iodide (0.230 g, 1.05 mmol) in one portion with stirring. After 5 min, H$_2$ evolution ceased, and after 15 min, a solution of 2-fluoro-4-[1-(3-methyl-3-H-imidazol-4-yl)-vinyl]-benzonitrile (as described above in Example 29, Step F) (0.240 g, 1.0 mmol) in DMF (4 mL) was added and the mixture was stirred at room temperature for 18 hr. The reaction mixture was partitioned between diethyl ether and ice water, the aqueous layer washed with ether, the organic layers combined, washed with brine, and dried (Na$_2$SO$_4$). Filtration and concentration to dryness gave the title compound after purification by RPLC on a Waters PrepPak column with a H$_2$O/CH$_3$CN gradient.

FAB MS (M+1) 242.

Step B: Preparation of 2-[3-(3-ethyl-1-methyl-2-oxo-azepan-3-yl)-phenoxy]-4-[-(3-methyl-3-H-imidazol-4-yl)-cyclopropyl]-benzonitrile Using the procedure described in Example 3, the title compound was prepared starting with 2-fluoro-4-[1-(3-methyl-3-H-imidazol-4-yl)-cyclopropyl]-benzonitrile (as described in Step A above) (0.050 g, 0.21 mmol) and 3-ethyl-3-(3-hydroxy-phenyl)-1-methyl-azepan-2-one (0.078 g, 0.21 mmol).

FAB mass spectrum m/e 469 (M+1). Analysis calculated for C$_{29}$H$_{32}$N$_4$O$_2$·1.00 H$_2$O: C, 71.57; H, 7.04; N, 11.51; Found: C, 71.35; H, 6.72; N, 11.49.

Example 31

Preparation of 2-[3-N,N-dimethylaminomethyl-1-methyl-2-oxo-azepan-3-yl)-phenoxy]-4-[1-hydroxy-1-(3-methyl-3H-imidazol-4-yl)-ethyl]-benzonitrile Step A: Preparation of 3-bromomethyl-3-(3-hydroxy-phenyl)-1-methyl-azepan-2-one 3-Hydroxymethyl-3-(3-hydroxy-phenyl)-1-methyl-azepan-2-one (as described in Example 6, Step B) (0.60 g, 2.40 mmol), triphenylphosphine (0.94 g, 3.60 mmol), and carbon tetrabromide (1.19 g, 3.60 mmol) were dissolved in CH$_2$Cl$_2$ (15 mL), stirred under Ar for 16 h, then the solution was concentrated in vacuo and purified using SiO$_2$ chromatography (0.5% MeOH/CH$_2$Cl$_2$) to give the title compound.

Step B: Preparation of 3-N,N-dimethylaminomethyl-3-(3-hydroxy-phenyl)-1-methyl-azepan-2-one 3-Bromomethyl-3-(3-hydroxy-phenyl)-1-methyl-azepan-2-one (as described above in Step A) (0.263 g, 0.842 mmol) was dissolved in DMF (5 mL) in a sealed vessel. The solution was cooled to −78° C. and saturated with dimethyl amine gas. The reaction vessel was sealed and heated at 80° C. for 16 h. The solution was concentrated to give the title compound.

Step C: Preparation of 2-[3-N,N-dimethylaminomethyl-1-methyl-2-oxo-azepan-3-yl)-phenoxy]-4-[1-hydroxy-1-(3-methyl-3H-imidazol-4-yl)-ethyl]-benzonitrile 2-Fluoro-4-[1-hydroxy-1-(3-methyl-3H-imidazol-4-yl)-ethyl]-benzonitrile (as described in Example 24A, Step D) and 3-N,N-dimethylaminomethyl-3-(3-hydroxy-phenyl)-1-methyl-azepan-2-one (as described above in Step B) were reacted as described in EXAMPLE 17, Step F, to give the title compound as its trifluoroacetate salt after purification by RPLC.

FAB MS (M+1)=502; HRMS measured 502.2824; theoretical 502.2812.

Example 32

Preparation of 2-[3-N,N-dimethylaminomethyl-1-methyl-2-oxo-azepan-3-yl)-phenoxy]-4-[1-amino-1-(3-methyl-3H-imidazol-4-yl)-ethyl]-benzonitrile Following the procedure described in Example 24A but using 2-[3-N,N-dimethylaminomethyl-1-methyl-2-oxo-azepan-3-yl)-phenoxy]-4-[1-hydroxy-1-(3-methyl-3H-imidazol-4-yl)-ethyl]-benzonitrile (as described in Example 31) as the starting material, the title compound was prepared.

FAB mass spectrum m/e 501 (M+1). Analysis calculated for C$_{29}$H$_{36}$N$_6$O$_2$·0.05 H$_2$O·0.55 CH$_2$Cl$_2$: C, 64.73; H, 6.84; N, 15.33; Found: C, 64.79; H, 6.50; N, 15.13.

Example 33

Preparation of 2-[3-(3-N,N-dimethylaminomethyl-1-methyl-2-oxo-azepan-3-yl)-phenoxy]-4-[1-(3-methyl-3-H-imidazol-4-yl)-vinyl]-benzonitrile From the methods described in Example 32, the title compound was obtained as a byproduct.

FAB MS (M+1)=484; HRMS measured 484.2730; theoretical 484.2707.

Example 34

Preparation of 4-[5-(2-N,N-dimethylaminoethyl)-2-methyl-imidazol-1-ylmethyl]-2-[3-(3(S)-ethyl-1-methyl-2-oxo-azepan-3-yl)-phenoxy]-benzonitrile bis trifluoroacetate Step A: Preparation of 4-[5-(2-amino-ethyl)-2-methyl-imidazol-1-ylmethyl]-2-fluoro-benzonitrile Dihydrochloride A solution of {2-[3-(4-cyano-3-fluoro-benzyl)-2-methyl-3H-imidazol-4-yl]-ethyl}-carbamic acid tert-butyl ester (as described in Example 11, Step A) (1.0 g, 2.9 mmol) in EtOAc (30 mL) was cooled to −20° C. and saturated with HCl gas. The cooling bath was removed and the reaction was stirred for 2 hr. The solvent was removed in vacuo to obtain the title compound.

Step B: Preparation of 4-[5-(2-(N,N-dimethylaminoethyl)-2-methyl-imidazol-1-ylmethyl]-2-fluoro-benzonitrile To a solution of 4-[5-(2-amino-ethyl)-2-methyl-imidazol-1-ylmethyl]-2-fluoro-benzonitrile dihydrochloride (as described above in Step A) (0.5 g, 1.65 mmol) in MeOH (5 mL) at pH=4 was added paraformaldehyde (300 mg) and NaCNBH$_3$ (0.311 g, 4.95 mmol). The reaction mixture was stirred for 2 h then additional NaCNBH$_3$ (0.311 g) was added. After 18 h, more NaCNBH$_3$ was added and stirring was continued for 24 h. The MeOH was removed in vacuo and the residue was partitioned between EtOAc and saturated NaHCO$_3$. The organic layer was washed with brine and dried (MgSO$_4$). Filtration and removal of EtOAc in vacuo gave the title compound as an oil.

Step C: Preparation of 4-[5-(2-N,N-dimethylaminoethyl)-2-methyl-imidazol-1-ylmethyl]-2-[3-(3(S)-ethyl-1-methyl-2-oxo-azepan-3-yl)-phenoxy]-benzonitrile Bis Trifluoroacetate To a solution of 4-[5-(2-(N,N-dimethylaminoethyl)-2-methyl-imidazol-1-ylmethyl]-2-fluoro-benzonitrile (as described above in Step B) (0.54 g, 1.86 mmol) in DMF (5 mL) was added 3(S)-ethyl-3-(3-hydroxy-phenyl)-1-methyl-azepan-2-one (0.80 g, 0.323 mmol) and Cs$_2$CO$_3$ (0.96 g, 2.95 mmol). The mixture was heated for 42 hr at 60° C., then partitioned with EtOAc and saturated NaHCO$_3$. The organic layer was separated, washed with H$_2$O, brine and dried (MgSO$_4$). Filtration and removal of the EtOAc in vacuo the title compound as its bis trifluoroacetate salt after purification by preparative HPLC eluting with 95:5 to 5:95 gradient of 0.1% TFA/H$_2$O: 0.1% TFA/CH$_3$CN.

FAB mass spectrum m/e 514 (m+1).

Example 35

Preparation of [2-(3-{4-cyano-3-[3-(3S-ethyl-1-methyl-2-oxo-azepan-3-yl)-phenoxy]-benzyl}-2-methyl-3H-imidazol-4-yl)-ethyl]-urea Step A: Preparation of {2-[3-(4-cyano-3-fluoro-benzyl)-2-methyl-3H-imidazol-4-yl]-ethyl}-tert-butyl Urea To a solution of 4-[5-(2-amino-ethyl)-2-methyl-imidazol-1-ylmethyl]-2-fluoro-benzonitrile dihydrochloride (as described in Example 34, Step A) (0.3 g, 0.97 mmol) in DMF (5.0 mL) was added NEt$_3$ (0.41 mL, 2.97 mmol) and t-butyl-isocyanate (0.125 mL, 1.07 mmol). After ½ hr the DMF was removed in vacuo and the residue partitioned between EtOAc and saturated NaHCO$_3$. The organic layer was separated, washed with brine and dried (MgSO$_4$). Filtration and concentration in vacuo gave the title compound as an oil.

Step B: Preparation of {2-[3-(4-cyano-3-fluoro-benzyl)-2-methyl-3H-imidazol-4-yl]-ethyl}-urea {2-[3-(4-cyano-3-fluoro-benzyl)-2-methyl-3H-imidazol-4-yl]-ethyl}-tert-butyl urea (as described above in Step A) (0.41 g) was dissolved in TFA/CH$_2$Cl$_2$ 3:1 (5.0 mL) and stirred at ambient temperature for 72 hr. The solvents were removed in vacuo to obtain the title compound.

Step C: Preparation of [2-(3-{4-cyano-3-[3-(3S-ethyl-1-methyl-2-oxo-azepan-3-yl)-phenoxy]-benzyl}-2-methyl-3H-imidazol-4-yl)-ethyl]-urea To a solution of {2-[3-(4-cyano-3-fluoro-benzyl)-2-methyl-3H-imidazol-4-yl]-ethyl}-urea (as described above in Step B) (0.15 g, 0.52 mmol) in DMF (5 mL) was added 3(S)-ethyl-3-(3-hydroxy-phenyl)-1-methyl-azepan-2-one (0.80 g, 0.323 mmol) and Cs$_2$CO$_3$ (0.96 g, 2.95 mmol). The mixture was heated for 18 hr at 60° C. The solution was partitioned with EtOAc and saturated NaHCO$_3$. The organic layer was washed with H$_2$O, brine and dried (MgSO$_4$). Filtration and concentration to dryness gave the title compound after purification by preparative RP HPLC.

FAB mass spectrum m/e 529 (M+1). Analysis calculated for C$_{30}$H$_{35}$N$_6$O$_3$.0.10 H$_2$O.0.4 CH$_2$Cl$_2$: C, 64.68; H, 6.61; N, 14.89; Found: C, 64.67; H, 6.45; N, 14.36.

Example 36

Preparation of 2-[3-(3-ethyl-1-methyl-2-oxo-azepan-3-yl)-phenoxy]-4-pyridin-N-oxide-3-ylmethyl-benzonitrile To a solution of 2-[3-(3-ethyl-1-methyl-2-oxo-azepan-3-yl)-phenoxy]-4-pyridin-3-ylmethyl-benzonitrile (as described in Example 21) (0.06 g, 0.137 mmol) in CH$_2$Cl$_2$ (5.0 mL) was added MCPBA (0.07 g, 0.41 mmol) and the reaction was stirred for 1 hr. The reaction mixture was partitioned between EtOAc and saturated NaHCO$_3$. The organic layer was washed with brine and dried (MgSO$_4$). Filtration and concentration to dryness gave the title compound after purification by preparative RP HPLC.

FAB mass spectrum m/e 456(M+1). Analysis calculated for C$_{28}$H$_{29}$N$_3$O$_3$.0.30 H$_2$O.1.4 CH$_2$Cl$_2$: C, 60.89; H, 5.63; N, 7.25; Found: C, 60.90; H, 5.68; N, 6.55.

Example 37

Preparation of 2-[3-(1-methyl-2-oxo-pyrrolidin-3-yl)-phenoxy]-4-[1-amino-1-(3-methyl-3H-imidazol-4-yl)-ethyl]-benzonitrile Using the methods described in Example 24A, but substituting racemic 3-(3-methoxy-phenyl)-1-methyl-pyrrolidin-2-one (prepared as described in Example 4, Step A, but using N-methyl-2-pyrrolidinone instead of N-methylcaprolactam), the title compound was prepared.

FAB mass spectrum m/e 416 (M+1).

Similarly, using 3-(3-hydroxy-phenyl)-1-methyl-azepan-2-one (Example 4, Step B) in the methods described in Example 24A, the following compound was prepared: 2-[3-(1-methyl-2-oxo-azepan-3-yl)-phenoxy]-4-[1-amino-1-(3-methyl-3H-imidazol-4-yl)-ethyl]-benzonitrile HRMS theoretical: 444.2393, measured: 444.2399; Analysis calculated for C$_{26}$H$_{31}$N$_5$O.$_2$0.25 H$_2$O.1.15 CF$_3$CO$_2$H: C, 60.89; H, 5.63; N, 7.25. Found: C, 60.90; H, 5.68; N, 6.55.

Using 3-hydroxymethyl-3-(3-hydroxy-phenyl)-1-methyl-azepan-2-one (Example 6, Step B) in the methods described in Example 24A, the following compound was prepared: 2-[3-(3-hydroxymethyl-1-methyl-2-oxo-azepan-3-yl)-phenoxy]-4-[1-amino-1-(3-methyl-3H-imidazol-4-yl)-ethyl]-benzonitrile HRMS theoretical: 474.2500, measured: 474.2498: Analysis calculated for C$_{27}$H$_{33}$N$_5$O$_3$.0.10 H$_2$O.0.40 CF$_3$CO$_2$H: C, 50.99; H, 4.52; N, 9.35. Found: C, 51.00; H, 4.50; N, 9.39.

Example 38

Preparation of 2-[3-(3-cyclopropylmethyl-1-methyl-2-oxo-pyrrolidin-3-yl)-phenoxy]-4-[1-amino-1-(3-methyl-3H-imidazol-4-yl)-ethyl]-benzonitrile Using the methods described in Example 24A, but substituting racemic 3-(3-methoxy-phenyl)-1-methyl-pyrrolidin-2-one (prepared using techniques described in Example 4, Step A, and in Example 6, Step A, but using N-methyl-2-pyrrolidinone instead of N-methylcaprolactam in Example 4 and using cyclopropylmethyl bromide in place of iodomethyl methylether in Example 6), the title compound was prepared.

FAB mass spectrum m/e 470 (M+1). Analysis calculated for C$_{28}$H$_{31}$N$_5$O$_2$.1.00 H$_2$O.2.5 CF$_3$CO$_2$H: C, 51.29; H, 4.63; N, 9.06; Found: C, 51.31; H, 4.42; N, 8.93.

Example 38A

Preparation of the diastereomers of 2-[3-3(R or S)-cyclopropyl-1-methyl-2-oxo-pyrrolidin-3-yl)-phenoxy]-4-[1-(R or S)amino-1-(3-methyl-3H-imidazol-4-yl)-ethyl]-benzonitrile Using the methods described in Example 24A, but substituting racemic 3-cycloproylmethyl-3-(3-methoxyphenyl)-1-methyl-pyrrolidin-2-one (prepared using techniques described in Example 4, Step A, and in Example 6, Step A, but using N-methyl-2-pyrrolidinone instead of N-methylcaprolactam in Example 4 and cyclopropylmethyl bromide in place of iodomethyl methylether in Example 6), the following compounds were prepared, wherein the "(−)" and "(+)" represent the optical rotation of the starting intermediates that are combined to obtain the compounds below:

2-[3-3(R or S)(−)-cyclopropylmethyl-1-methyl-2-oxo-pyrrolidin-3-yl)-phenoxy]-4-[1-(R or S)(+)amino-1-(3-methyl-3H-imidazol-4-yl)-ethyl]-benzonitrile
FAB MS (M+1)=470.

2-[3-3(R or S)(+)-cyclopropylmethyl-1-methyl-2-oxo-pyrrolidin-3-yl)-phenoxy]-4-[1-(R or S)(+)amino-1-(3-methyl-3H-imidazol-4-yl)-ethyl]-benzonitrile
FAB MS (M+1)=470.

2-[3-3(R or S)(−)-cyclopropylmethyl-1-methyl-2-oxo-pyrrolidin-3-yl)-phenoxy]-4-[1-(R or S)(−)amino-1-(3-methyl-3H-imidazol-4-yl)-ethyl]-benzonitrile
FAB MS (M+)=470.

2-[3-3(R or S)(+)-cyclopropylnethyl-1-methyl-2-oxo-pyrrolidin-3-yl)-phenoxy]-4-[1-(R or S)(−)amino-1-(3-methyl-3H-imidazol-4-yl)-ethyl]-benzonitrile
FAB MS (M+1)=470.

Example 38B

Preparation of the Diastereomers of 2-[3-3(R or S)-benzyl-1-methyl-2-oxo-pyrrolidin-3-yl)-phenoxy]-4-[1-(R or S)amino-1-(3-methyl-3H-imidazol-4-yl)-ethyl]-benzonitrile Using the methods described in Example 24A, but substituting racemic 3-benzyl-3-(3-methoxy-phenyl)-1-methyl-pyrrolidin-2-one (prepared using techniques described in Example 4, Step A, and in Example 6, Step A, but using N-methyl-2-pyrrolidinone instead of N-methylcaprolactam in Example 4 and benzyl bromide in place of iodomethyl methylether in Example 6), the following compounds were prepared, wherein the "(−)" and "(+)" represent the optical rotation of the starting intermediates that are combined to obtain the compounds below:

2-[3-3(R or S)(−)-benzyl-1-methyl-2-oxo-pyrrolidin-3-yl)-phenoxy]-4-[1-(R or S)(+)amino-1-(3-methyl-3H-imidazol-4-yl)-ethyl]-benzonitrile
FAB MS (M+1)=506.

2-[3-3(R or S)(+)-benzyl-1-methyl-2-oxo-pyrrolidin-3-yl)-phenoxy]-4-[1-(R or S)(+)amino-1-(3-methyl-3H-imidazol-4-yl)-ethyl]-benzonitrile
FAB MS (M+1)=506.

2-[3-3(R or S)(−)-benzyl-1-methyl-2-oxo-pyrrolidin-3-yl)-phenoxy]-4-[1-(R or S)(−)amino-1-(3-methyl-3H-imidazol-4-yl)-ethyl]-benzonitrile
FAB MS (M+)=506.

2-[3-3(R or S)(+)-benzyl-1-methyl-2-oxo-pyrrolidin-3-yl)-phenoxy]-4-[1-(R or S)(−)amino-1-(3-methyl-3H-imidazol-4-yl)-ethyl]-benzonitrile
FAB MS (M+1)=506.

Example 39

Preparation of 4-[1-(4-allyl-5-bromo-pyridin-3-yl)-1-hydroxy-ethyl]-2-[3-(3-ethyl-1-methyl-2-oxo-azepan-3-yl)-phenoxy]-benzonitrile Trifluoroacetate Step A: Preparation of 4-allyl-3,5-dibromo-pyridine A THF (100 mL) solution of 3,5-dibromopyridine (5 g, 21.1 mmol) at −78° C. was added via cannula to a solution of LDA (22.2 mmol) in THF (700 mL) at −78° C. keeping the temperature <60° C. After stirring for 10 min. at −78° C., allyl bromide (2.56 mL, 29.5 mmol) was added via syringe and the reaction mixture was stirred for 2 hr at −78° C. Saturated NH$_4$Cl (100 mL) was added slowly to quench the reaction. The organic layer was separated, washed with brine and dried (MgSO$_4$). Filtration and concentration in vacuo gave the title compound as an oil which was purified by chromatography on silica gel with hexane:ethyl acetate 9:1.

Step B: Preparation of 4-[(4-allyl-5-bromo-pyridin-3-yl)-hydroxy-methyl]-2-fluoro-benzonitrile To a solution of 4-allyl-3,5-dibromo-pyridine (as described above in Step A) (2.35 g, 8.48 mmol) in THF (100 mL) at −100° C. was added n-BuLi (8.48 mmol), and the mixture was stirred for 5 min. 2-Fluoro-4-formyl-benzonitrile (as described in Example 17, Step A) (1.39 g, 9.33 mmol) in THF (5 mL) was added dropwise via syringe. The reaction mixture was stirred at −78° C. for 1 hr, quenched with saturated NH$_4$Cl (50 mL), and partitioned between EtOAc and saturated NaHCO$_3$. The organic layer was washed with brine and dried (MgSO$_4$). Filtration and concentration to dryness gave the title compound which was purified by chromatography on silica gel with hexane: ethyl acetate 7:3–5:5.

Step C: Preparation of 4-(4-allyl-5-bromo-pyridine-3-carbonyl)-2-fluoro-benzonitrile To a solution of 4-[(4-allyl-5-bromo-pyridin-3-yl)-hydroxy-methyl]-2-fluoro-benzonitrile (as described above in Step B) (0.42 g, 1.21 mmol) in CH$_2$Cl$_2$ (50 mL) was added MnO$_2$ (1.58 g, 18.1 mmol). After 6 hr the reaction was filtered and the CH$_2$Cl$_2$ was removed in vacuo to obtain the title compound.

Step D: Preparation of 4-[1-(4-allyl-5-bromo-pyridin-3-yl)-1-hydroxy-ethyl]-2-fluoro-benzonitrile To a solution of 4-(4-allyl-5-bromo-pyridine-3-carbonyl)-2-fluoro-benzonitrile (as described above in Step C) (0.39 g, 1.13 mmol) in THF (20 mL) at 0° C. was added methylmagnesium bromide (1.13 mmol, 3M) and the reaction was monitored by TLC. Three more portions (1.13 mmol) of CH$_3$MgBr were added until the reaction was complete. The reaction was quenched with saturated NH$_4$Cl (20 mL), then partitioned between EtOAc and saturated NaHCO$_3$. The organic layer was washed with brine and dried (MgSO$_4$). Filtration and concentration to dryness gave the title compound after purification by chromatography on silica eluting with hexane:ethyl acetate 7:3.

Step E: Preparation of 4-[1-(4-allyl-5-bromo-pyridin-3-yl)-1-hydroxy-ethyl]- 2-[3-(3-ethyl-1-methyl-2-oxo-azepan-3-yl)-phenoxy]-benzonitrile Trifluoroacetate To a solution of 4-[1-(4-allyl-5-bromo-pyridin-3-yl)-1-hydroxy-ethyl]-2-fluoro-benzonitrile (as described above in Step D) (0.1 g, 0.277 mmol) in DMF (3 mL) was added 3(S)-ethyl-3-(3-hydroxy-phenyl)-1-methyl-azepan-2-one (0.068 g, 0.277 mmol) and Cs$_2$CO$_3$ (0.25 g, 0.831 mmol) and the mixture was heated at 60° C. for 16 hr. The DMF was removed in vacuo and the residue was partition with EtOAc and saturated NaHCO$_3$. The organic layer was separated, washed with brine and dried (MgSO$_4$). Filtration and concentration to dryness gave the title compound as the trifluoroacetate salt after purification by RP HPLC.

FAB mass spectrum m/e 703 (M+1).

Example 40

Preparation of 1-tert-butyl-3(R or S(+))-[1-{4-cyano-3-[3-(3S-ethyl-1-methyl-2-oxo-azepan-3-yl)-phenoxy]-phenyl}-1-(3-methyl-3H-imidazol-4-yl)-ethyl]-urea Trifluoracetate Step A: Preparation of 1-tert-butyl-3(R or S(+))-[1-(4-cyano-3-fluoro-phenyl)-1-(3-methyl-3H-imidazol-4-yl)-ethyl]-urea trifluoroacetate To a solution of (+)-2-fluoro-4-[1-amino-1-(3-methyl-3H-imidazol-4-yl)-ethyl]-benzonitrile (as described in Example 24A, Step F) (0.1 g, 0.41 mmol) in DMF (2 mL) was added NEt$_3$ (0.17 mL, 1.23 mmol) and t-butylisocyanate (0.102 mL, 0.9 mmol) and the reaction was stirred 18 hr. The DMF was removed in vacuo to obtain the title compound after purification by prep RP HPLC.

Step B: Preparation of 1-tert-butyl-3(R or S(+))-[1-{4-cyano-3-[3-(3S-ethyl-1-methyl-2-oxo-azepan-3-yl)-phenoxy]-phenyl}-1-(3-methyl-3H-imidazol-4-yl)-ethyl]-urea Trifluoracetate Following the methods described in Example 39, Step E but using 1-tert-butyl-3(R or S(+))-[1-(4-cyano-3-fluoro-phenyl)-1-(3-methyl-3H-imidazol-4-yl)-ethyl]-urea trifluoroacetate (as described above in Step A) (0.026 g, 0.057 mmol) and 3(S)-ethyl-3-(3-hydroxy-phenyl)-1-methyl-azepan-2-one (as described in Example 24A, Step B) (0.014 g, 0.057 mmol), the title compound was prepared.

FAB mass spectrum m/e 571 (M+1). Analysis calculated for $C_{33}H_{42}N_6O_3$.1.75 $CF_3CO_2H$.0.25 $H_2O$: C, 56.58; H, 5.76; N, 10.85; Found: C, 56.58; H, 5.77; N, 10.62.

Example 41

Preparation of 1-tert-butyl-3(R or S(−))-[1-{4-cyano-3-[3-(3S-ethyl-1-methyl-2-oxo-azepan-3-yl)-phenoxy]-phenyl}-1-(3-methyl-3H-imidazol-4-yl)-ethyl]-urea Trifluoracetate To a solution of 2-[3-(3S)-ethyl-1-methyl-2-oxo-azepan-3-yl)-phenoxy]-4-[1-(R or S)(−)amino-1-(3-methyl-3H-imidazol-4-yl)-ethyl]-benzonitrile (as described in Example 24D) (0.040 g, 0.086 mmol) in DMF (2 mL) was added NEt$_3$ (0.048 mL, 0.34 mmol) and t-butylisocyanate (0.039 mL, 0.34 mmol) and the reaction was stirred and heated at 80° C. for 72 hr. The DMF was removed in vacuo to obtain the title compound after purification by prep RP HPLC to obtain the title compound (0.023 g).

FAB mass spectrum m/e 571 (M+1). Analysis calculated for $C_{33}H_{42}N_6O_3$.1.95 $CF_3CO_2H$.0.10 $H_2O$: C, 55.75; H, 5.60; N, 10.57; Found: C, 55.74; H, 5.37; N, 10.63.

Using the Same Procedure but Substituting Appropriate Isocyanate for t-butyl Isocyanate the Following Compounds were Prepared:

1-[1-{4-cyano-3(R or S(−))-[3-(3S-ethyl-1-methyl-2-oxo-azepan-3-yl)-phenoxy]-phenyl}-1-(3-methyl-3H-imidazol-4-yl)-ethyl]-3-methyl-urea FAB mass spectrum m/e 529 (M+1). HRMS measured 529.2915; theoretical 529.2921.

1-[1-{4-cyano-3(R or S(−))-[3-(3S-ethyl-1-methyl-2-oxo-azepan-3-yl)-phenoxy]-phenyl}-1-(3-methyl-3H-imidazol-4-yl)-ethyl]-3-phenyl-urea FAB mass spectrum m/e 529 (M+1). HRMS measured 591.3080; theoretical 591.3078.

Example 42

Preparation of [1-{4-cyano-3(R or S(+))-[3-(3S-ethyl-1-methyl-2-oxo-azepan-3-yl)-phenoxy]-phenyl}-1-(3-methyl-3H-imidazol-4-yl)-ethyl]-urea Trifluoroacetate 1-tert-Butyl-3(R or S(+))-[1-{4-cyano-3-[3-(3 S-ethyl-1-methyl-2-oxo-azepan-3-yl)-phenoxy]-phenyl}-1-(3-methyl-3H-imidazol-4-yl)-ethyl]-urea Trifluoracetate (as described in Example 40) (0.02 g) was dissolved in TFA (6.0 mL) and CH$_2$Cl$_2$ (3.0 mL) and stirred for 18 hr. The solvents were removed in vacuo and the residue was lyophylized to obtain the title compound.

FAB mass spectrum m/e 515 (M+1). Analysis calculated for $C_{29}H_{34}N_6O_3$.2.5 $CF_3CO_2H$.1.65 $H_2O$: C, 49.23; H, 4.84; N, 10.13; Found: C, 49.17; H, 4.44; N, 10.45.

Using the Procedure Outlined above but Substituting 1-tert-Butyl-3(R or S(−))-[1-{4-cyano-3-[3-(3S-ethyl-1-methyl-2-oxo-azepan-3-yl)-phenoxy]-phenyl}-1-(3-methyl-3H-imidazol-4-yl)-ethyl]-urea Trifluoracetate (as described in Example 41), the following compound was prepared:

[1-{4-cyano-3(R or S(−))-[3-(3S-ethyl-1-methyl-2-oxo-azepan-3-yl)-phenoxy]-phenyl}-1-(3-methyl-3H-imidazol-4-yl)-ethyl]-urea Trifluoroacetate FAB mass spectrum m/e 515 (M+1).

Example 43

Preparation of N-[1-{4-cyano-3-[3-(3S-ethyl-1-methyl-2-oxo-azepan-3-yl)-phenoxy]-phenyl}-1-(3-methyl-3H-imidazol-4-yl)-ethyl]-acetamide Trifluoroacetate 4-[1-(R or S(−)amino-1-(3-methyl-3H-imidazol-4-yl)-ethyl]-2-[3-(3S-ethyl-1-methyl-2-oxo-azepan-3-yl)-phenoxy]-benzonitrile (as described in Example 24G (0.020 g, 0.042 mmol), Et$_3$N (0.009 mL, 0.063 mmol) and acetyl chloride (0.004 mL, 0.051 mmol) were dissolved in DMF (0.30 mL) and stirred at RT for 16 h. The reaction was quenched with H$_2$O (0.10 mL), purified using reverse phase chromatography (95/5 to 5/95 H$_2$O/CH$_3$CN w/0.1% TFA, flow=15 mL/min) and lyophilized to give the title compound.

FAB mass spectrum m/e 514 (M+1). HRMS measured 514.2819; theoretical 514.2818.

Example 44

Preparation of 2-[3-(3S-ethyl-1-methyl-2-oxo-azepan-3-yl)-phenoxy]-4-[1-methylamino-1-(3-methyl-3H-imidazol-4-yl)-ethyl]-benzonitrile Step A: Preparation of 2-fluoro-4-[1-methylamino-1-(3-methyl-3H-imidazol-4-yl)-ethyl]-benzonitrile 2-Fluoro-4-[1-hydroxy-1-(3-methyl-3H-imidazol-4-yl)-ethyl]-benzonitrile (as described in Example 24A, Step D) (0.400 g, 1.65 mmol) was added to SOCl$_2$ (5 mL) in an ice-H$_2$O bath, and stirred at RT for 45 min. The solution was concentrated in vacuo and azeotroped with anhydrous CH$_2$Cl$_2$ (3×). The solid was dissolved in CH$_2$Cl$_2$ (5 mL) and added via syringe to a −78° C. solution of CH$_3$NH$_2$ (1), then the solution was stirred for 2 h while warming to RT under Ar. The solution was concentrated in vacuo, partitioned between aq. NaHCO$_3$ and CH$_2$Cl$_2$, the aqueous layer was back extracted with CH$_2$Cl$_2$, and the organic layers were combined and dried (MgSO$_4$). Filtration, concentration and chromatographic purification using SiO$_2$ (1.0% MeOH/CH$_2$Cl$_2$ with NH$_4$OH) gave the title compound.

Step B: Preparation of 2-[3-(3S-ethyl-1-methyl-2-oxo-azepan-3-yl)-phenoxy]-4-[1-methylamino-1-(3-methyl-3H-imidazol-4-yl)-ethyl]-benzonitrile 2-Fluoro-4-[1-methylamino-1-(3-methyl-3H-imidazol-4-yl)-ethyl]-benzonitrile (as described above in Step A) (0.147 g, 0.569 mmol), 3-ethyl-3-(3-hydroxy-phenyl)-1-methyl-azepan-2-one (Example 24A, Step B) (0.140 g, 0.569 mmol), KF.Al$_2$O$_3$ (0.168 g) and 18-Crown-6 (0.014 g, 0.052 mmol) were refluxed in CH$_3$CN (10 mL) under Ar for 24 h. The solution was filtered, concentrated in vacuo, and purified using SiO$_2$ chromatography (0–1.5% MeOH/CH$_2$Cl$_2$ with NH$_4$OH) to give the title compound.

FTMS (M+1)=486; Analysis calculated for $C_{29}H_{35}N_5O_2$.0.35 $H_2O$: C, 70.80; H, 7.32; N, 14.24; Found: C, 70.46; H, 6.92; N, 14.37.

The individual diastereomers were separated by chiral HPLC on a ChirakPak AD column to give:
2-[3-(3S-ethyl-1-methyl-2-oxo-azepan-3-yl)-phenoxy]-4-[1(R or S)-methylamino-1-(3-methyl-3H-imidazol-4-yl)-ethyl]-benzonitrile HRMS theoretical: 486.2869, measured: 486.2851: Analysis calculated for $C_{29}H_{35}N_5O_2 \cdot 0.85\ H_2O$: C, 69.53; H, 7.38; N, 13.98. Found: C, 69.50; H, 7.05; N, 13.84.

2-[3-(3S-ethyl-1-methyl-2-oxo-azepan-3-yl)-phenoxy]-4-[1(R or S)-methylamino-1-(3-methyl-3H-imidazol-4-yl)-ethyl]-benzontrile HRMS theoretical: 486.2869, measured: 486.2863: Analysis calculated for $C_{29}H_{35}N_5O_2 \cdot 1.65\ H_2O$: C, 67.58; H, 7.49; N, 13.59. Found: C, 67.57; H, 7.12; N, 13.31.

Example 45

Preparation of 2-[5-(3S-ethyl-1-methyl-2-oxo-azepan-3-yl)-2-iodo-phenoxy]-4-imidazol-1-ylmethyl-benzonitrile Step A: Preparation of 3S-ethyl-3-(3-hydroxy-4-iodo-phenyl)-1-methyl-azepan-2-one To a solution of 3S-ethyl-3-(3-hydroxy-phenyl)-1-methyl-azepan-2-one (as described in Example 24A, Step B) (0.10 g, 0.404 mmol) in DMF (2 mL) was added a solution of N-iodosuccinimide in DMF (2 mL) with stirring under Ar at ambient temperature. After stirring for 16 hr the reaction mixture was partitioned between $CH_2Cl_2$ and $H_2O$, the organic layer separated, washed with $H_2O$, aqueous saturated $NaHCO_3$ solution, brine, and dried ($Na_2SO_4$). Filtration and concentration to dryness gave the title compound as a white solid after chromatography on silica gel eluting with EtOAc: hexane, 1:3 to 1:2. 1D-NOE NMR confirmed the position of the iodo substituent.

Step B: Preparation of 2-[5-(3S-ethyl-1-methyl-2-oxo-azepan-3-yl)-2-iodo-phenoxy]-4-imidazol-1-ylmethyl-benzonitrile 3S-Ethyl-3-(3-hydroxy-4-iodo-phenyl)-1-methyl-azepan-2-one (as described above in Step A) (0.118 g, 0.316 mmol), 2-fluoro-4-imidazol-1-ylmethyl-benzonitrile (as described in Example 1, Step E) (0.64 g, 0.316 mmol), $KF \cdot Al_2O_3$ (0.100 g) and 18-Crown-6 (0.010 g) were refluxed in $CH_3CN$ (10 mL) under Ar for 24 h. The solution was filtered, concentrated in vacuo, and purified using $SiO_2$ chromatography (1–2 % MeOH/$CH_2Cl_2$ with $NH_4OH$) followed by preparative RP HPLC to give the title compound.

FTMS (M+1)=555.

Using the Methods Outlined Above but Substituting N-bromosuccinimide for N-iodosuccinimide in Step A and 2-fluoro-4-[1-(−)amino-1-(3-methyl-3H-imidazol-4-yl)-ethyl]-benzonitrile (as described in Example 24A, Step F) for 2-fluoro-4-imidazol-1-ylmethyl-benzonitrile in Step B, the Following Compound was Prepared:

2-[5-(3S-ethyl-1-methyl-2-oxo-azepan-3-yl)-2-bromo-phenoxy]-4-imidazol-1-ylmethyl-benzonitrile FTMS (M+1)=552; Analysis calculated for $C_{28}H_{32}N_5O_2Br \cdot 2.4\ HCl$: C, 52.71; H, 5.43; N, 10.98; Found: C, 52.62; H, 5.44; N, 11.01.

Example 46

Preparation of 4-[1-amino-1-(3-methyl-3H-imidazol-4-yl)-ethyl]-2-[2-dimethylaminomethyl-5-(3S-ethyl-1-methyl-2-oxo-azepan-3-yl)-phenoxy]-benzonitrile Step A: Preparation of 3-(4-dimethylaminomethyl-3-hydroxy-phenyl)-3S-ethyl-1-methyl-azepan-2-one Formaldehyde (38% in $H_2O$) (0.084 mL, 0.0011 mol) was added to a mixture of 3S-ethyl-3-(3-hydroxy-phenyl)-1-methyl-azepan-2-one (as described in Example 24A, Step B) (0.25 g, 0.001 mol) and aqueous dimethylamine (40% in $H_2O$) (0.45 mL, 0.002 mol) in abs EtOH (3 mL) and the mixture was heated at reflux for 3 hr then concentrated to dryness to give the title compound.

Step B: Preparation of 4-[1-amino-1-(3-methyl-3H-imidazol-4-yl)-ethyl]-2-[2-dimethylaminomethyl-5-(3S-ethyl-1-methyl-2-oxo-azepan-3-yl)-phenoxy]-benzonitrile Using the methods described in Example 45, Step B, but substituting 3-(4-dimethylaminomethyl-3-hydroxy-phenyl)-3S-ethyl-1-methyl-azepan-2-one and 2-fluoro-4-[1-amino-1-(3-methyl-3H-imidazol-4-yl)-ethyl]-benzonitrile (as described in Example 24A, Step F) the title compound was prepared.

FTMS (M+1)=529; Analysis calculated for $C_{31}H_{40}N_6O_2$: C, 70.43; H, 7.63; N, 15.90; Found: C, 70.37; H, 7.61; N, 15.48.

Example 47

Preparation of 2-[3-(3-ethyl-1-methyl-2-oxo-azepan-3-yl)-phenoxy]-4-(4,5,6,7-tetrahydro-3H-imidazo[4,5-]pyridin-4-yl)-benzonitrile Step A: Preparation of 2-fluoro-4-(4,5,6,7-tetrahydro-3H-imidazo[4,5-c]pyridin-4-yl)-benzonitrile 2-Fluoro-4-formyl-benzonitrile (as described in Example 29, Step A) (0.268 g, 1.79 mmol) and histamine (0.200 g, 1.79 mmol) were heated neat at 120° C. for 1.5 h. The molten liquid was cooled to give the title compound.

Step B: Preparation of 4-(4-cyano-3-fluoro-phenyl)-6,7-dihydro-4H-imidazo [4,5-c]pyridine-3,5-dicarboxylic acid di-tert-butyl ester 2-Fluoro-4-(4,5,6,7-tetrahydro-3H-imidazo[4,5-c]pyridin-4-yl)-benzonitrile (as described above in Step A) (0.277 g, 1.143 mmol), $Boc_2O$ (1.10 g, 5.03 mmol), $Et_3N$ (0.70 mL, 5.03 mmol) were dissolved in $CH_2Cl_2$ (20 mL) and stirred at RT for 3 days. The reaction was concentrated and purified using $SiO_2$ chromatography (1% MeOH/$CH_2Cl_2$) to give the title compound.

Step C: Preparation of 2-[3-(3-ethyl-1-methyl-2-oxo-azepan-3-yl)-phenoxy]-4-(4,5,6,7-tetrahydro-3H-imidazo[4,5-]pyridin-4-yl)-benzonitrile 4-(4-Cyano-3-fluoro-phenyl)-6,7-dihydro-4H-imidazo[4,5-c]pyridine-3,5-dicarboxylic acid di-tert-butyl ester (as described above in Step B) (0.120 g, 0.270 mmol), 3-ethyl-3-(3-hydroxy-phenyl)-1-methyl-azepan-2-one (0.067 g, 0.270 mmol), $KF \cdot Al_2O_3$ (0.080 g) and 18-Crown-6 (0.007 g) were refluxed in $CH_3CN$ (5 mL) under Ar for 24 h. The solution was filtered and concentrated in vacuo. The residue was dissolved in $CH_2Cl_2$ (10 mL) and TFA (5 mL) and stirred at RT for ½ h. The solution was concentrated in vacuo, purified using reverse phase chromatography (95/5 to 5/95 $H_2O$/$CH_3CN$ w/0.1% TFA, flow=65 mL/min), lyophilized, and then further separated into two diastereomers using a Chiralpak AS column.

Diastereomer A:
HRMS Measured=470.2562, Theoretical=470.2550.

Diastereomer B:
HRMS Measured=470.2570, Theoretical=470.2550.

Example 48

Preparation of 2-[3-ethyl-2-oxo-azepan-3-yl)-phenoxy]-4-[1-amino-1-(3-methyl-3H-imidazol-4-yl)-ethyl]-benzonitrile Using the methods described in Example 24A, but substituting racemic 3-ethyl-3-(3-hydroxy-phenyl)-azepan-2- one (as described in Example 8, Step B) and racemic 2-fluoro-4-[1-amino-1-(3-methyl-3H-imidazol-4-yl)-ethyl]-benzonitrile (as described in Example 24A, Step F), the following compound was prepared: 2-[3-ethyl-2-oxo-azepan-3-yl)-phenoxy]-4-[1-amino-1-(3-methyl-3H-imidazol-4-yl)-ethyl]-benzonitrile FAB MS (M+1)=458; Analysis calculated for $C_{27}H_{31}N_5O_2 \cdot 0.65\ H_2O$: C, 69.10; H, 6.94; N, 14.92; Found: C, 69.08; H, 6.96; N, 13.86.

Example 49

Preparation of 4-[1-amino-1-(3-methyl-3H-imidazol-4-yl)-ethyl]-2-{3-[3-ethyl-1-(3-hydroxy-propyl)-2-oxo-azepan-3-yl]-phenoxy}-benzonitrile ditrifluoroacetate Step A: Preparation of 1-allyl-3-ethyl-3-(3-methoxy-phenyl)-azepan-2-one To a solution of 3-ethyl-3-(3-methoxy-phenyl)-azepan-2-one (as described in Example 8, Step A) (2.62 g, 10.6 mmol) in DMF (20 mL) at 0° C. was added NaH (0.47 g, 11.6 mmol) and the mixture was stirred for 20 min at 0° C. and 20 min at 25° C. Allyl bromide (1.1 mL, 12.7 mmol) was added. After 5 hr, additional NaH (0.12 g, 3 mmol) and allyl bromide (0.3 mL, 3.5 mmol) were added and stirring was continued for 16 hr. The reaction was quenched with $H_2O$ and the solvents removed in vacuo. The residue was partitioned between EtOAc and saturated $NaHCO_3$ solution. The organic layer was separated, washed with brine and dried ($MgSO_4$). Filtration and concentration gave the title compound after chromatography on silica gel with hexane and ethyl acetate 9:1.

Step B: Preparation of 3-ethyl-1-(3-hydroxy-propyl)-3-(3-methoxy-phenyl)-azepan-2-one To a solution of 1-allyl-3-ethyl-3-(3-methoxy-phenyl)-azepan-2-one (as described above in Step A) (0.83 g, 2.89 mmol) in THF (20 mL) at 0° C. was added $BH_3 \cdot THF$ (1M, 2.85 mL, 2.89 mmol) with stirring. After 1 hr at 25° C. the reaction mixture was cooled to 0° C. and EtOH (5 mL), 1M NaOH (5 mL), and 30% $H_2O_2$ (10 mL) were added. The reaction mixture was stirred for 1 hr at 25° C. The solvents were removed in vacuo and the residue was partitioned between EtOAc and saturated $NaHCO_3$ solution. The organic layer was washed with brine and dried ($MgSO_4$), the solvents removed in vacuo and the crude product chromatographed on silica gel with hexane and ethyl acetate 1:1 to obtain the title compound.

Step C: Preparation of 3-ethyl-3-(3-hydroxy-phenyl)-1-(3-hydroxy-propyl)-azepan-2-one To a solution of 3-ethyl-1-(3-hydroxy-propyl)-3-(3-methoxy-phenyl)-azepan-2-one (as described above in Step B) (0.12 g, 0.393 mmol) in $CH_2Cl_2$ (20 mL) at −78° C. was added $BBr_3$ (1M, 0.786 mL, 0.786 mmol). The reaction mixture was stirred for 3 hr at 25° C. then quenched with $H_2O$ and extracted with EtOAc. The organic layer was separated, washed with brine and dried ($MgSO_4$). Filtration and concentration to dryness gave the title compound after purification by preparative RP HPLC.

Step D: Preparation of 4-[1-amino-1-(3-methyl-3H-imidazol-4-yl)-ethyl]-2-{3-[3-ethyl-1-(3-hydroxy-propyl)-2-oxo-azepan-3-yl]-phenoxy}-benzonitrile Ditrifluoroacetate Using the procedure described in Example 47, Step C, 3-ethyl-3-(3-hydroxyphenyl)-1-(3-hydroxy-propyl)-azepan-2-one (as described above in Step C) (0.036 g, 0.124 mmol) and 2-fluoro-4-[1-amino-1-(3-methyl-3H-imidazol-4-yl)-ethyl]-benzonitrile (as described in Example 24A, Step F) (0.030 g, 0.124 mmol) were reacted to obtain the title compound after purification by RP HPLC.

FAB MS; M+1=516. Analysis calculated for $C_{30}H_{37}N_5O_3 \cdot 2.5\ CF_3CO_2H \cdot 2.15\ H_2O$: C, 50.07; H, 5.26; N, 8.34; Found: C, 50.07; H, 4.91; N, 8.49.

Example 50

Preparation of 4-[1-amino-1-(3-methyl-3H-imidazol-4-yl)-ethyl]-2-{3-[3-ethyl-1-propyl-2-oxo-azepan-3-yl]-phenoxy}-benzonitrile ditrifluoroacetate Step A: Preparation of 1-propyl-3-ethyl-3-(3-methoxy-phenyl)-azepan-2-one Hydrogenation of 1-allyl-3-ethyl-3-(3-methoxy-phenyl)-azepan-2-one (as described in Example 49, Step A) in a Parr apparatus in EtOH with 10% Pd/C provided the title compound after filtration and concentration.

Step B: Preparation of 1-propyl-3-ethyl-3-(3-hydroxy-phenyl)-azepan-2-one

Using the method described in Example 49, Step C, the title compound was prepared.

Step C: Preparation of 4-[1-amino-1-(3-methyl-3H-imidazol-4-yl)-ethyl]-2-{3-[3-ethyl-1-propyl-2-oxo-azepan-3-yl]-phenoxy}-benzonitrile Ditrifluoroacetate Using the procedure described in Example 47, Step C, 3-ethyl-3-(3-hydroxy-phenyl)-1-propyl-azepan-2-one (as described above in Step B) (0.036 g, 0.124 mmol) and 2-fluoro-4-[1-amino-1-(3-methyl-3H-imidazol-4-yl)-ethyl]-benzonitrile (as described in Example 24A, Step F) (0.030 g, 0.124 mmol) were reacted to obtain the title compound after purification by RP HPLC.

FAB MS; M+1=500. Analysis calculated for $C_{30}H_{37}N_5O_3 \cdot 2.5\ CF_3CO_2H \cdot 0.1\ H_2O$: C, 53.44; H, 5.09; N, 8.91; Found: C, 53.46; H, 4.77; N, 8.70.

Example 51

Preparation of 2-{3-[1-(2-amino-ethyl)-3-ethyl-2-oxo-azepan-3-yl]-phenoxy}-4-1-amino-1-(3-methyl-3H-imidazol-4-yl)-ethyl]-benzonitrile tris-trifluoroacetate Step A: Preparation of 3-ethyl-1-(2-hydroxy-ethyl)-3-(3-methoxy-phenyl)-azepan-2-one A solution of 1-allyl-3-ethyl-3-(3-methoxy-phenyl)-azepan-2-one (as described in Example 49, Step A) (0.9 g, 3.1 mmol) in MeOH (20 mL) at −78° C. was saturated with O3 for 20 min. The solution was warmed to −40° C. for 10 min then $NaBH_4$ (0.36 g, 9.4 mmol) was added and the reaction mixture was stirred at 25° C. for 1 hr. The MeOH was removed in vacuo, and the residue was partitioned between EtOAc and saturated $NaHCO_3$ solution. The organic layer was washed with brine and dried ($MgSO_4$). Filtration and concentration to dryness gave the title compound.

Step B: Preparation of 1-(2-azido-ethyl)-3-ethyl-3-(3-methoxy-phenyl)-azepan-2-one To a solution of 3-ethyl-1-(2-hydroxy-ethyl)-3-(3-methoxyphenyl)-azepan-2-one (as described above in Step A) (0.6 g, 2.05 mmol) in $CH_2Cl_2$ (15 mL) at 0° C. was added $NEt_3$ (0.85 mL, 6.15 mmol) and methanesulfonyl chloride (0.19 mL, 2.45 mmol). The mixture was stirred for 30 min at 25° C. then $NaN_3$ (0.27 g, 4.1 mmol) in DMF (3 mL) was added. The reaction was stirred for 18 hr then partitioned between EtOAc and saturated $NaHCO_3$ solution. The organic layer was washed with brine and dried ($MgSO_4$) Filtration and concentration to dryness gave the title compound.

FAB MS; M+1=317.

Step C: Preparation of 1-(2-amino-ethyl)-3-ethyl-3-(3-methoxy-phenyl)-azepan-2-one Hydrochloride To a solution of 1-(2-azido-ethyl)-3-ethyl-3-(3-methoxy-phenyl)-azepan-2-one (as described above in Step B) (0.56 g, 1.94 mmol) in MeOH (20 mL) and 10% HCl (5 mL) was added 10% Pd/C (0.1 g) under argon. The mixture was placed under 1 atm of $H_2$ and stirred for 2 hr. Filtration and concentration to dryness gave the title compound.

Step D: Preparation of 1-(2-amino-ethyl)-3-ethyl-3-(3-hydroxy-phenyl)-azepan-2-one Trifluoroacetate To a solution of 1-(2-amino-ethyl)-3-ethyl-3-(3-methoxy-phenyl)-azepan-2-one hydrochloride (as described above in Step C) (0.1 g, 0.306 mmol) in $CH_2Cl_2$ (10 mL) at −78° C. was added $BBr_3$ (1M, 0.60 mL, 0.60 mmol). After stirring for 2 hr at 25° C. the reaction mixture was quenched with $H_2O$, the solvents removed in vacuo and the residue purified by prep RP HPLC to obtain the title compound.

Step E: Preparation of 2-{3-[1-(2-amino-ethyl)-3-ethyl-2-oxo-azepan-3-yl]-phenoxy}-4-[1-amino-1-(3-methyl-3H-imidazol-4-yl)-ethyl]-benzonitrile Tri-trifluoroacetate Using the procedure described in Example 47, Step C, 1-(2-amino-ethyl)-3-ethyl-3-(3-hydroxy-phenyl)-azepan-2-one trifluoroacetate (as described above in Step D) (0.070 g, 0.18 mmol) and 2-fluoro-4-[1-(−)amino-1-(3-methyl-3H-imidazol-4-yl)-ethyl]-benzonitrile (as described in Example 24A, step F) (0.044 g, 0.18 mmol) were reacted to obtain the title compound.

FAB MS; M+1=501. Analysis calculated for $C_{29}H_{36}N_6O_2 \cdot 3.45\ CF_3CO_2H$: C, 48.23; H, 4.45; N, 9.40; Found: C, 48.59; H, 4.05; N, 9.28.

Example 52

Preparation of {2-[3-(3-{5-[1-amino-1-(3-methyl-3H-imidazol-4-yl)-ethyl]2-cyano-phenoxy}-phenyl)-3-ethyl-2-oxo-azepan-1-yl]-ethyl}-urea Ditrifluoroacetate Step A: Preparation of 1-tert-butyl-3-{2-[3-ethyl-3-(3-methoxy-phenyl)-2-oxo-azepan-1-yl]-ethyl}-urea To a solution of 1-(2-amino-ethyl)-3-ethyl-3-(3-methoxy-phenyl)-azepan-2-one hydrochloride (as described in Example 51, Step C) (0.27 g, 0.826 mmol) in DMF (5.0 mL) was added $NEt_3$ (0.35 mL, 2.48 mmol) and t-butylisocyanate (0.29 mL, 2.48 mmol) and the solution was stirred for 18 hr. The DMF was removed in vacuo, and the residue partitioned between EtOAc and $H_2O$. The organic layer was washed with brine and dried ($MgSO_4$), and the solvents removed in vacuo to obtain the title compound.

Step B: Preparation of {2-[3-ethyl-3-(3-methoxy-phenyl)-2-oxo-azepan-1-yl]-ethyl}-urea To a solution of 1-tert-butyl-3-{2-[3-ethyl-3-(3-methoxy-phenyl)-2-oxo-azepan-1-yl]-ethyl}-urea (as described above in Step A) (0.35 g, 0.93 mmol) in $CH_2Cl_2$ (2.0 mL) was added TFA (6.0 mL) and the solution was stirred for 72 hr. The solvents were removed in vacuo to obtain the title compound.

Step C: Preparation of {2-[3-ethyl-3-(3-hydroxy-phenyl)-2-oxo-azepan-1-yl]-ethyl}-urea To a solution of {2-[3-ethyl-3-(3-methoxy-phenyl)-2-oxo-azepan-1-yl]-ethyl}-urea (as described above in Step B) (0.14 g, 0.421 mmol) in $CH_2Cl_2$ (10 mL) at −78° C. was added $BBr_3$ (1M, 0.842 mL, 0.842 mmol). After stirring for 1 hr at 25° C. the reaction was quenched with $H_2O$ and partitioned with EtOAc and 10% HCl. The organic layer was washed with brine and dried ($MgSO_4$), and the solvent removed in vacuo to obtain the title compound.

Step D: Preparation of {2-[3-(3-{5-[1-amino-1-(3-methyl-3H-imidazol-4-yl)-ethyl]2-cyano-phenoxy}-phenyl)-3-ethyl-2-oxo-azepan-1-yl]-ethyl}-urea Ditrifluoroacetate Using the procedure described in Example 47, Step C, {2-[3-ethyl-3-(3-hydroxy-phenyl)-2-oxo-azepan-1-yl]-ethyl}-urea (as described above in Step C) (0.070 g, 0.23 mmol) and 2-fluoro-4-[1-(−)amino-1-(3-methyl-3H-imidazol-4-yl)-ethyl]-benzonitrile (as described in Example 24A, Step F) (0.058 g, 0.23 mmol) were reacted to prepare the title compound.

FAB MS; M+1=544. Analysis calculated for $C_{30}H_{37}N_7O_3 \cdot 2.5\ CF_3CO_2H \cdot 0.9\ H_2O$: C, 49.81; H, 4.81; N, 11.62; Found: C, 49.81; H, 4.55; N, 11.47.

In a Similar Manner, Using Methylisocyanate in Place of t-butylisocyanate in Step A, the Following Compound was Prepared:

N-{2-[3-(3-{5-[1-amino-1-(3-methyl-3H-imidazol-4-yl)-ethyl]2-cyano-phenoxy}-phenyl)-3-ethyl-2-oxo-azepan-1-yl]-ethyl}-N'-methyl urea Ditrifluoroacetate FAB MS; M+1=558. Analysis calculated for $C_{31}H_{41}N_7O_3 \cdot 2.5\ CF_3CO_2H \cdot 0.4\ H_2O$: C, 50.87; H, 5.02; N, 11.54; Found: C, 50.87; H, 4.73; N, 11.33.

Example 53

Preparation of 4-[1-amino-1-(3-methyl-3H-imidazol-4-yl)-ethyl]-2-{3-[1-(2-dimethylamino-ethyl)-3-ethyl-2-oxo-azepan-3-yl]-phenoxy}-benzonitrile tri-trifluoroacetate Step A: Preparation of 1-(2-dimethylamino-ethyl)-3-ethyl-3-(3-methoxy-phenyl)-azepan-2-one Trifluoroacetate To a solution of 1-(2-amino-ethyl)-3-ethyl-3-(3-methoxy-phenyl)-azepan-2-one hydrochloride (as described in Example 51, Step C) (0.2 g, 0.612 mmol) in MeOH (7.0 mL) was added paraformaldehyde (0.1 g) and $NaCNBH_3$ (0.115 g, 1.84 mmol) and the solution was stirred for 18 hr. The MeOH was removed in vacuo and the residue partitioned between EtOAc and saturated $NaHCO_3$ solution. The organic layer was washed with brine and dried ($MgSO_4$), and the solvents removed in vacuo to obtain the title compound after purification by preparative RP HPLC.

Step B: Preparation of 1-(2-dimethylamino-ethyl)-3-ethyl-3-(3-hydroxy-phenyl)-azepan-2-one Trifluoroacetate To a solution of 1-(2-dimethylamino-ethyl)-3-ethyl-3-(3-methoxy-phenyl)-azepan-2-one Trifluoroacetate (as described above in Step A) (0.1 g, 0.23 mmol) in $CH_2Cl_2$ (10 mL) at −78° C. was added $BBr_3$ (1M, 0.46 mL, 0.46 mmol). After stirring for 2 hr at 25° C. the reaction mixture was quenched with $H_2O$, the solvents removed in vacuo, and the residue purified by prep RP HPLC to obtain the title compound.

Step C: Preparation of 4-[1-amino-1-(3-methyl-3H-imidazol-4-yl)-ethyl]-2-{3-[1-(2-dimethylamino-ethyl)-3-ethyl-2-oxo-azepan-3-yl]-phenoxy}-benzonitrile Tri-trifluoroacetate Using the procedure described in Example 47, Step C, 1-(2-dimethylamino-ethyl)-3-ethyl-3-(3-hydroxy-phenyl)-azepan-2-one trifluoroacetate (as described above in Step B) (0.060 g, 0.154 mmol) and 2-fluoro-4-[1-(−)amino-1-(3-methyl-3H-imidazol-4-yl)-ethyl]-benzonitrile (as described in Example 24A, Step F) (0.040 g, 0.16 mmol) were reacted to obtain the title after purification by preparative RP HPLC.

FAB MS; M+1=529. Analysis calculated for $C_{31}H_{40}N_6O_2 \cdot 3.70\ CF_3CO_2H$: C, 48.52; H, 4.63; N, 8.84; Found: C, 48.55; H, 4.26; N, 8.67.

Example 54

Preparation of 4-[1-(R or S)amino-1-(3-methyl-3H-imidazol-4-yl)-ethyl]-2-{3-[1-(2-hydroxyethyl)-3-ethyl-2-oxo-azepan-3-yl]-phenoxy}-benzonitrile Tris trifluoroacetate Step A: Preparation of 3-ethyl-3-(3-benzyloxy-phenyl)-azepan-2-one To a solution of 3-ethyl-3-(3-hydroxy-phenyl)-azepan-2-one (Example 8, Step B) (1.28 g, 0.0055 mol) in DMF (50 mL) was added Cs$_2$CO$_3$ (1.79 g, 0.055 mmol) and benzyl bromide (0.653 mL, 0.0055 mmol) at ambient temperature. After 1.5 h the reaction was concentrated to remove most of the DMF and the residue was partitioned between EtOAc and H$_2$O. The aqueous layer was washed with EtOAc, the organics combined, washed with brine, and dried (MgSO$_4$). Filtration and concentration to dryness gave the title compound.

Step B: Preparation of 1-allyl-3-ethyl-3-(3-benzyloxy-phenyl)-azepan-2-one

To a solution of 3-ethyl-3-(3-benzyloxy-phenyl)-azepan-2-one, as described above in Step A, (1.65 g, 5.1 mmol) in DMF (25 mL) at 0° C. was added NaH (0.265 g, 6.63 mmol) and the mixture was stirred for 20 min at 0° C. and 20 min at 25° C. Allyl bromide (0.66 mL, 7.65 mmol) was added. After 5 hr, additional NaH (0.13 g, 3 mmol) and allyl bromide (0.33 mL, 3.5 mmol) were added and stirring was continued for 16 hr. The reaction was quenched with H$_2$O and the solvents removed in vacuo. The residue was partitioned between EtOAc and saturated NaHCO$_3$ solution. The organic layer was separated, washed with brine and dried (MgSO$_4$). Filtration and concentration gave the title compound after chromatography on silica gel with hexane and ethyl acetate 9:1.

Step C: Preparation of 3-ethyl-1-(2-hydroxy-ethyl)-3-(3-benzyloxy-phenyl)-azepan-2-one A solution of 1-allyl-3-ethyl-3-(3-benzyloxy-phenyl)-azepan-2-one, as described in Step B above, (0.87 g, 2.4 mmol) in MeOH (20 mL) at –78° C. was saturated with O3 for 25 min. The solution was warmed to –40° C. for 10 min then NaBH$_4$ (0.363 g, 9.6 mmol) was added and the reaction mixture was stirred at 25° C. for 1 hr. The MeOH was removed in vacuo, and the residue was partitioned between EtOAc and saturated NaHCO$_3$ solution. The organic layer was washed with brine and dried (MgSO$_4$). Filtration and concentration to dryness gave the title compound after chromatography on silica gel eluting with hexane/EtOAc, 1/1.

Step D: Preparation of 3-ethyl-1-(2-hydroxy-ethyl)-3-(3-hydroxy-phenyl)-azepan-2-one To a solution of 3-ethyl-1-(2-hydroxy-ethyl)-3-(3-benzyloxy-phenyl)-azepan-2-one, as described in Step C, (0.270 g, 0.735 mmol) in MeOH (15 mL) was added 10% Pd on C (0.06 g), and the mixture was hydrogenated under a H$_2$ balloon at ambient temperature for 16 h. The reaction mixture was filtered, and the filtrate concentrated to dryness to give the title compound.

Step E: Preparation of 4-[1-(R or S)amino-1-(3-methyl-3H-imidazol-4-yl)-ethyl]-2-{3-[1-(2-hydroxyethyl)-3-ethyl-2-oxo-azepan-3-yl]-phenoxy}-benzonitrile Tris trifluoroacetate Using the procedure described in Example 47, Step C, 3-ethyl-1-(2-hydroxy-ethyl)-3-(3-hydroxy-phenyl)-azepan-2-one (0.060 g, 0.216 mmol) and 2-fluoro-4-[1-(–)amino-1-(3-methyl-3H-imidazol-4-yl)-ethyl]-benzonitrile (as described in Example 24A, Step F) (0.053 g, 0.216 mmol) were reacted to prepare the title compound.

FAB MS; M+1=502; Analysis calculated for C$_{29}$H$_{35}$N$_5$O$_3$.2.5 CF$_3$CO$_2$H.0.1 H$_2$O: C, 51.79; H, 4.82; N, 8.88; Found: C, 51.78; H. 4.68; N, 8.77.

Example 55

Preparation of 4-[1-amino-1-(3-methyl-3H-imidazol-4-yl)-ethyl]-2-{3-[1-(2-methoxyethyl)-3R-ethyl-2-oxo-azepan-3-yl]-phenoxy}-benzonitrile tris trifluoroacetate Step A: Preparation of 3-ethyl-1-(2-methoxy-ethyl)-3-(3-benzyloxy-phenyl)-azepan-2-one Sodium hydride (0.017 g, 0.425 mmol) was added to a solution of 3-ethyl-1-(2-hydroxy-ethyl)-3-(3-benzyloxyphenyl)-azepan-2-one, as described in Example 54, Step C, (0.12 g, 0.327 mmol) in DMF (5 mL) at 0° C. with stirring. After 20 min CH$_3$I (0.041 mL, 0.653 mmol) was added and stirring was continued at room temperature for 16 h. The reaction was quenched with H$_2$O and the solvents removed in vacuo. The residue was partitioned between EtOAc and saturated NaHCO$_3$ solution. The organic layer was separated, washed with brine and dried (MgSO$_4$). Filtration and concentration gave the title compound.

Step B: Preparation of 3-ethyl-1-(2-methoxyethyl)-3-(3-hydroxy-phenyl)-azepan-2-one To a solution of 3-ethyl-1-(2-methoxy-ethyl)-3-(3-benzyloxy-phenyl)-azepan-2-one, as described above in Step A, (0.120 g, 0.412 mmol) in MeOH (20 mL) was added 10% Pd on C (0.025 g), and the mixture was hydrogenated under a H$_2$ balloon at ambient temperature for 48 h. The reaction mixture was filtered, and the filtrate concentrated to dryness to give the title compound.

Step C: Preparation of 4-[1-amino-1-(3-methyl-3H-imidazol-4-yl)-ethyl]-2-{3-[1-(2-methoxyethyl)-3-ethyl-2-oxo-azepan-3-yl]-phenoxy}-benzonitrile Tris trifluoroacetate Using the procedure described in Example 47, Step C, 3-ethyl-1-(2-methoxy-ethyl)-3-(3-hydroxy-phenyl)-azepan-2-one, as described above in Step B, (0.090 g, 0.309 mmol) and 2-fluoro-4-[1-(–)amino-1-(3-methyl-3H-imidazol-4-yl)-ethyl]-benzonitrile (as described in Example 24A, Step F) (0.075 g, 0.309 mmol) were reacted to prepare the title compound.

FAB MS; M+1=516; Analysis calculated for C$_{30}$H$_{37}$N$_5$O$_3$.2.4 CF$_3$CO$_2$H: C, 52.95; H, 5.03; N, 8.87; Found: C, 53.08; H, 4.65; N, 8.79.

Example 56

Preparation of 4-Imidazol-1-ylmethyl-2-[3-(1-methyl-7-oxo-azepan-2-yl)-phenoxy]-benzonitrile Hydrochloride Step A: Preparation of 2-(3-methoxyphenyl)-cyclohexanone To 1.6 M n-BuLi in hexane (12.5 mL, 20 mmol) at 0° C. was added a solution of 2,2,6,6-tetramethyl piperidine (3.4 mL, 20 mmol) in anhydrous THF (40 mL) over 5 min. Cyclohexanone (2.1 mL, 20 mmol) was added dropwise. After stirring the reaction mixture for 10 min, a further portion of 1.6M n-BuLi in hexane (12.5 mL, 20 mmol) was added, the mixture stirred for 10 min, and 2-chloroanisole (2.5 mL, 20 mmol) was added. After stirring for 30 min under Ar, the reaction mixture was quenched with H$_2$O (300 mL) and extracted with EtOAc (150 mL). The organic layer was separated, washed with 2N HCl (100 mL), H$_2$O (200 mL) and brine, then dried (MgSO$_4$). Filtration and concentration gave the title compound after SiO$_2$ chromatography (CHCl$_3$:MeOH, 200:1).

Step B: Preparation of 2-(3-methoxyphenyl)-cyclohexanone Oxime 2-(3-Methoxyphenyl)-cyclohexanone, as described in Step A above, (0.61 g, 3 mmol), hydroxylamine hydrochloride (0.40 g, 6 mmol) and sodium acetate (0.80, 6.2 mmol) were combined in EtOH (4 mL): H$_2$O (2 mL) and heated at reflux for 3 h. The reaction mixture was concentrated, then partitioned between EtOAc (100 mL) and H$_2$O (100 mL), the organic layer separated, washed with H$_2$O, brine, and dried (MgSO$_4$). Filtration and concentration to dryness gave the title compound.

Step C: Preparation of 7-(3-methoxyphenyl)-azepan-2-one 2-(3-Methoxyphenyl)-cyclohexanone oxime, as described above in Step B, (0.62 g, 2.8 mmol) and polyphosphoric acid (20 g) were combined and heated at 115–120° C. with stirring for 20 min. The dark mixture was poured into ice (100 g) with stirring, diluted with $H_2O$ (200 mL), then extracted with $CHCl_3$ (5×100 mL), the organic layers combined, washed with brine, dried ($MgSO_4$), filtered, and concentrated to dryness to give the title compound after $SiO_2$ chromatography ($CHCl_3$:MeOH, 100:1 to 20:1).

FAB MS (M+1) 220;

Step D: Preparation of 7-(1-methyl-3-methoxyphenyl)-azepan-2-one 7-(3-Methoxyphenyl)-azepan-2-one, as described above in Step C, (0.13 g, 0.6 mmol) and NaH (60% dispersion in mineral oil) (0.03 g, 0.75 mmol) were dissolved in THF (5 mL) under Ar at ambient temperature. After 0.25 hours, iodomethane (0.064 mL, 1.0 mmol) was added and stirring was continued for 20 h. The reaction mixture was partitioned between EtOAc (100 mL)—$H_2O$ (100 mL), the organic layer separated, washed with $H_2O$, dried ($MgSO_4$), filtered and concentrated to give the title compound after $SiO_2$ chromatography ($CHCl_3$:MeOH, 100:1 to 50:1).

FAB MS (M+1) 234.

Step E: Preparation of 7-(1-methyl-3-hydroxyphenyl)-azepan-2-one

BBr3 (1M in $CH_2Cl_2$) (1 mL, 1 mmol) was added dropwise to a solution of 7-(1-methyl-3-methoxyphenyl)-azepan-2-one, as described in Step D above, (0.06 g, 0.26 mmol) in $CHCl_3$ (1 mL) at 0° C. with stirring. The ice bath was removed and stirring was continued for 1 h. The reaction mixture was partitioned between EtOAc (100 mL)—$H_2O$ (100 mL), the organic layer separated, washed with $H_2O$, dried ($MgSO_4$), filtered and concentrated to give the title compound after $SiO_2$ chromatography ($CHCl_3$:MeOH, 10:1).

FAB MS (M+1) 219.

Step F: Preparation of 4-Imidazol-1-ylmethyl-2-[3-(1-methyl-7-oxo-azepan-2-yl)-phenoxy]-benzonitrile 7-(1-Methyl-3-hydroxyphenyl)-azepan-2-one, as described above in Step E, (0.055 g, 0.25 mmol), 2-fluoro-4-imidazol-1-ylmethyl-benzonitrile, as described in Example 1, Step E, (0.055 g, 0.27 mmol) and $Cs_2CO_3$ (0.490 g, 0.75 mmol) were dissolved in DMSO (4 mL) and stirred at 50° C. under Ar for 3 h. The reaction mixture was cooled and partitioned between EtOAc (120 mL) and $H_2O$ (150 mL). The organic layer was separated, washed with H2O (2×100 mL), dried ($MgSO_4$). Filtration, concentration and RPLC (eluting with a 0.1% TFA/H2O: 0.1% TFA/$CH_3CN$ gradient, 95:5 to 5:95) gave the title compound after conversion to the hydrochloride salt.

HRMS theoretical: 401.1972, measured: 401.1980. Analysis calculated for $C_{24}H_{24}N_4O_2 \cdot 0.55$ HCl$\cdot 0.25$ $C_2H_5OH$: C, 62.81; H, 5.82; N, 11.96; Found: C, 62.83; H, 5.56; N, 11.77.

Example 57

Preparation of 4-[1-Amino-1-(3-methyl-3H-imidazol-4-yl)-ethyl]-2-[3-(4-methyl-3-oxo-2-propyl-morpholin-2-yl)-phenoxy]-benzonitrile Step A: Preparation of 4-Methyl-morpholine-2,3-dione Following the procedure of G. Drefahl, M. Hartmann and A. Skurk, Chem. Ber. 1966, 99, diethyl oxalate (1.81 mL, 0.0133 mol) and N-methylamino-ethanol (1 g, 0.0133 mol) were dissolved in toluene(50 mL) and heated at reflux for 5 h. The reaction mixture was concentrated to dryness, triturated with ether, and the residue chromatographed ($SiO_2$, 0–5% MeOH in $CH_2Cl_2$) to give the title compound.

$^1$H NMR ($CDCl_3$) δ 4.53 (t, 2H), 3.70 (t, 2H), 3.18 (s, 3H).

Step B: Preparation 2-Hydroxy-2-(3-methoxy-phenyl)-4-methyl-morpholin-3-one

Following the procedure described by S. Murahashi et al., Bull. Chem. Soc. Japan, 69, 2079–2090 (1996), 3-bromoanisole (0.633 mL, 5 mmol) in dry THF (2 mL) was added dropwise to a mixture of Mg (0.121 g, 5 mmol) and a few crystals of $I_2$ in THF (2 mL) at ambient temperature under Ar. After stirring for 1 h, this solution was added dropwise to a solution of 4-methyl-morpholine-2,3-dione (0.15 g, 1.16 mmol) in $CH_2Cl_2$ (2 mL) under Ar at 0° C. and the reaction mixture stirred for 1 h at 0° C. then left to warm to room temperature for 1 h. The reaction was quenched with aqueous ammonium chloride solution and partitioned between $CH_2Cl_2$ and $H_2O$. The aqueous layer was washed with $CH_2Cl_2$, the organic layers combined, dried ($MgSO_4$), filtered and concentrated to dryness to give the title compound after chromatography (($SiO_2$, 1% MeOH in $CH_2Cl_2$). FAB MS (M+1) 238.

Step C: Preparation of 2-Allyl-2-(-3-methoxy-phenyl)-4-methyl-morpholine-3-one

Following the procedure described by S. Pansare et al., J. Org. Chem. 1998, 63, 4120–4124, 2-hydroxy-2-(3-methoxy-phenyl)-4-methyl-morpholin-3-one, as described in Step C above, (0.133 g, 0.56 mmol) was dissolved in anhydrous $CH_2Cl_2$ (10 mL) under Ar, treated with allyltrimethylsilane (0.534 mL, 3.36 mmol), the mixture cooled to −23° C., then treated with $TiCl_4$ (0.37 mL, 3.36 mmol). After 15 min the reaction mixture was quenched slowly with saturated aqueous $NH_4Cl$ solution, left to warm to room temperature, and partitioned between $CH_2Cl_2$ and $H_2O$. The aqueous layer was washed with $CH_2Cl_2$, the organic layers combined, dried ($Na_2SO_4$), filtered and concentrated to dryness to give the title compound after chromatography ($SiO_2$, 0–1% MeOH in $CH_2Cl_2$).

FAB MS (M+1) 262.

Step D: Preparation of 2-(-3-methoxy-phenyl)-4-methyl-2-propyl-morpholine-3-one

2-Allyl-2-(-3-methoxy-phenyl)-4-methyl-morpholine-3-one, as described above in Step C, (0.400 g, 1.53 mmol) was dissolved in MeOH (20 mL), the solution purged with Ar, treated with 10% Pd/C (0.060 g), and hydrogenated under a $H_2$ balloon. After 2 h the reaction mixture was filtered through a celite pad and concentrated to dryness to give the title compound.

Step E: Preparation of 2-(-3-hydroxy-phenyl)-4-methyl-2-propyl-morpholine-3-one $BBr_3$ (1M in $CH_2Cl_2$) (0.341 mL, 0.341 mmol) was added dropwise to a solution of 2-(-3-methoxy-phenyl)-4-methyl-2-propyl-morpholine-3-one, as described above in Step D, (0.06 g, 0.227 mmol) in $CH_2Cl_2$ (3 mL) at 0° C. with stirring. The ice bath was removed and stirring was continued for 16 h. The reaction mixture was quenched with $H_2O$, concentrated to dryness, then dissolved in MeOH and purified by RP preparative HPLC on a PrepPak (95/5 to 5/95 $H_2O/CH_3CN$ w/0.1% TFA, flow=65 mL/min) to give the title compound. FAB MS (M+1) 250.

Step F: Preparation of 4-[1-Amino-1-(3-methyl-3H-imidazol-4-yl)-ethyl]-2-[3-(4-methyl-3-oxo-2-propyl-morpholin-2-yl)-phenoxy]-benzonitrile Bistrifluoroacetate Using the procedure described in Example 47, Step C, 2-(-3-hydroxy-phenyl)-4-methyl-2-propyl-morpholine-3-one, as described above in Step E, (0.026 g, 0.104 mmol) and 2-fluoro-4-[1-(−)amino-1-(3-methyl-3H-imidazol-4- yl)-ethyl]-benzonitrile (as described in Example 24A, Step F) (0.026 g, 0.104 mmol) were reacted to prepare the title compound which was purified by RP preparative HPLC on a PrepPak (95/5 to 5/95 $H_2O/CH_3CN$ w/0.1% TFA, flow=65 mL/min).

HRMS Theoretical=474.2500, Measured=474.2484, Analysis calculated for $C_{29}H_{33}F_3N_5O_5$.2.5 $CF_3CO_2H$.0.75 $H_2O$: C, 49.77; H, 4.57; N, 9.07; Found: C, 49.76; H, 4.23; N, 9.22.

Example 58

Preparation of 4-[1-amino-1-(3-methyl-3H-imidazol-4-yl)-ethyl]-2-[3-(morpholine-4-sulfonyl)-phenoxy]-benzonitrile Step A: Preparation of 3-Methoxy Benzenesulfonyl Morpholine 3-Methoxybenzenesulfonyl chloride (0.20 g, 0.968 mmol) in acetone (2 mL) at 0° C. was treated with excess morpholine (0.253 mL, 2.9 mmol) with stirring. After 0.5 hr the reaction mixture was partitioned between $CH_2Cl_2$ (1 mL) and 1N HCl, the organic layer separated, washed with brine, dried ($Na_2SO_4$), filtered and concentrated to dryness to give the title compound.

Step B: Preparation of 3-Hydroxybenzenesulfonylmornholine

Boron tribromide in $CH_2Cl_2$ (1 M) (3.84 mL, 3.84 mmol) was added to a solution of 3-methoxy benzenesulfonyl morpholine (0.3297 g, 1.28 mmol) in anhydrous $CH_2Cl_2$ (25 mL) at 0° C. under $N_2$. After stirring overnight the reaction was partitioned between $CH_2Cl_2$ and aqueous saturated $NaHCO_3$ solution, the organic layer separated, washed with $H_2O$, brine, and dried ($Na_2SO_4$). Filtration and concentration to dryness gave the title compound.

Step C: Preparation of 4-[1-amino-1-(3-methyl-3H-imidazol-4-yl)-ethyl]-2-[3-(morpholine-4-sulfonyl)-phenoxy]-benzonitrile Using the methods described in Example 24A, but substituting 3-hydroxybenzenesulfonylmorpholine (0.015 g, 0.061 mmol) and 2-fluoro-4-[1-amino-1-(3-methyl-3H-imidazol-4-yl)-ethyl]-benzonitrile (as described in Example 24A, Step F), the title compound was prepared.

FAB MS (M+1)=468.

Example 59

Preparation of 2-[3-(3R-ethyl-1-methyl-2-oxo-azepan-3-yl)-phenoxy]-4-[5-(2-morpholin-4-yl-ethyl)-imidazol-1-ylmethyl benzonitrile Step A: Preparation of {2-[3-(4-cyano-3-fluoro-benzyl)-3H-imidazol-4-yl]-ethyl}-carbamic Acid Tert-butyl Ester To a solution of $N^\tau$-pivaloyloxymethyl-$N^\alpha$-phthaloylhistamine (J. C. Emmett, F. H. Holloway, and J. L. Turner, *J. Chem. Soc., Perkin Trans.* 1, 1341, (1979)) (4.59 g, 0.0124 mmol) in acetonitrile (40 mL) was added 4-bromomethyl-2-fluoro-benzonitrile (as described in Example 1, Step D) (2.8 g, 0.013 mmol) and the mixture was heated to reflux for 18 hr. A white solid precipitate formed which after cooling to 0° C. was collected by filtration to obtain the quaternary salt. This intermediate was dissolved in EtOH (100 mL), hydrazine (1.46 mL, 0.046 mmol) was added, and the mixture was heated at reflux for 4 hr. A white precipitate was observed and the reaction was cooled to 25° C. Dimethylphthalate (11.4 mL, 0.0699 mmol) was added and the mixture was again refluxed for 18 hr. After cooling to 25° C. the precipitate was removed by filtration and washed with EtOAc. The filtrate was evaporated in vacuo and the residue was dissolved in THF (125 mL) and $H_2O$ (25 mL). To this solution was added solid $Na_2CO_3$ (4.0 g, 0.0377 mmol) and $BOC_2O$ (4.47 g, 0.020 mmol) and the reaction was stirred for 18 hr. The THF was removed in vacuo and the mixture was partitioned with EtOAc and saturated $NaHCO_3$. The EtOAc layer was washed with brine, dried with $MgSO_4$, and evaporated in vacuo to obtain the title product after chromatography (silica gel, $CH_2Cl_2$:MeOH:$NH_4OH$/97:3:0.3.

Step B: Preparation of 4-[5-(2-amino-ethyl)-imidazol-1-ylmethyl]-2-fluoro-benzonitrile Dihydrochloride A solution of {2-[3-(4-cyano-3-fluoro-benzyl)-3H-imidazol-4-yl]-ethyl}-carbamic acid tert-butyl ester (1.0 g, 0.0029 mmol) in EtOAc (30 mL) was cooled to –20° C. and saturated with HCl gas. The cooling bath was removed and the reaction was stirred for 2 hr. The solvent was removed in vacuo to obtain the title compound.

Step C: Preparation of 2-fluoro-4-[5-(2-morpholin-4-yl-ethyl)-imidazol-1-ylmethyl]-benzonitrile To a solution of 4-[5-(2-amino-ethyl)-imidazol-1-ylmethyl]-2-fluoro-benzonitrile dihydrochloride (0.92 g, 0.0029 mmol) in acetonitrile (150 mL) and triethylamine (3.2 mL) was added 2-bromoethyl ether (0.839 mL, 0.0067 mmol) and the mixture was refluxed for 48 hr. The solvents were removed in vacuo and the residue was dissolved in EtOAc which was washed twice with 1M HCl (100 mL). The HCl layers were combined and adjusted to pH=9 with solid $Na_2CO_3$ and extraxcted 3 times with EtOAc. The EtOAc layers were combined and dried with brine and $MgSO_4$. Removal of the EtOAc in vacuo yielded the title compound.

Step D: Preparation of 2-[3-(3R-ethyl-1-methyl-2-oxo-azepan-3-yl)-phenoxy]-4-[5-(2-morpholin-4-yl-ethyl)-imidazol-1-ylmethyl Benzonitrile Using the methods described in Example 24A, but substituting 3R-ethyl-3-(3-hydroxy-phenyl)-azepan-2-one (as described in Example 8, Step B) and 2-fluoro-4-[5-(2-morpholin-4-yl-ethyl)-imidazol-1-ylmethyl]-benzonitrile (as described above in Step C), the following compound was prepared:

2-[3-(3R-ethyl-1-methyl-2-oxo-azepan-3-yl)-phenoxy]-4-[5-(2-morpholin-4-yl-ethyl)imidazol-1-ylmethyl benzonitrile

FAB MS (M+1)=542.

Example 60

In vitro Inhibition of Ras Farnesyl Transferase

Transferase Assays. Isoprenyl-protein transferase activity assays are carried out at 30° C. unless noted otherwise. A typical reaction contains (in a final volume of 50 $\mu$L): [$^3$H]farnesyl diphosphate, Ras protein, 50 mM HEPES, pH 7.5, 5 mM $MgCl_2$, 5 mM dithiothreitol, 10 $\mu$M $ZnCl_2$, 0.1% polyethyleneglycol (PEG) (15,000–20,000 mw) and isoprenyl-protein transferase. The FPTase employed in the assay is prepared by recombinant expression as described in Omer, C. A., Kral, A. M., Diehl, R. E., Prendergast, G. C., Powers, S., Allen, C. M., Gibbs, J. B. and Kohl, N. E. (1993) *Biochemistry* 32:5167–5176. After thermally pre-equilibrating the assay mixture in the absence of enzyme, reactions are initiated by the addition of isoprenyl-protein transferase and stopped at timed intervals (typically 15 min) by the addition of 1 M HCl in ethanol (1 mL). The quenched reactions are allowed to stand for 15 m (to complete the precipitation process). After adding 2 mL of 100% ethanol, the reactions are vacuum-filtered through Whatman GF/C filters. Filters are washed four times with 2 mL aliquots of 100% ethanol, mixed with scintillation fluid (10 mL) and then counted in a Beckman LS3801 scintillation counter.

For inhibition studies, assays are run as described above, except inhibitors are prepared as concentrated solutions in 100% dimethyl sulfoxide and then diluted 20 fold into the enzyme assay mixture. Substrate concentrations for inhibitor IC$_{50}$ determinations are as follows: FTase, 650 nM Ras-CVLS (SEQ.ID.NO.: 1), 100 nM farnesyl diphosphate.

The compounds of the instant invention described in the above Examples 1–59 were tested for inhibitory activity against human FPTase by the assay described above and were found to have IC$_{50}$ of ≦30 μM.

Example 61
Modified In vitro GGTase Inhibition Assay

The modified geranylgeranyl-protein transferase inhibition assay is carried out at room temperature. A typical reaction contains (in a final volume of 50 μL): [$^3$H] geranylgeranyl diphosphate, biotinylated Ras peptide, 50 mM HEPES, pH 7.5, a modulating anion (for example 10 mM glycerophosphate or 5 mM ATP), 5 mM MgCl$_2$, 10 μM ZnCl$_2$, 0.1% PEG (15,000–20,000 mw), 2 mM dithiothreitol, and geranylgeranyl-protein transferase type I(GGTase). The GGTase-type I enzyme employed in the assay is prepared as described in U.S. Pat. No. 5,470,832, incorporated by reference. The Ras peptide is derived from the K4B-Ras protein and has the following sequence: biotinyl-GKKKKKKSKTKCVIM (single amino acid code) (SEQ. ID.NO.: 2). Reactions are initiated by the addition of GGTase and stopped at timed intervals (typically 15 min) by the addition of 200 μL of a 3 mg/mL suspension of streptavidin SPA beads (Scintillation Proximity Assay beads, Amersham) in 0.2 M sodium phosphate, pH 4, containing 50 mM EDTA, and 0.5% BSA. The quenched reactions are allowed to stand for 2 hours before analysis on a Packard TopCount scintillation counter.

For inhibition studies, assays are run as described above, except inhibitors are prepared as concentrated solutions in 100% dimethyl sulfoxide and then diluted 25 fold into the enzyme assay mixture. IC$_{50}$ values are determined with Ras peptide near K$_M$ concentrations. Enzyme and substrate concentrations for inhibitor IC$_{50}$ determinations are as follows: 75 pM GGTase-I, 1.6 μM Ras peptide, 100 μM geranylgeranyl diphosphate.

The compounds of the instant invention described in the above Examples 1–59 are tested for inhibitory activity against human GGTase type I by the assay described above.

Example 62
Cell-based In vitro Ras Farnesylation Assay

The cell line used in this assay is a v-ras line derived from either RatI or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labeled in 3 ml methionine-free DMEM supplemented with 10% regular DMEM, 2% fetal bovine serum and 400 μCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., *J. Virol.* 43:294–304, (1982)). Following a 2 hour antibody incubation at 4° C., 200 μL of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 63
Cell-based In vitro Growth Inhibition Assay

To determine the biological consequences of FPTase inhibition, the effect of the compounds of the instant invention on the anchorage-independent growth of RatI cells transformed with either a v-ras, v-raf or v-mos oncogene is tested. Cells transformed by v-Raf and v-Mos maybe included in the analysis to evaluate the specificity of compounds for Ras-induced cell transformation.

Rat 1 cells transformed with either v-ras, v-raf, or v-mos are seeded at a density of 1×10$^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

Example 64
Construction of SEAP Reporter Plasmid pDSE100

The SEAP reporter plasmid, pDSE100 was constructed by ligating a restriction fragment containing the SEAP coding sequence into the plasmid pCMV-RE-AKI. The SEAP gene is derived from the plasmid pSEAP2-Basic (Clontech, Palo Alto, Calif.). The plasmid pCMV-RE-AKI contains 5 sequential copies of the 'dyad symmetry response element' cloned upstream of a 'CAT-TATA' sequence derived from the cytomegalovirus immediate early promoter. The plasmid also contains a bovine growth hormone poly-A sequence.

The plasmid, pDSE100 was constructed as follows. A restriction fragment encoding the SEAP coding sequence was cut out of the plasmid pSEAP2-Basic using the restriction enzymes EcoR1 and HpaI. The ends of the linear DNA fragments were filled in with the Klenow fragment of *E. coli* DNA Polymerase I. The "blunt ended" DNA containing the SEAP gene was isolated by electrophoresing the digest in an agarose gel and cutting out the 1694 base pair fragment. The vector plasmid pCMV-RE-AKI was linearized with the restriction enzyme Bgl-II and the ends filled in with Klenow DNA Polymerase I. The SEAP DNA fragment was blunt end ligated into the pCMV-RE-AKI vector and the ligation products were transformed into DH$_5$-alpha *E. coli* cells (Gibco-BRL). Transformants were screened for the proper insert and then mapped for restriction fragment orientation. Properly oriented recombinant constructs were sequenced across the cloning junctions to verify the correct sequence. The resulting plasmid contains the SEAP coding sequence downstream of the DSE and CAT-TATA promoter elements and upstream of the BGH poly-A sequence.

Alternative Construction of SEAP Reporter Plasmid, pDSE101

The SEAP repotrer plasmid, pDSE101 is also constructed by ligating a restriction fragment containing the SEAP coding sequence into the plasmid pCMV-RE-AKI. The SEAP gene is derived from plasmid pGEM7zf(−)/SEAP.

The plasmid pDSE101 was constructed as follows: A restriction fragment containing part of the SEAP gene coding sequence was cut out of the plasmid pGEM7zf(−)/SEAP using the restriction enzymes Apa I and KpnI. The ends of the linear DNA fragments were chewed back with the Klenow fragment of *E. coli* DNA Polymerase I. The "blunt ended" DNA containing the truncated SEAP gene was isolated by electrophoresing the digest in an agarose gel and cutting out the 1910 base pair fragment. This 1910 base pair fragment was ligated into the plasmid pCMV-RE-AKI which had been cut with Bgl-II and filled in with *E. coli* Klenow fragment DNA polymerase. Recombinant plasmids were screened for insert orientation and sequenced through the ligated junctions. The plasmid pCMV-RE-AKI is derived from plasmid pCMVIE-AKI-DHFR (Whang, Y., Silberklang, M., Morgan, A., Munshi, S., Lenny, A. B., Ellis, R. W., and Kieff, E. (1987) J. Virol., 61, 1796–1807) by removing an EcoRI fragment containing the DHFR and Neomycin markers. Five copies of the fos promoter serum response element were inserted as described previously (Jones, R. E., Defeo-Jones, D., McAvoy, E. M., Vuocolo, G. A., Wegrzyn, R. J., Haskell, K. M. and Oliff, A. (1991) Oncogene, 6, 745–751) to create plasmid pCMV-RE-AKI.

The plasmid pGEM7zf(−)/SEAP was constructed as follows. The SEAP gene was PCRed, in two segments from a human placenta cDNA library (Clontech) using the following oligos.
Sense Strand N-terminal SEAP:
   5' GAGAGGGAATTCGGGCCCTTCCTGCAT GCT-GCTGCTGCTGCTGCTGGGC 3' (SEQ.ID.NO.:3)
Antisense Strand N-terminal SEAP:
   5' GAGAGAGCTCGAGGTTAACCCGGGT GCGCG-GCGTCGGTGGT 3' (SEQ.ID.NO.: 4)
Sense Strand C-terminal SEAP:
   5' GAGAGAGTCTAGAGTTAACCCGTGGTCC CCGCGTTGCTTCCT 3' (SEQ.ID.NO.: 5)
Antisense Strand C-terminal SEAP:
   5' GAAGAGGAAGCTTGGTACCGCCACTG GGCTG-TAGGTGGTGGCT 3' (SEQ.ID.NO.: 6).

The N-terminal oligos (SEQ.ID.NO.: 4 and SEQ.ID.NO.: 5) were used to generate a 1560 bp N-terminal PCR product that contained EcoRI and HpaI restriction sites at the ends. The Antisense N-terminal oligo (SEQ.ID.NO.: 4) introduces an internal translation STOP codon within the SEAP gene along with the HpaI site. The C-terminal oligos (SEQ.ID.NO.: 5 and SEQ.ID.NO.: 6) were used to amplify a 412 bp C-terminal PCR product containing HpaI and HindIII restriction sites. The sense strand C-terminal oligo (SEQ.ID.NO.: 5) introduces the internal STOP codon as well as the HpaI site. Next, the N-terminal amplicon was digested with EcoRI and HpaI while the C-terminal amplicon was digested with HpaI and HindIII. The two fragments comprising each end of the SEAP gene were isolated by electrophoresing the digest in an agarose gel and isolating the 1560 and 412 base pair fragments. These two fragments were then co-ligated into the vector pGEM7zf(−) (Promega) which had been restriction digested with EcoRI and HindIII and isolated on an agarose gel. The resulting clone, pGEM7zf(−)/SEAP contains the coding sequence for the SEAP gene from amino acids.

Construction of a Constitutively Expressing SEAP Plasmid pCMV-SEAP

An expression plasmid constitutively expressing the SEAP protein was created by placing the sequence encoding a truncated SEAP gene downstream of the cytomegalovirus (CMV) IE-1 promoter. The expression plasmid also includes the CMV intron A region 5' to the SEAP gene as well as the 3' untranslated region of the bovine growth hormone gene 3' to the SEAP gene.

The plasmid pCMVIE-AKI-DHFR (Whang et al, 1987) containing the CMV immediate early promoter was cut with EcoRI generating two fragments. The vector fragment was isolated by agarose electrophoresis and religated. The resulting plasmid is named pCMV-AKI. Next, the cytomegalovirus intron A nucleotide sequence was inserted downstream of the CMV IE1 promter in pCMV-AKI. The intron A sequence was isolated from a genomic clone bank and subcloned into pBR322 to generate plasmid p16T-286. The intron A sequence was mutated at nucleotide 1856 (nucleotide numbering as in Chapman, B. S., Thayer, R. M., Vincent, K. A. and Haigwood, N. L., Nuc.Acids Res. 19, 3979–3986) to remove a SacI restriction site using site directed mutagenesis. The mutated intron A sequence was PCRed from the plasmid p16T-287 using the following oligos.
Sense Strand:
   5' GGCAGAGCTCGTTTAGTGAACCGTCAG 3' (SEQ.ID.NO.: 7)
Antisense Strand:
   5' GAGAGATCTCAAGGACGGTGACTGCAG 3' (SEQ.ID.NO.: 8).

These two oligos generate a 991 base pair fragment with a Sacd site incorporated by the sense oligo and a Bgl-II fragment incorporated by the antisense oligo. The PCR fragment is trimmed with SacI and Bgl-II and isolated on an agarose gel. The vector pCMV-AKI is cut with Sacd and Bgl-II and the larger vector fragment isolated by agarose gel electrophoresis. The two gel isolated fragments are ligated at their respective Sacd and Bgl-II sites to create plasmid pCMV-AKI-InA.

The DNA sequence encoding the truncated SEAP gene is inserted into the pCMV-AKI-InA plasmid at the Bgl-II site of the vector. The SEAP gene is cut out of plasmid pGEM7zf (−)/SEAP (described above) using EcoRI and HindIII. The fragment is filled in with Klenow DNA polymerase and the 1970 base pair fragment isolated from the vector fragment by agarose gel electrophoresis. The pCMV-AKI-InA vector is prepared by digesting with Bgl-II and filling in the ends with Kienow DNA polymerase. The final construct is generated by blunt end ligating the SEAP fragment into the pCMV-AKI-InA vector. Transformants were screened for the proper insert and then mapped for restriction fragment orientation. Properly oriented recombinant constructs were sequenced across the cloning junctions to verify the correct sequence. The resulting plasmid, named pCMV-SEAP, contains a modified SEAP sequence downstream of the cytomegalovirus immediately early promoter IE-1 and intron A sequence and upstream of the bovine growth hormone poly-A sequence. The plasmid expresses SEAP in a constitutive manner when transfected into mammalian cells.

Cloning of a Myristylated Viral-H-ras Expression Plasmid

A DNA fragment containing viral-H-ras can be PCRed from plasmid "H-1" (Ellis R. et al. J. Virol. 36, 408, 1980) or "HB-11 (deposited in the ATCC under Budapest Treaty on Aug. 27, 1997, and designated ATCC 209,218) using the following oligos.
Sense Strand:
   5'TCTCCTCGAGGCCACCATGGGGAGTAG-CAAGAGCAAGCCTAAGGACCC CAGC-CAGCGCCGGATGACAGAATACAAGCT-TGTGGTGG 3'. (SEQ.ID.NO.: 9)

Antisense:

5'CACATCTAGATCAGGACAGCACAGACT-TGCAGC 3'. (SEQ.ID.NO.: 10).

A sequence encoding the first 15 aminoacids of the v-src gene, containing a myristylation site, is incorporated into the sense strand oligo. The sense strand oligo also optimizes the 'Kozak' translation initiation sequence immediately 5' to the ATG start site.

To prevent prenylation at the viral-ras C-terminus, cysteine 186 would be mutated to a serine by substituting a G residue for a C residue in the C-terminal antisense oligo. The PCR primer oligos introduce an XhoI site at the 5' end and a XbaI site at the 3'end. The XhoI-XbaI fragment can be ligated into the mammalian expression plasmid pCI (Promega) cut with XhoI and XbaI. This results in a plasmid in which the recombinant myr-viral-H-ras gene is constitutively transcribed from the CMV promoter of the pCI vector.

Cloning of a Viral-H-ras-CVLL Expression Plasmid

A viral-H-ras clone with a C-terminal sequence encoding the amino acids CVLL can be cloned from the plasmid "H-1" (Ellis R. et al., *J. Virol.* 36, 408, 1980) or "HB-11 (deposited in the ATCC under Budapest Treaty on Aug. 27, 1997, and designated ATCC 209,218) by PCR using the following oligos.

Sense Strand:

5 'TCTCCTCGAGGCCACCATGACAGAATACA AGCTTGTGGTGG-3' (SEQ.ID.NO.: 11)

Antisense Strand:

5' CACTCTAGACTGGTGTCAGAGCAGCACAC ACTTGCAGC-3' (SEQ.ID.NO.: 12).

The sense strand oligo optimizes the 'Kozak' sequence and adds an XhoI site. The antisense strand mutates serine 189 to leucine and adds an XbaI site. The PCR fragment can be trimmed with XhoI and XbaI and ligated into the XhoI-XbaI cut vector pCI (Promega). This results in a plasmid in which the mutated viral-H-ras-CVLL gene is constitutively transcribed from the CMV promoter of the pCI vector.

Cloning of c-H-ras-Leu61 Expression Plasmid

The human c-H-ras gene can be PCRed from a human cerebral cortex cDNA library (Clontech) using the following oligonucleotide primers.

Sense Strand:
5'-GAGAGAATTCGCCACCATGACGGAATATAAG CTGGTGG-3' (SEQ.ID.NO.: 13)

Antisense Strand:

5'-GAGAGTCGACGCGTCAGGAGAGCACA CACTTGC-3' (SEQ.ID.NO.: 14).

The primers will amplify a c-H-ras encoding DNA fragment with the primers contributing an optimized "Kozak" translation start sequence, an EcoRI site at the N-terminus and a Sal I stite at the C-terminal end. After trimming the ends of the PCR product with EcoRI and Sal I, the c-H-ras fragment can be ligated ligated into an EcoRI-Sal I cut mutagenesis vector pAlter-1 (Promega). Mutation of glutamine-61 to a leucine can be accomplished using the manufacturer's protocols and the following oligonucleotide:

5'-CCGCCGGCCTGGAGGAGTACAG-3' (SEQ.ID.NO.: 15)

After selection and sequencing for the correct nucleotide substitution, the mutated c-H-ras-Leu61 can be excised from the pAlter-1 vector, using EcoRI and Sal I, and be directly ligated into the vector pCI (Promega) which has been digested with EcoRI and Sal I. The new recombinant plasmid will constitutively transcribe c-H-ras-Leu61 from the CMV promoter of the pCI vector.

Cloning of a c-N-ras-Val-12 Expression Plasmid

The human c-N-ras gene can be PCRed from a human cerebral cortex cDNA library (Clontech) using the following oligonucleotide primers.

Sense Strand:

5'-GAGAGAATTCGCCACCATGACTGAGTAC AAACTGGTGG-3' (SEQ.ID.NO.: 16)

Antisense Strand:

5'-GAGAGTCGACTTGTTACATCACCACACATGGC-3' (SEQ.ID.NO.: 17).

The primers will amplify a c-N-ras encoding DNA fragment with the primers contributing an optimized 'Kozak' translation start sequence, an EcoRI site at the N-terminus and a Sal I stite at the C-terminal end. After trimming the ends of the PCR product with EcoRI and Sal I, the c-N-ras fragment can be ligated into an EcoRI-Sal I cut mutagenesis vector pAlter-1 (Promega). Mutation of glycine-12 to a valine can be accomplished using the manufacturer's protocols and the following oligonucleotide:

5'-GTTGGAGCAGTTGGTGTTGGG-3' (SEQ.ID.NO.: 18).

After selection and sequencing for the correct nucleotide substitution, the mutated c-N-ras-Val-12 can be excised from the pAlter-1 vector, using EcoRI and Sal I, and be directly ligated into the vector pCI (Promega) which has been digested with EcoRI and Sal I. The new recombinant plasmid will constitutively transcribe c-N-ras-Val-12 from the CMV promoter of the pCI vector.

Cloning of a c-K-ras-Val-12 Expression Plasmid

The human c-K-ras gene can be PCRed from a human cerebral cortex cDNA library (Clontech) using the following oligonucleotide primers.

Sense Strand:

5'-GAGAGGTACCGCCACCATGACTGAATAT AAACTTGTGG-3' (SEQ.ID.NO.: 19)

Antisense Strand:

5'-CTCTGTCGACGTATTTACATAATTACACA CTTTGTC-3' (SEQ.ID.NO.: 20).

The primers will amplify a c-K-ras encoding DNA fragment with the primers contributing an optimized 'Kozak' translation start sequence, a KpnI site at the N-terminus and a Sal I site at the C-terminal end. After trimming the ends of the PCR product with Kpn I and Sal I, the c-K-ras fragment can be ligated into a KpnI-Sal I cut mutagenesis vector pAlter-1 (Promega). Mutation ofcysteine-12 to a valine can be accomplished using the manufacturer's protocols and the following oligonucleotide:

5'-GTAGTTGGAGCTGTTGGCGTAGGC-3' (SEQ.ID.NO.: 21).

After selection and sequencing for the correct nucleotide substitution, the mutated c-K-ras-Val-12 can be excised from the pAlter-1 vector, using KpnI and Sal I, and be directly ligated into the vector pCI (Promega) which has been digested with KpnI and Sal I. The new recombinant plasmid will constitutively transcribe c-K-ras-Val-12 from the CMV promoter of the pCI vector.

SEAP Assay

Human C33A cells (human epitheial carcenoma—ATTC collection) are seeded in 10 cm tissue culture plates in DMEM+10% fetal calf serum+1×Pen/Strep+1×glutamine+ 1×NEAA. Cells are grown at 37° C. in a 5% $CO_2$ atmosphere until they reach 50–80% of confluency.

The transient transfection is performed by the $CaPO_4$ method (Sambrook et al., 1989). Thus, expression plasmids for H-ras, N-ras, K-ras, Myr-ras or H-ras-CVLL are co-precipitated with the DSE-SEAP reporter construct. For 10 cm plates 600 ml of CaCl$_2$-DNA solution is added dropwise while vortexing to 600 ml of 2×HBS buffer to give 1.2 ml of precipitate solution (see recipes below). This is allowed to sit at room temperature for 20 to 30 minutes. While the precipitate is forming, the media on the C33A cells is replaced with DMEM (minus phenol red; Gibco cat. # 31053-028)+0.5% charcoal stripped calf serum+1×(Pen/Strep, Glutamine and nonessential aminoacids). The CaPO$_4$-DNA precipitate is added dropwise to the cells and the plate rocked gently to distribute. DNA uptake is allowed to proceed for 5–6 hrs at 37° C. under a 5% CO$_2$ atmosphere.

Following the DNA incubation period, the cells are washed with PBS and trypsinized with 1 ml of 0.05% trypsin. The 1 ml of trypsinized cells is diluted into 10 ml of phenol red free DMEM+0.2% charcoal stripped calf serum+1×(Pen/Strep, Glutamine and NEAA). Transfected cells are plated in a 96 well microtiter plate (100 ml/well) to which drug, diluted in media, has already been added in a volume of 100 ml. The final volume per well is 200 ml with each drug concentration repeated in triplicate over a range of half-log steps.

Incubation of cells and test compound is for 36 hrs at 37° C. under CO$_2$. At the end of the incubation period, cells are examined microscopically for evidence of cell distress. Next, 100 ml of media containing the secreted alkaline phosphatase is removed from each well and transferred to a microtube array for heat treatment at 65° C. for 1 hr to inactivate endogenous alkaline phosphatases (but not the heat stable secreted phosphatase).

The heat treated media is assayed for alkaline phosphatase by a luminescence assay using the luminescence reagent CSPD® (Tropix, Bedford, Mass.). A volume of 50 ml media is combined with 200 ml of CSPD cocktail and incubated for 60 minutes at room temperature. Luminesence is monitored using an ML2200 microplate luminometer (Dynatech). Luminescence reflects the level of activation of the fos reporter construct stimulated by the transiently expressed protein.

| DNA-CaPO$_4$ precipitate for 10 cm. plate of cells | |
|---|---|
| Ras Expression plasmid (1 mg/ml) | 10 ml |
| DSE-SEAP Plasmid (1 mg/ml) | 2 ml |
| Sheared Calf Thymus DNA (1 mg/ml) | 8 ml |
| 2M CaCl$_2$ | 74 ml |
| dH$_2$O | 506 ml |

2×HBS Buffer
  280 mM NaCl
  10 mM KCl
  1.5 mM Na$_2$HPO$_4$ 2H$_2$O
  12 mM dextrose
  50 mM HEPES
  Final pH=7.05
Luminesence Buffer (26 ml)

| Luminesence Buffer (26 ml) | |
|---|---|
| Assay Buffer | 20 ml |
| Emerald Reagent ™ (Tropix) | 2.5 ml |
| 100 mM homoarginine | 2.5 ml |
| CSPD Reagent ® (Tropix) | 1.0 ml |

Assay Buffer
  Add 0.05M Na$_2$CO$_3$ to 0.05M NaHCO$_3$ to obtain pH 9.5. Make 1 mM in MgCl$_2$.

Example 65

The processing assays employed in this example and in Example 66 modifications of that described by DeClue et al [Cancer Research 51, 712–717, 1991].
K4B-Ras Processing Inhibition Assay PSN-1 (human pancreatic carcinoma) cells are used for analysis of protein processing. Subconfluent cells in 100 mm dishes are fed with 3.5 ml of media (methionine-free RPMI supplemented with 2% fetal bovine serum or cysteine-free/methionine-free DMEM supplemented with 0.035 ml of 200 mM glutamine (Gibco), 2% fetal bovine serum, respectively) containing the desired concentration of test compound, lovastatin or solvent alone. Cells treated with lovastatin (5–10 $\mu$M), a compound that blocks Ras processing in cells by inhibiting a rate-limiting step in the isoprenoid biosynthetic pathway, serve as a positive control. Test compounds are prepared as 1000× concentrated solutions in DMSO to yield a final solvent concentration of 0.1%. Following incubation at 37° C. for two hours 204 $\mu$Ci/ml [$^{35}$S]Pro-Mix (Amersham, cell labeling grade) is added.

After introducing the label amino acid mixture, the cells are incubated at 37° C. for an additional period of time (typically 6 to 24 hours). The media is then removed and the cells are washed once with cold PBS. The cells are scraped into 1 ml of cold PBS, collected by centrifugation (10,000×g for 10 sec at room temperature), and lysed by vortexing in 1 ml of lysis buffer (1% Nonidet P-40, 20 mM HEPES, pH 7.5, 150 mM NaCl, 1 mM EDTA, 0.5% deoxycholate, 0.1% SDS, 1 mM DTT, 10 $\mu$g/ml AEBSF, 10 $\mu$g/ml aprotinin, 2 $\mu$g/ml leupeptin and 2 $\infty$g/ml antipain). The lysate is then centrifuged at 15,000×g for 10 min at 4° C. and the supernatant saved.

For immunoprecipitation of Ki4B-Ras, samples of lysate supernatant containing equal amounts of protein are utilized. Protein concentration is determined by the bradford method utilizing bovine serum albumin as a standard. The appropriate volume of lysate is brought to 1 ml with lysis buffer lacking DTT and 8 $\mu$g of the pan Ras monoclonal antibody, Y13-259, added. The protein/antibody mixture is incubated on ice at 4° C. for 24 hours. The imrnmune complex is collected on pansorbin (Calbiochem) coated with rabbit antiserum to rat IgG (Cappel) by tumbling at 4° C. for 45 minutes. The pellet is washed 3 times with 1 ml of lysis buffer lacking DTT and protease inhibitors and resuspended in 100 ml elution buffer (10 mM Tris pH 7.4, 1% SDS). The Ras is eluted from the beads by heating at 95° C. for 5 minutes, after which the beads are pelleted by brief centrifugation (15,000×g for 30 sec. at room temperature).

The supernatant is added to 1 ml of Dilution Buffer 0.1% Triton X-100, 5 mM EDTA, 50 mM NaCl, 10 mM Tris pH 7.4) with 2 mg Kirsten-ras specific monoclonal antibody, c-K-ras Ab-1 (Calbiochem). The second protein/antibody mixture is incubated on ice at 4° C. for 1–2 hours. The immune complex is collected on pansorbin (Calbiochem) coated with rabbit antiserum to rat IgG (Cappel) by tumbling at 4° C. for 45 minutes. The pellet is washed 3 times with 1 ml of lysis buffer lacking DTT and protease inhibitors and resuspended in Laemmli sample buffer. The Ras is eluted from the beads by heating at 95° C. for 5 minutes, after which the beads are pelleted by brief centrifugation. The supernatant is subjected to SDS-PAGE on a 12% acrylamide gel (bis-acrylamide:acrylamide, 1:100), and the Ras visualized by fluorography.

hDJ Processing Inhibition Assay

PSN-1 cells are seeded in 24-well assay plates. For each compound to be tested, the cells are treated with a minimum of seven concentrations in half-log steps. The final solvent (DMSO) concentration is 0.1%. A vehicle-only control is included on each assay plate. The cells are treated for 24 hours at 37° C./5% $CO_2$.

The growth media is then aspirated and the samples are washed with PBS. The cells are lysed with SDS-PAGE sample buffer containing 5% 2-mercaptoethanol and heated to 95° C. for 5 minutes. After cooling on ice for 10 minutes, a mixture of nucleases is added to reduce viscosity of the samples.

The plates are incubated on ice for another 10 minutes. The samples are loaded onto pre-cast 8% acrylamide gels and electrophoresed at 15 mA/gel for 3–4 hours. The samples are then transferred from the gels to PVDF membranes by Western blotting.

The membranes are blocked for at least 1 hour in buffer containing 2% nonfat dry milk. The membranes are then treated with a monoclonal antibody to HDJ-2 (Neomarkers Cat. # MS-225), washed, and treated with an alkaline phosphatase-conjugated secondary antibody. The membranes are then treated with a fluorescent detection reagent and scanned on a phosphorimager.

For each sample, the percent of total signal corresponding to the unprenylated species of HDJ (the slower-migrating species) is calculated by densitometry. Dose-response curves and $IC_{50}$ values are generated using 4-parameter curve fits in SigmaPlot software.

Example 66

K4B-Ras Processing Inhibition Assay

PSN-1 (human pancreatic carcinoma) cells are used for analysis of protein processing. Subconfluent cells in 150 mm dishes are fed with 20 ml of media (RPMI supplemented with 15% fetal bovine serum) containing the desired concentration of prenyl-protein transferase inhibitor or solvent alone. Cells treated with lovastatin (5–10 $\mu$M), a compound that blocks Ras processing in cells by inhibiting a rate-limiting step in the isoprenoid biosynthetic pathway, serve as a positive control. Test compounds are prepared as 1000× concentrated solutions in DMSO to yield a final solvent concentration of 0.1%.

The cells are incubated at 37° C. for 24 hours, the media is then removed and the cells are washed twice with cold PBS. The cells are scraped into 2 ml of cold PBS, collected by centrifugation (10,000×g for 5 min at 4° C.) and frozen at –70° C. Cells are lysed by thawing and addition of lysis buffer (50 mM HEPES, pH 7.2, 50 mM NaCl, 1% CHAPS, 0.7 $\mu$g/ml aprotinin, 0.7 $\mu$g/ml leupeptin 300 $\mu$g/ml pefabloc, and 0.3 mM EDTA). The lysate is then centrifuged at 100,000×g for 60 min at 4° C. and the supernatant saved. The supernatant may be subjected to SDS-PAGE, HPLC analysis, and/or chemical cleavage techniques.

The lysate is applied to a HiTrap-SP (Pharmacia Biotech) column in buffer A (50 mM HEPES pH 7.2) and resolved by gradient in buffer A plus 1 M NaCl. Peak fractions containing Ki4B-Ras are pooled, diluted with an equal volume of water and immunoprecipitated with the pan Ras monoclonal antibody, Y13-259 linked to agarose. The protein/antibody mixture is incubated at 4° C. for 12 hours. The immune complex is washed 3 times with PBS, followed by 3 times with water. The Ras is eluted from the beads by either high pH conditions (pH>10) or by heating at 95° C. for 5 minutes, after which the beads are pelleted by brief centrifugation. The supernatant may be subjected to SDS-PAGE, HPLC analysis, and/or chemical cleavage techniques.

Example 67

Rap1 Processing Inhibition Assay

Protocol A:

Cells are labeled, incubated and lysed as described in Example 65.

For immunoprecipitation of Rap1, samples of lysate supernatant containing equal amounts of protein are utilized. Protein concentration is determined by the bradford method utilizing bovine serum albumin as a standard. The appropriate volume of lysate is brought to 1 ml with lysis buffer lacking DTT and 2 $\mu$g of the Rap1 antibody, Rap1/Krev1 (121) (Santa Cruz Biotech), is added. The protein/antibody mixture is incubated on ice at 4° C. for 1 hour. The immune complex is collected on pansorbin (Calbiochem) by tumbling at 4° C. for 45 minutes. The pellet is washed 3 times with 1 ml of lysis buffer lacking DTT and protease inhibitors and resuspended in 100 ml elution buffer (10 mM Tris pH 7.4, 1% SDS). The Rap1 is eluted from the beads by heating at 95° C. for 5 minutes, after which the beads are pelleted by brief centrifugation (15,000×g for 30 sec. at room temperature).

The supernatant is added to 1 ml of Dilution Buffer (0.1% Triton X-100, 5 mM EDTA, 50 mM NaCl, 10 mM Tris pH 7.4) with 2 mg Rap1 antibody, Rap1/Krev1 (121) (Santa Cruz Biotech). The second protein/antibody mixture is incubated on ice at 4° C. for 1–2 hours. The immune complex is collected on pansorbin (Calbiochem) by tumbling at 4° C. for 45 minutes. The pellet is washed 3 times with 1 ml of lysis buffer lacking DTT and protease inhibitors and resuspended in Laemmli sample buffer. The Rap1 is eluted from the beads by heating at 95° C. for 5 minutes, after which the beads are pelleted by brief centrifugation. The supernatant is subjected to SDS-PAGE on a 12% acrylamide gel (bis-acrylamide:acrylamide, 1:100), and the Rap1 visualized by fluorography.

Protocol B:

PSN-1 cells are passaged every 3–4 days in 10 cm plates, splitting near-confluent plates 1:20 and 1:40. The day before the assay is set up, 5×10 cells are plated on 15 cm plates to ensure the same stage of confluency in each assay. The media for these cells is RPM1 1640 (Gibco), with 15% fetal bovine serum and 1×Pen/Strep antibiotic mix.

The day of the assay, cells are collected from the 15 cm plates by trypsinization and diluted to 400,000 cells/ml in media. 0.5 ml of these diluted cells are added to each well of 24-well plates, for a final cell number of 200,000 per well. The cells are then grown at 37$\geqq$ C. overnight.

The compounds to be assayed are diluted in DMSO in ½-log dilutions. The range of final concentrations to be assayed is generally 0.1–100 $\mu$M. Four concentrations per compound is typical. The compounds are diluted so that each concentration is 1000× of the final concentration (i.e., for a 10 $\mu$M data point, a 10 mM stock of the compound is needed).

2 $\mu$L of each 1000× compound stock is diluted into 1 ml media to produce a 2× stock of compound. A vehicle control solution (2 $\mu$L DMSO to 1 ml media), is utilized. 0.5 ml of the 2× stocks of compound are added to the cells.

After 24 hours, the media is aspirated from the assay plates. Each well is rinsed with 1 ml PBS, and the PBS is aspirated. 180 $\mu$L SDS-PAGE sample buffer (Novex) containing 5% 2-mercaptoethanol is added to each well. The plates are heated to 100° C. for 5 minutes using a heat block containing an adapter for assay plates. The plates are placed on ice. After 10 minutes, 20 $\mu$L of an RNAse/DNase mix is added per well. This mix is 1 mg/ml DNaseI (Worthington Enzymes), 0.25 mg/ml RNAse A (Worthington Enzymes), 0.5M Tris-HCl pH8.0 and 50 mM MgCl$_2$. The plate is left on ice for 10 minutes. Samples are then either loaded on the gel, or stored at −70° C. until use.

Each assay plate (usually 3 compounds, each in 4-point titrations, plus controls) requires one 15-well 14% Novex gel. 25 μl of each sample is loaded onto the gel. The gel is run at 15 mA for about 3.5 hours. It is important to run the gel far enough so that there will be adequate separation between 21 kd (Rap1) and 29 kd (Rab6).

The gels are then transferred to Novex pre-cut PVDF membranes for 1.5 hours at 30V (constant voltage). Immediately after transferring, the membranes are blocked overnight in 20 ml Western blocking buffer (2% nonfat dry milk in Western wash buffer (PBS+0.1% Tween-20). If blocked over the weekend, 0.02% sodium azide is added. The membranes are blocked at 4° C. with slow rocking. The blocking solution is discarded and 20 ml fresh blocking solution containing the anti Rap1a antibody (Santa Cruz Biochemical SC1482) at 1:1000 (diluted in Western blocking buffer) and the anti Rab6 antibody (Santa Cruz Biochemical SC310) at 1:5000 (diluted in Western blocking buffer) are added. The membranes are incubated at room temperature for 1 hour with mild rocking. The blocking solution is then discarded and the membrane is washed 3 times with Western wash buffer for 15 minutes per wash. 20 ml blocking solution containing 1:1000 (diluted in Western blocking buffer) each of two alkaline phosphatase conjugated antibodies (Alkaline phosphatase conjugated Anti-goat IgG and Alkaline phosphatase conjugated anti-rabbit IgG [Santa Cruz Biochemical]) is then added. The membrane is incubated for one hour and washed 3× as above.

About 2 ml per gel of the Amersham ECF detection reagent is placed on an overhead transparency (ECF) and the PVDF membranes are placed face down onto the detection reagent. This is incubated for one minute, then the membrane is placed onto a fresh transparency sheet.

The developed transparency sheet is scanned on a phosphorimager and the Rap1a Minimum Inhibitory Concentration is determined from the lowest concentration of compound that produces a detectable Rap1a Western signal. The Rap1a antibody used recognizes only unprenylated/unprocessed Rap1a, so that the precence of a detectable Rap1a Western signal is indicative of inhibition of Rap1a prenylation.

Protocol C:

This protocol allows the determination of an EC$_{50}$ for inhibition of processing of Rap1a. The assay is run as described in Protocol B with the following modifications. 20 μl of sample is run on pre-cast 10–20% gradient acrylamide mini gels (Novex Inc.) at 15 mA/gel for 2.5–3 hours. Prenylated and unprenylated forms of Rap1a are detected by blotting with a polyclonal antibody (Rap1/Krev-1 Ab#121; Santa Cruz Research Products #sc-65), followed by an alkaline phosphatase-conjugated anti-rabbit IgG antibody. The percentage of unprenylated Rap1a relative to the total amount of Rap1a is determined by peak integration using Imagequant" software (Molecular Dynamics). Unprenylated Rap1a is distinguished from prenylated protein by virtue of the greater apparent molecular weight of the prenylated protein. Dose-response curves and EC$_{50}$ values are generated using 4-parameter curve fits in SigmaPlot software.

Example 68

In vivo Tumor Growth Inhibition Assay (nude mouse)

In vivo efficacy as an inhibitor of the growth of cancer cells may be confirmed by several protocols well known in the art. Examples of such in vivo efficacy studies are described by N. E. Kohl et al. (*Nature Medicine*, 1:792–797 (1995)) and N. E. Kohl et al. (*Proc. Nat. Acad. Sci. U.S.A.*, 91:9141–9145 (1994)).

Rodent fibroblasts transformed with oncogenically mutated human Ha-ras or Ki-ras (10$^6$ cells/animal in 1 ml of DMEM salts) are injected subcutaneously into the left flank of 8–12 week old female nude mice (Harlan) on day 0. The mice in each oncogene group are randomly assigned to a vehicle or compound treatment group. Animals are dosed subcutaneously starting on day 1 and daily for the duration of the experiment. Alternatively, the prenyl-protein transferase inhibitor may be administered by a continuous infusion pump. Compound or vehicle is delivered in a total volume of 0.1 ml. Tumors are excised and weighed when all of the vehicle-treated animals exhibited lesions of 0.5–1.0 cm in diameter, typically 11–15 days after the cells were injected. The average weight of the tumors in each treatment group for each cell line is calculated.

What is claimed is:
1. A compound of the formula I:

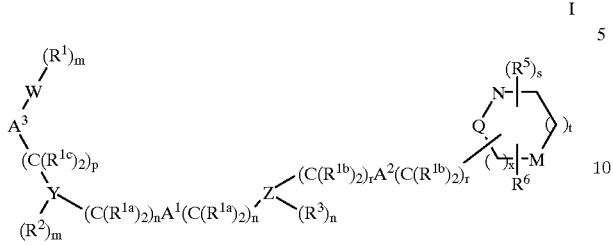

wherein:
$R^{1a}$, $R^{1b}$ and $R^{1c}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^9S(O)_q$—, CN, $NO_2$, $R^8C(O)$—, $R^8OC(O)$—, $(R^8)_2NC(O)$—, —$N(R^{15})_2$, —$OR^{15}$, —$N(R^8)S(O)_qR^8$ or $N_3$;
c) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$R^1$ is independently selected from:
a) H,
b) unsubstituted or substituted $C_1$–$C_6$ alkyl,
c) unsubstituted or substituted aryl,
d) unsubstituted or substituted heterocycle,
e) —$(C_1$–$C_6$ alkyl$)N(R^8)_2$,
f) —$R^8C(O)R^8$,
g) —$(C_1$–$C_6$ alkyl$)OR^8$,
h) —$N(R^8)_2$,
i) —$OR^8$,
j) —$R^8NHC(O)R^8$,
k) —$R^8C(O)N(R^8)_2$,
l) $CF_3$,
m) halo,
n) —$C(O)OR^8$,
o) $C_2$–$C_6$ alkynyl,
p) $C_2$–$C_6$ alkenyl,
q) perfluoroalkyl,
r) $N_3$,
s) $NO_2$,
t) CN,
u) $R^9S(O)_q$—,
v) —$(C_1$–$C_6$ alkyl$)NR^8C(O)N(R^8)_2$, and
w) —$(C_1$–$C_6$ alkyl$)R^{14}$;

$R^2$ is independently selected from:
a) hydrogen,
b) CN,
c) $NO_2$,
d) halogen,
e) aryl, unsubstituted or substituted,
f) heteroaryl, unsubstituted or substituted,
g) $C_1$–$C_6$ alkyl, unsubstituted or substituted,
h) $OR^8$,
i) $N_3$,
j) $R^9S(O)_q$,
k) $R^8HC=CH$—, and
l) $R^8C\equiv C$—;

$R^3$ is independently selected from:
a) H,
b) CN,
c) $NO_2$,
d) halogen,
e) $C_1$–$C_6$ alkyl, unsubstituted or substituted,
f) $OR^8$,
g) aryl, unsubstituted or substituted,
h) heteroaryl, unsubstituted or substituted, and
i) $CF_3$;

$R^5$ and $R^6$ are independently selected from:
a) H,
b) CN,
c) $NO_2$,
d) halogen,
e) $C_1$–$C_6$ alkyl, unsubstituted or substituted,
f) $N_3$,
g) $R^9S(O)_q$,
h) —$HC=CH_2$,
i) $HC\equiv C$—,
j) aryl, unsubstituted or substituted,
k) heterocycle, unsubstituted or substituted,
l) $CF_3O$—,
m) $CF_3CH_2O$—,
n) $C_3$–$C_{10}$ cycloalkyl,
o) $CF_3$,
p) —$(C_1$–$C_6$ alkyl$)N(R^8)_2$,
q) —$(C_1$–$C_6$ alkyl$)OR^8$,
r) $OR^8$,
s) $N(R^8)_2$,
t) —$C(O)(C_1$–$C_6$ alkyl),
u) —$(C_1$–$C_6$ alkyl$)C(O)R^8$,
v) —$C(O)O(C_1$–$C_6$ alkyl),
w) —$C(O)N(R^8)_2$,
x) —$(C_1$–$C_6$ alkyl$)NR^8C(O)N(R^8)_2$,
y) —$(C_1$–$C_6$ alkyl$)NR^8C(O)R^8$,
z) —$C_2$–$C_6$ alkynyl,
aa) —$C_2$–$C_6$ alkenyl,
bb) —$(C_1$–$C_6$ alkyl$)N_3$,
cc) —$(C_1$–$C_6$ alkyl$)NR^8S(O)_q$, and
dd) —$(C_1$–$C_6$ alkyl$)NR^8(C_1$–$C_6$ alkyl$)N(R^8)_2$;

$R^8$ is independently selected from hydrogen, unsubstituted or substituted $C_1$–$C_6$ alkyl, unsubstituted or substituted aralkyl, unsubstituted or substituted heterocycle and unsubstituted or substituted aryl;

$R^9$ is independently selected from unsubstituted or substituted $C_1$–$C_6$ alkyl, unsubstituted or substituted benzyl and unsubstituted or substituted aryl;

$R^{14}$ is unsubstituted saturated heterocycle;

$R^{15}$ is independently selected from
a) hydrogen, unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^9S(O)_2$—, $R^8C(O)$—, $R^8OC(O)$—, $(R^8)_2NC(O)$—, and
b) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$A^1$ and $A^2$ are independently selected from:
a) a bond,
b) —$HC=CH$—,
c) —$C\equiv C$—,
d) O,
e) $S(O)_q$,
f) OC(O),
g) C(O),
h) C(O)O, and
i) $NR^8$;

$A^3$ is selected from a bond, —C(=O)—,

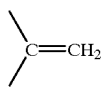

and $C_3$–$C_6$ cycloalkyl;

M is $CH_2$;

Q is C(=O);

W is selected from:
 a) heterocycle, and
 b) aryl;

Y is selected from:
 a) aryl, and
 b) heterocycle;

Z is selected from:
 a) aryl,
 b) heterocycle,
 c) $C_3$–$C_6$ cycloalkyl, and
 d) a bond;

m is 0, 1, 2, 3 or 4;

n is 0, 1, 2, 3 or 4;

p is 0, 1, 2, 3 or 4;

q is 0, 1 or 2;

r is 0, 1, 2, 3, or 4;

s is 0, 1, 2, 3 or 4;

t is 0, 1, 2 or 3; and x is 0, 1, 2 or 3;
 provided that the moiety

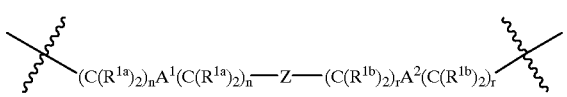

does not represent a bond; and
 provided that if attachment of

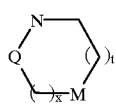

to the rest of the molecule is through a nitrogen ring atom, then $A^1$ is $NR^8$, O, or $S(O)_q$;
 provided that the sum of variables x and t will be equal to 3;

or a pharmaceutically acceptable salt, an optical isomer or stereoisomer thereof.

2. A compound of the formula A:

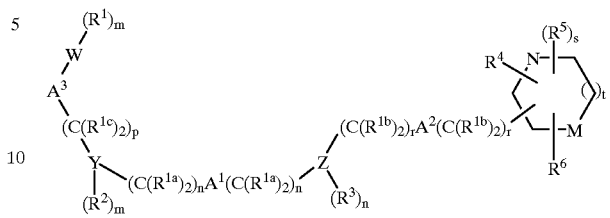

wherein:
$R^{1a}$, $R^{1b}$ and $R^{1c}$ are independently selected from:
 a) hydrogen,
 b) unsubstituted or substituted aryl; unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, $N(R^8)_2$, $(R^8)_2NC(O)$—, $C(O)N(R^8)$—, or $N_3$;
 c) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$R^1$ is selected from:
 a) H,
 b) unsubstituted or substituted $C_1$–$C_6$ alkyl,
 c) unsubstituted or substituted aryl,
 d) unsubstituted or substituted heterocycle,
 e) —($C_1$–$C_6$ alkyl)$N(R^8)_2$,
 f) —$R^8C(O)R^8$,
 g) —($C_1$–$C_6$ alkyl)$OR^8$,
 h) —$N(R^8)_2$,
 i) —$OR^8$,
 j) —$R^8NHC(O)R^8$,
 k) —$R^8C(O)N(R^8)_2$,
 l) $CF_3$,
 m) halo,
 n) —$C(O)OR^8$,
 o) $C_2$–$C_6$ alkynyl,
 p) $C_2$–$C_6$ alkenyl,
 q) perfluoroalkyl,
 r) $N_3$,
 s) $NO_2$,
 t) CN, and
 u) $R^9S(O)_q$—;

$R^2$ is selected from:
 a) hydrogen,
 b) CN,
 c) $NO_2$,
 d) halogen,
 e) aryl, unsubstituted or substituted,
 f) heteroaryl, unsubstituted or substituted,
 g) $C_1$–$C_6$ alkyl, unsubstituted or substituted,
 h) $OR^8$,
 i) $N_3$,
 j) $R^9S(O)_q$,
 k) $R^8HC=CH$—, and
 l) $R^8C\equiv C$—;

$R^3$ is selected from:
 a) H,
 b) CN,
 c) $NO_2$,
 d) halogen, e) $C_1$–$C_6$ alkyl, unsubstituted or substituted,
f) $OR^8$,
g) aryl, unsubstituted or substituted,
h) heteroaryl, unsubstituted or substituted, and
i) $CF_3$;

$R^4$ is =O;

$R^5$ is selected from:
a) H,
b) CN,
c) $NO_2$,
d) halogen,
e) $C_1$–$C_6$ alkyl, unsubstituted or substituted,
f) $N_3$,
g) $R^9S(O)_q$,
h) —HC=$CH_2$,
i) HC≡C—,
j) aryl, unsubstituted or substituted,
k) heterocycle, unsubstituted or substituted,
l) $CF_3O$—,
m) $CF_3CH_2O$—,
n) $C_3$–$C_{10}$ cycloalkyl,
o) $CF_3$,
p) —($C_1$–$C_6$ alkyl)$N(R^8)_2$,
q) —($C_1$–$C_6$ alkyl)$OR^8$,
r) $OR^8$,
s) $N(R^8)_2$,
t) —C(O)($C_1$–$C_6$ alkyl), and
u) —($C_1$–$C_6$ alkyl)$C(O)R^8$;

$R^6$ is selected from:
a) H,
b) $C_1$–$C_6$ alkyl, unsubstituted or substituted,
c) $OR^8$, and
d) —C(O)($C_1$–$C_6$ alkyl);

$R^8$ is independently selected from hydrogen, unsubstituted or substituted $C_1$–$C_6$ alkyl, unsubstituted or substituted benzyl, unsubstituted or substituted heterocycle and unsubstituted or substituted aryl;

$R^9$ is independently selected from unsubstituted or substituted $C_1$–$C_6$ alkyl, unsubstituted or substituted benzyl and unsubstituted or substituted aryl;

$A^1$ and $A^2$ are independently selected from:
a) a bond,
b) —HC=CH—,
c) —C≡C—,
d) O,
e) $S(O)_q$,
f) OC(O),
g) C(O),
h) C(O)O, and
i) $NR^8$;

$A^3$ is selected from a bond, —C(=O)—, $$\diagdown_{C=CH_2}^{\diagup}$$

and $C_3$–$C_6$ cycloalkyl;

M is $CH_2$;

W is selected from:
a) heterocycle, and
b) aryl;

Y is selected from:
a) aryl, and
b) heterocycle;

Z is selected from:
a) aryl,
b) heterocycle,
c) $C_3$–$C_6$ cycloalkyl, and
d) a bond;

m is 0, 1, 2, 3 or 4;
n is 0, 1, 2, 3 or 4;
p is 0, 1, 2, 3 or 4;
q is 0, 1 or 2;
r is 0, 1, 2, 3, or 4;
s is 0, 1, 2, 3 or 4; and
t is 2;

or a pharmaceutically acceptable salt, an optical isomer or stereoisomer thereof.

3. The compound according to claim 2 of formula A:

A wherein:

$R^{1a}$, $R^{1b}$ and $R^{1c}$ are independently selected from:
a) hydrogen,
b) unsubstituted or substituted aryl; unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, $N(R^8)_2$, $(R^8)_2NC(O)$—, $C(O)N(R^8)$—, or $N_3$;
c) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$R^1$ is selected from:
a) H,
b) unsubstituted or substituted $C_1$–$C_6$ alkyl,
c) unsubstituted or substituted aryl,
d) unsubstituted or substituted heterocycle,
e) —($C_1$–$C_6$ alkyl)$N(R^8)_2$,
f) —($C_1$–$C_6$ alkyl)$C(O)R^8$,
g) —($C_1$–$C_6$ alkyl)$OR^8$,
h) —$N(R^8)_2$,
i) —$OR^8$,
j) —($C_1$–$C_6$ alkyl)$NHC(O)R^8$,
k) —($C_1$–$C_6$ alkyl)$C(O)N(R^8)_2$,
l) $CF_3$, and
m) halo;

$R^2$ is selected from:
a) hydrogen,
b) CN,
c) $NO_2$,
d) halogen,
e) aryl, unsubstituted or substituted,
f) heteroaryl, unsubstituted or substituted,
g) $C_1$–$C_6$ alkyl, unsubstituted or substituted,
h) $OR^8$,
i) $N_3$,
j) $R^9S(O)_q$, k) $R^8HC=CH-$, and
l) $R^8C≡C-$;

$R^3$ is selected from:
  a) H,
  b) CN,
  c) $NO_2$,
  d) halogen,
  e) $C_1-C_6$ alkyl, unsubstituted or substituted,
  f) $OR^8$,
  g) aryl, unsubstituted or substituted,
  h) heteroaryl, unsubstituted or substituted, and
  i) $CF_3$;

$R^4$ is =O;

$R^5$ is selected from:
  a) H,
  b) CN,
  c) $NO_2$,
  d) halogen,
  e) $C_1-C_6$ alkyl, unsubstituted or substituted,
  f) $N_3$,
  g) $R^9S(O)_q$,
  h) $-HC=CH_2$,
  i) $HC≡C-$,
  j) aryl, unsubstituted or substituted,
  k) heterocycle, unsubstituted or substituted,
  l) $CF_3O-$,
  m) $CF_3CH_2O-$,
  n) $C_3-C_{10}$ cycloalkyl,
  o) $CF_3$,
  p) $-(C_1-C_6$ alkyl$)N(R^8)_2$,
  q) $-(C_1-C_6$ alkyl$)OR^8$,
  r) $OR^8$,
  s) $N(R^8)_2$,
  t) $-C(O)(C_1-C_6$ alkyl), and
  u) $-(C_1-C_6$ alkyl$)C(O)R^8$;

$R^6$ is selected from:
  a) H,
  b) $C_1-C_6$ alkyl, unsubstituted or substituted,
  c) $OR^8$, and
  d) $-C(O)(C_1-C_6$ alkyl);

$R^8$ is independently selected from hydrogen, unsubstituted or substituted $C_1-C_6$ alkyl, benzyl and unsubstituted or substituted aryl;

$R^9$ is independently selected from unsubstituted or substituted $C_1-C_6$ alkyl, benzyl and unsubstituted or substituted aryl;

$A^1$ is selected from:
  a) a bond,
  b) $-HC=CH-$,
  c) $-C≡C-$,
  d) O,
  e) $S(O)_q$,
  f) OC(O),
  g) C(O),
  h) C(O)O, and
  i) $NR^8$;

$A^2$ is selected from:
  a) a bond,
  b) O,
  c) $S(O)_q$,
  d) C(O), and
  e) $NR^8$;

$A^3$ is seected from a bond, $-C(=O)-$, $$\underset{/}{\overset{\backslash}{C}}=CH_2$$

and $C_3-C_6$ cycloalkyl;

M is $CH_2$;

W is selected from:
  a) heterocycle, and
  b) aryl;

Y is selected from:
  a) aryl, and
  b) heterocycle;

Z is selected from:
  a) aryl,
  b) heterocycle, and
  c) a bond;

m is 0, 1, 2, 3 or 4;
n is 0, 1, 2, 3 or 4;
p is 0, 1, 2, 3 or 4;
q is 0, 1 or 2;
r is 0, 1, 2, 3, or 4;
s is 0, 1, 2, 3 or 4; and
t is 2;

or a pharmaceutically acceptable salt, an optical isomer or stereoisomer thereof.

4. The compound according to claim 3 of formula B:

wherein:

$R^{1a}$ and $R^{1c}$ are independently selected from:
  a) hydrogen,
  b) unsubstituted or substituted aryl; unsubstituted or substituted heterocycle, $C_3-C_{10}$ cycloalkyl, $C_2-C_6$ alkenyl, $C_2-C_6$ alkynyl, $R^8O-$, $R^9S(O)_q-$, CN, $NO_2$, $R^8C(O)-$, $R^8OC(O)-$, $N(R^8)_2$, $(R^8)_2NC(O)-$, $C(O)N(R^8)-$, or $N_3$;
  c) $C_1-C_6$ alkyl, unsubstituted or substituted by unsubstituted or substituted aryl, unsubstituted or substituted heterocycle, $C_3-C_{10}$ cycloalkyl, $C_2-C_6$ alkenyl, $C_2-C_6$ alkynyl, $R^8O-$, $R^9S(O)_q-$, CN, $R^8C(O)-$, $R^8OC(O)-$, $N(R^8)_2$, $N_3$, or $R^8C(O)O-$;

$R^1$ is selected from:
  a) H,
  b) unsubstituted or substituted $C_1-C_6$ alkyl,
  c) unsubstituted or substituted aryl,
  d) unsubstituted or substituted heterocycle,
  e) $-(C_1-C_6$ alkyl$)N(R^8)_2$,
  f) $-(C_1-C_6$ alkyl$)C(O)R^8$,
  g) $-(C_1-C_6$ alkyl$)OR^8$,
  h) $-N(R^8)_2$,
  i) $-OR^8$,
  j) $-(C_1-C_6$ alkyl$)NHC(O)R^8$,
  k) $-(C_1-C_6$ alkyl$)C(O)N(R^8)_2$, l) CF$_3$, and
m) halo;

R$^2$ is selected from:
a) hydrogen,
b) CN,
c) NO$_2$,
d) halogen,
e) aryl, unsubstituted or substituted,
f) heteroaryl, unsubstituted or substituted,
g) C$_1$–C$_6$ alkyl, unsubstituted or substituted,
h) OR$^8$,
i) N$_3$,
j) R$^9$S(O)$_q$,
k) R$^8$HC=CH—, and
l) R$^8$C≡C—;

R$^3$ is selected from:
a) H,
b) CN,
c) NO$_2$,
d) halogen,
e) C$_1$–C$_6$ alkyl, unsubstituted or substituted,
f) OR$^8$,
g) aryl, unsubstituted or substituted,
h) heteroaryl, unsubstituted or substituted, and
i) CF$_3$;

R$^4$ is =O;

R$^5$ is selected from:
a) H,
b) CN,
c) NO$_2$,
d) halogen,
e) C$_1$–C$_6$ alkyl, unsubstituted or substituted,
f) N$_3$,
g) R$^9$S(O)$_q$,
h) —HC=CH$_2$,
i) HC≡C—,
j) aryl, unsubstituted or substituted,
k) heterocycle, unsubstituted or substituted,
l) CF$_3$O—,
m) CF$_3$CH$_2$O—,
n) C$_3$–C$_{10}$ cycloalkyl,
o) CF$_3$,
p) —(C$_1$–C$_6$ alkyl)N(R$^8$)$_2$,
q) —(C$_1$–C$_6$ alkyl)OR$^8$,
r) OR$^8$,
s) N(R$^8$)$_2$,
t) —C(O)(C$_1$–C$_6$ alkyl), and
u) —(C$_1$–C$_6$ alkyl)C(O)R$^8$;

R$^6$ is selected from:
a) H,
b) C$_1$–C$_6$ alkyl, unsubstituted or substituted,
c) OR$^8$, and
d) —C(O)(C$_1$–C$_6$ alkyl);

R$^8$ is independently selected from hydrogen, unsubstituted or substituted C$_1$–C$_6$ alkyl, benzyl and unsubstituted or substituted aryl;

R$^9$ is independently selected from unsubstituted or substituted C$_1$–C$_6$ alkyl, benzyl and unsubstituted or substituted aryl;

A$^1$ is selected from:
a) a bond,
b) —HC=CH—,
c) —C≡C—,
d) O,
e) S(O)$_q$,
f) OC(O),
g) C(O),
h) C(O)O, and
i) NR$^8$;

W is selected from:
a) heterocycle, and
b) aryl;

Y is selected from:
a) aryl, and
b) heterocycle;

Z is selected from:
a) aryl, and
b) heterocycle;

m is 0, 1, 2, 3 or 4;
n is 0, 1, 2, 3 or 4;
p is 0, 1, 2, 3 or 4;
q is 0, 1 or 2;
s is 0, 1, 2, 3 or 4; and
t is 2;

or a pharmaceutically acceptable salt, an optical isomer or stereoisomer thereof.

5. The compound according to claim 1 of formula II:

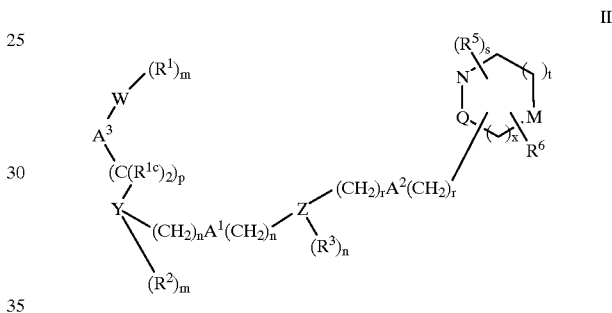

II wherein:
R$^{1c}$ is independently selected from:
a) hydrogen,
b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, R$^9$S(O)$_q$—, CN, NO$_2$, R$^8$C(O)—, R$^8$OC(O)—, (R$^8$)$_2$NC(O)—, —N(R$^{15}$)$_2$, —OR$^{15}$, —N(R$^8$)S(O)$_q$R$^8$ or N$_3$;
c) C$_1$–C$_6$ alkyl, unsubstituted or substituted by unsubstituted or substituted aryl, unsubstituted or substituted heterocycle, C$_3$–C$_{10}$ cycloalkyl, C$_2$–C$_6$ alkenyl, C$_2$–C$_6$ alkynyl, R$^8$O—, R$^9$S(O)$_q$—, CN, R$^8$C(O)—, R$^8$OC(O)—, N(R$^8$)$_2$, N$_3$, or R$^8$C(O)O—;

R$^1$ is independently selected from:
a) H,
b) unsubstituted or substituted C$_1$–C$_6$ alkyl,
c) unsubstituted or substituted aryl,
d) unsubstituted or substituted heterocycle,
e) —(C$_1$–C$_6$ alkyl)N(R$^8$)$_2$,
f) —R$^8$C(O)R$^8$,
g) —(C$_1$–C$_6$ alkyl)OR$^8$,
h) —N(R$^8$)$_2$,
i) —OR$^8$,
j) —R$^8$NHC(O)R$^8$,
k) —R$^8$C(O)N(R$^8$)$_2$,
l) CF$_3$,
m) halo,
n) —C(O)OR$^8$,
o) C$_2$–C$_6$ alkynyl,
p) C$_2$–C$_6$ alkenyl,
q) perfluoroalkyl, r) $N_3$,
s) $NO_2$,
t) CN,
u) $R^9S(O)_q$—,
v) —($C_1$–$C_6$ alkyl)$NR^8C(O)N(R^8)_2$, and
w) —($C_1$–$C_6$ alkyl)$R^{14}$;

$R^2$ is independently selected from:
a) hydrogen,
b) CN,
c) $NO_2$,
d) halogen,
e) aryl, unsubstituted or substituted,
f) heteroaryl, unsubstituted or substituted,
g) $C_1$–$C_6$ alkyl, unsubstituted or substituted,
h) $OR^8$,
i) $N_3$,
j) $R^9S(O)_q$,
k) $R^8HC=CH$—, and
l) $R^8C\equiv C$—;

$R^3$ is independently selected from:
a) H,
b) CN,
c) $NO_2$,
d) halogen,
e) $C_1$–$C_6$ alkyl, unsubstituted or substituted,
f) $OR^8$,
g) aryl, unsubstituted or substituted,
h) heteroaryl, unsubstituted or substituted, and
i) $CF_3$;

$R^5$ and $R^6$ are independently selected from:
a) H,
b) CN,
c) $NO_2$,
d) halogen,
e) $C_1$–$C_6$ alkyl, unsubstituted or substituted,
f) $N_3$,
g) $R^9S(O)_q$,
h) —$HC=CH_2$,
i) $HC\equiv C$—,
j) aryl, unsubstituted or substituted,
k) heterocycle, unsubstituted or substituted,
l) $CF_3O$—,
m) $CF_3CH_2O$—,
n) $C_3$–$C_{10}$ cycloalkyl,
o) $CF_3$,
p) —($C_1$–$C_6$ alkyl)$N(R^8)_2$,
q) —($C_1$–$C_6$ alkyl)$OR^8$,
r) $OR^8$,
s) $N(R^8)_2$,
t) —$C(O)(C_1$–$C_6$ alkyl),
u) —($C_1$–$C_6$ alkyl)$C(O)R^8$,
v) —$C(O)O(C_1$–$C_6$ alkyl),
w) —$C(O)N(R^8)_2$,
x) —($C_1$–$C_6$ alkyl)$NR^8C(O)N(R^8)_2$,
y) —($C_1$–$C_6$ alkyl)$NR^8C(O)R^8$,
z) —$C_2$–$C_6$ alkynyl,
aa) —$C_2$–$C_6$ alkenyl,
bb) —($C_1$–$C_6$ alkyl)$N_3$,
cc) —($C_1$–$C_6$ alkyl)$NR^8S(O)_q$, and
dd) —($C_1$–$C_6$ alkyl)$NR^8(C_1$–$C_6$ alkyl)$N(R^8)_2$;

$R^8$ is independently selected from hydrogen, unsubstituted or substituted $C_1$–$C_6$ alkyl, unsubstituted or substituted aralkyl, unsubstituted or substituted heterocycle and unsubstituted or substituted aryl;

$R^9$ is independently selected from unsubstituted or substituted $C_1$–$C_6$ alkyl, unsubstituted or substituted benzyl and unsubstituted or substituted aryl;

$R^{14}$ is unsubstituted saturated heterocycle;

$R^{15}$ is independently selected from
a) hydrogen, unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^9S(O)_2$—, $R^8C(O)$—, $R^8OC(O)$—, $(R^8)_2NC(O)$—, and
b) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$A^1$ and $A^2$ are independently selected from:
a) a bond,
b) —$HC=CH$—,
c) —$C\equiv C$—,
d) O,
e) $S(O)_q$,
f) OC(O),
g) C(O),
h) C(O)O, and
i) $NR^8$;

$A^3$ is selected from a bond, —$C(=O)$—,

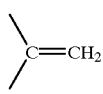

and $C_3$–$C_6$ cycloalkyl;

M is $CH_2$;

Q is $C(=O)$;

W is a heterocycle;

Y is selected from
a) aryl, and
b) heterocycle;

Z is selected from
a) aryl, and
b) heterocycle;

m is 0, 1, 2, 3 or 4;

n is 0, 1, 2, 3 or 4;

p is 0, 1, 2, 3 or 4;

q is 0, 1 or 2;

r is 0, 1, 2, 3, or 4;

s is 0, 1, 2, 3 or 4;

t is 0, 1, 2 or 3; and x is 0, 1, 2 or 3;

provided that if attachment of

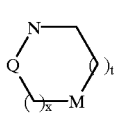

to the rest of the molecule is through a nitrogen ring atom, then $A^1$ is $NR^8$, O, or $S(O)_q$;

provided that the sum of variables x and t equals 3;

or a pharmaceutically acceptable salt, an optical isomer or stereoisomer thereof.

6. The compound according to claim 1 of formula III:

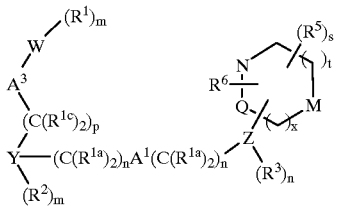

III wherein:
R$^{1a}$ and R$^{1c}$ are independently selected from:
  a) hydrogen,
  b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, R$^9$S(O)$_q$—, CN, NO$_2$, R$^8$C(O)—, R$^8$OC(O)—, (R$^8$)$_2$NC(O)—, —N(R$^{15}$)$_2$, —OR$^{15}$, —N(R$^8$)S(O)$_q$R$^8$ or N$_3$;
  c) C$_1$–C$_6$ alkyl, unsubstituted or substituted by unsubstituted or substituted aryl, unsubstituted or substituted heterocycle, C$_3$–C$_{10}$ cycloalkyl, C$_2$–C$_6$ alkenyl, C$_2$–C$_6$ alkynyl, R$^8$O—, R$^9$S(O)$_q$—, CN, R$^8$C(O)—, R$^8$OC(O)—, N(R$^8$)$_2$, N$_3$, or R$^8$C(O)O—;
R$^1$ is independently selected from:
  a) H,
  b) unsubstituted or substituted C$_1$–C$_6$ alkyl,
  c) unsubstituted or substituted aryl,
  d) unsubstituted or substituted heterocycle,
  e) —(C$_1$–C$_6$ alkyl)N(R$^8$)$_2$,
  f) —R$^8$C(O)R$^8$,
  g) —(C$_1$–C$_6$ alkyl)OR$^8$,
  h) —N(R$^8$)$_2$,
  i) —OR$^8$,
  j) —R$^8$NHC(O)R$^8$,
  k) —R$^8$C(O)N(R$^8$)$_2$,
  l) CF$_3$,
  m) halo,
  n) —C(O)OR$^8$,
  o) C$_2$–C$_6$ alkynyl,
  p) C$_2$–C$_6$ alkenyl,
  q) perfluoroalkyl,
  r) N$_3$,
  s) NO$_2$,
  t) CN,
  u) R$^9$S(O)$_q$—,
  v) —(C$_1$–C$_6$ alkyl)NR$^8$C(O)N(R$^8$)$_2$, and
  w) —(C$_1$–C$_6$ alkyl)R$^{14}$;
R$^2$ is independently selected from:
  a) hydrogen,
  b) CN,
  c) NO$_2$,
  d) halogen,
  e) aryl, unsubstituted or substituted,
  f) heteroaryl, unsubstituted or substituted,
  g) C$_1$–C$_6$ alkyl, unsubstituted or substituted,
  h) OR$^8$,
  i) N$_3$,
  j) R$^9$S(O)$_q$,
  k) R$^8$HC=CH—, and
  l) R$^8$C≡C—;
R$^3$ is independently selected from:
  a) H,
  b) CN,
  c) NO$_2$,
  d) halogen,
  e) C$_1$–C$_6$ alkyl, unsubstituted or substituted,
  f) OR$^8$,
  g) aryl, unsubstituted or substituted,
  h) heteroaryl, unsubstituted or substituted, and
  i) CF$_3$;
R$^5$ and R$^6$ are independently selected from:
  a) H,
  b) CN,
  c) NO$_2$,
  d) halogen,
  e) C$_1$–C$_6$ alkyl, unsubstituted or substituted,
  f) N$_3$,
  g) R$^9$S(O)$_q$,
  h) —HC=CH$_2$,
  i) HC≡C—,
  j) aryl, unsubstituted or substituted,
  k) heterocycle, unsubstituted or substituted,
  l) CF$_3$O—,
  m) CF$_3$CH$_2$O—,
  n) C$_3$–C$_{10}$ cycloalkyl,
  o) CF$_3$,
  p) —(C$_1$–C$_6$ alkyl)N(R$^8$)$_2$,
  q) —(C$_1$–C$_6$ alkyl)OR$^8$,
  r) OR$^8$,
  s) N(R$^8$)$_2$,
  t) —C(O)(C$_1$–C$_6$ alkyl),
  u) —(C$_1$–C$_6$ alkyl)C(O)R$^8$,
  v) —C(O)O(C$_1$–C$_6$ alkyl),
  w) —C(O)N(R$^8$)$_2$,
  x) —(C$_1$–C$_6$ alkyl)NR$^8$C(O)N(R$^8$)$_2$,
  y) —(C$_1$–C$_6$ alkyl)NR$^8$C(O)R$^8$,
  z) —C$_2$–C$_6$ alkynyl,
  aa) —C$_2$–C$_6$ alkenyl,
  bb) —(C$_1$–C$_6$ alkyl)N$_3$,
  cc) —(C$_1$–C$_6$ alkyl)NR$^8$S(O)$_q$, and
  dd) —(C$_1$–C$_6$ alkyl)NR$^8$(C$_1$–C$_6$ alkyl)N(R$^8$)$_2$;
R$^8$ is independently selected from hydrogen, unsubstituted or substituted C$_1$–C$_6$ alkyl, unsubstituted or substituted aralkyl, unsubstituted or substituted heterocycle and unsubstituted or substituted aryl;
R$^9$ is independently selected from unsubstituted or substituted C$_1$–C$_6$ alkyl, unsubstituted or substituted benzyl and unsubstituted or substituted aryl;
R$^{14}$ is unsubstituted saturated heterocycle;
R$^{15}$ is independently selected from
  a) hydrogen, unsubstituted or substituted aryl, unsubstituted or substituted heterocycle, C$_3$–C$_{10}$ cycloalkyl, C$_2$–C$_6$ alkenyl, C$_2$–C$_6$ alkynyl, R$^9$S(O)$_2$—, R$^8$C(O)—, R$^8$OC(O)—, (R$^8$)$_2$NC(O)—, and
  b) C$_1$–C$_6$ alkyl, unsubstituted or substituted by unsubstituted or substituted aryl, unsubstituted or substituted heterocycle, C$_3$–C$_{10}$ cycloalkyl, C$_2$–C$_6$ alkenyl, C$_2$–C$_6$ alkynyl, R$^8$O—, R$^9$S(O)$_q$—, CN, R$^8$C(O)—, R$^8$OC(O)—, N(R$^8$)$_2$, N$_3$, or R$^8$C(O)O—;
A$^1$ is selected from:
  a) a bond,
  b) —HC=CH—,
  c) —C≡C—,
  d) O,
  e) S(O)$_q$,
  f) OC(O),
  g) C(O),
  h) C(O)O, and
  i) NR$^8$;

$A^3$ is selected from a bond, —C(=O)—,

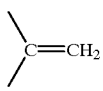

and $C_3$–$C_6$ cycloalkyl;

M is $CH_2$;

Q is (=O);

W is a heterocycle selected from pyrrolidinyl, imidazolyl, pyridyl, triazolyl, pyridonyl, 2-oxopiperidinyl, indolyl, quinolinyl, isoquinolinyl, and tetrahydroimidazopyridinyl, Y is selected from:
a) aryl, and
b) pyridyl;

Z is selected from:
a) aryl, and
b) pyridyl;

m is 0, 1, 2, 3 or 4;
n is 0, 1, 2, 3 or 4;
p is 0, 1, 2, 3 or 4;
q is 0, 1 or 2;
s is 0, 1, 2, 3 or 4;
t is 0, 1, 2 or 3; and
x is 0, 1, 2 or 3;
provided that if attachment of

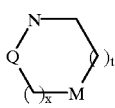

to the rest of the molecule is through a nitrogen ring atom, then $A^1$ is $NR^8$, O, or $S(O)_q$;

provided that the sum of the variables x and t equals 3; or a pharmaceutically acceptable salt, an optical isomer or stereoisomer thereof.

7. The compound according to claim 2 of formula C:

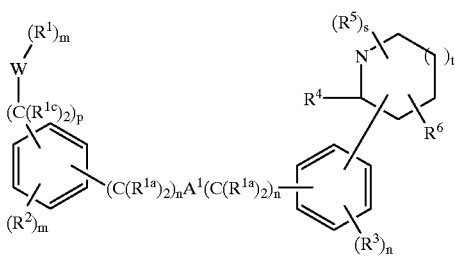

wherein:

$R^{1a}$ and $R^{1c}$ are independently selected from:
a) hydrogen,
b) unsubstituted or substituted aryl; unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, $N(R^8)_2$, $(R^8)_2NC(O)$—, $C(O)N(R^8)$—, or $N_3$;
c) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$R^1$ is selected from:
a) H,
b) unsubstituted or substituted $C_1$–$C_6$ alkyl,
c) unsubstituted or substituted aryl,
d) unsubstituted or substituted heterocycle,
e) —($C_1$–$C_6$ alkyl)$N(R^8)_2$,
f) —($C_1$–$C_6$ alkyl)$C(O)R^8$,
g) —($C_1$–$C_6$ alkyl)$OR^8$,
h) —$N(R^8)_2$,
i) —$OR^8$,
j) —($C_1$–$C_6$ alkyl)$NHC(O)R^8$,
k) —($C_1$–$C_6$ alkyl)$C(O)N(R^8)_2$,
l) $CF_3$, and
m) halo;

$R^2$ is selected from:
a) hydrogen,
b) CN,
c) $NO_2$,
d) halogen,
e) aryl, unsubstituted or substituted,
f) heteroaryl, unsubstituted or substituted,
g) $C_1$–$C_6$ alkyl, unsubstituted or substituted,
h) $OR^8$,
i) $N_3$,
j) $R^9S(O)_q$,
k) $R^8HC=CH$—, and
l) $R^8C\equiv C$—;

$R^3$ is selected from:
a) H,
b) CN,
c) $NO_2$,
d) halogen,
e) $C_1$–$C_6$ alkyl, unsubstituted or substituted,
f) $OR^8$,
g) aryl, unsubstituted or substituted,
h) heteroaryl, unsubstituted or substituted, and
i) $CF_3$;

$R^4$ is =O;

$R^5$ is selected from:
a) H,
b) CN,
c) $NO_2$,
d) halogen,
e) $C_1$–$C_6$ alkyl, unsubstituted or substituted,
f) $N_3$,
g) $R^9S(O)_q$,
h) —$HC=CH_2$,
i) $HC\equiv C$—,
j) aryl, unsubstituted or substituted,
k) heterocycle, unsubstituted or substituted,
l) $CF_3O$—,
m) $CF_3CH_2O$—,
n) $C_3$–$C_{10}$ cycloalkyl,
o) $CF_3$,
p) —($C_1$–$C_6$ alkyl)$N(R^8)_2$,
q) —($C_1$–$C_6$ alkyl)$OR^8$,
r) $OR^8$,
s) $N(R^8)_2$,
t) —$C(O)(C_1$–$C_6$ alkyl), and
u) —($C_1$–$C_6$ alkyl)$C(O)R^8$;

$R^6$ is selected from:
  a) H,
  b) $C_1$–$C_6$ alkyl, unsubstituted or substituted,
  c) $OR^8$, and
  d) —C(O)($C_1$–$C_6$ alkyl);
$R^8$ is independently selected from hydrogen, unsubstituted or substituted $C_1$–$C_6$ alkyl, benzyl and unsubstituted or substituted aryl;
$R^9$ is independently selected from unsubstituted or substituted $C_1$–$C_6$ alkyl, benzyl and unsubstituted or substituted aryl;
$A^1$ is selected from:
  a) a bond,
  b) —HC=CH—,
  c) —C≡C—,
  d) O,
  e) $S(O)_q$,
  f) OC(O),
  g) C(O),
  h) C(O)O, and
  i) $NR^8$;
W is selected from:
  a) heterocycle, and
  b) aryl;
m is 0, 1, 2, 3 or 4;
n is 0, 1, 2, 3 or 4;
p is 0, 1, 2, 3 or 4;
q is 0, 1 or 2;
s is 0, 1, 2, 3 or 4; and
t is 2;
or a pharmaceutically acceptable salt, an optical isomer or stereoisomer thereof.

8. The compound according to claim 1 of formula IV:

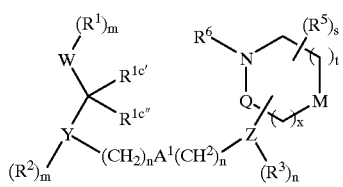

IV wherein:
$R^{1c'}$ is selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl;
  c) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;
$R^{1c''}$ is selected from:
  a) hydrogen,
  b) $N(R^{15})_2$, and
  c) $OR^{15}$;
$R^1$ is independently selected from:
  a) H,
  b) unsubstituted or substituted $C_1$–$C_6$ alkyl,
  c) unsubstituted or substituted aryl,
  d) unsubstituted or substituted heterocycle,
  e) —($C_1$–$C_6$ alkyl)$N(R^8)_2$,
  f) —$R^8C(O)R^8$,
  g) —($C_1$–$C_6$ alkyl)$OR^8$,
  h) —$N(R^8)_2$,
  i) —$OR^8$,
  j) —$R^8NHC(O)R^8$,
  k) —$R^8C(O)N(R^8)_2$,
  l) $CF_3$,
  m) halo,
  n) —$C(O)OR^8$,
  o) $C_2$–$C_6$ alkynyl,
  p) $C_2$–$C_6$ alkenyl,
  q) perfluoroalkyl,
  r) $N_3$,
  s) $NO_2$,
  t) CN,
  u) $R^9S(O)_q$—,
  v) —($C_1$–$C_6$ alkyl)$NR^8C(O)N(R^8)_2$, and
  w) —($C_1$–$C_6$ alkyl)$R^{14}$;
$R^2$ is independently selected from:
  a) hydrogen,
  b) CN,
  c) $NO_2$,
  d) halogen,
  e) aryl, unsubstituted or substituted,
  f) heteroaryl, unsubstituted or substituted,
  g) $C_1$–$C_6$ alkyl, unsubstituted or substituted,
  h) $OR^8$,
  i) $N_3$,
  j) $R^8S(O)_q$,
  k) $R^8HC=CH$—, and
  l) $R^8C≡C$—;
$R^3$ is independently selected from:
  a) H,
  b) CN,
  c) $NO_2$,
  d) halogen,
  e) $C_1$–$C_6$ alkyl, unsubstituted or substituted,
  f) $OR^8$,
  g) aryl, unsubstituted or substituted,
  h) heteroaryl, unsubstituted or substituted, and
  i) $CF_3$;
$R^5$ is independently selected from:
  a) H,
  b) CN,
  c) $NO_2$,
  d) halogen,
  e) $C_1$–$C_6$ alkyl, unsubstituted or substituted,
  f) $N_3$,
  g) $R^9S(O)_q$,
  h) —$HC=CH_2$,
  i) $HC≡C$—,
  j) aryl, unsubstituted or substituted,
  k) heterocycle, unsubstituted or substituted,
  l) $CF_3O$—,
  m) $CF_3CH_2O$—,
  n) $C_3$–$C_{10}$ cycloalkyl,
  o) $CF_3$,
  p) —($C_1$–$C_6$ alkyl)$N(R^8)_2$,
  q) —($C_1$–$C_6$ alkyl)$OR^8$,
  r) $OR^8$,
  s) $N(R^8)_2$,
  t) —C(O)($C_1$–$C_6$ alkyl),
  u) —($C_1$–$C_6$ alkyl)$C(O)R^8$,
  v) —$C(O)O(C_1$–$C_6$ alkyl),
  w) —$C(O)N(R^8)_2$,
  x) —($C_1$–$C_6$ alkyl)$NR^8C(O)N(R^8)_2$,
  y) —($C_1$–$C_6$ alkyl)$NR^8C(O)R^8$,
  z) —$C_2$–$C_6$ alkynyl, aa) —$C_2$–$C_6$ alkenyl,
bb) —($C_1$–$C_6$ alkyl)$N_3$,
cc) —($C_1$–$C_6$ alkyl)$NR^8S(O)_q$, and
dd) —($C_1$–$C_6$ alkyl)$NR^8$($C_1$–$C_6$ alkyl)$N(R^8)_2$;

$R^6$ is selected from
a) H,
b) $C_1$–$C_6$ alkyl, unsubstituted or substituted,
c) aryl, unsubstituted or substituted,
d) heterocycle, unsubstituted or substituted,
e) $C_3$–$C_{10}$ cycloalkyl,
f) —($C_1$–$C_6$ alkyl)$N(R^8)_2$,
g) —($C_1$–$C_6$ alkyl)$OR^8$,
h) —C(O)($C_1$–$C_6$ alkyl),
i) —($C_1$–$C_6$ alkyl)$C(O)R^8$,
j) —C(O)O($C_1$–$C_6$ alkyl),
k) —C(O)$N(R^8)_2$,
l) —($C_1$–$C_6$ alkyl)$NR^8C(O)N(R^8)_2$,
m) —($C_1$–$C_6$ alkyl)$NR^8C(O)R^8$,
n) —$C_2$–$C_6$ alkynyl,
o) —$C_2$–$C_6$ alkenyl,
p) —($C_1$–$C_6$ alkyl)$N_3$,
q) —($C_1$–$C_6$ alkyl)$NR^8S(O)_q$, and
r) —($C_1$–$C_6$ alkyl)$NR^8$($C_1$–$C_6$ alkyl)$N(R^8)_2$;

$R^8$ is independently selected from hydrogen, unsubstituted or substituted $C_1$–$C_6$ alkyl, unsubstituted or substituted aralkyl, unsubstituted or substituted heterocycle and unsubstituted or substituted aryl;

$R^9$ is independently selected from unsubstituted or substituted $C_1$–$C_6$ alkyl, unsubstituted or substituted benzyl and unsubstituted or substituted aryl;

$R^{14}$ is unsubstituted saturated heterocycle;

$R^{15}$ is independently selected from
a) hydrogen, unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^9S(O)_2$—, $R^8C(O)$—, $R^8OC(O)$—, $(R^8)_2NC(O)$—, and
b) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$A^1$ is selected from
a) O,
b) $S(O)_q$,
c) C(O), and
d) $NR^8$;

M is $CH_2$;

Q is C(=O);

W is a heterocycle selected from imidazolyl, triazolyl or pyridyl;

Y is selected from phenyl or pyridyl;

Z is selected from phenyl or pyridyl;

m is 0, 1, 2, 3 or 4;

n is 0, 1, 2, 3 or 4;

q is 0, 1 or 2;

s is 0, 1, 2, 3 or 4;

t is 0, 1, 2 or 3; and x is 0, 1, 2 or 3;

provided that if attachment of

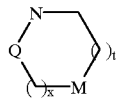

to the rest of the molecule is through a nitrogen ring atom, then $A^1$ is $NR^8$, O, or $S(O)_q$;

provided that the sum of variables x and t equals 3;

or a pharmaceutically acceptable salt, an optical isomer or stereoisomer thereof.

9. The compound according to claim 2 of formula D:

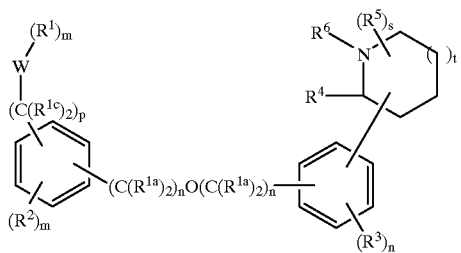

D $R^{1a}$ and $R^{1c}$ are independently selected from:
a) hydrogen,
b) unsubstituted or substituted aryl; unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, $N(R^8)_2$, $(R^8)_2NC(O)$—, $C(O)N(R^8)$—, or $N_3$;
c) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$R^1$ is selected from:
a) H,
b) unsubstituted or substituted $C_1$–$C_6$ alkyl,
c) unsubstituted or substituted aryl,
d) unsubstituted or substituted heterocycle,
e) —($C_1$–$C_6$ alkyl)$N(R^8)_2$,
f) —($C_1$–$C_6$ alkyl)$C(O)R^8$,
g) —($C_1$–$C_6$ alkyl)$OR^8$,
h) —$N(R^8)_2$,
i) —$OR^8$,
j) —($C_1$–$C_6$ alkyl)$NHC(O)R^8$,
k) —($C_1$–$C_6$ alkyl)$C(O)N(R^8)_2$,
l) $CF_3$, and
m) halo;

$R^2$ is selected from:
a) hydrogen,
b) CN,
c) $NO_2$,
d) halogen,
e) aryl, unsubstituted or substituted,
f) heteroaryl, unsubstituted or substituted,
g) $C_1$–$C_6$ alkyl, unsubstituted or substituted,
h) $OR^8$,
i) $N_3$,
j) $R^9S(O)_q$,
k) $R^8HC$=CH—, and
l) $R^8C$≡C—;

R³ is selected from:
  a) H,
  b) CN,
  c) NO₂,
  d) halogen,
  e) C₁–C₆ alkyl, unsubstituted or substituted,
  f) OR⁸,
  g) aryl, unsubstituted or substituted,
  h) heteroaryl, unsubstituted or substituted, and
  i) CF₃;
R⁴ is =O;
R⁵ is selected from:
  a) H,
  b) CN,
  c) NO₂,
  d) halogen,
  e) C₁–C₆ alkyl, unsubstituted or substituted,
  f) N₃,
  g) R⁹S(O)$_q$,
  h) —HC=CH₂,
  i) HC≡C—,
  j) aryl, unsubstituted or substituted,
  k) heterocycle, unsubstituted or substituted,
  l) CF₃O—,
  m) CF₃CH₂O—,
  n) C₃–C₁₀ cycloalkyl,
  o) CF₃,
  p) —(C₁–C₆ alkyl)N(R⁸)₂,
  q) —(C₁–C₆ alkyl)OR⁸,
  r) OR⁸,
  s) N(R⁸)₂,
  t) —C(O)(C₁–C₆ alkyl), and
  u) —(C₁–C₆ alkyl)C(O)R⁸;
R⁶ is selected from:
  a) H,
  b) C₁–C₆ alkyl, unsubstituted or substituted, and
  c) —C(O)(C₁–C₆ alkyl);
R⁸ is independently selected from hydrogen, unsubstituted or substituted C₁–C₆ alkyl, benzyl and unsubstituted or substituted aryl;
R⁹ is independently selected from unsubstituted or substituted C₁–C₆ alkyl, benzyl and unsubstituted or substituted aryl;
W is a heterocycle, selected from imidazolyl or pyridyl;
m is 0, 1, 2, 3 or 4;
n is 0, 1, 2, 3 or 4;
p is 0, 1, 2, 3 or 4;
q is 0, 1 or 2;
s is 0, 1, 2, 3 or 4; and
t is 2;
or a pharmaceutically acceptable salt, an optical isomer or stereoisomer thereof.

10. A compound which is selected from the group consisting of:
  4-imidazol-1-ylmethyl-2-[3-(2-oxo-azepan-1-yl)-phenoxy]-benzonitrile
  2-[3-(3-ethyl-1-methyl-2-oxo-azepan-3-yl)-phenoxy]-4-imidazol-1-ylmethyl-benzonitrile
  2-[3-(3(S)-ethyl-1-methyl-2-oxo-azepan-3-yl)-phenoxy]-4-imidazol-1-ylmethyl-benzonitrile
  2-[3-(3(R)-ethyl-1-methyl-2-oxo-azepan-3-yl)-phenoxy]-4-imidazol-1-ylmethyl-benzonitrile
  2-[3-(3-ethyl-1-methyl-2-oxo-azepan-3-yl)-phenoxy]-4-(2-methyl-imidazol-1-yl)methyl-benzonitrile
  2-[3-(3-ethyl-1-methyl-2-oxo-azepan-3-yl)-phenoxy]-4-(5-methyl-imidazol-1-yl)methyl-benzonitrile
  2-[3-(3-ethyl-1-methyl-2-oxo-azepan-3-yl)-phenoxy]-4-(2,5-dimethyl-imidazol-1-yl)methyl-benzonitrile
  2-[3-(3-ethyl-1-methyl-2-oxo-azepan-3-yl)-phenoxy]-4-[1,2,4]triazol-4-ylmethyl-benzonitrile
  2-[3-(3-ethyl-1-methyl-2-oxo-azepan-3-yl)-phenoxy]-4-[1,2,4]triazol-1-ylmethyl-benzonitrile
  4-imidazol-1-ylmethyl-2-[3-(1-methyl-2-oxo-azepan-3-yl)-phenoxy]-benzonitrile
  4-imidazol-1-ylmethyl-2-[3-(2-oxo-azepan-3-yl)-phenoxy]-benzonitrile
  2-[3-(3-hydroxymethyl-1-methyl-2-oxo-azepan-3-yl)-phenoxy]-4-imidazol-1-ylmethyl-benzonitrile
  2-[3-(3-cyclopropylmethyl-1-methyl-2-oxo-azepan-3-yl)-phenoxy]-4-imidazol-1-ylmethyl-benzonitrile
  2-[4-bromo-3-(3-cyclopropylmethyl-1-methyl-2-oxo-azepan-3-yl)-phenoxy]-4-imidazol-1-ylmethyl-benzonitrile
  2-[3-(3-methoxymethyl-1-methyl-2-oxo-azepan-3-yl)-phenoxy]-4-imidazol-1-ylmethyl-benzonitrile
  2-[3-(3-ethyl-2-oxo-azepan-3-yl)-phenoxy]-4-imidazol-1-ylmethyl-benzonitrile
  4-[5-(2-amino-ethyl)-2-methyl-imidazol-1-ylmethyl]-2-[3-(3-ethyl-1-methyl-2-oxo-azepan-3-yl)-phenoxy]-benzonitrile
  2-[3-(3-ethyl-1-methyl-2-oxo-azepan-3-yl)-phenoxy]-4-[2-methyl-5-(2-morpholin-4-yl-ethyl-imidazol-1-ylmethyl]-benzonitrile
  N-[2-(3-{4-cyano-3-[3-(3-ethyl-1-methyl-2-oxo-azepan-3-yl)-phenoxy]-benzyl}-2-methyl-3H-imidazol-4-yl)-ethyl]-acetamide
  3-ethyl-3-[3-(3-imidazol-1-ylmethyl-phenoxy)-phenyl]-1-methyl-azepan-2-one
  2-[3-(3-ethyl-1-methyl-2-oxo-azepan-3-yl)-phenoxy]-4-(3-methyl-3-H-imidazol-4-ylmethyl)-benzonitrile
  2-[3-(3-ethyl-1-methyl-2-oxo-azepan-3-yl)-phenoxy]-4-(3H-imidazol-4-ylmethyl)-benzonitrile
  2-[3-(3-ethyl-1-methyl-2-oxo-azepan-3-yl)-phenoxy]-4-[hydroxy-(3-methyl-3-H-imidazol-4-yl)-methyl]-benzonitrile
  4-[amino-(3-methyl-3-H-imidazol-4-yl)-methyl]-2-[3-(3-ethyl-1-methyl-2-oxo-azepan-3yl)-phenoxy]-benzonitrile
  2-[3-(3-ethyl-1-methyl-2-oxo-azepan-3-yl)-benzyl]-4-(3-methyl-3H-imidazole-4-carbonyl)-benzonitrile
  2-[3-(3-ethyl-1-methyl-2-oxo-azepan-3-yl)-phenoxy]-4-(hydroxy-pyridin-3-yl-methyl)-benzonitrile
  2-[3-(3-ethyl-1-methyl-2-oxo-azepan-3-yl)-phenoxy]-4-pyridin-3-ylmethyl-benzonitrile
  2-[3-(3-ethyl-1-methyl-2-oxo-azepan-3-yl)-phenoxy]-4-pyridin-2-ylmethyl-benzonitrile
  2-[3-(3-ethyl-1-methyl-2-oxo-azepan-3-yl)-phenoxy]-4-[1-hydroxy-1-(3-methyl-3H-imidazol-4-yl)-ethyl]-benzonitrile
  2-[3-(3R)-ethyl-1-methyl-2-oxo-azepan-3-yl)-phenoxy]-4-[1-(R)amino-1-(3-methyl-3H-imidazol-4-yl)-ethyl]-benzonitrile
  2-[3-(3S)-ethyl-1-methyl-2-oxo-azepan-3-yl)-phenoxy]-4-[1-(S)amino-1-(3-methyl-3H-imidazol-4-yl)-ethyl]-benzonitrile
  2-[3-(3S)-ethyl-1-methyl-2-oxo-azepan-3-yl)-phenoxy]-4-[1-(R)amino-1-(3-methyl-3H-imidazol-4-yl)-ethyl]-benzonitrile 2-[3-(3R)-ethyl-1-methyl-2-oxo-azepan-3-yl)-phenoxy]-4-[1-(S)amino-1-(3-methyl-3H-imidazol-4-yl)-ethyl]-benzonitrile 2-[3-3(R)-n-butyl-1-methyl-2-oxo-azepan-3-yl)-phenoxy]-4-[1-(R)amino-1-(3-methyl-3H-imidazol-4-yl)-ethyl]-benzonitrile 2-[3-3(S)-n-butyl-1-methyl-2-oxo-azepan-3-yl)-phenoxy]-4-[1-(S)amino-1-(3-methyl-3H-imidazol-4-yl)-ethyl]-benzonitrile 2-[3-3(S)-n-butyl-1-methyl-2-oxo-azepan-3-yl)-phenoxy]-4-[1-(R)amino-1-(3-methyl-3H-imidazol-4-yl)-ethyl]-benzonitrile 2-[3-3(R)-n-butyl-1-methyl-2-oxo-azepan-3-yl)-phenoxy]-4-[1-(S)amino-1-(3-methyl-3H-imidazol-4-yl)-ethyl]-benzonitrile 2-[3-3(R)-cyclopropylmethyl-1-methyl-2-oxo-azepan-3-yl)-phenoxy]-4-[1-(R)amino-1-(3-methyl-3H-imidazol-4-yl)-ethyl]-benzonitrile 2-[3-3(S)-cyclopropylmethyl-1-methyl-2-oxo-azepan-3-yl)-phenoxy]-4-[1-(S)amino-1-(3-methyl-3H-imidazol-4-yl)-ethyl]-benzonitrile 2-[3-3(R)-cyclopropylmethyl-1-methyl-2-oxo-azepan-3-yl)-phenoxy]-4-[1-(S)amino-1-(3-methyl-3H-imidazol-4-yl)-ethyl]-benzonitrile 2-[3-3(S)-cyclopropylmethyl-1-methyl-2-oxo-azepan-3-yl)-phenoxy]-4-[1-(R)-amino-1-(3-methyl-3H-imidazol-4-yl)-ethyl]-benzonitrile 2-[3-3(R)-cyclopropylethyl-1-methyl-2-oxo-azepan-3-yl)-phenoxy]-4-[1-(R)-amino-1-(3-methyl-3H-imidazol-4-yl)-ethyl]-benzonitrile 2-[3-3(S)-cyclopropylethyl-1-methyl-2-oxo-azepan-3-yl)-phenoxy]-4-[1-(S)-amino-1-(3-methyl-3H-imidazol-4-yl)-ethyl]-benzonitrile 2-[3-3(R)-cyclopropylethyl-1-methyl-2-oxo-azepan-3-yl)-phenoxy]-4-[1-(S)-amino-1-(3-methyl-3H-imidazol-4-yl)-ethyl]-benzonitrile 2-[3-3(S)-cyclopropylethyl-1-methyl-2-oxo-azepan-3-yl)-phenoxy]-4-[1-(R)-amino-1-(3-methyl-3H-imidazol-4-yl)-ethyl]-benzonitrile 2-[3-3(R)-propyl-1-methyl-2-oxo-azepan-3-yl)-phenoxy]-4-[1-(R)-amino-1-(3-methyl-3H-imidazol-4-yl)-ethyl]-benzonitrile 2-[3-3(S)-propyl-1-methyl-2-oxo-azepan-3-yl)-phenoxy]-4-[1-(S)amino-1-(3-methyl-3H-imidazol-4-yl)-ethyl]-benzonitrile 2-[3-3(R)-propyl-1-methyl-2-oxo-azepan-3-yl)-phenoxy]-4-[1-(S)amino-1-(3-methyl-3H-imidazol-4-yl)-ethyl]-benzonitrile 2-[3-3(S)-propyl-1-methyl-2-oxo-azepan-3-yl)-phenoxy]-4-[1-(R)-amino-1-(3-methyl-3H-imidazol-4-yl)-ethyl]-benzonitrile 2-[3-3(R)-methoxymethyl-1-methyl-2-oxo-azepan-3-yl)-phenoxy]-4-[1-(R)-amino-1-(3-methyl-3H-imidazol-4-yl)-ethyl]-benzonitrile 2-[3-3(S)-methoxymethyl-1-methyl-2-oxo-azepan-3-yl)-phenoxy]-4-[1-(S)-amino-1-(3-methyl-3H-imidazol-4-yl)-ethyl]-benzonitrile 2-[3-3(R)-methoxymethyl-1-methyl-2-oxo-azepan-3-yl)-phenoxy]-4-[1-(S)-amino-1-(3-methyl-3H-imidazol-4-yl)-ethyl]-benzonitrile 2-[3-3(S)-methoxymethyl-1-methyl-2-oxo-azepan-3-yl)-phenoxy]-4-[1-(R)-amino- 2-[3-3(R)-ethoxymethyl-1-methyl-2-oxo-azepan-3-yl)-phenoxy]-4-[1-(R)-amino-1-(3-methyl-3H-imidazol-4-yl)-ethyl]-benzonitrile 2-[3-3(S)-ethoxymethyl-1-methyl-2-oxo-azepan-3-yl)-phenoxy]-4-[1-(S)-amino-1-(3-methyl-3H-imidazol-4-yl)-ethyl]-benzonitrile 2-[3-3(R)-ethoxymethyl-1-methyl-2-oxo-azepan-3-yl)-phenoxy]-4-[1-(S)-amino-1-(3-methyl-3H-imidazol-4-yl)-ethyl]-benzonitrile 2-[3-3(S)-ethoxymethyl-1-methyl-2-oxo-azepan-3-yl)-phenoxy]-4-[1-(R)-amino-1-(3-methyl-3H-imidazol-4-yl)-ethyl]-benzonitrile 2-[3-methyl-1-methyl-2-oxo-azepan-3-yl)-phenoxy]-4-[1-amino-1-(3-methyl-3H-imidazol-4yl)-ethyl]-benzonitrile 2-[3-(3-ethyl-1-methyl-2-oxo-azepan-3-yl)-phenoxy]-4-[1-(3-methyl-3-H-imidazol-4-yl)-vinyl]-benzonitrile 2-[3-(3-ethyl-1-methyl-2-oxo-azepan-3-yl)-phenoxy]-4-[1-(3-methyl-3-H-imidazol-4-yl)-cyclopropyl]-benzonitrile 2-[3-N,N-dimethylaminomethyl-1-methyl-2-oxo-azepan-3-yl)-phenoxy]-4-[1-hydroxy-1-(3-methyl-3H-imidazol-4-yl)-ethyl]-benzonitrile 2-[3-N,N-dimethylaminomethyl-1-methyl-2-oxo-azepan-3-yl)-phenoxy]-4-[1-amino-1-(3-methyl-3H-imidazol-4-yl)-ethyl]-benzonitrile 2-[3-(3-N,N-dimethylaminomethyl-1-methyl-2-oxo-azepan-3-yl)-phenoxy]-4-[1-(3-methyl-3-H-imidazol-4-yl)-vinyl]-benzonitrile 4-[5-(2-N,N-dimethylaminoethyl)-2-methyl-imidazol-1-ylmethyl]-2-[3-(3S-ethyl-1-methyl-2-oxo-azepan-3-yl)-phenoxy]-benzonitrile 4-[5-(2-N,N-dimethylaminoethyl)-2-methyl-imidazol-1-ylmethyl]-2-[3-(3R-ethyl-1-methyl-2-oxo-azepan-3-yl)-phenoxy]-benzonitrile

[2-(3-{4-cyano-3-[3-(3S-ethyl-1-methyl-2-oxo-azepan-3-yl)-phenoxy]-benzyl}-2-methyl-3H-imidazol-4-yl)-ethyl]-urea

[2-(3-{4-cyano-3-[3-(3R-ethyl-1-methyl-2-oxo-azepan-3-yl)-phenoxy]-benzyl}-2-methyl-3H-imidazol-4-yl)-ethyl]-urea 2-[3-(3-ethyl-1-methyl-2-oxo-azepan-3-yl)-phenoxy]-4-pyridin-N-oxide-3-ylmethyl-benzonitrile 2-[3-(1-methyl-2-oxo-azepan-3-yl)-phenoxy]-4-[1-amino-1-(3-methyl-3H-imidazol-4yl)-ethyl]-benzonitrile 2-[3-(3-hydroxymethyl-1-methyl-2-oxo-azepan-3-yl)-phenoxy]-4-[1-amino-1-(3-methyl-3H-imidazol-4-yl)-ethyl]-benzonitrile 4-[1-(4-allyl-5-bromo-pyridin-3-yi)-1-hydroxy-ethyl]-2-[3-(3-ethyl-1-methyl-2-oxo-azepan-3-yl)-phenoxy]-benzonitrile 1-tert-butyl-3(R)-[1-{4-cyano-3-[3-(3R-ethyl-1-methyl-2-oxo-azepan-3-yl)-phenoxy]-phenyl}-1-(3-methyl-3H-imidazol-4-yl)-ethyl]-urea 1-tert-butyl-3(S)-[1-{4-cyano-3-[3-(3S-ethyl-1-methyl-2-oxo-azepan-3-yl)-phenoxy]-phenyl}-1-(3-methyl-3H-imidazol-4-yl)-ethyl]-urea 1-tert-butyl-3(R)-[1-{4-cyano-3-[3-(3S-ethyl-1-methyl-2-oxo-azepan-3-yl)-phenoxy]-phenyl}-1-(3-methyl-3H-imidazol-4-yl)-ethyl]-urea 1-tert-butyl-3(S)-[1-{4-cyano-3-[3-(3R-ethyl-1-methyl-2-oxo-azepan-3-yl)-phenoxy]-phenyl}-1-(3-methyl-3H-imidazol-4-yl)-ethyl]-urea 1-[1-{4-cyano-3(R)-[3-(3R-ethyl-1-methyl-2-oxo-azepan-3-yl)-phenoxy]-phenyl}-1-(3-methyl-3H-imidazol-4-yl)-ethyl]-3-methyl-urea 1-[1-{4-cyano-3(S)-[3-(3S-ethyl-1-methyl-2-oxo-azepan-3-yl)-phenoxy]-phenyl}-1(3-methyl-3H-imidazol-4-yl)-ethyl]-3-methyl-urea 1-[1-{4-cyano-3(R)-[3-(3S-ethyl-1-methyl-2-oxo-azepan-3-yl)-phenoxy]-phenyl}-1-(3methyl-3H-imidazol-4-yl)-ethyl]-3-methyl-urea 1-[1-{4-cyano-3(S)-[3-(3R-ethyl-1-methyl-2-oxo-azepan-3-yl)-phenoxy]-phenyl}-1-(3-methyl-3H-imidazol-4-yl)-ethyl]-3-methyl-urea 1-[1-{4-cyano-3(R)-[3-(3S-ethyl-1-methyl-2-oxo-azepan-3-yl)-phenoxy]-phenyl}-1-(3-methyl-3H-imidazol-4-yl)-ethyl]-3-phenyl-urea 1-[1-{4-cyano-3(S)-[3-(3S-ethyl-1-methyl-2-oxo-azepan-3-yl)-phenoxy]-phenyl}-1-(3-methyl-3H-imidazol-4-yl)-ethyl]-3-phenyl-urea 1-[1-{4-cyano-3(R)-[3-(3R-ethyl-1-methyl-2-oxo-azepan-3-yl)-phenoxy]-phenyl}-1-(3-methyl-3H-imidazol-4-yl)-ethyl]-3-phenyl-urea 1-[1-{4-cyano-3(R)-[3-(3S-ethyl-1-methyl-2-oxo-azepan-3-yl)-phenoxy]-phenyl}-1-(3-methyl-3H-imidazol-4-yl)-ethyl]-3-phenyl-urea

[1-{4-cyano-3(R)-[3-(3R-ethyl-1-methyl-2-oxo-azepan-3-yl)-phenoxy]-phenyl}-1-(3-methyl-3H-imidazol-4-yl)-ethyl]-urea

[1-{4-cyano-3(S)-[3-(3S-ethyl-1-methyl-2-oxo-azepan-3-yl)-phenoxy]-phenyl}-1-(3-methyl-3H-imidazol-4-yl)-ethyl]-urea

[1-{4-cyano-3(R)-[3-(3S-ethyl-1-methyl-2-oxo-azepan-3-yl)-phenoxy]-phenyl}-1-(3-methyl-3H-imidazol-4-yl)-ethyl]-urea

[1-{4-cyano-3(S)-[3-(3R-ethyl-1-methyl-2-oxo-azepan-3-yl)-phenoxy]-phenyl}-1-(3-methyl-3H-imidazol-4-yl)-ethyl]-urea N-[1-{4-cyano-3-[3-(3-ethyl-1-methyl-2-oxo-azepan-3-yl)-phenoxy]-phenyl}-1-(3-methyl-3H-imidazol-4-yl)-ethyl]-acetamide 2-[3-(3S-ethyl-1-methyl-2-oxo-azepan-3-yl)-phenoxy]-4-[1-methylamino-1-(3-methyl-3H-imidazol-4-yl)-ethyl]-benzonitrile 2-[3 (3R-ethyl-1-methyl-2-oxo-azepan-3-yl)-phenoxy]-4-[1-methylamino-1-(3-methyl-3H-imidazol-4-yl)-ethyl]-benzonitrile 2-[3-(3S-ethyl-1-methyl-2-oxo-azepan-3-yl)-phenoxy]-4-[1(R)-methylamino-1-(3-methyl-3H-imidazol-4-yl)-ethyl]-benzonitrile 2-[3-(3S-ethyl-1-methyl-2-oxo-azepan-3-yl)-phenoxy]-4-[1(S)-methylamino-1-(3methyl-3H-imidazol-4-yl)-ethyl]-benzonitrile 2-[5-(3S-ethyl-1-methyl-2-oxo-azepan-3-yl)-2-iodo-phenoxy]-4-imidazol-1-ylmethyl-benzonitrile 2-[5-(3R-ethyl-1-methyl-2-oxo-azepan-3-yl)-2-iodo-phenoxy]-4-imidazol-1-ylmethyl-benzonitrile 2-[5-(3S-ethyl-1-methyl-2-oxo-azepan-3-yl)-2-bromo-phenoxy]-4-imidazol-1-ylmethyl-benzonitrile 2-[5-(3R-ethyl-1-methyl-2-oxo-azepan-3-yl)-2-bromo-phenoxy]-4-imidazol-1-ylmethyl-benzonitrile 4-[1-amino-1-(3-methyl-3H-imidazol-4-yl)-ethyl]-2-[2-dimethyl aminomethyl-5-(3S-ethyl-1-methyl-2-oxo-azepan-3-yl)-phenoxy]-benzonitrile 2-[3-(3-ethyl-1-methyl-2-oxo-azepan-3-yl)-phenoxy]-4-(4,5,6,7-tetrahydro-3H-imidazo]4,5-]pyridin-4-yl)-benzonitrile 2-[3-ethyl -2-oxo-azepan-3-yl)-phenoxy]-4-[1-amino-1-(3-methyl-3H-imidazol-4-yl)-ethyl]-benzonitrile 4-[1-amino-1-(3-methyl-3H-imidazol-4-yl)-ethyl]-2-{3-[3-ethyl-1-(3-hydroxy-propyl)-2oxo-azepan-3-yl]-phenoxy}-benzonitrile 4-[1-amino-1-(3-methyl-3H-imidazol-4-yl)-ethyl]-2-{3-[3-ethyl-1-propyl-2-oxo-azepan-3-yl]-phenoxy}-benzonitrile 2-{3-[1-(2-amino-ethyl)-3-ethyl-2-oxo-azepan-3-yl]-phenoxy}-4-[1-amino-1-(3-methyl-3H-imidazol-4-yl)-ethyl]-benzonitrile {2-[3-(3-{5-[1-amino-1-(3-methyl-3H -imidazol-4-yl)-ethyl]2-cyano-phenoxy}-phenyl)-3-ethyl-2-oxo-azepan-1-yl]-ethyl}-urea N-{2-[3-(3-{5-[1-amino-1-(3-methyl-3H-imidazol-4-yl)-ethyl]2-cyano-phenoxy}-phenyl)-3-ethyl-2-oxo-azepan-1-yl]-ethyl}-N'-methyl urea 4-[1(R)-amino-1-(3-methyl-3H-imidazol-4-yl)-ethyl]-2-{3-[1-methyl-2-oxo-3(R)-(3,3,3-trifluoro-propyl)-azepan-3-yl]-phenoxy}-benzonitrile 4-[1(S)-amino-1-(3-methyl-3H-imidazol-4-yl)-ethyl]-2-{3-[1-methyl-2-oxo-3(S)-(3,3,3-triflouro-propyl)-azepan-3-yl]-phenoxy}-benzonitrile 4-[1(R)-amino-1-(3-methyl-3H-imidazol-4-yl)-ethyl]-2-{3-[1-methyl-2-oxo-3(S)-(3,3,3-trifluoro-propyl)-azepan-3-yl]-phenoxy}-benzonitrile 4-[1(S)-amino-1-(3-methyl-3H-imidazol-4-yl)-ethy]-2-{3-[1-methyl-2-oxo-3(R)-(3,3,3-trifluoro-propyl)-azepan-3-yl]-phenoxy}-benzonitrile 4-[1-amino-1-(3-methyl-3H-imidazol-4-yl)-ethyl]-2-{3-[1-(2-dimethylamino-ethyl)-3-ethyl-2-oxo-azepan-3-yl]-phenoxy}-benzonitrile 4-[1-(R or S)amino-1-(3-methyl-3H-imidazol-4-yl)-ethyl]-2-{3-[1-(2-hydroxyethyl)-3-ethyl-2-oxo-azepan-3-yl]-phenoxy}-benzonitrile 4-[1-amino-1-(3-methyl-3H-imidazol-4-yl)-ethyl]-2-{3-[1-(2-methoxyethyl)-3R-ethyl-2-oxo-azepan-3-yl]-phenoxy}-benzonitrile 4-Imidazol-1-ylmethyl-2-[3-(1-methyl-7-oxo-azepan-2-yl)-phenoxy]-benzonitrile hydrochloride 4-[1-amino-1-(3-methyl-3H-imidazol-4-yl)-ethyl]-2-{3-[1-(2-methoxyethyl)-3R-ethyl-2-oxo-azepan-3-yl]-phenoxy}-benzonitrile;

2-[3-(3R-ethyl-1-methyl-2-oxo-azepan-3-yl)-phenoxy]-4-[5-(2-morpholin-4-yl-ethyl)-imidazol-1-ylmethyl benzonitrile;

or a pharmaceutically acceptable salt, an optical isomer or stereoisomer thereof.

11. The compound according to claim 10 which is

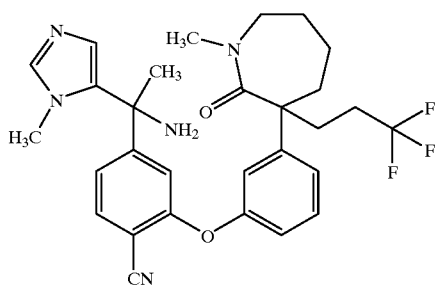

2-{3-[1-methyl-2-oxo-3-(R or S)-(3,3,3-trifluoro-propyl)-azepan-3-yl]-phenoxy}-4-[1(R or S)-amino-1-(3-methyl-3H-imidazol-4-yl)-ethyl]-benzonitrile;

or a pharmaceutically acceptable salt, an optical isomer or stereoisomer thereof.

12. The compound according to claim 10 which is

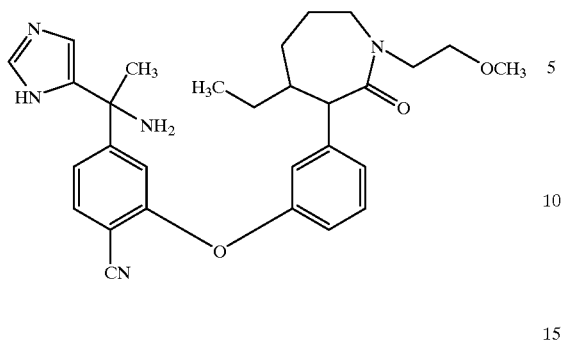

4-[1-amino-1-(3-methyl-3H-imidazol-4-yl)-ethyl]-2-{3-[1-(2-methoxyethyl)-3R-ethyl-2-oxo-azepan-3-yl]-phenoxy}-benzonitrile;

or a pharmaceutically acceptable salt, an optical isomer or stereoisomer thereof.

13. The compound according to claim 10 which is:

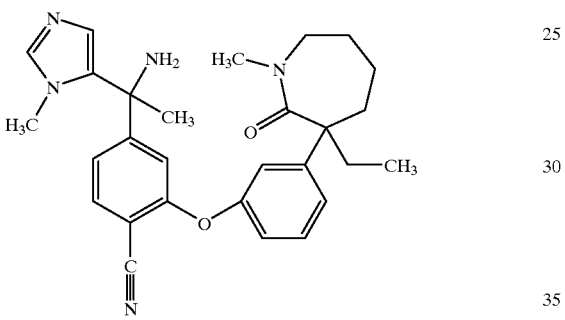

2-[3-(3-ethyl-1-methyl-2-oxo-azepan-3-yl)-phenoxy]-4-[1-amino-1-(3-methyl-3-H-imidazol-4-yl)-ethyl]-benzonitrile or a pharmaceutically acceptable salt, an optical isomer or stereoisorer thereof.

14. The compound according to claim 10 which is:

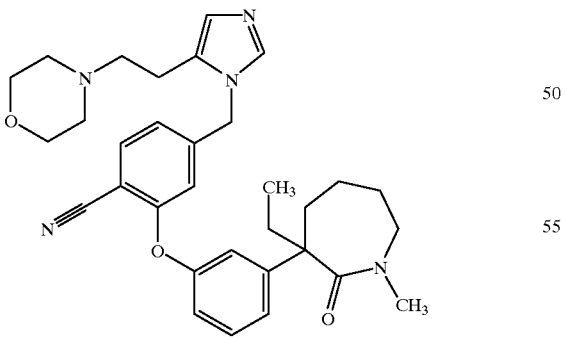

2-[3-(3R-ethyl-1-methyl-2-oxo-azepan-3-yl)-phenoxy]-4-[5-(2-morpholin-4-yl-ethyl)-imidazol-1-ylmethyl benzonitrile;

or a pharmaceutically acceptable salt, an optical isomer or stereoisomer thereof.

15. The compound according to claim 10 which is:

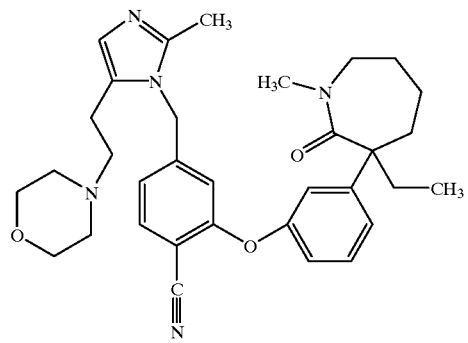

2-[3-(3-ethyl-1-methyl-2-oxo-azepan-3-yl)-phenoxy]-4-[2-methyl-5-(2-morpholin-4-ethyl)-yl-ethyl)-imidazol-1-ylmethyl]-benzonitrile;

or a pharmaceutically acceptable salt, an optical isomer or stereoisomer thereof.

16. The compound according to claim 10 which is:

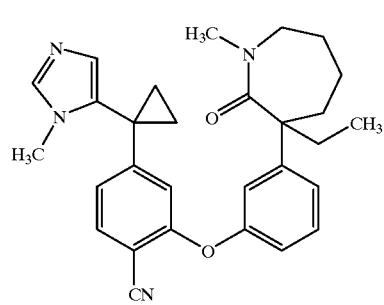

2-[3-(3-ethyl-1-methyl-2-oxo-azepan-3-yl)-phenoxy]-4-[1-(3-methyl-3-H-imidazol-4-yl)-cyclopropyl]-benzonitrile or a pharmaceutically acceptable salt, an optical isomer or stereoisomer thereof.

17. The compound according to claim 10 which is:

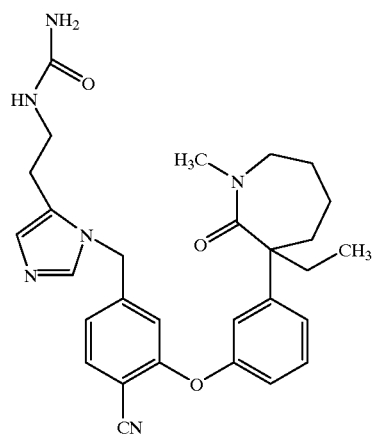

[2-(3-{4-cyano-3-[3-(3-ethyl-1-methyl-2-oxo-azepan-3-yl)-phenoxy]-benzyl}methyl-3H-imidazol-4-yl)-ethyl]-urea or a pharmaceutically acceptable salt, an optical isomer or stereoisomer thereof.

18. The compound according to claim 10 which is:

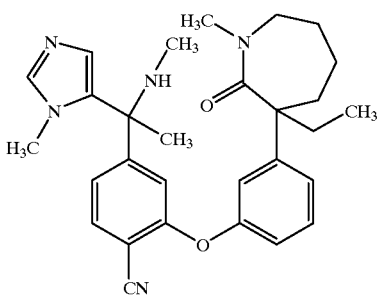

2-[3-(3-ethyl-1-methyl-2-oxo-azepan-3-yl)-phenoxy]-4-[1-methylamino-1-(3-methyl-3H-imidazol-4-yl)-ethyl]-benzonitrile
or a pharmaceutically acceptable salt, an optical isomer or stereoisomer thereof.

19. The compound according to claim 10 which is:

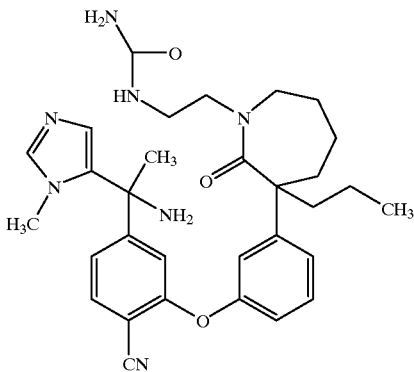

{2-[3-(3-{5-[1-amino-1-(3-methyl-3H-imidazol-4-yl)-ethyl]2-cyano-phenoxy}-phenyl)-3-ethyl-2-oxo-azepan-1-yl]-ethyl}-urea
or a pharmaceutically acceptable salt, an optical isomer or stereoisomer thereof.

20. A pharmaceutical composition comprising a pharmaceutical carrier, and dispersed therein, a therapeutically effective amount of a compound of claim 1.

21. A pharmaceutical composition comprising a pharmaceutical carrier, and dispersed therein, a therapeutically effective amount of a compound of claim 2.

22. A pharmaceutical composition comprising a pharmaceutical carrier, and dispersed therein, a therapeutically effective amount of a compound of claim 4.

23. A pharmaceutical composition comprising a pharmaceutical carrier, and dispersed therein, a therapeutically effective amount of a compound of claim 10.

24. A pharmaceutical composition made by combining the compound of claim 1 and a pharmaceutically acceptable carrier.

25. A pharmaceutical composition made by combining the compound of claim 2 and a pharmaceutically acceptable carrier.

26. A process for making a pharmaceutical composition comprising combining a compound of claim 1 and a pharmaceutically acceptable carrier.

27. A process for making a pharmaceutical composition comprising combining a compound of claim 2 and a pharmaceutically acceptable carrier.

28. A method for treating a cancer, selected from colorectal carcinoma, exocrine pancreatic carcinoma, myeloid leukemias and neurological tumors, which comprises administering to a mammal in need thereof a therapeutically effective amount of a composition of claim 20.

29. A method for treating a cancer, selected from colorectal carcinoma, exocrine pancreatic carcinoma, myeloid leukemias and neurological tumors, which comprises administering to a mammal in need thereof a therapeutically effective amount of a composition of claim 21.

30. A method for treating a cancer, selected from colorectal carcinoma, exocrine pancreatic carcinoma, myeloid leukemias and neurological tumors, which comprises administering to a mammal in need thereof a therapeutically effective amount of a composition of claim 22.

31. A method for treating a cancer, selected from colorectal carcinoma, exocrine pancreatic carcinoma, myeloid leukemias and neurological tumors, which comprises administering to a mammal in need thereof a therapeutically effective amount of a composition of claim 24.

32. A method for treating neurofibromen benign proliferative disorder which comprises administering to a mammal in need thereof a therapeutically effective amount of a composition of claim 20.

33. A method for treating blindness related to retinal vascularization which comprises administering to a mammal in need thereof a therapeutically effective amount of a composition of claim 20.

34. A method for treating infections from hepatitis delta which comprises administering to a mammal in need thereof a therapeutically effective amount of a composition of claim 20.

35. A method for treating polycystic kidney disease which comprises administering to a mammal in need thereof a therapeutically effective amount of a composition of claim 20.

* * * * *

UNITED STATES PATENT AND TRADEMARK OFFICE
CERTIFICATE OF CORRECTION

PATENT NO. : 6,284,755 B1
DATED : September 4, 2001
INVENTOR(S) : S. Jane deSolms, Samuel L. Graham, Anthony W. Shaw, Terrence M. Ciccarone and Gerald E. Stokker It is certified that error appears in the above-identified patent and that said Letters Patent is hereby corrected as shown below:

Column 149,
Line 10 should read as follows: -- Q is C(=O); --.

Column 157,
Lines 34 and 35 should read as follows:
--  imidazol-4-yl)-ethyl]-benzonitrile
2-{3-3(R)-cyclopropylethyl-1-methyl-2-oxo-azepan-3-yl)- --.
Line 64 should read as follows:
-- phenoxy]-4-[1-(R)-amino-1-(3-methyl-3H-imidazol-4-yl)-ethyl]-benzonitrile --.

Column 158,
Line 44 should read as follows: -- amino-1-(3-methyl-3H-imidazol-4-yl)-ethyl]- --.
Line 49 should read as follows:
-- 4-[1-(4-allyl-5-bromo-pyridin-3-yl)-1-hydroxy-ethyl]-2- --.

Column 159,
Line 49 should read as follows:
-- [1(S)-methylamino-1-(3-methyl-3H-imidazol-4-yl)- --.

Column 160,
Line 2 should read as follows: -- [3-ethyl-1-(3-hydroxy-propyl)-2-oxo-azepan-3-yl]- --.

Column 161,
Line 40 should read as follows: -- [1-amino-1-(3-methyl-3H-imidazol-4-yl)-ethyl]- --.

UNITED STATES PATENT AND TRADEMARK OFFICE
CERTIFICATE OF CORRECTION

PATENT NO.   : 6,284,755 B1
DATED        : September 4, 2001
INVENTOR(S)  : S. Jane deSolms, Samuel L. Graham, Anthony W. Shaw, Terrence M. Ciccarone and Gerald E. Stokker It is certified that error appears in the above-identified patent and that said Letters Patent is hereby corrected as shown below:

<u>Column 162,</u>
Line 19 should read as follows: -- [2-methyl-5-(2-morpholin-4-yl-ethyl)-imidazol- --.
Line 64 should read as follows:
-- yl)-phenoxy]-benzyl}-2-methyl-3H-imidazol-4-yl)- --.

Signed and Sealed this

Fourteenth Day of May, 2002

*Attest:*

*Attesting Officer*

JAMES E. ROGAN
*Director of the United States Patent and Trademark Office*